(12) United States Patent
Tang et al.

(10) Patent No.: US 11,724,997 B2
(45) Date of Patent: Aug. 15, 2023

(54) COMPOUNDS AND COMPOSITIONS FOR TREATING CONDITIONS ASSOCIATED WITH APJ RECEPTOR ACTIVITY

(71) Applicant: Annapurna Bio, Inc., South San Francisco, CA (US)

(72) Inventors: Haifeng Tang, South San Francisco, CA (US); Sarah Boyce, South San Francisco, CA (US); Michael Hanson, South San Francisco, CA (US); Zhe Nie, South San Francisco, CA (US)

(73) Assignee: Annapurna Bio, Inc., South San Francisco, CA (US)

( * ) Notice: Subject to any disclaimer, the term of this patent is extended or adjusted under 35 U.S.C. 154(b) by 0 days.

(21) Appl. No.: 16/971,227

(22) PCT Filed: Feb. 28, 2019

(86) PCT No.: PCT/US2019/020138
§ 371 (c)(1),
(2) Date: Aug. 19, 2020

(87) PCT Pub. No.: WO2019/169193
PCT Pub. Date: Sep. 6, 2019

(65) Prior Publication Data
US 2021/0053936 A1    Feb. 25, 2021

Related U.S. Application Data

(60) Provisional application No. 62/637,207, filed on Mar. 1, 2018.

(51) Int. Cl.
| | | |
|---|---|---|
| *C07D 401/04* | (2006.01) | |
| *C07D 249/14* | (2006.01) | |
| *C07D 401/14* | (2006.01) | |
| *C07D 403/04* | (2006.01) | |
| *C07D 405/04* | (2006.01) | |
| *C07D 405/14* | (2006.01) | |
| *C07D 413/04* | (2006.01) | |

(52) U.S. Cl.
CPC ......... *C07D 401/04* (2013.01); *C07D 249/14* (2013.01); *C07D 401/14* (2013.01); *C07D 403/04* (2013.01); *C07D 405/04* (2013.01); *C07D 405/14* (2013.01); *C07D 413/04* (2013.01)

(58) Field of Classification Search
CPC .................................................. C07D 401/04
See application file for complete search history.

(56) References Cited

U.S. PATENT DOCUMENTS

| | | |
|---|---|---|
| 7,112,601 B2 | 9/2006 | Glunz et al. |
| 7,214,802 B2 | 5/2007 | Cogan et al. |
| 9,156,796 B2 | 10/2015 | Hachtel et al. |
| 9,758,514 B2 | 9/2017 | Muthuppalaniappan et al. |
| 10,344,016 B2 * | 7/2019 | Dransfield ................ A61P 9/04 |

FOREIGN PATENT DOCUMENTS

| | | |
|---|---|---|
| WO | WO 2004/037809 | 5/2004 |
| WO | WO 2004/101555 | 11/2004 |
| WO | WO 2004/111015 | 12/2004 |
| WO | WO 2008/056150 | 5/2008 |
| WO | WO 2008/130021 | 10/2008 |
| WO | WO 2010/017479 | 2/2010 |
| WO | WO 2010/017545 | 2/2010 |
| WO | WO 2011/143466 | 11/2011 |

(Continued)

OTHER PUBLICATIONS

Venkatesh, J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Coquerel et al., "The apelinergic system as an alternative to catecholamines in low-output septic shock," Critical Care, Dec. 1, 2018, 22(1):10, 7 Pages.
International Preliminary Report on Patentability in International Appln. No. PCT/US2019/020138, dated Sep. 1, 2020, 7 Pages.
International Search Report and Written Opinion in International Appln. No. PCT/US2019/020138, dated Apr. 25, 2019, 14 Pages.
Kim, "Apelin-APJ signaling: a potential therapeutic target for pulmonary arterial hypertension," Molecules and cells, Mar. 31, 2014, 37(3):196-201.

(Continued)

*Primary Examiner* — Nizal S Chandrakumar
(74) *Attorney, Agent, or Firm* — Sheppard Mullin Richter & Hampton LLP

(57) ABSTRACT

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

20 Claims, No Drawings

(56) References Cited

FOREIGN PATENT DOCUMENTS

| WO | WO 2014/150326 | 9/2014 | | |
|----|----------------|--------|---|---|
| WO | WO 2016/187308 | 11/2016 | | |
| WO | 2017/096130 A1 | 6/2017 | | |
| WO | WO 2017/091513 | 6/2017 | | |
| WO | WO 2017/091513 | * | 6/2017 | ............. G06F 19/00 |
| WO | WO 2018/093579 | 5/2018 | | |

OTHER PUBLICATIONS

Lau et al., "Epidemiology and treatment of pulmonary arterial hypertension," Nature Reviews Cardiology, Jun. 8, 2017, 14(10): 1-12.
O'Carroll et al., "APJ: journey from an orphan to a multifaceted regulator of homeostasis," J Endocrinol, Oct. 1, 2013, 219(1):R13-R35.
Scimia et al., "APJ acts as a dual receptor in cardiac hypertrophy," Nature, Aug. 2012, 488(7411):394-398.
Chinese Office Action dated Dec. 28, 2022, in corresponding Chinese Appln. No. 201980029435.X (14 pages).

* cited by examiner

COMPOUNDS AND COMPOSITIONS FOR TREATING CONDITIONS ASSOCIATED WITH APJ RECEPTOR ACTIVITY

PRIORITY CLAIM

This application is a National Stage application under 35 U.S.C. § 371 of International Application No. PCT/US2019/020138 having an International Filing Date of Feb. 28, 2019, which claims the benefit of U.S. Provisional Application No. 62/637,207, filed on Mar. 1, 2018, which are incorporated herein by reference in their entirety.

TECHNICAL FIELD

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

BACKGROUND

Pulmonary arterial hypertension (PAH) is a severe cardiopulmonary disorder characterized by the vascular remodeling of the pulmonary arterioles, including formation of plexiform and concentric lesions comprised of proliferative vascular cells. PAH is believed to be caused by cellular proliferation and fibrosis of the small pulmonary arteries. Clinically, PAH leads to increased pulmonary arterial pressure and subsequent right ventricular failure, which is one of the major causes of morbidity and mortality. Mortality rates remain exceedingly high with 15%, 30%, and 45% mortality at 1, 2, and 3 years after diagnosis, respectively. See, e.g., Kim, J., *Mol. Cells* 2014; 37(3): 196-201 and Lau, E. M. T., *Nature Reviews*, 2017, 1-12.

Diabetes mellitus type 2 (type-2 diabetes) is characterized by high blood glucose and insulin resistance. Type 2 diabetes as well as conditions that are co-morbid or sequela with type-2 diabetes affect tens of millions of people in the United States alone. Type-2 diabetes is frequently associated with obesity.

The apelin or APJ receptor is a G protein-coupled receptor containing seven hydrophobic transmembrane domains (see, e.g., Kim, supra). Apelin (also known as APLN) is a 36 amino acid peptide that in humans is encoded by the APLN gene and is the endogenous ligand for the APJ receptor (see, e.g., O'Carroll, A-M., et al., *J Endocrinol* 2013, 219, R13-R35).

The apelin/APJ system is present in many tissues such as heart, kidney, pancreas, lung, vasculature, central nervous system, liver, adipose, gastrointestinal tract, brain, adrenal glands, endothelium, and human plasma.

Additionally, there is evidence showing that both apelin and APJ are regulators of central and peripheral responses to multiple homeostatic perturbations such as cardiovascular control and function; angiogenesis; fluid homeostasis; water balance; hypothalamic-pituitary-adrenal (HPA) axis regulation; metabolic homeostasis; energy metabolism; and kidney function. For example, there is emerging evidence that APJ-apelin signaling plays a role in the maintenance of pulmonary vascular homeostasis (see, e.g., Kim supra). Evidence also points to a nexus between apelinergic system (e.g., apelin and APJ receptor) and the treatment of conditions such as sepsis, septic shock, and renal failure (see, e.g., Coquerel, D., et al., *Critical Care* 2018, 22: 10). As another example, apelin, synthesized and secreted by adipocytes, has been described as a beneficial adipokine related to obesity, and there is additional evidence of a potential role for apelin and APJ receptor in glucose and energy metabolism (see e.g., O'Carroll supra).

WO2016187308 discloses "Triazole Agonists of the APJ Receptor."

SUMMARY

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

An "agonist" of the APJ receptor includes compounds that, at the protein level, directly bind or modify the APJ receptor such that an activity of the APJ receptor is increased, e.g., by activation, stabilization, altered distribution, or otherwise.

Certain chemical entities described herein that agonize the APJ receptor to a lesser extent than an APJ receptor full agonist can function in assays as antagonists as well as agonists. These chemical entities antagonize activation of the APJ receptor by an APJ receptor full agonist because they prevent the full effect of APJ receptor interaction. However, the chemical entities also, on their own, activate some APJ receptor activity, typically less than a corresponding amount of the APJ receptor full agonist. Such chemical entities are sometimes referred to herein as "partial agonists of the APJ receptor".

In some embodiments, the chemical entities described herein are agonists (e.g. full agonists) of the APJ receptor. In other embodiments, the chemical entities described herein are partial agonists of the APJ receptor.

In other embodiments, the chemical entities described herein modulate (e.g., agonize) the APJ receptor in a pathway-specific manner. Accordingly, this disclosure also features chemical entities that exhibit activity as ligand-biased modulators (e.g., ligand-biased agonists). APJ receptor activity can modulate (e.g., alter or bias) competing levels of downstream G-protein signaling (activation) and β-arrestin recruitment. APJ receptor signaling through β-arrestin has been shown to mediate stretch-induced myocardial hypertrophy. See, e.g., Scimia, M. C., et al., *Nature* 2012, 488, 394-398. In certain embodiments, the chemical entities described herein modulate (e.g., reduce, e.g., attenuate, disrupt, inhibit) β-arrestin signaling. In certain embodiments, the chemical entities described herein modulate (e.g., reduce, e.g., attenuate, disrupt, inhibit) recruitment of β-arrestin.

In certain embodiments, the chemical entities described herein activate or increase the levels of downstream G-protein signaling.

In certain embodiments, the chemical entities described herein inhibit or decrease the levels of β-arrestin recruitment.

In certain embodiments, the chemical entities described herein activate or increase the levels of β-arrestin recruitment.

In certain embodiments, the chemical entities described herein selectively modulate (e.g., increase) one of the pathways over the other. For example, the chemical entities described herein can activate or increase the levels of downstream G-protein signaling, and inhibit or decrease the levels of β-arrestin recruitment.

In other embodiments, the chemical entities described herein can activate or increase the levels of downstream G-protein signaling, and activate or increase the levels of β-arrestin recruitment. For example, the chemical entities described herein can fully agonize both β-arrestin and G protein signaling pathways.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In one aspect, the featured peptide-based chemical entities include compounds of Formula I, or a pharmaceutically acceptable salt thereof:

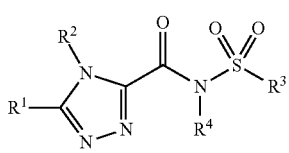

(I)

in which $R^1$, $R^2$, $R^3$, and $R^4$ can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing,) APJ receptor activity are featured that include contacting the APJ receptor with a chemical entity described herein (e.g., a compound described generically or specifically herein or a pharmaceutically acceptable salt thereof or compositions containing the same). Methods include in vitro methods, e.g., contacting a sample that includes one or more cells, each independently comprising one or more APJ receptors with the chemical entity. Methods can also include in vivo methods. Such methods can include, e.g., administering the chemical entity to a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition (e.g., PAH; heart failure; type II diabetes; sepsis; renal failure; and systemic hypertension). In vivo methods include, but are not limited to modulating (e.g., decreasing) right ventricular afterload; modulating (e.g., decreasing) mean pulmonary artery pressure; modulating (e.g., increasing) insulin levels; and modulating (e.g., decreasing) glucose levels in a subject (e.g., a human).

In a further aspect, methods of treatment of a disease, disorder, or condition are featured, in a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. The methods include administering to a subject in need of such treatment an effective amount of a chemical entity described herein (e.g., a compound described generically or specifically herein, a pharmaceutically acceptable salt thereof, or compositions containing the same).

In another aspect, this disclosure features methods of treating a subject having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. The methods include administering a chemical entity described herein (e.g., a compound described generically or specifically herein, a pharmaceutically acceptable salt thereof or compositions containing the same) in an amount effective to treat the disease, disorder, or condition.

In a further aspect, methods of treatment are featured that include administering to a subject chemical entity described herein (e.g., a compound described generically or specifically herein, a pharmaceutically acceptable salt thereof, or compositions containing the same). The methods include administering the chemical entity in an amount effective to treat a disease, disorder, or condition, wherein a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition, thereby treating the disease, disorder, or condition.

A non-limiting example of such diseases, disorders, and conditions is PAH. In some embodiments, the PAH is idiopathic. In other embodiments, the PAH is heritable PAH, toxin or drug-induced PAH; or a PAH associated with one or more of the following: congenital heart disease, connective tissue disorders (e.g., scleroderma, systemic lupus erythematosus, systemic sclerosis, Hashimoto's thyroiditis, Sjogren's Syndrome, and the antiphospholipid antibody syndrome), portal hypertension, BMPR2 mutations, Schistosomiasis, and HIV infection.

Another non-limiting example of such diseases, disorders, and conditions is cardiovascular disease, e.g., coronary heart disease and heart failure. In certain embodiments, the cardiovascular disease is heart failure; e.g., systolic heart failure, diastolic heart failure, diabetic heart failure and heart failure with preserved ejection fraction, cardiomyopathy, myocardial infarction, left ventricular dysfunction including left ventricular dysfunction after myocardial infarction, right ventricular dysfunction, right ventricular failure, cardiac hypertrophy, myocardial remodeling including myocardial remodeling after infarction or after cardiac surgery, and valvular heart diseases.

Still another non-limiting example of such diseases, disorders, and conditions is a metabolic disorder, such as metabolic syndrome; diabetes (e.g., type 2 diabetes); obesity; obesity-related disorders; impaired glucose tolerance; and insulin resistance.

Other non-limiting examples of such diseases, disorders, and conditions include sepsis, septic shock, renal failure, and systemic hypertension.

Further non-limiting examples include coronary artery disease (CAD), non-CAD atherosclerotic conditions, including peripheral vascular disease (PVD), aortic atherosclerosis, and cerebral arteriosclerosis, diabetic retinopathy, ischemia-reperfusion injury, emphysema, radiation-induced organ and tissue injury, corpus luteum regression, scleroderma, systemic sclerosis, and diseases of immune dysregulation.

In one aspect, this disclosure features methods for identifying and/or selecting a subject (e.g., a human) likely to benefit from the methods described herein, as well as methods for determining whether a subject (e.g., a human) is responding to such methods. In certain embodiments, a biological sample, which may be, for example and without limitation, a breath, sputum, tissue, plasma or serum sample, urine, is obtained from the subject, and the level of a particular parameter in the sample is determined and compared to a control value. In some instances, the control value may be determined from one or more normal individuals not suffering from the disease, disorder, or conditions being treated. In other instances, the control value can also be determined from a sample previously obtained from the subject. Generally, higher (or elevated) levels of the measured parameter relative to a control value determined from a normal, non-diseased individual or population indicate that a subject will benefit from methods described herein. Lower levels generally indicate that a patient is responding to therapy or, for a subject not on such therapy, that the therapeutic methods may not be as beneficial for that subject.

In certain of the foregoing embodiments, the subject is suffering from, or at risk of suffering from PAH. Non-limiting, exemplary parameters related to PAH are delineated below.

In certain embodiments, the parameter is LTB4 level. For example, a baseline or reference value of LTB4 can be 100 pg/mL or greater, 200 pg/mL or greater, 300 pg/mL or greater, 400 pg/mL or greater, 500 pg/mL or greater, 600 pg/mL or greater, or 100 pg/mL or greater. In certain embodiments, the treatment provided is efficacious if, after treatment has started, the endpoint LTB4 level of the subject decreases from the baseline or reference LTB4 level. For example, the endpoint LTB4 level of the subject decreases to 600 pg/mL or less, 500 pg/mL or less, 400 pg/mL or less, 300 pg/mL or less, 200 pg/mL or less, or 100 pg/mL or less. In certain embodiments, the treatment provided is efficacious if, after treatment has started, the endpoint LTB4 level is 30 pg/mg of tissue or lower, 20 pg/mg of tissue of lower, 10 pg/mg of tissue or lower, 7.5 pg/mg of tissue or lower, or 5 pg/mg of tissue or lower. In other embodiments, the treatment provided is efficacious if, after treatment has started, the endpoint LTB4 level is lower than the baseline LTB4 level by 2-fold or more, 3-fold or more, 4-fold or more, or 5-fold or more.

In certain embodiments, the parameter is pulmonary vascular resistance (PVR). The baseline or reference PVR level can be 200 $dynsec/cm^5$ or greater, 240 $dynsec/cm^5$ or greater, 300 $dynsec/cm^5$ or greater, 400 $dynsec/cm^5$ or greater, 500 $dynsec/cm^5$ or greater, 600 $dynsec/cm^5$ or greater, 700 $dynsec/cm^5$ or greater, or 800 $dynsec/cm^5$ or greater. In certain embodiments, the treatment provided is efficacious if, after treatment has started, the endpoint PVR level of the subject decreases from the baseline or reference PVR level by 70 $dynsec/cm^5$ or more, 100 $dynsec/cm^5$ or more, 130 $dynsec/cm^5$ or more, or 160 $dynsec/cm^5$ or more.

In certain embodiments, the parameter is pulmonary arterial pressure (PAP). The baseline or reference PAP level can be 20 mmHg or greater, 25 mmHg or greater, 30 mmHg or greater, 35 mmHg or greater, 40 mmHg or greater, 45 mmHg or greater, 50 mmHg or greater, 60 mmHg or greater, or 70 mmHg or greater. In certain embodiments, the treatment provided is efficacious if, after treatment has started, the endpoint PAP level of the subject decreases from the baseline or reference PAP level by 0.5 mmHg or more, 1 mmHg or more, 1.5 mmHg or more, 5 mmHg or more, 10 mmHg or more, 20 mmHg or more, 30 mmHg or more, 40 mmHg or more, or 50 mmHg. In certain embodiments, the subject exhibits a mean pulmonary artery pressure of greater than 25 mmHg.

In certain embodiments, the parameter is cardiac index (CI). A baseline or reference CI level can be 5 L/min/m.sup.2 or lower, 2.5 L/min/m.sup.2 or lower, 2 L/min/m.sup.2 or lower, 1.5 L/min/m.sup.2 or lower, or 1 L/min/m.sup.2 or lower. In certain embodiments, the treatment provided is efficacious if, after treatment has started, the endpoint CI level increases from the baseline or reference CI level by 0.1 or more, 0.2 or more, 0.3 or more, 0.4 or more, 0.5 or more, 1 or more, or 2 or more.

In certain embodiments, the parameter is pulmonary capillary wedge pressure (PCWP). A baseline or reference PCWP level can be 36 mmHg or less, 24 mmHg or less, 18 mmHg or less, 10 mmHg, or 5 mmHg or less. In certain embodiments, the treatment provided is efficacious if, after treatment has started, the endpoint PCWP level increases from the baseline or reference PCWP level by 0.2 mmHg or more, 0.3 mmHg or more, 0.4 mmHg or more, 0.5 mmHg or more, 0.6 mmHg or more, 1 mmHg or more, or 5 mmHg or more.

In certain embodiments, the parameter is right atrial pressure (RAP). A baseline or reference RAP level can be 4 mmHg or more, 6 mmHg or more, 8 mmHg or more, 10 mmHg or more, 12 mmHg or more, 16 mmHg or more, 20 mmHg or more, or 25 mmHg or more. In certain embodiments, the treatment provided is efficacious if, after treatment has started, the endpoint RAP level of the subject decreases from the baseline or reference RAP level by 5 mmHg or more 2.5 mmHg or more, 1 mmHg or more, 0.5 mmHg or more, or 0.2 mmHg or more.

In certain embodiments, the parameter is the six-minute walk distance (6 MWD). A baseline or reference 6 MWD can be 50 m or less, 100 m or less, 200 m or less, 300 m or less, 400 m or less, or 500 m or less. In certain embodiments, the treatment provided is efficacious it after treatment has started, the endpoint 6 MWD of the subject increases from the baseline or reference 6 MWD by 10 m or more, 15 m or more, 20 m or more, 25 m or more, 30 m or more, or 50 m or more. Alternatively or in addition, treatment provided in the invention is efficacious if, after treatment has started, the endpoint 6 MWD of the subject increases by 3% or more, 4% or more, 5% or more, 10% or more, or 20% or more of the baseline level.

In certain embodiments, the parameter is brain natriuretic peptide (BNP) level. A baseline or reference BNP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. In certain embodiments, the treatment provided is efficacious if, after treatment has started, the endpoint BNP level of the subject decreases from the baseline or reference BNP level. For example, the endpoint BNP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

In certain embodiments, the parameter is atrial natriuretic peptide (ANP) level. A baseline or reference ANP level can be 60 pg/mL or higher, 80 pg/mL or higher, 100 pg/mL or higher, 120 pg/mL or higher, 140 pg/mL or higher, 200 pg/mL or higher, 500 pg/mL or higher, or 1000 pg/mL or higher. In certain embodiments, the treatment provided is efficacious if, after treatment has started, the endpoint ANP level of the subject decreases from the baseline or reference ANP level. For example, the endpoint ANP level of the subject can decrease by 1 pg/mL or more, 2 pg/mL or more, 5 pg/mL or more, 10 pg/mL or more, 20 pg/mL or more, 100 pg/mL or more, 500 pg/mL or more, or 1000 pg/mL or more.

In certain embodiments, the parameter is Diffusion of lung capacity (DLCO), or diffusion capacity of CO, can also be used in the methods as a parameter to determine efficacy. A baseline or reference DLCO can be 90% or less, 80% or less, 70% or less, 50% or less, 45% or less, or 40% or less. In certain embodiments, the treatment provided is efficacious if, after treatment has started, the endpoint DLCO is increased from the baseline level. For example, the endpoint DLCO can be increased from the baseline or reference DLCO by 1% or more, 5% or more, 10% or more, 15% or more, 20% or more, or 50% or more.

In another aspect, this disclosure features methods for reducing the risk of right ventricular failure in a subject in need of such reducing, the method comprising administering to the subject an effective amount of a chemical entity described herein.

The methods described herein can further include treating one or more conditions that are associated, co-morbid or sequela with any one or more of the conditions described herein.

For example, the methods can further include treating one or more conditions that are associated, co-morbid or sequela with PAH, e.g., coronary heart disease or heart failure. In certain embodiments, the cardiovascular disease is heart failure, e.g., systolic heart failure, diastolic heart failure, diabetic heart failure and heart failure with preserved ejection fraction, cardiomyopathy, myocardial infarction, left ventricular dysfunction including left ventricular dysfunction after myocardial infarction, right ventricular dysfunction, right ventricular failure, cardiac hypertrophy, myocardial remodeling including myocardial remodeling after infarction or after cardiac surgery, and valvular heart diseases.

As another example, the methods can further include treating one or more conditions that are co-morbid or sequela with diabetes (e.g., type 2 diabetes), such as obesity, obesity-related disorders, metabolic syndrome, impaired glucose tolerance; insulin resistance; cardiovascular risk factors. (e.g., coronary artery disease, peripheral artery disease, cerebrovascular disease, hypertension, and risk factors related to unmanaged cholesterol and/or lipid levels, and/or inflammation), retinopathy, nephropathy, neuropathy, NASH, bone fracture and cognitive dysfunction.

The methods can further include administering one or more other therapeutic agents (e.g., in combination with a chemical entity described herein).

Embodiments can include one of more of the following advantageous properties.

Apelin peptide is labile; as such, only acute pharmacodynamics effect of apelin peptide is observable. In some embodiments, the compounds described herein exhibit relatively high metabolic stability to allow observations of non-acute pharmacodynamics effect.

In some embodiments, the compounds described herein can lead to reduced atrial pressure in addition to enhancing cardiac output.

In some embodiments, the compounds described herein can selectively activate the G-protein pathway through APJ receptor, thereby reducing tachyphylaxis often associated with dosing potent agonists. As such, in certain embodiments, compounds described herein can reduce arrestin-associated cardiac hypertrophy.

In some embodiments, the compounds described herein can exhibit pleiotropic properties (e.g., inodilator activity, cardio-renal protection, and control of fluid homeostasis).

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "APJ receptor" is meant to include, without limitation, nucleic acids, polynucleotides, oligonucleotides, sense and antisense polynucleotide strands, complementary sequences, peptides, polypeptides, proteins, homologous and/or orthologous APJ or APJ receptor molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The term "IC50" or "EC50" refers an amount, concentration, or dosage of a compound that is required for 50% inhibition or activation of a maximal response in an assay that measures such response.

The terms "effective amount" or "therapeutically effective amount," as used herein, refer to a sufficient amount of a chemical entity (e.g., a compound described generically or specifically herein, a pharmaceutically acceptable salt thereof, or compositions containing the same) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21*st ed.*; Lippincott Williams & Wilkins: Philadelphia, Pa., 2005; *Handbook of Pharmaceutical Excipients*, 6*th ed.*; Rowe et al., Eds.; The Pharmaceutical Press and the American Pharmaceutical Association: 2009; *Handbook of Pharmaceutical Additives*, 3*rd ed.*; Ash and Ash Eds.; Gower Publishing Company: 2007; *Pharmaceutical Preformulation and Formulation*, 2*nd ed.*; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl radical (e.g., —OCF$_3$).

The term "cycloalkoxy" refers to an —O-cycloalkyl radical (e.g., —O-cyclohexyl or —O-cyclopropyl).

The term "alkylene" refers to a branched or unbranched divalent alkyl (e.g., —CH$_2$—).

The term "arylene" and the like refer to divalent forms of the ring system, here divalent aryl.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene [1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the description below and in the accompanying Appendix, which is expressly considered part of this disclosure. Other features and advantages will also be apparent from the claims.

DETAILED DESCRIPTION

This disclosure features chemical entities (e.g., a compound or a pharmaceutically acceptable salt and/or hydrate and/or prodrug of the compound) that modulate (e.g., agonize) the apelin receptor (also referred to herein as the APJ receptor; gene symbol "APLNR"). This disclosure also features compositions containing the same as well as other methods of using and making the same. The chemical entities are useful, e.g., for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. Non-limiting examples of such diseases, disorders, or conditions include: (i) cardiovascular disease; (ii) metabolic disorders; (iii) diseases, disorders, and conditions associated with vascular pathology; and (iv) organ failure; (v) diseases, disorders, and conditions associated with infections (e.g., microbial infections); and (vi) diseases, disorders, or conditions that are sequela or comorbid with any of the foregoing or any disclosed herein. More particular non-limiting examples of such diseases, disorders, or conditions include pulmonary hypertension (e.g., PAH); heart failure; type II diabetes; renal failure; sepsis; and systemic hypertension.

Formula (I) Compounds

In one aspect, this disclosure features compounds of Formula I, or a pharmaceutically acceptable salt thereof:

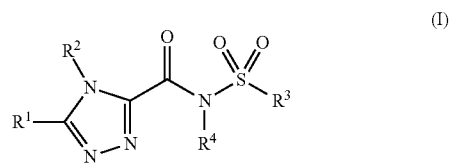

or a pharmaceutically acceptable salt thereof;
wherein:
$R^1$ is:
(i) —$(Y^1)_n$—$Y^2$, wherein:
n is 0 or 1;
$Y^1$ is $C_{1-6}$ alkylene, which is optionally substituted with from 1-6 $R^a$; and
$Y^2$ is:
  (a) $C_{3-10}$ cycloalkyl, which is optionally substituted with from 1-4 $R^b$,
  (b) $C_{6-10}$ aryl, which is optionally substituted with from 1-4 $R^c$;
  (c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
  (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
OR
(ii) —$Z^1$—$Z^2$—$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;
OR
(iii) $C_{3-10}$ alkyl, optionally substituted with from 1-6 independently selected $R^a$;
OR
(iv) —$Z^4$—$Z^5$—$Z^6$—$Y^2$ wherein:
$Z^4$ is $C_{1-3}$ alkylene, which is optionally substituted with from 1-4 $R^a$;
$Z^5$ is —N(H)—, —N($R^d$)—, —O—, or —S—;
$Z^6$ is $C_{1-4}$ alkylene, which is optionally substituted with from 1-4 $R^a$; and
$Y^2$ is as defined above;
$R^2$ is:
(i) $C_{6-10}$ aryl, which is optionally further substituted with from 1-4 $R^c$; or
(ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$,
$R^3$ is:
(i) —$(Y^3)_p$—$Y^4$, wherein:
p is 0 or 1;
$Y^3$ is $C_{1-6}$ alkylene, which is optionally substituted with from 1-6 $R^a$; and
$Y^4$ is:
(a) $C_{3-6}$ cycloalkyl, which is optionally substituted with from 1-4 $R^b$,
(b) $C_{6-10}$ aryl, which is optionally further substituted with from 1-4 $R^c$;
(c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$,
OR
(ii) $C_{1-10}$ alkyl, optionally substituted with from 1-6 independently selected $R^a$;
OR
(iii) —$Z^7$—$Z^8$—$Z^9$—$Y^4$ wherein:
$Z^7$ is a bond or $C_{1-3}$ alkylene, which is optionally substituted with from 1-4 $R^a$;
$Z^8$ is —N(H)— or —N($R^d$)—;
$Z^9$ is a bond or $C_{1-4}$ alkylene, which is optionally substituted with from 1-4 $R^a$; and
$Y^4$ is as defined above;
$R^4$ is H or $C_{1-3}$ alkyl;
each occurrence of $R^a$ is independently selected from the group consisting of: —OH; —F; —Cl; —Br; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;
each occurrence of $R^b$ is independently selected from the group consisting of: $C_{1-6}$ alkyl; $C_{1-4}$ haloalkyl; —OH; oxo; —F; —Cl; —Br; —$NR^eR^f$; $C_{1-4}$ alkoxy; $C_{1-4}$ haloalkoxy;
—C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl;
each occurrence of $R^c$ is independently selected from the group consisting of:
(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —S(O)$_{1-2}$($C_{1-4}$ alkyl);
(xi) —$NR^eR^f$;
(xii) —OH;
(xiii) —S(O)$_{1-2}$(NR'R'');
(xiv) —$C_{1-4}$ thioalkoxy;
(xv) —$NO_2$;
(xvi) —C(=O)($C_{1-4}$ alkyl);
(xvii) —C(=O)O($C_{1-4}$ alkyl);
(xviii) —C(=O)OH;
(xix) —C(=O)N(R')(R''); and
(xx) $C_{3-6}$ cycloalkoxy,
$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; $C_{1-4}$ alkoxy; and —($C_{0-3}$ alkylene)-$C_{6-10}$ aryl optionally substituted with from 1-4 independently selected $C_{1-4}$ alkyl, $C_{1-4}$ alkoxy, $C_{1-4}$ haloalkyl, or $C_{1-4}$ haloalkoxy;
each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of N($R^d$), O, and S; and
each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S.

In another aspect, this disclosure features compounds of Formula I, or a pharmaceutically acceptable salt thereof:

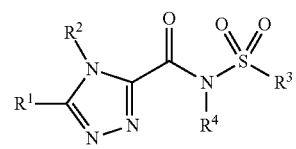

(I)

or a pharmaceutically acceptable salt thereof;
wherein:
$R^1$ is:
(i) —$(Y^1)_n$—$Y^2$, wherein:
n is 0 or 1;
$Y^1$ is $C_{1-6}$ alkylene, which is optionally substituted with from 1-6 $R^a$; and
$Y^2$ is:
  (a) $C_{3-10}$ cycloalkyl, which is optionally substituted with from 1-4 $R^b$,
  (b) $C_{6-10}$ aryl, which is optionally substituted with from 1-4 $R^c$;
  (c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
  (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,
OR
(ii) —$Z^1$—$Z^2$—$Z^3$, wherein:
$Z^1$ is $C_{1-3}$ alkylene, which is optionally substituted with from 1-4 $R^a$;
$Z^2$ is —N(H)—, —N($R^d$)—, —O—, or —S—; and
$Z^3$ is $C_{2-7}$ alkyl, which is optionally substituted with from 1-4 $R^a$;
OR
(iii) $C_{3-10}$ alkyl, optionally substituted with from 1-6 independently selected $R^a$;
OR
(iv) —$Z^4$—$Z^5$—$Z^6$—$Y^2$ wherein:
$Z^4$ is $C_{1-3}$ alkylene, which is optionally substituted with from 1-4 $R^a$;
$Z^5$ is —N(H)—, —N($R^d$)—, —O—, or —S—;
$Z^6$ is $C_{1-4}$ alkylene, which is optionally substituted with from 1-4 $R^a$; and
$Y^2$ is as defined above;
$R^2$ is:
(i) $C_{6-10}$ aryl, which is optionally further substituted with from 1-4 $R^c$; or
(ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$,
$R^3$ is:
(i) —$(Y^3)_p$—$Y^4$, wherein:
p is 0 or 1;
$Y^3$ is $C_{1-6}$ alkylene, which is optionally substituted with from 1-6 $R^a$; and
$Y^4$ is:
  (a) $C_{3-6}$ cycloalkyl, which is optionally substituted with from 1-4 $R^b$,
  (b) $C_{6-10}$ aryl, which is optionally further substituted with from 1-4 $R^c$;
  (c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$,
OR
(ii) $C_{1-10}$ alkyl, optionally substituted with from 1-6 independently selected $R^a$;
OR
(iii) —$Z^7$—$Z^8$—$Z^9$—$Y^4$ wherein:
$Z^7$ is a bond or $C_{1-3}$ alkylene, which is optionally substituted with from 1-4 $R^a$;
$Z^8$ is —N(H)— or —N($R^d$)—;
$Z^9$ is a bond or $C_{1-4}$ alkylene, which is optionally substituted with from 1-4 $R^a$; and
$Y^4$ is as defined above;
$R^4$ is H or $C_{1-3}$ alkyl;
each occurrence of $R^a$ is independently selected from the group consisting of: —OH; —F; —Cl; —Br; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;
each occurrence of $R^b$ is independently selected from the group consisting of: $C_{1-6}$ alkyl; $C_{1-4}$ haloalkyl; —OH; oxo; —F; —Cl; —Br; —NR$^e$R$^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl;
each occurrence of $R^c$ is independently selected from the group consisting of:
(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —S(O)$_{1-2}$($C_{1-4}$ alkyl);
(xi) —NR$^e$R$^f$;
(xii) —OH;
(xiii) —S(O)$_{1-2}$(NR'R'');
(xiv) —$C_{1-4}$ thioalkoxy;
(xv) —NO$_2$;
(xvi) —C(=O)($C_{1-4}$ alkyl);
(xvii) —C(=O)O($C_{1-4}$ alkyl);
(xviii) —C(=O)OH, and
(xix) —C(=O)N(R')(R'');
$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy;
each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S; and
each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of $N(R^d)$, O, and S.

Variable $R^1$

In some embodiments, $R^1$ is $—(Y^1)_n—Y^2$.

In some embodiments, n is 0.

In other embodiments, n is 1. In certain of these embodiments, $Y^1$ is $C_{1-3}$ alkylene.

In some embodiments, $Y^2$ is heteroaryl including from 5-10 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-4 independently selected $R^c$. In certain of these embodiments, n is 0.

In certain embodiments, $Y^2$ is heteroaryl including from 5-6 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-4 independently selected $R^c$. In certain of these embodiments, n is 0.

In certain embodiments, $Y^2$ is heteroaryl including 6 ring atoms, wherein from 1-2 ring atoms are N, and wherein one or more of the heteroaryl ring carbon atoms are optionally substituted with from 1-4 independently selected $R^c$. For example, $Y^2$ can be pyridyl (e.g., 2-pyridyl or 6-pyridyl), wherein one or more of the ring carbon atoms are optionally substituted with from 1-4 independently selected $R^c$. In certain of these embodiments, n is 0.

In certain embodiments, $Y^2$ is heteroaryl including 5 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-2 independently selected $R^c$. For example, $Y^2$ can be pyrazolyl, oxazolyl, or thiazolyl, wherein any substitutable nitrogen atom is optionally substituted with $R^d$, and wherein one or more of the ring carbon atoms are optionally substituted with from 1-2 independently selected $R^c$. In certain of these embodiments, n is 0. As another non-limiting example, $Y^2$ can be furanyl, wherein one or more of the ring carbon atoms are optionally substituted from 1-2 independently selected $R^c$. As another non-limiting example, $Y^2$ can be isoxazolyl, pyrimidinyl, or triazolyl, wherein any substitutable nitrogen atom is optionally substituted with $R^d$, and wherein one or more of the ring carbon atoms are optionally substituted with from 1-2 independently selected $R^c$.

In certain of the foregoing embodiments when $Y^2$ is heteroaryl, each occurrence of $R^c$ is independently selected from the group consisting of:
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) $—(C_{0-3}$ alkylene$)-C_{3-6}$ cycloalkyl optionally substituted with from 1-4 independently selected $C_{1-4}$ alkyl;
(xiv) $—C_{1-4}$ thioalkoxy; and
(xx) $C_{3-6}$ cycloalkoxy.

In certain of the foregoing embodiments when $Y^2$ is heteroaryl, each occurrence of $R^c$ is independently selected from the group consisting of:
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) $—(C_{0-3}$ alkylene$)-C_{3-6}$ cycloalkyl optionally substituted with from 1-4 independently selected $C_{1-4}$ alkyl; and
(xiv) $—C_{1-4}$ thioalkoxy.

In certain of the foregoing embodiments when $Y^2$ is heteroaryl, each occurrence of $R^c$ is independently selected from the group consisting of: (vii) $C_{1-4}$ alkoxy; (viii) $C_{1-4}$ haloalkoxy; and (xiv) $—C_{1-4}$ thioalkoxy. For example, each occurrence of $R^c$ is an independently selected $C_{1-4}$ alkoxy (e.g., $—OCH_3$, $—OCH_2CH_3$).

In certain of the foregoing embodiments when $Y^2$ is heteroaryl, each occurrence of $R^d$ is an independently selected $C_{1-6}$ alkyl.

In certain of the foregoing embodiments when $Y^2$ is heteroaryl and n is 0, $R^1$ can be selected from the group consisting of:

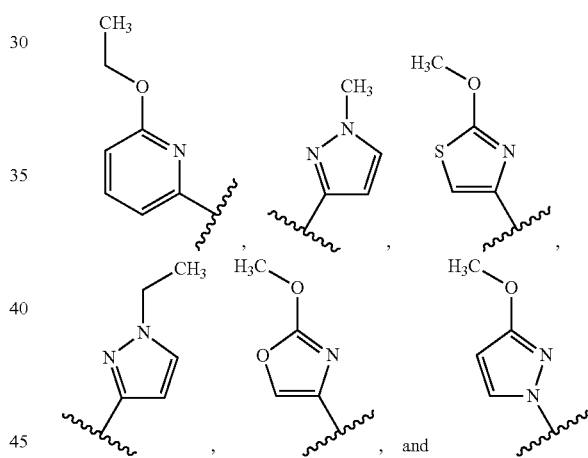

In certain embodiments when $Y^2$ is heteroaryl and n is 0, $R^1$ can be selected from the group consisting of:

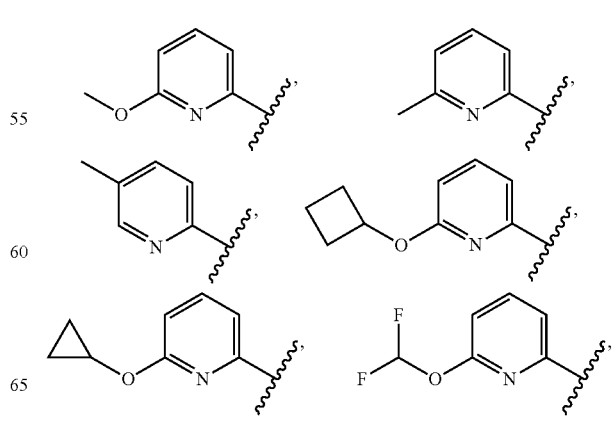

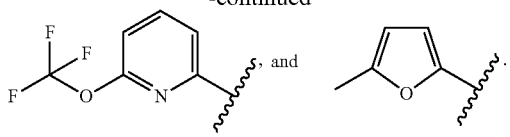

In some embodiments, $Y^2$ is $C_{3-10}$ cycloalkyl, which is optionally substituted with from 1-4 $R^b$. In certain of these embodiments, n is 0.

In some embodiments, $R^1$ is —$Z^1$—$Z^2$—$Z^3$.

In some embodiments, $Z^1$ is $CH_2$.

In some embodiments, $Z^2$ is —O—, or —S—. For example, $Z^2$ can be —O—.

In some embodiments, $Z^3$ is $C_{2-3}$ alkylene.

In certain embodiments, $Z^1$ is $CH_2$, and $Z^2$ is —O—, or —S— (e.g., —O—).

In certain embodiments, $Z^2$ is —O—, or —S— (e.g., —O—), and $Z^3$ is $C_{2-3}$ alkylene.

In certain embodiments, $Z^1$ is $CH_2$, and $Z^2$ is —O—, or —S— (e.g., —O—), and $Z^3$ is $C_{2-3}$ alkylene.

In certain of the foregoing embodiments when $R^1$ is —$Z^1$—$Z^2$—$Z^3$, $R^1$ is

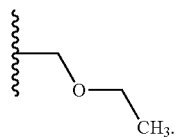

Variable $R^2$

In some embodiments, $R^2$ is $C_{6-10}$ aryl, which is optionally substituted with from 1-4 $R^c$.

In certain embodiments, $R^2$ is phenyl, which is optionally substituted with from 1-4 $R^c$. For example, $R^2$ can be phenyl, which is optionally substituted with from 1-2 $R^c$.

In certain of the foregoing embodiments when $R^2$ is aryl (e.g., phenyl), each occurrence of $R^c$ is independently selected from the group consisting of: (vii) $C_{1-4}$ alkoxy; (viii) $C_{1-4}$ haloalkoxy; (xiv) —$C_{1-4}$ thioalkoxy; and (xx) $C_{3-6}$ cycloalkoxy. For example, each occurrence of $R^c$ is an independently selected $C_{1-4}$ alkoxy (e.g., —$OCH_3$).

In certain of the foregoing embodiments when $R^2$ is aryl (e.g., phenyl), each occurrence of $R^c$ is independently selected from the group consisting of: (vii) $C_{1-4}$ alkoxy; (viii) $C_{1-4}$ haloalkoxy; and (xiv) —$C_{1-4}$ thioalkoxy. For example, each occurrence of $R^c$ is an independently selected $C_{1-4}$ alkoxy (e.g., —$OCH_3$).

In certain of the foregoing embodiments when $R^2$ is aryl (e.g., phenyl), $R^2$ has the following formula (A):

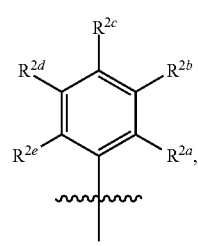

in which each of $R^{2a}$, $R^{2b}$, $R^{2c}$, $R^{2d}$, and $R^{2e}$ are each independently selected from the group consisting of H and $R^c$.

Formula (A) as disclosed in U.S. Provisional Application Ser. No. 62/637,207, filed on Mar. 1, 2018, includes two recitations of $R^{2a}$. The occurrence between $R^{2b}$ and $R^{2d}$ should have been labelled $R^{2c}$ as shown above. The references to $R^{2a}$ in U.S. Provisional Application Ser. No. 62/637,207 that follow formula (A) refer only to the $R^{2a}$ substituent that is ortho to the point of connection of formula (A) to the remainder of the formula (I).

In certain embodiments, four of $R^{2a}$, $R^{2b}$, $R^{2c}$, $R^{2d}$, and $R^{2e}$ are each an independently selected $R^c$, and the other is H.

In certain embodiments, three of $R^{2a}$, $R^{2b}$, $R^{2c}$, $R^{2d}$, and $R^{2e}$ are each an independently selected $R^c$, and the others are H.

In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and —$C_{1-4}$ thioalkoxy; e.g., each occurrence of $R^c$ is an independently selected $C_{1-4}$ alkoxy (e.g., —$OCH_3$). For example, $R^{2a}$ and $R^{2e}$ are each $OCH_3$.

In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., halo; $C_{1-4}$ haloalkyl; $C_{1-4}$ alkoxy; $C_{1-4}$ haloalkoxy; and —$C_{1-4}$ thioalkoxy; e.g., each occurrence of $R^c$ is an independently selected $C_{1-4}$ alkoxy (e.g., —$OCH_3$). For example, $R^{2a}$ and $R^{2e}$ are each $OCH_3$.

In certain of the foregoing embodiments when $R^2$ is aryl (e.g., phenyl), $R^2$ has formula (B)

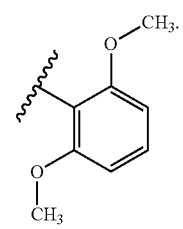

Variable $R^3$

In some embodiments, $R^3$ is —$(Y^3)_p$—$Y^4$.

In some embodiments, p is 1. In certain of these embodiments, $Y^3$ is $C_{1-3}$ alkylene. For example, $Y^3$ can be —$CH_2$— or —$CH(CH_3)$—. For example, $Y^3$ can be —$CH_2CH_2$—, —$CH_2CH(CH_3)$—, or —$CH(CH_3)CH_2$—.

In some embodiments, p is 0.

In some embodiments, $Y^4$ is $C_{6-10}$ aryl, which is optionally substituted with from 1-4 $R^c$. In certain of these embodiments, p is 1. In certain of these embodiments, $Y^3$ is $C_{1-3}$ alkylene. For example, $Y^3$ can be —$CH_2$— or —$CH(CH_3)$—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —$CH(CH_3)$—; or $Y^3$ can be —$CH_2CH_2$—, —$CH_2CH(CH_3)$—, or —$CH(CH_3)CH_2$—.

In certain embodiments, $Y^4$ is phenyl, which is optionally substituted with from 1-4 $R^c$. For example, $Y^4$ can be phenyl, which is optionally substituted with from 1-2 $R^c$. In certain of these embodiments, p is 1. In certain of these embodiments, $Y^3$ is $C_{1-3}$ alkylene. For example, $Y^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—. In certain of these embodiments, p is 1, and Y$^3$ is C$_{1-3}$ alkylene; e.g., Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—.

In certain embodiments, Y$^4$ is unsubstituted phenyl. In certain of these embodiments, p is 1. In certain of these embodiments, Y$^3$ is C$_{1-3}$ alkylene. For example, Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—. In certain of these embodiments, p is 1, and Y$^3$ is C$_{1-3}$ alkylene; e.g., Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—.

In certain embodiments, Y$^4$ is a C$_{10}$ bicyclic aryl, which is optionally substituted with from 1-4 R$^c$. In certain of these embodiments, p is 1. In certain of these embodiments, Y$^3$ is C$_{1-3}$ alkylene. For example, Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—. In certain of these embodiments, p is 1, and Y$^3$ is C$_{1-3}$ alkylene; e.g., Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—.

In certain embodiments, Y$^4$ is unsubstituted tetrahydronaphthyl. In certain of these embodiments, p is 1. In certain of these embodiments, Y$^3$ is C$_{1-3}$ alkylene. For example, Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—. In certain of these embodiments, p is 1, and Y$^3$ is C$_{1-3}$ alkylene; e.g., Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—.

In certain embodiments, when Y$^4$ is aryl, each occurrence of R$^c$ is independently selected from the group consisting of:
(i) halo;
(ii) C$_{1-4}$ alkyl;
(vi) C$_{1-4}$ haloalkyl;
(vii) C$_{1-4}$ alkoxy; and
(viii) C$_{1-4}$ haloalkoxy.

In certain of the foregoing embodiments when Y$^4$ is aryl (e.g., phenyl) and p is 1, R$^3$ is selected from the group consisting of:

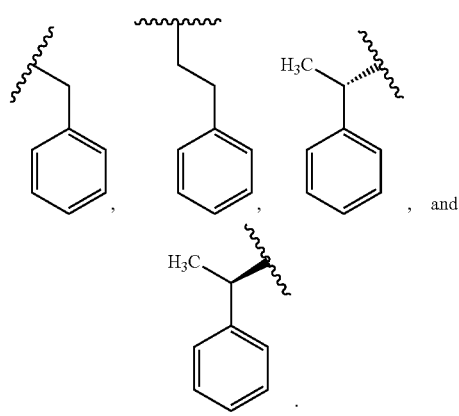

In certain embodiments when Y$^4$ is aryl (e.g., phenyl) and p is 1, R$^3$ is selected from the group consisting of:

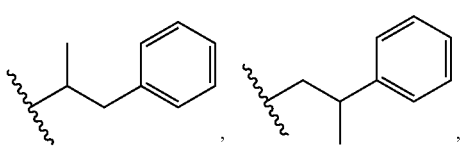

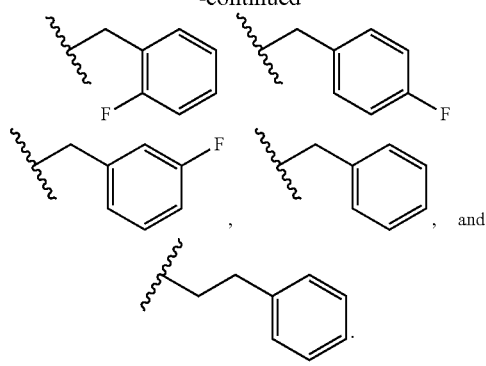

In certain embodiments when Y$^4$ is aryl (e.g., C$_{10}$ bicyclic aryl) and p is 0, R$^3$ is:

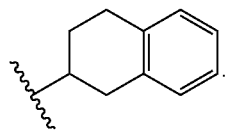 [SMILES: *C1CCc2ccccc2C1]

In certain of the foregoing embodiments when Y$^4$ is aryl (e.g., phenyl) and p is 0, R$^3$ is:

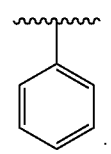

In some embodiments, Y$^4$ is heteroaryl including from 5-10 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-4 independently selected R$^c$. In certain of these embodiments, p is 1. In certain of these embodiments, Y$^3$ is C$_{1-3}$ alkylene. For example, Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—. In certain of these embodiments, p is 1, and Y$^3$ is C$_{1-3}$ alkylene; e.g., Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—.

In certain embodiments, Y$^4$ is heteroaryl including from 5-6 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-4 independently selected R$^c$. In certain of these embodiments, p is 1. In certain of these embodiments, Y$^3$ is C$_{1-3}$ alkylene. For example, Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—. In certain of these embodiments, p is 1, and Y$^3$ is C$_{1-3}$ alkylene; e.g., Y$^3$ can be —CH$_2$— or —CH(CH$_3$)—; or Y$^3$ can be —CH$_2$CH$_2$—, —CH$_2$CH(CH$_3$)—, or —CH(CH$_3$)CH$_2$—.

In certain embodiments, Y$^4$ is heteroaryl including 6 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-4 independently selected $R^c$. In certain of these embodiments, p is 1. In certain of these embodiments, $Y^3$ is $C_{1-3}$ alkylene. For example, $Y^3$ can be —$CH_2$— or —CH($CH_3$)—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —CH($CH_3$)—; or $Y^3$ can be —$CH_2CH_2$—, —$CH_2CH(CH_3)$—, or —$CH(CH_3)CH_2$—.

In certain embodiments, $Y^4$ is pyridyl, pyrimidyl, or pyrazinyl, each of which is optionally substituted with from 1-2 independently selected $R^c$. In certain of these embodiments, p is 1. In certain of these embodiments, $Y^3$ is $C_{1-3}$ alkylene. For example, $Y^3$ can be —$CH_2$— or —CH($CH_3$)—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —CH($CH_3$)—; or $Y^3$ can be —$CH_2CH_2$—, —$CH_2CH(CH_3)$—, or —$CH(CH_3)CH_2$—.

In certain embodiments, $Y^4$ is heteroaryl including 5 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$. In certain of these embodiments, p is 1. In certain of these embodiments, $Y^3$ is $C_{1-3}$ alkylene. For example, $Y^3$ can be —$CH_2$— or —CH($CH_3$)—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —CH($CH_3$)—; or $Y^3$ can be —$CH_2CH_2$—, —$CH_2CH(CH_3)$—, or —$CH(CH_3)CH_2$—.

In certain embodiments, $Y^4$ is triazolyl, wherein the ring carbon atom is optionally substituted with one independently selected R; and any substitutable nitrogen atom is optionally substituted with $R^d$. In certain of these embodiments, p is 1. In certain of these embodiments, $Y^3$ is $C_{1-3}$ alkylene. For example, $Y^3$ can be —$CH_2$— or —CH($CH_3$)—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —CH($CH_3$)—; or $Y^3$ can be —$CH_2CH_2$—, —$CH_2CH(CH_3)$—, or —$CH(CH_3)CH_2$—.

In certain embodiments, when $Y^4$ is heteroaryl, each occurrence of $R^c$ is independently selected from the group consisting of:
(i) halo;
(ii) $C_{1-4}$ alkyl;
(vi) $C_{1-4}$ haloalkyl;
(vii) $C_{1-4}$ alkoxy; and
(viii) $C_{1-4}$ haloalkoxy.

In certain of the foregoing embodiments when $Y^4$ is heteroaryl and p is 1, $R^3$ is:

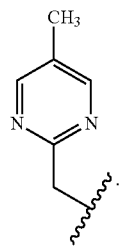

In certain embodiments when $Y^4$ is heteroaryl (e.g., heteroaryl including 6 ring atoms) and p is 1, $R^3$ is selected from the group consisting of:

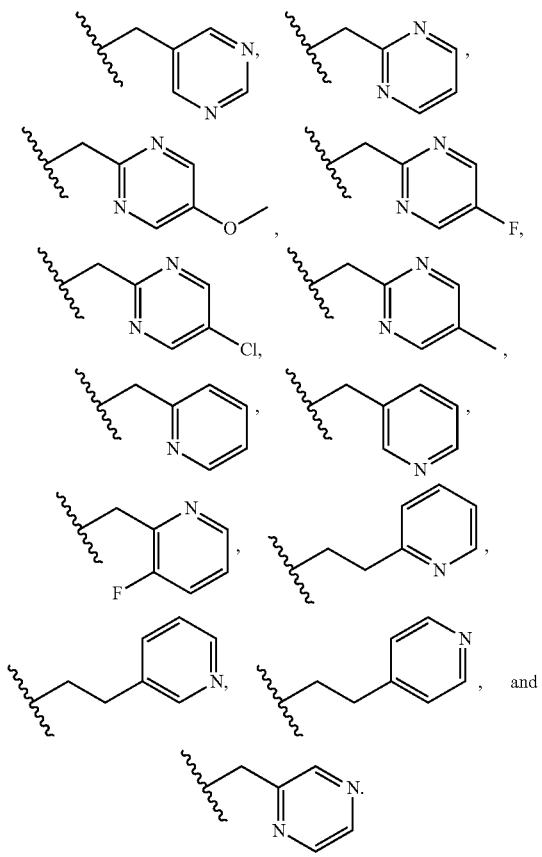

In certain embodiments when $Y^4$ is heteroaryl (e.g., heteroaryl including 5 ring atoms) and p is 1, $R^3$ is:

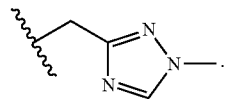 [SMILES: *Cc1ncn(C)n1]

In some embodiments, $Y^4$ is $C_{3-6}$ cycloalkyl, which is optionally substituted with from 1-4 $R^b$. In certain of these embodiments, p is 1. In certain of these embodiments, $Y^3$ is $C_{1-3}$ alkylene. For example, $Y^3$ can be —$CH_2$— or —CH($CH_3$)—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —CH($CH_3$)—; or $Y^3$ can be —$CH_2CH_2$—, —$CH_2CH(CH_3)$—, or —$CH(CH_3)CH_2$—.

In certain embodiments, $Y^4$ is $C_{3-6}$ cycloalkyl, which is optionally substituted with from 1-2 $R^b$. For example, $Y^4$ can be cyclohexyl or cyclopropyl, each of which is optionally substituted with from 1-2 $R^b$ (e.g., unsubstituted cyclohexyl or cyclopropyl). In certain of these embodiments, p is 1. In certain of these embodiments, $Y^3$ is $C_{1-3}$ alkylene. For example, $Y^3$ can be —$CH_2$— or —CH($CH_3$)—; or $Y^3$ can be —$CH_2CH_2$—, —$CH_2CH(CH_3)$—, or —$CH(CH_3)CH_2$—. In certain of these embodiments, p is 1, and $Y^3$ is $C_{1-3}$ alkylene; e.g., $Y^3$ can be —$CH_2$— or —CH($CH_3$)—; or $Y^3$ can be —$CH_2CH_2$—, —$CH_2CH(CH_3)$—, or —$CH(CH_3)CH_2$—.

In certain embodiments, when $Y^4$ is $C_{3-6}$ cycloalkyl and p is 1, $R^3$ is —$CH_2$— cyclopropyl or —$CH_2$-cyclohexyl.

In some embodiments, $R^3$ is $C_{1-10}$ alkyl, optionally substituted with from 1-6 independently selected $R^a$.

In certain embodiments, $R^3$ is $C_{1-6}$ alkyl, optionally substituted with from 1-6 independently selected $R^a$.

In certain embodiments, $R^3$ is unsubstituted $C_{1-6}$ alkyl (e.g., —$CH_3$).

In some embodiments, $R^3$ is —$Z^7$—$Z^8$—$Z^9$—$Y^4$.

In some embodiments, $Z^7$ is a bond.

In some embodiments, $Z^8$ is —N(H)—. In other embodiments, $Z^8$ is —N($R^d$)—.

In some embodiments, $Z^9$ is a bond. In other embodiments, $Z^9$ is $C_{1-4}$ alkylene, which is optionally substituted with from 1-4 $R^a$.

In some embodiments, $Z^7$ is a bond, and $Z^9$ is a bond.

In some embodiments, $Z^7$ is a bond, and $Z^9$ is $C_{1-4}$ alkylene, which is optionally substituted with from 1-4 $R^a$ (e.g., $CH_2$— or —$CH(CH_3)$—).

In any of the foregoing embodiments, in which $R^3$ is —$Z^7$—$Z^8$—$Z^9$—$Y^4$, $Y^4$ can be as defined anywhere herein (e.g., as defined in conjunction with embodiments wherein $R^3$ is —$(Y^3)_p$—$Y^4$).

Variable $R^4$

In some embodiments, $R^4$ is H.

Non-Limiting Combinations

This specification concluded with 122 claims, which are incorporated herein in this disclosure in their entireties and included as numbered Embodiments 1-122. For ease of exposition, certain variable definitions refer to one or more specific Embodiment numbers. For the avoidance of doubt, use of a phrase, such as "$R^1$ can be defined according to Embodiment 21 or 22" is intended to mean that:

$R^1$ can be selected from the group consisting of:

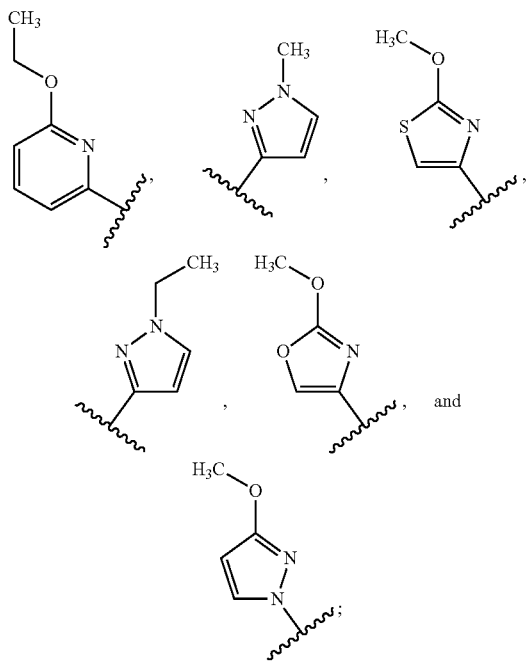

or $R^1$ can be selected from the group consisting of:

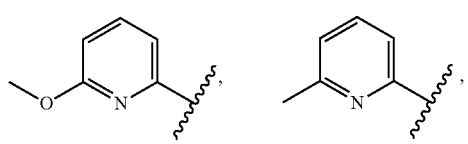

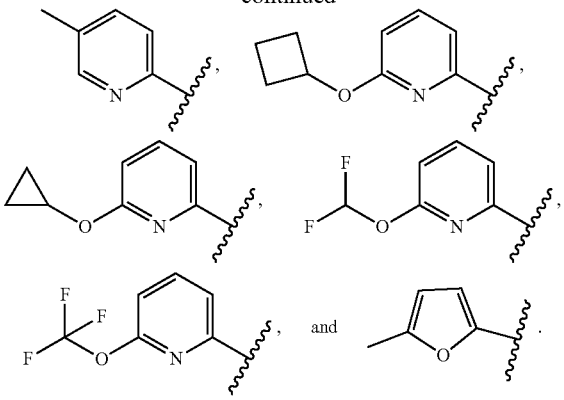

Embodiment 1. A compound having formula (I):

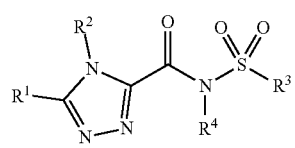

or a pharmaceutically acceptable salt thereof;

wherein:

$R^1$ is:

(i) —$(Y^1)_n$—$Y^2$, wherein:

n is 0 or 1;

$Y^1$ is $C_{1-6}$ alkylene, which is optionally substituted with from 1-6 $R^a$; and $Y^2$ is:

(a) $C_{3-10}$ cycloalkyl, which is optionally substituted with from 1-4$R^b$, (b) $C_{6-10}$ aryl, which is optionally substituted with from 1-4 $R^c$;

(c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$,

OR (ii) —$Z^1$—$Z^2$—$Z^3$, wherein:

$Z^1$ is $C_{1-3}$ alkylene, which is optionally substituted with from 1-4 $R^a$;

$Z^2$ is —N(H)—, —N($R^d$)—, —O—, or —S—; and $Z^3$ is $C_{2-7}$ alkyl, which is optionally substituted with from 1-4 $R^a$;

OR (iii) $C_{3-10}$ alkyl, optionally substituted with from 1-6 independently selected $R^a$;

OR (iv) —$Z^4$—$Z^5$—$Z^6$—$Y^2$ wherein:

$Z^4$ is $C_{1-3}$ alkylene, which is optionally substituted with from 1-4 $R^a$;

$Z^5$ is —N(H)—, —N($R^d$)—, —O—, or —S—;

$Z^6$ is $C_{1-4}$ alkylene, which is optionally substituted with from 1-4 $R^a$; and $Y^2$ is as defined above;

$R^2$ is:

(i) $C_{6-10}$ aryl, which is optionally further substituted with from 1-4 $R^c$; or (ii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, $R^3$ is:

(i) —$(Y^3)_p$—$Y^4$, wherein:

p is 0 or 1;

$Y^3$ is $C_{1-6}$ alkylene, which is optionally substituted with from 1-6 $R^a$; and $Y^4$ is:

(a) $C_{3-6}$ cycloalkyl, which is optionally substituted with from 1-4 $R^b$, (b) $C_{6-10}$ aryl, which is optionally further substituted with from 1-4 $R^c$;

(c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$,

OR (ii) $C_{1-10}$ alkyl, optionally substituted with from 1-6 independently selected $R^a$;

OR (iii) —$Z^7$—$Z^8$—$Z^9$—$Y^4$ wherein:

$Z^7$ is a bond or $C_{1-3}$ alkylene, which is optionally substituted with from 1-4 $R^a$;

$Z^8$ is —N(H)—or —N($R^d$)—;

$Z^9$ is a bond or $C_{1-4}$ alkylene, which is optionally substituted with from 1-4 $R^a$; and $Y^4$ is as defined above;

$R^4$ is H or $C_{1-3}$ alkyl;

each occurrence of $R^a$ is independently selected from the group consisting of: —OH; —F; —Cl; —Br; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R"); —S(O)$_{1-2}$(NR'R"); —S(O)$_{1-2}$($C_{1-4}$ alkyl); cyano, and $C_{3-6}$ cycloalkyl optionally substituted with from 1-4 independently selected $C_1$-4 alkyl;

each occurrence of $R^b$ is independently selected from the group consisting of: $C_{1-6}$ alkyl; $C_{1-4}$ haloalkyl; —OH; oxo; —F; —Cl; —Br; —$NR^eR^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R"); —S(O)$_{1-2}$(NR'R"); —S(O)$_{1-2}$($C_{1-4}$ alkyl); cyano; and $C_{3-6}$ cycloalkyl optionally substituted with from 1-4 independently selected $C_{1-4}$ alkyl;

each occurrence of $R^c$ is independently selected from the group consisting of:

(i) halo;

(ii) cyano;

(iii) $C_{1-6}$ alkyl;

(iv) $C_{2-6}$ alkenyl;

(v) $C_{2-6}$ alkynyl;

(vi) $C_{1-4}$ haloalkyl;

(vii) $C_{1-4}$ alkoxy;

(viii) $C_{1-4}$ haloalkoxy;

(ix) —($C_{0-3}$ alkylene)—$C_{3-6}$ cycloalkyl optionally substituted with from 1-4 independently selected $C_{1-4}$ alkyl;

(x) —S(O)$_{1-2}$($C_{1-4}$ alkyl);

(xi) —$NR^eR^f$;

(xiii) —S(O)$_{1-2}$ (NR'R");

(xiv) —$C_{1-4}$ thioalkoxy;

(xv) —$NO_2$;

(xvi) —C(=O)($C_{1-4}$ alkyl);

(xvii) —C(=O)O($C_{1-4}$ alkyl);

(xviii) —C(=O)OH;

(xix) —C(=O)N(R')(R"); and (xx) $C_{3-6}$ cycloalkoxy, $R^d$ is selected from the group consisting of: $C_{1-6}$ alkyl; $C_{3-6}$ cycloalkyl;—C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; $C_{1-4}$ alkoxy; and —($C_{0-3}$ alkylene)—$C_{6-10}$ aryl optionally substituted with from 1-4 independently selected $C_{1-4}$ alkyl, $C_{1-4}$ alkoxy, $C_{1-4}$ haloalkyl, or $C_{1-4}$ haloalkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of N($R^d$), O, and S; and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of N($R^d$), O, and S.

Embodiment 2. The compound of Embodiment 1, wherein $R^1$ is —$(Y^1)_n$—$Y^2$.

Embodiment 3. The compound of Embodiment 1 or 2, wherein n is 0.

Embodiment 4. The compound of Embodiment 1 or 2, wherein n is 1.

Embodiment 5. The compound of Embodiment 4, wherein $Y^1$ is $C_{1-3}$ alkylene.

Embodiment 6. The compound of any one of Embodiments 1-5, wherein $Y^2$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

Embodiment 7. The compound of any one of Embodiments 1-6, wherein $Y^2$ is heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

Embodiment 8. The compound of any one of Embodiments 1-7, wherein $Y^2$ is heteroaryl including 6 ring atoms, wherein from 1-2 ring atoms are N, and wherein one or more of the heteroaryl ring carbon atoms are optionally substituted with from 1-4 independently selected $R^c$.

Embodiment 9. The compound of Embodiment 8, wherein $Y^2$ is pyridyl (e.g., 2-pyridyl or 6-pyridyl), wherein one or more of the ring carbon atoms are optionally substituted with from 1-4 independently selected $R^c$.

Embodiment 10. The compound of any one of Embodiments 1-7, wherein $Y^2$ is heteroaryl including 5 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$.

Embodiment 11. The compound of Embodiment 10, wherein $Y^2$ is pyrazolyl, oxazolyl, or thiazolyl, wherein any substitutable nitrogen atom is optionally substituted with $R^d$, and wherein one or more of the ring carbon atoms are optionally substituted with from 1-2 independently selected $R^c$.

Embodiment 12. The compound of Embodiment 10, wherein $Y^2$ is furanyl, wherein one or more of the ring carbon atoms are optionally substituted from 1-2 independently selected $R^c$.

Embodiment 13. The compound of any one of Embodiments 6-12, wherein each occurrence of $R^c$ is independently selected from the group consisting of:
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(xiv) —$C_{1-4}$ thioalkoxy; and
(xx) $C_{3-6}$ cycloalkoxy.

Embodiment 14. The compound of any one of Embodiments 6-13, wherein each occurrence of $R^c$ is independently selected from the group consisting of:
(vii) $C_{1-4}$ alkoxy;
(viii) $C_{1-4}$ haloalkoxy;
(xiv) —$C_{1-4}$ thioalkoxy; and
(xx) $C_{3-6}$ cycloalkoxy.

Embodiment 15. The compound of any one of Embodiments 6-14, wherein each occurrence of $R^c$ is an independently selected $C_{1-4}$ alkoxy (e.g., —OCH$_3$, —OCH$_2$CH$_3$).

Embodiment 16. The compound of any one of Embodiments 6-14, wherein each occurrence of $R^c$ is an independently selected $C_{1-4}$ haloalkoxy (e.g., —OCHF$_2$, —OCF$_3$).

Embodiment 17. The compound of any one of Embodiments 6-14, wherein each occurrence of $R^c$ is an independently selected $C_{3-6}$ cycloalkoxy (e.g., —O—cyclopropyl, —O—cyclobutyl).

Embodiment 18. The compound of any one of Embodiments 6-17, wherein each occurrence of $R^d$ is an independently selected $C_{1-6}$ alkyl.

Embodiment 19. The compound of any one of Embodiments 1-5, wherein $Y^2$ is $C_{3-10}$ cycloalkyl, which is optionally substituted with from 1-4 $R^b$.

Embodiment 20. The compound of any one of Embodiments 6-19, wherein n is 0.

Embodiment 21. The compound of any one of Embodiments 1-3, 6-18, and 20, wherein $R^1$ is selected from the group consisting of:

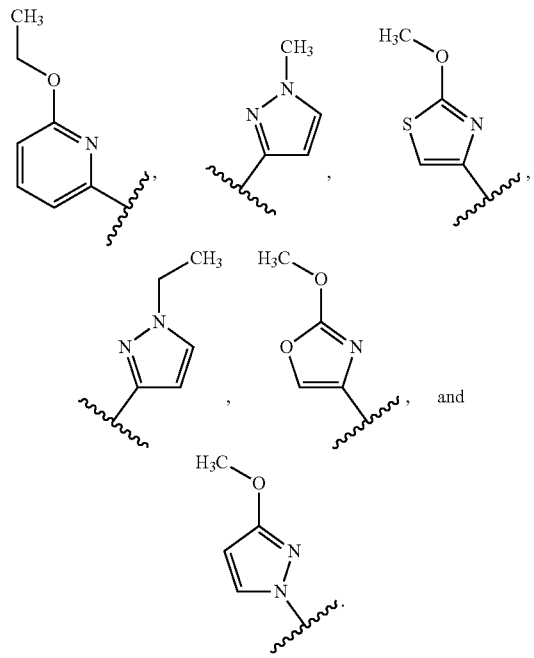

Embodiment 22. The compound of any one of Embodiments 1-3, 6-18, and 20, wherein $R^1$ is selected from the group consisting of:

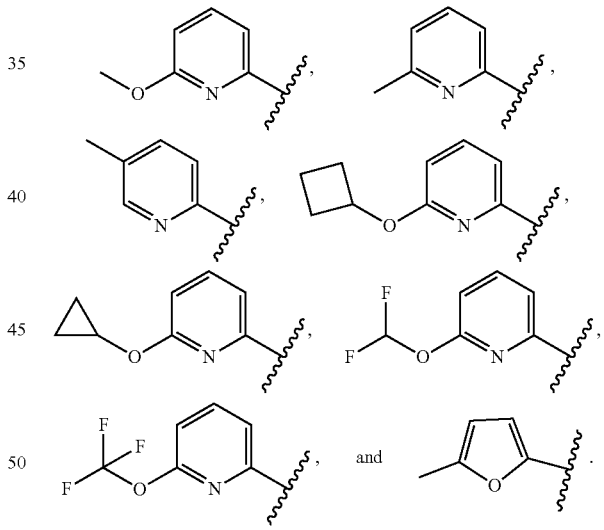

Embodiment 23. The compound of Embodiment 1, wherein $R^1$ is —$Z^1$—$Z^2$—$Z^3$.

Embodiment 24. The compound of Embodiment 23, wherein $Z^1$ is CH$_2$.

Embodiment 25. The compound of Embodiment 23 or 24, wherein $Z^2$ is —O—, or —S—.

Embodiment 26. The compound of any one of Embodiments 23-25, wherein $Z^2$ is —O—.

Embodiment 27. The compound of any one of Embodiments 23-26, wherein $Z^3$ is $C_{2-3}$ alkylene.

Embodiment 28. The compound of any one of Embodiments 23-27, wherein $R^1$ is

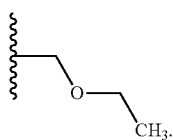

Embodiment 29. The compound of any one of Embodiments 1-28, wherein $R^2$ is $C_{6-10}$ aryl, which is optionally substituted with from 1-4 $R^c$.

Embodiment 30. The compound of any one of Embodiments 1-29, wherein $R^2$ is phenyl, which is optionally substituted with from 1-4 $R^c$.

Embodiment 31. The compound of any one of Embodiments 1-30, wherein $R^2$ is phenyl, which is optionally substituted with from 1-2 $R^c$.

Embodiment 32. The compound of any one of Embodiments 29-31, wherein each occurrence of $R^c$ is independently selected from the group consisting of:
(i) halo;
(vi) $C_{1-4}$ haloalkyl;
(vii) $C_{1-4}$ alkoxy;
(viii) $C_{1-4}$ haloalkoxy;
(xiv) —$C_{1-4}$ thioalkoxy; and
(xx) $C_{3-6}$ cycloalkoxy.

Embodiment 33. The compound of any one of Embodiments 29-32, wherein each occurrence of $R^c$ is an independently selected $C_{1-4}$ alkoxy.

Embodiment 34. The compound of any one of Embodiments 29-33, wherein each occurrence of $R^c$ is —$OCH_3$.

Embodiment 35. The compound of any one of Embodiments 1-34, wherein $R^2$ is:

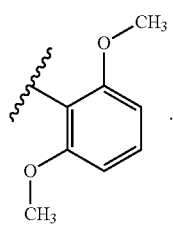

Embodiment 36. The compound of any one of Embodiments 1-35, wherein $R^3$ is —$(Y^3)_p$—$Y^4$.

Embodiment 37. The compound of any one of Embodiments 1-36, wherein p is 1;

Embodiment 38. The compound of any one of Embodiments 1-37, wherein $Y^3$ is $C_{1-3}$ alkylene.

Embodiment 39. The compound of any one of Embodiments 1-38, wherein $Y^3$ is —$CH_2$— or —$CH(CH_3)$—.

Embodiment 40. The compound of any one of Embodiments 1-38, wherein $Y^3$ is —$CH_2CH^2$—, —$CH_2CH(CH_3)$—, or —$CH(CH_3)CH_2$—.

Embodiment 41. The compound of any one of Embodiments 1-36, wherein p is 0.

Embodiment 42. The compound of any one of Embodiments 1-41, $Y^4$ is $C_{6-10}$ aryl, which is optionally substituted with from 1-4 $R^c$.

Embodiment 43. The compound of any one of Embodiments 1-42, wherein $Y^4$ is phenyl, which is optionally substituted with from 1-4 $R^c$.

Embodiment 44. The compound of any one of Embodiments 1-43, $Y^4$ is unsubstituted phenyl.

Embodiment 45. The compound of any one of Embodiments 1-42, $Y^4$ is a $C_{10}$ bicyclic aryl, which is optionally substituted with from 1-4 $R^c$.

Embodiment 46. The compound of Embodiment 45, wherein $Y^4$ is unsubstituted tetrahydronaphthyl.

Embodiment 47. The compound of any one of Embodiments 1-41, wherein $Y^4$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

Embodiment 48. The compound of any one of Embodiments 1-41, wherein $Y^4$ is heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

Embodiment 49. The compound of any one of Embodiments 1-41 and 48, wherein $Y^4$ is heteroaryl including 5 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

Embodiment 50. The compound of Embodiment 49, wherein $Y^4$ is triazolyl, wherein the ring carbon atom is optionally substituted with one independently selected $R^c$; and any substitutable nitrogen atom is optionally substituted with $R^d$ Embodiment 51. The compound of any one of Embodiments 1-41, wherein $Y^4$ is heteroaryl including 6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

Embodiment 52. The compound of Embodiment 51, wherein $Y^4$ is pyridyl, pyrimidyl, or pyrazinyl, each of which is optionally substituted with from 1-2 independently selected $R^c$.

Embodiment 53. The compound of any one of Embodiments 42-43, 45, and 47-52, wherein each $R^c$ is independently selected from the group consisting of:
(i) halo;
(ii) $C_{1-4}$ alkyl;
(vi) $C_{1-4}$ haloalkyl;
(vii) $C_{1-4}$ alkoxy; and
(viii) $C_{1-4}$ haloalkoxy.

Embodiment 54. The compound of any one of Embodiments 42-53, wherein p is 1.

Embodiment 55. The compound of any one of Embodiments 1-39 and 42-54, wherein $R^3$ is selected from the group consisting of:

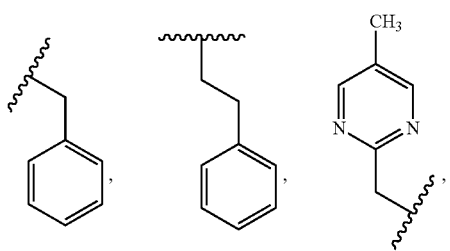

-continued

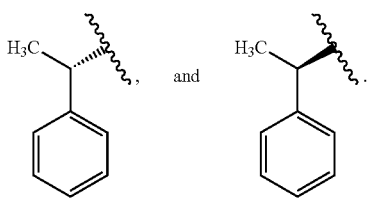

Embodiment 56. The compound of any one of Embodiments 1-38 and 42-43, wherein $R^3$ is selected from the group consisting of:

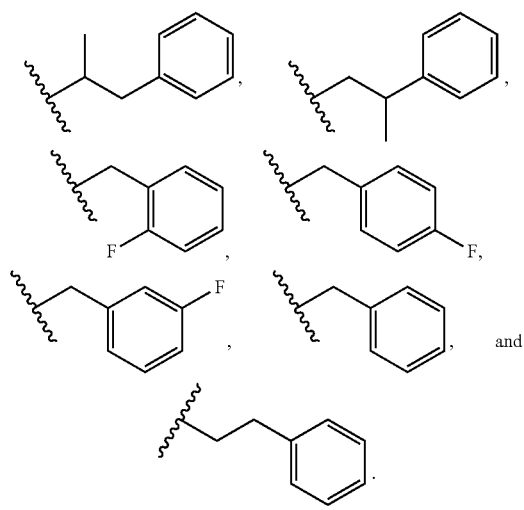

Embodiment 57. The compound of any one of Embodiments 1-38 and 45-46, wherein $R^3$ is

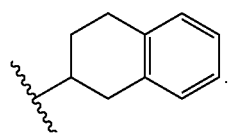 [SMILES: *C1CCc2ccccc2C1]

Embodiment 58. The compound of any one of Embodiments 1-38 and 47-50, wherein $R^3$ is:

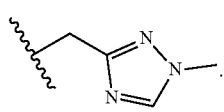 [SMILES: *Cc1ncn(C)n1]

Embodiment 59. The compound of any one of Embodiments 1-38, 47-48, and 51-52, wherein $R^3$ is selected from the group consisting of the following:

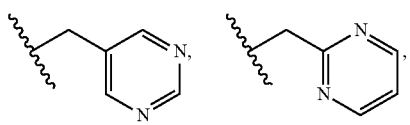

-continued

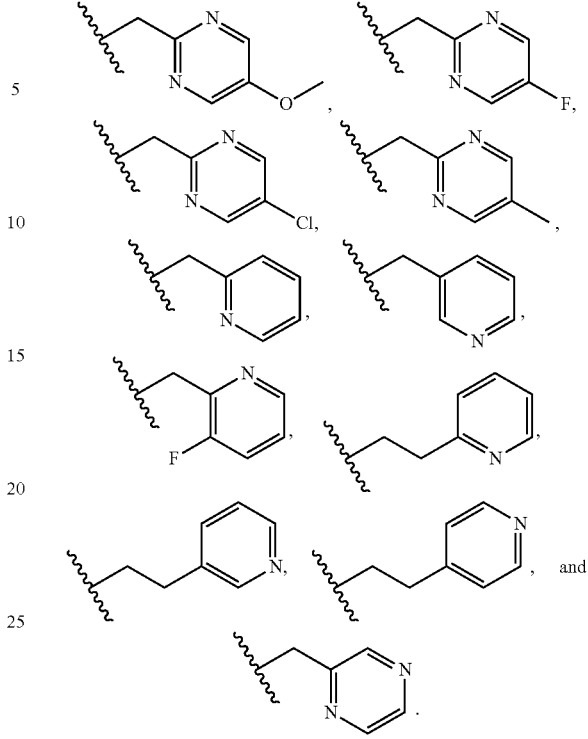

Embodiment 60. The compound of any one of Embodiments 1-36 and 41-53, wherein $R^3$ is:

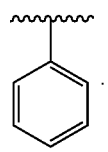

Embodiment 61. The compound of any one of Embodiments 1-40, wherein $Y^4$ is $C_{3-6}$ cycloalkyl, which is optionally substituted with from 1-4 $R^b$.

Embodiment 62. The compound of any one of Embodiments 1-40 and 61, wherein $Y^4$ is $C_{3-6}$ cycloalkyl, which is optionally substituted with from 1-2 $R^b$.

Embodiment 63. The compound of any one of Embodiments 1-40 and 61, wherein $Y^4$ is cyclohexyl or cyclopropyl, each of which is optionally substituted with from 1-2 $R^b$.

Embodiment 64. The compound of Embodiment 63, wherein $Y^4$ is unsubstituted cyclohexyl or cyclopropyl.

Embodiment 65. The compound of any one of Embodiments 62-64, wherein p is 1.

Embodiment 66. The compound of any one of Embodiments 1-38 and 61-65, wherein $R^3$ is —$CH_2$-cyclopropyl or —$CH_2$-cyclohexyl.

Embodiment 67. The compound of any one of Embodiments 1-35, wherein $R^3$ is $C_{1-10}$ alkyl, optionally substituted with from 1-6 independently selected $R^a$.

Embodiment 68. The compound of Embodiment 67, wherein $R^3$ is $C_{1-6}$ alkyl, optionally substituted with from 1-6 independently selected $R^a$.

Embodiment 69. The compound of Embodiment 67 or 68, wherein $R^3$ is unsubstituted $C_{1-6}$ alkyl.

Embodiment 70. The compound of any one of Embodiments 67-69, wherein $R^3$ is —$CH_3$.

Embodiment 71. The compound of am one of Embodiments 1-70, wherein $R^4$ is H.

Embodiment 72. The compound of any one of Embodiments 1-70, wherein $R^4$ is $C_{1-3}$ alkyl.

Embodiment 73. The compound of Embodiment 1, wherein:
$R^1$ is —$(Y^1)_n$—$Y^2$; and
$R^2$ is $C_{6-10}$ aryl, which is optionally substituted with from 1-4 $R^c$.

Embodiment 74. The compound of Embodiment 73, wherein n is 0.

Embodiment 75. The compound of Embodiment 1, wherein:
$R^1$ is —$Z^1$—$Z^2$—$Z^3$; and
$R^2$ is $C_{6-10}$ aryl, which is optionally substituted with from 1-4 $R^c$.

Embodiment 76. The compound of Embodiment 1, wherein:
$R^2$ is $C_{6-10}$ aryl, which is optionally substituted with from 1-4 $R^c$; and
$R^3$ is —$(Y^3)_p$—$Y^4$.

Embodiment 77. The compound of Embodiment 76, wherein p is 1.

Embodiment 78. The compound of Embodiment 1, wherein:
$R^2$ is $C_{6-10}$ aryl, which is optionally substituted with from 1-4 $R^c$; and
$R^3$ is $C_1$-10 alkyl, optionally substituted with from 1-6 independently selected $R^a$.

Embodiment 79. The compound of Embodiment 1, wherein:
$R^1$ is —$(Y^1)_n$—$Y^2$;
$R^2$ is $C_{6-10}$ aryl, which is optionally substituted with from 1-4 $R^c$; and
$R^3$ is —$(Y^3)_p$—$Y^4$.

Embodiment 80. The compound of Embodiment 79, wherein n is 0.

Embodiment 81. The compound of Embodiment 79 or 80, wherein p is 1.

Embodiment 82. The compound of Embodiment 1, wherein:
$R^1$ is —$Z^1$—$Z^2$—$Z^3$; and
$R^2$ is $C_{6-10}$ aryl, which is optionally substituted with from 1-4 $R^c$; and
$R^3$ is —$(Y^3)_p$—$Y^4$.

Embodiment 83. The compound of Embodiment 82, wherein p is 1.

Embodiment 84. The compound of Embodiment 1, wherein:
$R^1$ is —$(Y^1)_n$—$Y^2$;
$R^2$ is $C_{6-10}$ aryl, which is optionally substituted with from 1-4 $R^c$; and
$R^3$ is $C_{1-10}$ alkyl, optionally substituted with from 1-6 independently selected $R^a$.

Embodiment 85. The compound of Embodiment 84, wherein n is 0.

Embodiment 86. The compound of Embodiment 1, wherein:
$R^1$ is —$Z^1$—$Z^3$—$Z^3$; and
$R^2$ is $C_{6-10}$ aryl, which is optionally substituted with from 1-4 $R^c$; and
$R^3$ is $C_{1-10}$ alkyl, optionally substituted with from 1-6 independently selected $R^a$.

Embodiment 87. The compound of any one of Embodiments 73, 79, and 84, wherein $Y^2$ is defined according to any one or more of Embodiments 6-19.

Embodiment 88. The compound of any one of Embodiments 73, 79, and 84, wherein $R^1$ is defined according to any one or more of Embodiments 21-22.

Embodiment 89. The compound of any one of Embodiments 75, 82, and 86, wherein $R^1$ is defined according to any one or more of Embodiments 24-27.

Embodiment 90. The compound of any one of Embodiments 75, 82, and 86, wherein $R^1$ is defined according to Embodiment 28.

Embodiment 91. The compound of any one of Embodiments 76, 79, and 82, wherein $Y^3$ is defined according to Embodiment 38, 39, or 40.

Embodiment 92. The compound of any one of Embodiments 76, 79, 82, and 91, wherein $Y^4$ is defined according to any one or more of Embodiments 42-52.

Embodiment 93. The compound of any one of Embodiments 76, 79, and 82, wherein $R^3$ is defined according to any one or more of Embodiments 55-60.

Embodiment 94. The compound of any one of Embodiments 76, 79, and 82, wherein $Y^4$ is defined according to any one or more of Embodiments 61-64.

Embodiment 95. The compound of any one of Embodiments 76, 79, and 82, wherein $R^3$ is defined according to Embodiment 66

Embodiment 96. The compound of any one of Embodiments 78, 84, and 86, wherein $R^3$ is defined according to any one of Embodiments 67-70.

Embodiment 97. The compound of any one of Embodiments 73-96, wherein $R^2$ $C_{6-10}$ aryl, which is optionally substituted with from 1-4 $R^c$.

Embodiment 98. The compound of any one of Embodiments 73-97, wherein $R^2$ is phenyl, which is optionally substituted with from 1-4 (e.g., 1-2) $R^c$.

Embodiment 99. The compound of any one of Embodiments 73-98, wherein each occurrence of $R^c$ is independently selected from the group consisting of: $C_{1-4}$ alkoxy;, $C_{1-4}$ haloalkoxy; and —$C_{1-4}$ thioalkoxy (e g. each occurrence of $R^c$ is an independently selected $C_{1-4}$ alkoxy; e.g., each occurrence of $R^c$ is —$OCH_3$).

Embodiment 100. The compound of any one of Embodiments 73-99, wherein each occurrence of $R^2$ is:

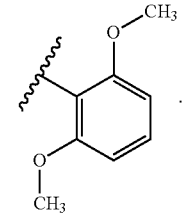 [SMILES: *c1c(OC)cccc1OC]

Embodiment 101. The compound of any one of Embodiments 73-100, wherein $R^4$ is H.

Embodiment 102. The compound of Embodiment 1, wherein the compound is selected from the group consisting of those in the table below.

| Ex. number | Structure | IUPAC name |
|---|---|---|
| 1 | 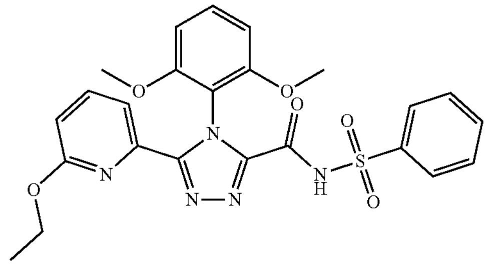 [SMILES: CCOc1cccc(-c2nnc(C(=O)NS(=O)(=O)c3ccccc3)n2-c2c(OC)cccc2OC)n1] | 4-(2,6-dimethoxyphenyl)-5-(6-ethoxypyridin-2-yl)-N-(phenylsulfonyl)-4H-1,2,4-triazole-3-carboxamide |
| 2 | 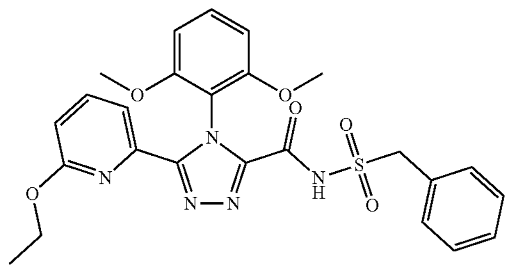 [SMILES: CCOc1cccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(6-ethoxypyridin-2-yl)-4H-1,2,4-triazole-3-carboxamide |
| 3 | 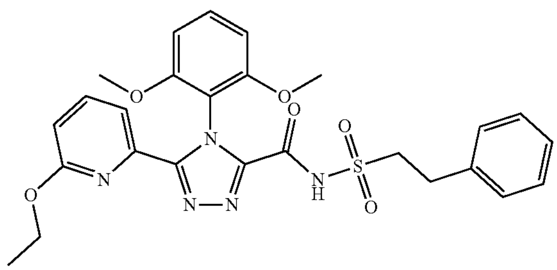 [SMILES: CCOc1cccc(-c2nnc(C(=O)NS(=O)(=O)CCc3ccccc3)n2-c2c(OC)cccc2OC)n1] | 4-(2,6-dimethoxyphenyl)-5-(6-ethoxypyridin-2-yl)-N-(phenethylsulfonyl)-4H-1,2,4-triazole-3-carboxamide |
| 4 | 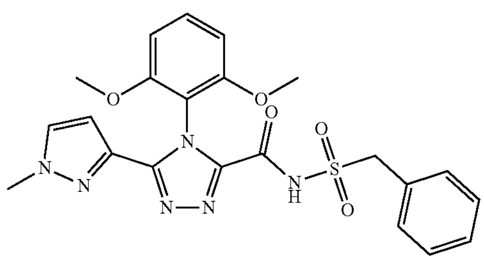 [SMILES: COc1cccc(OC)c1-n1c(C(=O)NS(=O)(=O)Cc2ccccc2)nnc1-c1ccn(C)n1] | N-(benzylsulfonyl)-4-(2,6-dimethoxyphenyl)-5-(1-methyl-1H-pyrazol-3-yl)-4H-1,2,4-triazole-3-carboxamide |
| 5 | 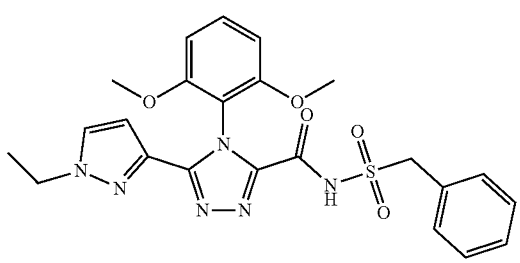 [SMILES: CCn1ccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(1-ethyl-1H-pyrazol-3-yl)-4H-1,2,4-triazole-3-carboxamide |
| 6 | 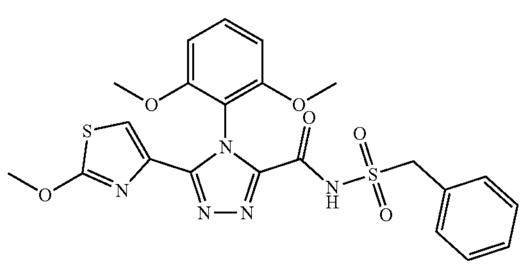 [SMILES: COc1nc(-c2nnc(C(=O)NS(=O)(=O)Cc3ccccc3)n2-c2c(OC)cccc2OC)cs1] | N-(benzylsulfonyl)-4-(2,6-dimethoxyphenyl)-5-(2-methoxythiazol-4-yl)-4H-1,2,4-triazole-3-carboxamide |

| Ex. number | Structure | IUPAC name |
|---|---|---|
| 7 | 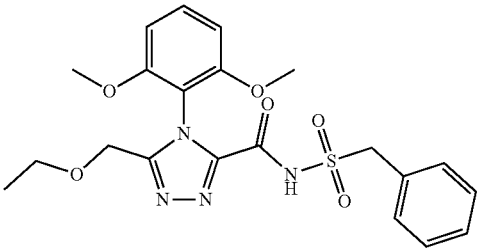 [SMILES: CCOCc1nnc(C(=O)NS(=O)(=O)Cc2ccccc2)n1-c1c(OC)cccc1OC] | N-(benzylsulfonyl)-4-(2,6-dimethoxyphenyl)-5-(ethoxymethyl)-4H-1,2,4-triazole-3-carboxamide |
| 8 | 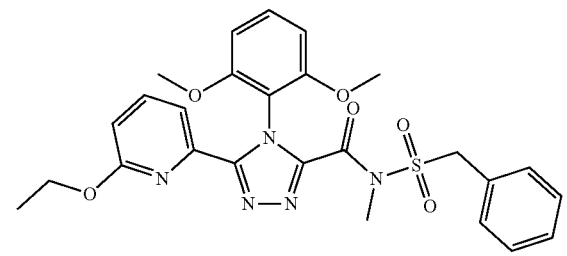 [SMILES: CCOc1cccc(-c2nnc(C(=O)N(C)S(=O)(=O)Cc3ccccc3)n2-c2c(OC)cccc2OC)n1] | N-(benzylsulfonyl)-4-(2,6-dimethoxyphenyl)-5-(6-ethoxypyridin-2-yl)-N-methyl-4H-1,2,4-triazole-3-carboxamide |
| 9 | 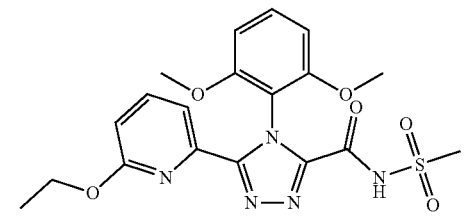 [SMILES: CCOc1cccc(-c2nnc(C(=O)NS(C)(=O)=O)n2-c2c(OC)cccc2OC)n1] | 4-(2,6-Dimethoxyphenyl)-5-(6-ethoxypyridin-2-yl)-N-(methylsulfonyl)-4H-1,2,4-triazole-3-carboxamide |
| 10 | 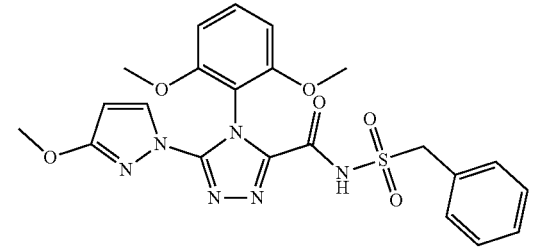 [SMILES: COc1ccn(-c2nnc(C(=O)NS(=O)(=O)Cc3ccccc3)n2-c2c(OC)cccc2OC)n1] | N-(enzylsulfonyl)-4-(2,6-dimethoxyphenyl)-5-(3-methoxy-1H-pyrazol-1-yl)-4H-1,2,4-triazole-3-carboxamide |
| 11 | 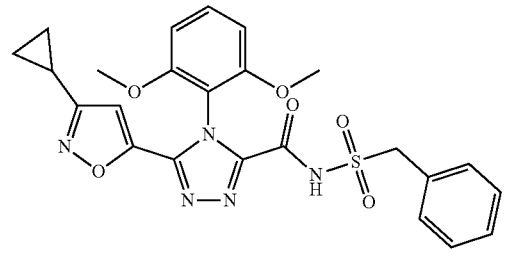 [SMILES: COc1cccc(OC)c1-n1c(C(=O)NS(=O)(=O)Cc2ccccc2)nnc1-c1cc(C2CC2)no1] | N-(benzylsulfonyl)-5-(3-cyclopropylisoxazol-5-yl)-4-(2,6-dimethoxyphenyl)-4H-1,2,4-triazole-3-carboxamide |
| 12 | 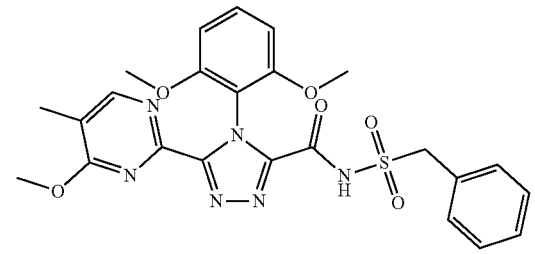 [SMILES: COc1cccc(OC)c1-n1c(C(=O)NS(=O)(=O)Cc2ccccc2)nnc1-c1ncc(C)c(OC)n1] | N-(benzylsulfonyl)-4-(2,6-dimethoxyphenyl)-5-(4-methoxy-5-methylpyrimidin-2-yl)-4H-1,2,4-triazole-3-carboxamide |

-continued

| Ex. number | Structure | IUPAC name |
|---|---|---|
| 13 | 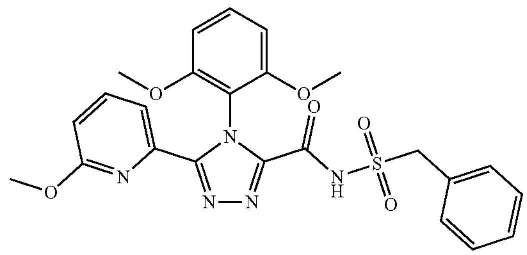 [SMILES: COc1cccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(6-methoxypyridin-2-yl)-4H-1,2,4-triazole-3-carboxamide |
| 14 | 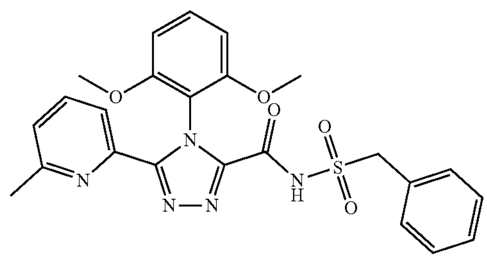 [SMILES: COc1cccc(OC)c1-n1c(C(=O)NS(=O)(=O)Cc2ccccc2)nnc1-c1cccc(C)n1] | N-(benzylsulfonyl)-4-(2,6-dimethoxyphenyl)-5-(6-methylpyridin-2-yl)-4H-1,2,4-triazole-3-carboxamide |
| 15 | 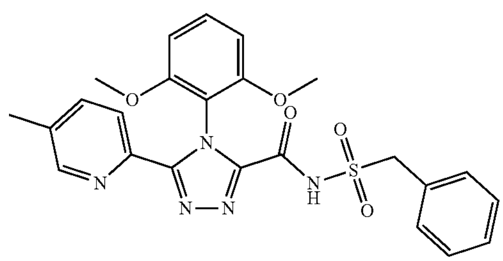 [SMILES: COc1cccc(OC)c1-n1c(C(=O)NS(=O)(=O)Cc2ccccc2)nnc1-c1ccc(C)cn1] | N-(benzylsulfonyl)-4-(2,6-dimethoxyphenyl)-5-(5-methylpyridin-2-yl)-4H-1,2,4-triazole-3-carboxamide |
| 16 | 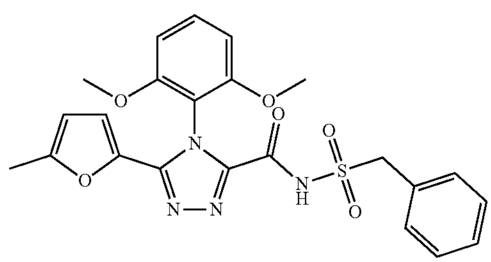 [SMILES: COc1cccc(OC)c1-n1c(C(=O)NS(=O)(=O)Cc2ccccc2)nnc1-c1ccc(C)o1] | N-(benzylsulfonyl)-4-(2,6-dimethoxyphenyl)-5-(5-methylfuran-2-yl)-4H-1,2,4-triazole-3-carboxamide |
| 17 | 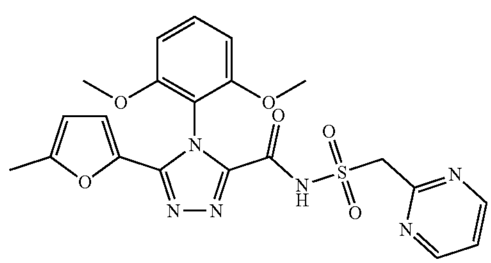 [SMILES: COc1cccc(OC)c1-n1c(C(=O)NS(=O)(=O)Cc2ncccn2)nnc1-c1ccc(C)o1] | 4-(2,6-Dimethoxyphenyl)-5-(5-methylfuran-2-yl)-N-((pyrimidin-2-ylmethyl)sulfonyl)-4H-1,2,4-triazole-3-carboxamide |
| 18 | 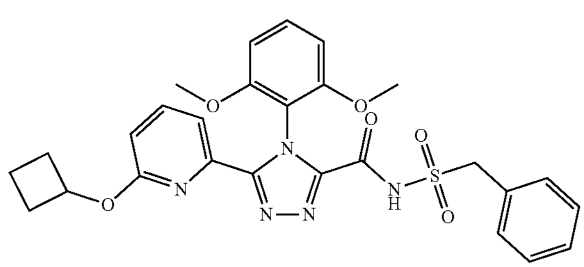 [SMILES: COc1cccc(OC)c1-n1c(C(=O)NS(=O)(=O)Cc2ccccc2)nnc1-c1cccc(OC2CCC2)n1] | N-(benzylsulfonyl)-5-(6-cyclobutoxypyridin-2-yl)-4-(2,6-dimethoxyphenyl)-4H-1,2,4-triazole-3-carboxamide |

-continued

| Ex. number | Structure | IUPAC name |
|---|---|---|
| 19 | 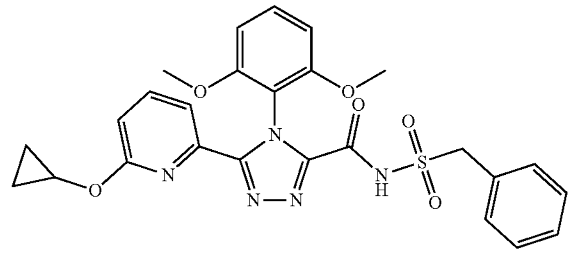 [SMILES: COc1cccc(OC)c1-n1c(C(=O)NS(=O)(=O)Cc2ccccc2)nnc1-c1cccc(OC2CC2)n1] | N-(benzylsulfonyl)-5-(6-cyclopropoxypyridin-2-yl)-4-(2,6-dimethoxyphenyl)-4H-1,2,4-triazole-3-carboxamide |
| 20 | 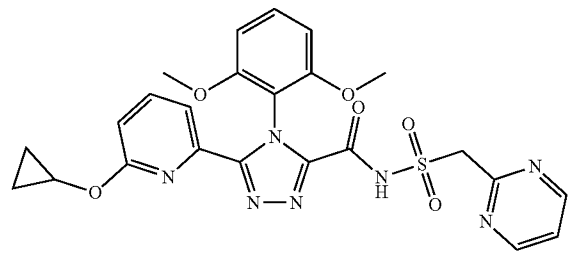 [SMILES: COc1cccc(OC)c1-n1c(C(=O)NS(=O)(=O)Cc2ncccn2)nnc1-c1cccc(OC2CC2)n1] | 5-(6-Cyclopropoxypyridin-2-yl)-4-(2,6-dimethoxyphenyl)-N-((pyrimidin-2-ylmethyl)sulfonyl)-4H-1,2,4-triazole-3-carboxamide |
| 21 | 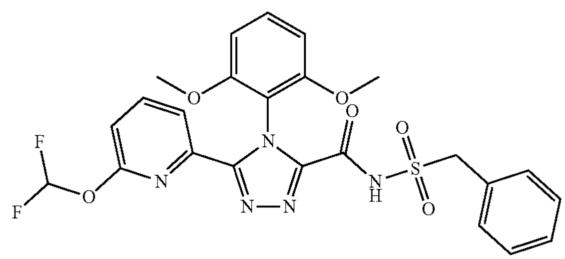 [SMILES: COc1cccc(OC)c1-n1c(C(=O)NS(=O)(=O)Cc2ccccc2)nnc1-c1cccc(OC(F)F)n1] | N-(benzylsulfonyl)-5-(6-(difluoromethoxy)pyridin-2-yl)-4-(2,6-dimethoxyphenyl)-4H-1,2,4-triazole-3-carboxamide |
| 22 | 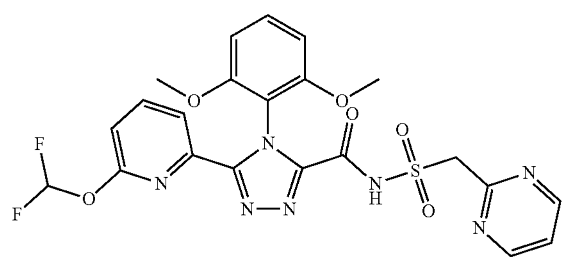 [SMILES: COc1cccc(OC)c1-n1c(C(=O)NS(=O)(=O)Cc2ncccn2)nnc1-c1cccc(OC(F)F)n1] | 5-(6-(Difluoromethoxy)pyridin-2-yl)-4-(2,6-dimethoxyphenyl)-N-((pyrimidin-2-ylmethyl)sulfonyl)-4H-1,2,4-triazole-3-carboxamide |
| 23 | 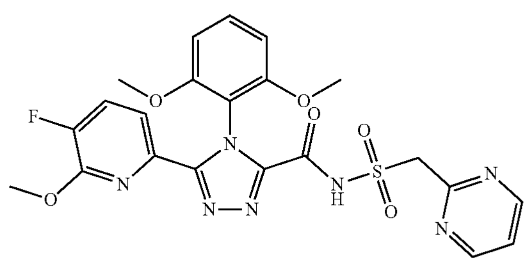 [SMILES: COc1cccc(OC)c1-n1c(C(=O)NS(=O)(=O)Cc2ncccn2)nnc1-c1ccc(F)c(OC)n1] | 4-(2,6-Dimethoxyphenyl)-5-(5-fluoro-6-methoxypyridin-2-yl)-N-((pyrimidin-2-ylmethyl)sulfonyl)-4H-1,2,4-triazole-3-carboxamide |
| 24 | 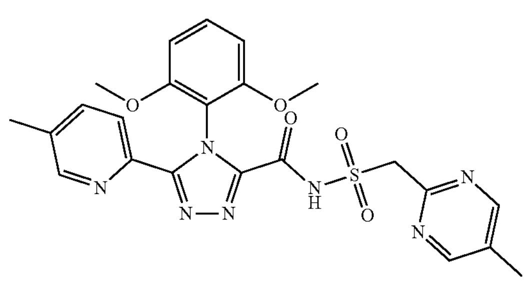 | 4-(2,6-Dimethoxyphenyl)-5-(5-methylpyridin-2-yl)-N-(((5-methylpyrimidin-2-yl)methyl)sulfonyl)-4H-1,2,4-triazole-3-carboxamide |

-continued

| Ex. number | Structure | IUPAC name |
|---|---|---|
| 25 | 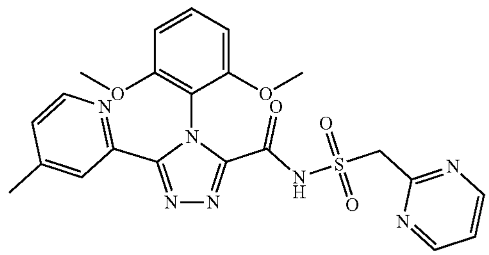 [SMILES: COc1cccc(OC)c1-n1c(C(=O)NS(=O)(=O)Cc2ncccn2)nnc1-c1cc(C)ccn1] | 4-(2,6-Dimethoxyphenyl)-5-(4-methylpyridin-2-yl)-N-((pyrimidin-2-ylmethyl)sulfonyl)-4H-1,2,4-triazole-3-carboxamide |
| 26 | 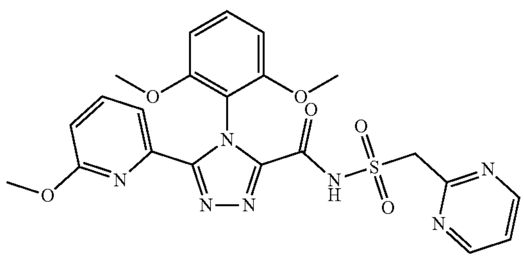 [SMILES: COc1cccc(-c2nnc(C(=O)NS(=O)(=O)Cc3ncccn3)n2-c2c(OC)cccc2OC)n1] | 4-(2,6-dimethoxyohenyl)-5-(6-methoxypyridin-2-yl)-N-((pyrimidin-2-ylmethyl)sulfonyl)-4H-1,2,4-triazole-3-carboxamide |
| 27 | 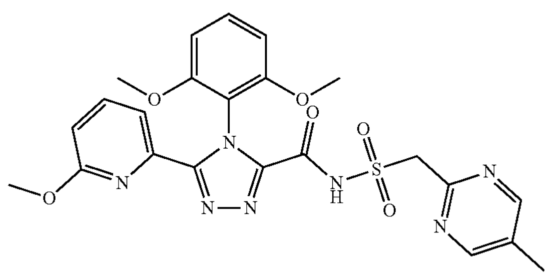 | 4-(2,6-Dimethoxyphenyl)-5-(6-methoxypyridin-2-yl)-N-(((5-methylpyrimidin-2-yl)methyl)sulfonyl)-4H-1,2,4-triazole-3-carboxamide |
| 28 | 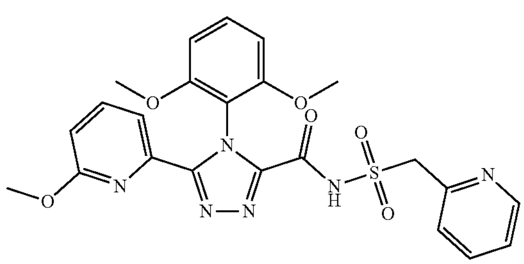 [SMILES: COc1cccc(-c2nnc(C(=O)NS(=O)(=O)Cc3ccccn3)n2-c2c(OC)cccc2OC)n1] | 4-(2,6-Dimethoxyphenyl)-5-(6-methoxypyridin-2-yl)-N-((pyridin-2-ylmethyl)sulfonyl)-4H-1,2,4-triazole-3-carboxamide |
| 29 | 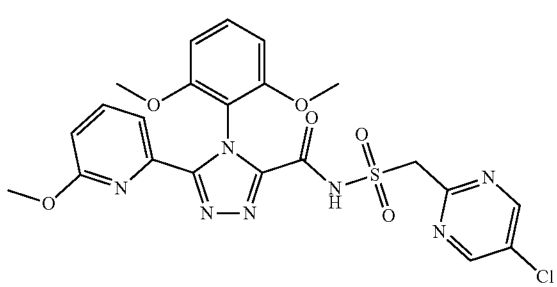 [SMILES: COc1cccc(-c2nnc(C(=O)NS(=O)(=O)Cc3ncc(Cl)cn3)n2-c2c(OC)cccc2OC)n1] | N-(((5-chloropyrimidin-2-yl)methyl)sulfonyl)-4-(2,6-dimethoxyphenyl)-5-(6-methoxypyridin-2-yl)-4H-1,2,4-triazole-3-carboxamide |

-continued

| Ex. number | Structure | IUPAC name |
|---|---|---|
| 30 | 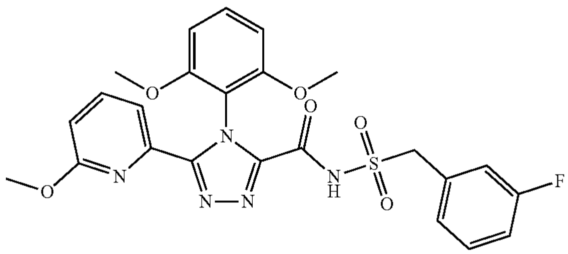 [SMILES: COc1cccc(-c2nnc(C(=O)NS(=O)(=O)Cc3cccc(F)c3)n2-c2c(OC)cccc2OC)n1] | 4-(2,6-Dimethoxyphenyl)-N-((3-fluorobenzyl)sulfonyl)-5-(6-methoxypyridin-2-yl)-4H-1,2,4-triazole-3-carboxamide |
| 31 | 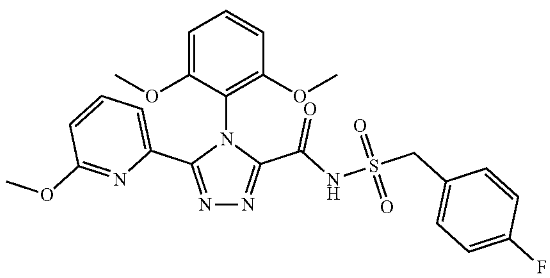 [SMILES: COc1cccc(-c2nnc(C(=O)NS(=O)(=O)Cc3ccc(F)cc3)n2-c2c(OC)cccc2OC)n1] | 4-(2,6-Dimethoxyphenyl)-N-((4-fluorobenzyl)sulfonyl)-5-(6-methoxypyridin-2-yl)-4H-1,2,4-triazole-3-carboxamide |
| 32 | 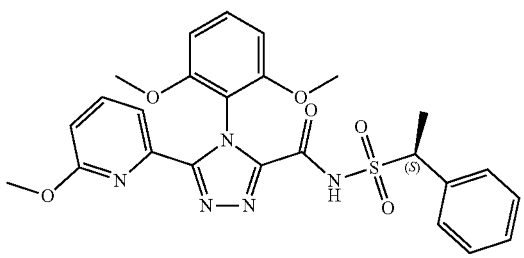 | (S)-4-(2,6-Dimethoxyphenyl)-5-(6-methoxypyridin-2-yl-N-((1-phenylethyl)sulfonyl)-4H-1,2,4-triazole-3-carboxamide |
| 33 | 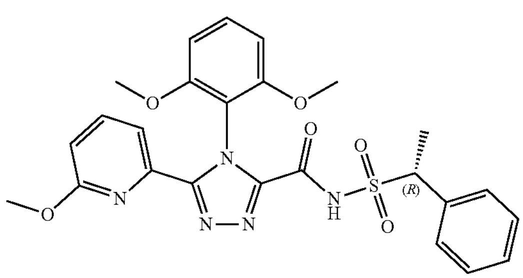 | (R)-4-(2,6-Dimethoxyohenyl)-5-(6-methoxypyridin-2-yl)-N-((1-phenylethyl)sulfonyl)-4H-1,2,4-triazole-3-carboxamide |
| 34 | 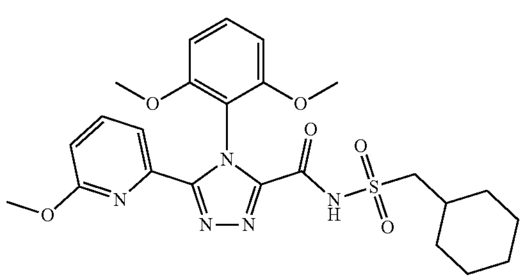 [SMILES: COc1cccc(-c2nnc(C(=O)NS(=O)(=O)CC3CCCCC3)n2-c2c(OC)cccc2OC)n1] | N-((cyclohexylmethyl)sulfonyl)-4-(2,6-dimethoxyphenyl)-5-(6-methoxypyridin-2-yl)-4H-1,2,4-triazole-3-carboxamide |

| Ex. number | Structure | IUPAC name |
|---|---|---|
| 35 | 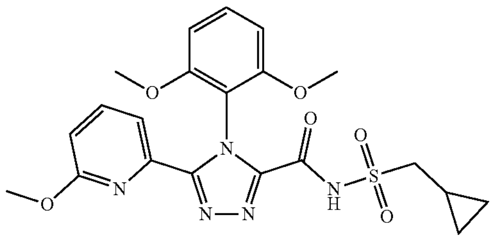 [SMILES: COc1cccc(-c2nnc(C(=O)NS(=O)(=O)CC3CC3)n2-c2c(OC)cccc2OC)n1] | N-((cyclopropylmethyl)sulfonyl)-4-(2,6-dimethoxyphenyl)-5-(6-methoxypyridin-2-yl)-4H-1,2,4-triazole-3-carboxamide |
| 36 | 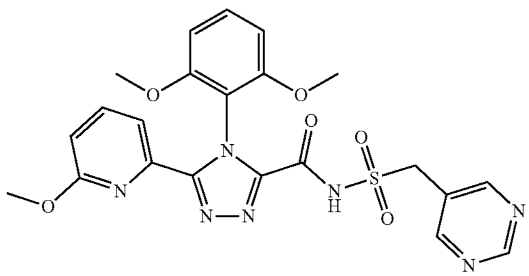 [SMILES: COc1cccc(-c2nnc(C(=O)NS(=O)(=O)Cc3cncnc3)n2-c2c(OC)cccc2OC)n1] | 4-(2,6-Dimethoxyphenyl)-5-(6-methoxypyridin-2-yl)-N-((pyrimidin-5-ylmethyl)sulfonyl)-4H-1,2,4-triazole-3-carboxamide |
| 37 | 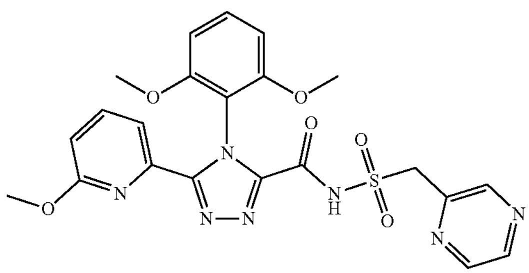 [SMILES: COc1cccc(-c2nnc(C(=O)NS(=O)(=O)Cc3cnccn3)n2-c2c(OC)cccc2OC)n1] | 4-(2,6-Dimethoxyphenyl)-5-(6-methoxypyridin-2-yl)-N-((pyrazin-2-ylmethyl)sulfonyl)-4H-1,2,4-triazole-3-carboxamide |
| 38 | 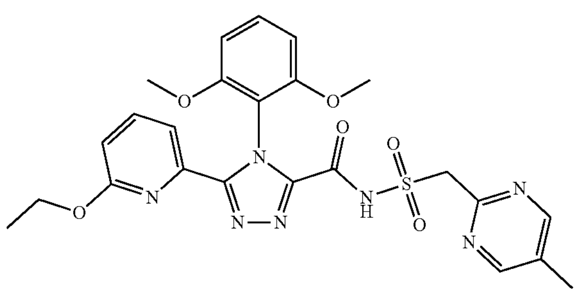 [SMILES: CCOc1cccc(-c2nnc(C(=O)NS(=O)(=O)Cc3ncc(C)cn3)n2-c2c(OC)cccc2OC)n1] | 4-(2,6-Dimethoxyphenyl)-5-(6-ethoxypyridin-2-yl)-N-(((5-methylpyrimidin-2-yl)methyl)sulfonyl)-4H-1,2,4-triazole-3-carboxamide |
| 39 | 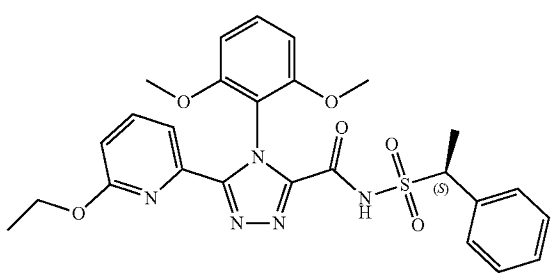 | (S)-4-(2,6-dimethoxyphenyl)-5-(6-ethoxypyridin-2-yl)-N-((1-phenylethyl)sulfonyl)-4H-1,2,4-triazole-3-carboxamide |

| Ex. number | Structure | IUPAC name |
|---|---|---|
| 40 | 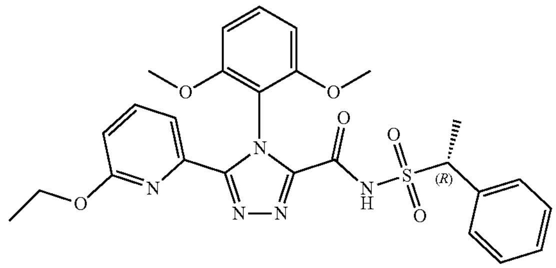 | (R)-4-(2,6-dimethoxyphenyl)-5-(6-ethoxypyridin-2-yl)-N-((1-phenylethyl)sulfonyl)-4H-1,2,4-triazole-3-carboxamide |
| 41 | 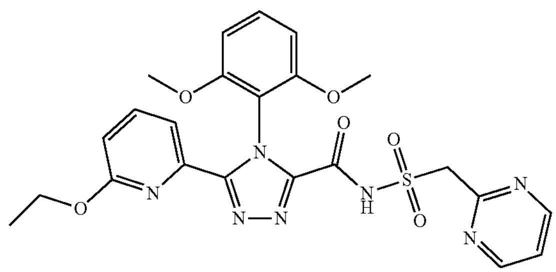 [SMILES: CCOc1cccc(-c2nnc(C(=O)NS(=O)(=O)Cc3ncccn3)n2-c2c(OC)cccc2OC)n1] | 4-(2,6-Dimethoxyphenyl)-5-(6-ethoxypyridin-2-yl)-N-((pyrimidin-2-ylmethyl)sulfonyl)-4H-1,2,4-triazole-3-carboxamide |
| 42 | 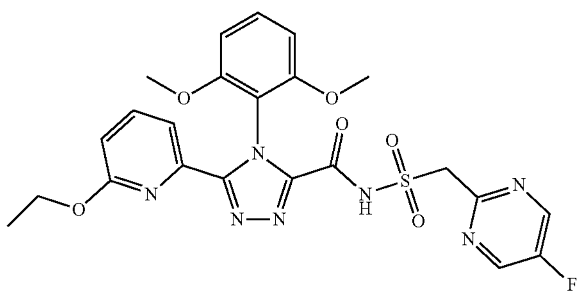 [SMILES: CCOc1cccc(-c2nnc(C(=O)NS(=O)(=O)Cc3ncc(F)cn3)n2-c2c(OC)cccc2OC)n1] | 4-(2,6-Dimethoxyphenyl)-5-(6-ethoxypyridin-2-yl)-N-(((5-fluoropyrimidin-2-yl)methylsulfonyl)-4H-1,2,4-triazole-3-carboxamide |
| 43 | 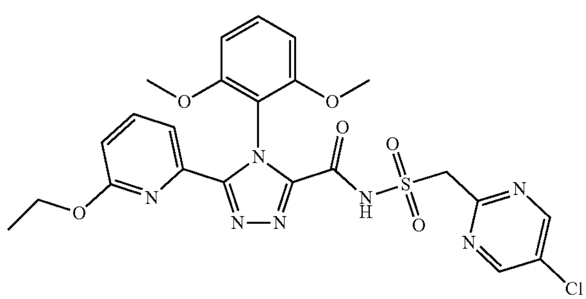 [SMILES: CCOc1cccc(-c2nnc(C(=O)NS(=O)(=O)Cc3ncc(Cl)cn3)n2-c2c(OC)cccc2OC)n1] | N-(((5-chloropyrimidin-2-yl)methyl)sulfonyl)-4-(2,6-dimethoxyphenyl)-5-(6-ethoxypyridin-2-yl)-4H-1,2,4-triazole-3-carboxamide |
| 44 | 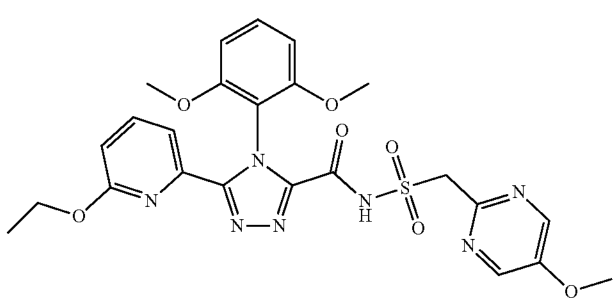 [SMILES: CCOc1cccc(-c2nnc(C(=O)NS(=O)(=O)Cc3ncc(OC)cn3)n2-c2c(OC)cccc2OC)n1] | 4-(2,6-Dimethoxyphenyl)-5-(6-ethoxypyridin-2-yl)-N-(((5-methoxypyrimidin-2-yl)methylsulfonyl)-4H-1,2,4-triazole-3-carboxamide |

-continued

| Ex. number | Structure | IUPAC name |
|---|---|---|
| 45 | 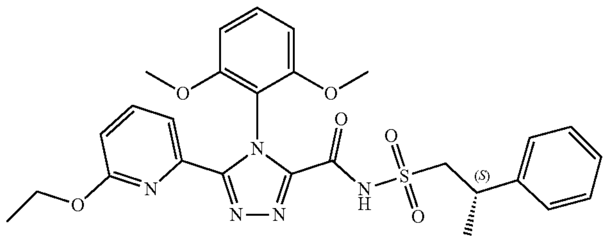 | (S)-4-(2,6-Dimethoxyphenyl)-5-(6-ethoxypyridin-2-yl)-N-((2-phenylpropyl)sulfonyl)-4H-1,2,4-triazole-3-carboxamide |
| 46 | 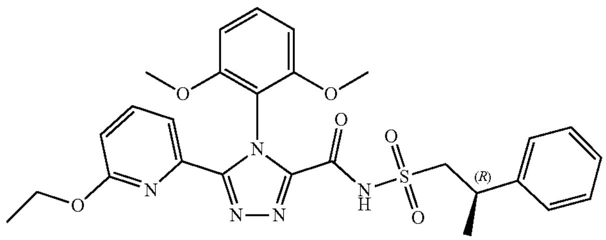 | (R)-4-(2,6-Dimethoxyphenyl)-5-(6-ethoxypyridin-2-yl)-N-((2-phenylpropyl)sulfonyl)-4H-1,2,4-triazole-3-carboxamide |
| 47 | 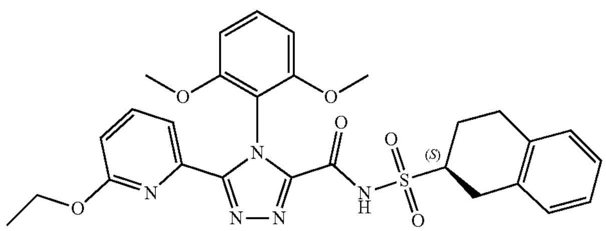 | (S)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide |
| 48 | 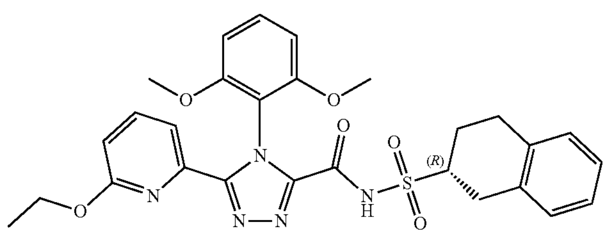 | (R)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide |
| 49 | 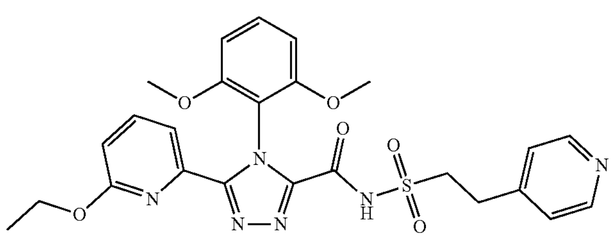 [SMILES: CCOc1cccc(-c2nnc(C(=O)NS(=O)(=O)CCc3ccncc3)n2-c2c(OC)cccc2OC)n1] | 4-(2,6-Dimethoxyphenyl)-5-(6-ethoxypyridin-2-yl)-N-((2-(pyridin-4-yl)ethyl)sulfonyl)-4H-1,2,4-triazole-3-carboxamide |
| 50 | 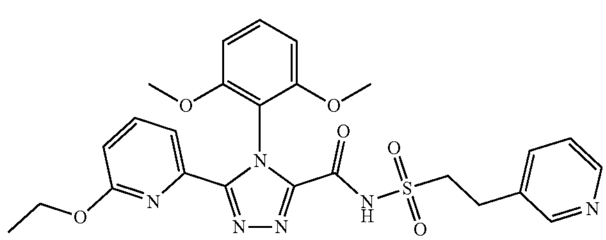 [SMILES: CCOc1cccc(-c2nnc(C(=O)NS(=O)(=O)CCc3cccnc3)n2-c2c(OC)cccc2OC)n1] | 4-(2,6-Dimethoxyphenyl)-5-(6-ethoxypyridin-2-yl)-N-((2-(pyridin-3-yl)ethyl)sulfonyl)-4H-1,2,4-triazole-3-carboxamide |

-continued

| Ex. number | Structure | IUPAC name |
|---|---|---|
| 51 | 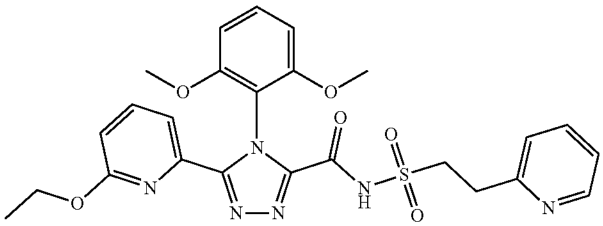 [SMILES: CCOc1cccc(-c2nnc(C(=O)NS(=O)(=O)CCc3ccccn3)n2-c2c(OC)cccc2OC)n1] | 4-(2,6-Dimethoxyphenyl)-5-(6-ethoxypyridin-2-yl)-N-((2-(pyridin-2-yl)ethyl)sulfonyl)-4H-1,2,4-triazole-3-carboxamide |
| 52 | 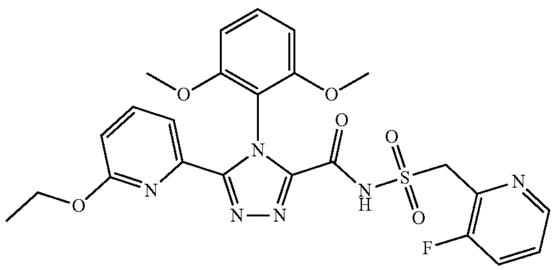 [SMILES: CCOc1cccc(-c2nnc(C(=O)NS(=O)(=O)Cc3ncccc3F)n2-c2c(OC)cccc2OC)n1] | 4-(2,6-Dimethoxyphenyl)-5-(6-ethoxypyridin-2-yl)-N-(((3-fluoropyridin-2-yl)methyl)sulfonyl)-4H-1,2,4-triazole-3-carboxamide |
| 53 | 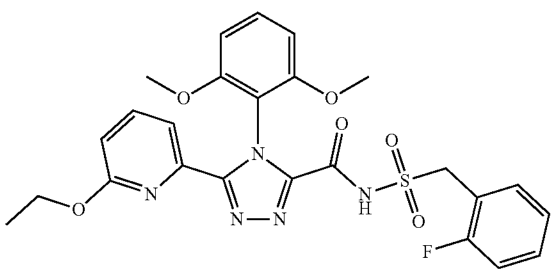 [SMILES: CCOc1cccc(-c2nnc(C(=O)NS(=O)(=O)Cc3ccccc3F)n2-c2c(OC)cccc2OC)n1] | 4-(2,6-Dimethoxyphenyl)-5-(6-ethoxypyridin-2-yl)-N-((2-fluorobenzyl)sulfonyl)-4H-1,2,4-triazole-3-carboxamide |
| 54 | 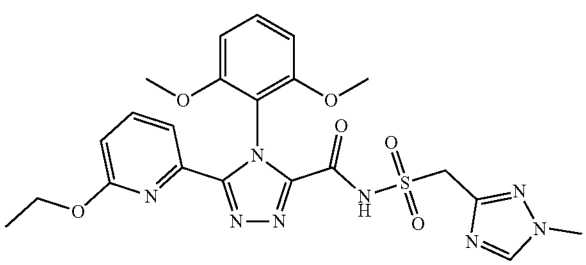 [SMILES: CCOc1cccc(-c2nnc(C(=O)NS(=O)(=O)Cc3ncn(C)n3)n2-c2c(OC)cccc2OC)n1] | 4-(2,6-Dimethoxyphenyl)-5-(6-ethoxypyridin-2-yl)-N-(((1-methyl-1H-1,2,4-triazol-3-yl)methyl)sulfonyl)-4H-1,2,4-triazole-3-carboxamide |
| 55 | 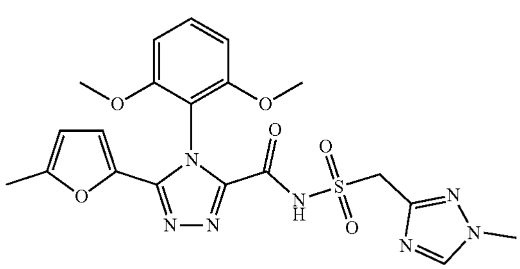 | 4-(2,6-Dimethoxyphenyl)-N-(((1-methyl-1H-1,2,4-triazol-3-yl)methyl)sulfonyl)-5-(5-methylfuran-2-yl)-4H-1,2,4-triazole-3-carboxamide |

| Ex. number | Structure | IUPAC name |
|---|---|---|
| 56 | 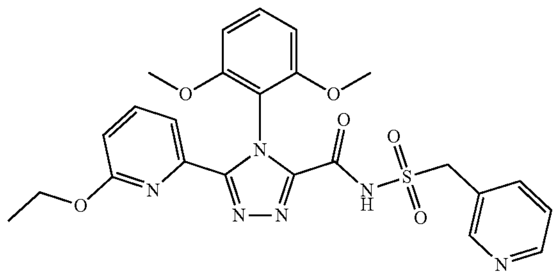 [SMILES: CCOc1cccc(-c2nnc(C(=O)NS(=O)(=O)Cc3cccnc3)n2-c2c(OC)cccc2OC)n1] | 4-(2,6-Dimethoxyphenyl)-5-(6-ethoxypyridin-2-yl)-N-((pyridin-3-ylmethyl)sulfonyl)-4H-1,2,4-triazole-3-carboxamide |
| 57 | 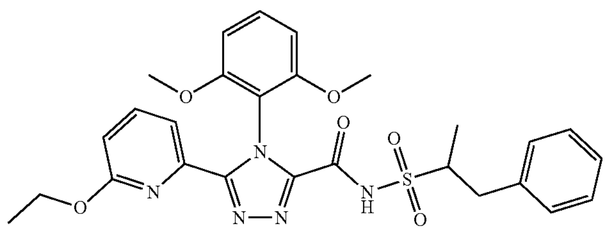 [SMILES: CCOc1cccc(-c2nnc(C(=O)NS(=O)(=O)C(C)Cc3ccccc3)n2-c2c(OC)cccc2OC)n1] | 4-(2,6-Dimethoxyphenyl)-5-(6-ethoxypyridin-2-yl)-N-((1-phenylpropan-2-yl)sulfonyl)-4H-1,2,4-triazole-3-carboxamide |
| 58 | 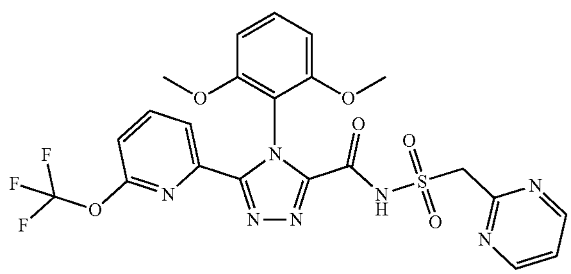 [SMILES: COc1cccc(OC)c1-n1c(C(=O)NS(=O)(=O)Cc2ncccn2)nnc1-c1cccc(OC(F)(F)F)n1] | 4-(2,6-Dimethoxyphenyl)-N-((pyrimidin-2-ylmethyl)sulfonyl)-5-(6-(trifluoromethoxy)pyridin-2-yl)-4H-1,2,4-triazole-3-carboxamide |
| 59 | 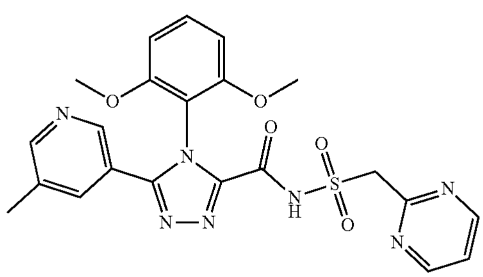 [SMILES: COc1cccc(OC)c1-n1c(C(=O)NS(=O)(=O)Cc2ncccn2)nnc1-c1cncc(C)c1] | 4-(2,6-Dimethoxyphenyl)-5-(5-methylpyridin-3-yl)-N-((pyrimidin-2-ylmethyl)sulfonyl)-4H-1,2,4-triazole-3-carboxamide |
| 60 | 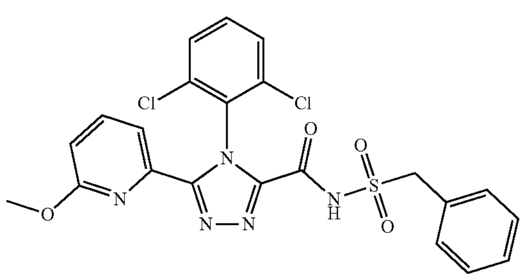 [SMILES: COc1cccc(-c2nnc(C(=O)NS(=O)(=O)Cc3ccccc3)n2-c2c(Cl)cccc2Cl)n1] | N-(benzylsulfonyl)-4-(2,6-dichlorophenyl)-5-(6-methoxypyridin-2-yl)-4H-1,2,4-triazole-3-carboxamide |

-continued

| Ex. number | Structure | IUPAC name |
|---|---|---|
| 61 | 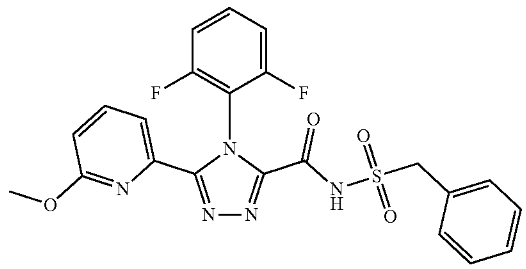 [SMILES: COc1cccc(-c2nnc(C(=O)NS(=O)(=O)Cc3ccccc3)n2-c2c(F)cccc2F)n1] | N-(benzylsulfonyl)-4-(2,6-difluorophenyl)-5-(6-methoxypyridin-2-yl)-4H-1,2,4-triazole-3-carboxamide |
| 62 | 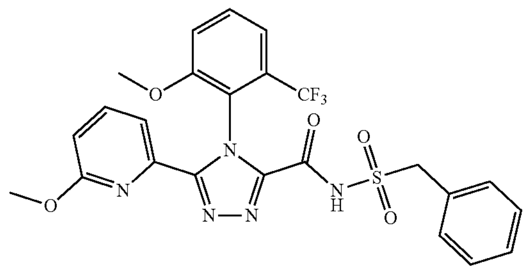 [SMILES: COc1cccc(-c2nnc(C(=O)NS(=O)(=O)Cc3ccccc3)n2-c2c(OC)cccc2C(F)(F)F)n1] | N-(benzylsulfonyl)-4-(2-methoxy-6-(trifluoromethyl)phenyl)-5-(6-methoxypyridin-2-yl)-4H-1,2,4-triazole-3-carboxamide |
| 63 | 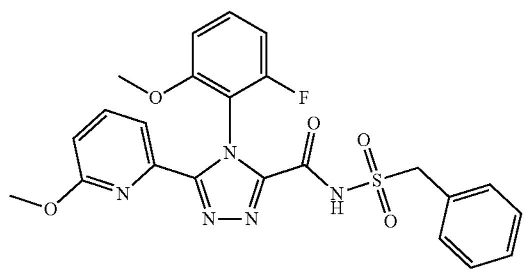 [SMILES: COc1cccc(-c2nnc(C(=O)NS(=O)(=O)Cc3ccccc3)n2-c2c(F)cccc2OC)n1] | N-(benzylsulfonyl)-4-(2-fluoro-6-methoxyphenyl)-5-(6-methoxypyridin-2-yl)-4H-1,2,4-triazole-3-carboxamide |
| 64 | 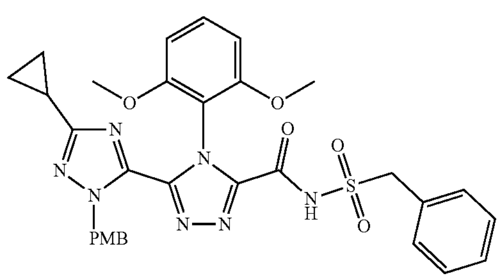 | N-(benzylsulfonyl)-5-cyclopropyl-4'-(2,6-dimethoxyphenyl)-2-(4-methoxybenzyl)-2H,4'H-[3,3'-bi(1,2,4-triazole)]-5'-carboxamide |
| 65 | 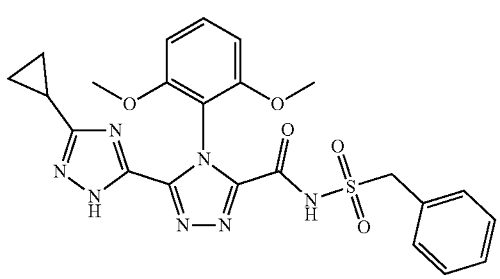 [SMILES: COc1cccc(OC)c1-n1c(C(=O)NS(=O)(=O)Cc2ccccc2)nnc1-c1nc(C2CC2)n[nH]1] | N-(benzylsulfonyl)-5-cyclopropyl-4'-(2,6-dimethoxyphenyl)-2H,4'H-[3,3'-bi(1,2,4-triazole)]-5'-carboxamide |

| Ex. number | Structure | IUPAC name |
|---|---|---|
|  |  | N-(benzylsulfonyl)-4-(2,6-dimethoxyphenyl)-5-(2-methoxyoxazol-4-yl)-4H-1,2,4-triazole-3-carboxamide |

Embodiment 103. The compound of Embodiment 1, wherein the compound is selected from the group consisting of those in the table below,

| Ex. number | Structure | IUPAC name |
|---|---|---|
| 1 | 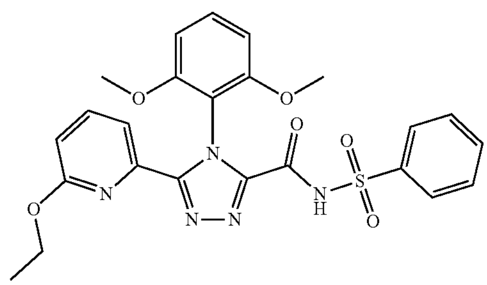 [SMILES: CCOc1cccc(-c2nnc(C(=O)NS(=O)(=O)c3ccccc3)n2-c2c(OC)cccc2OC)n1] | 4-(2,6-dimethoxyphenyl)-5-(6-ethoxypyridin-2-yl)-N-(phenylsulfonyl)-4H-1,2,4-triazole-3-carboxamide |
| 3 | 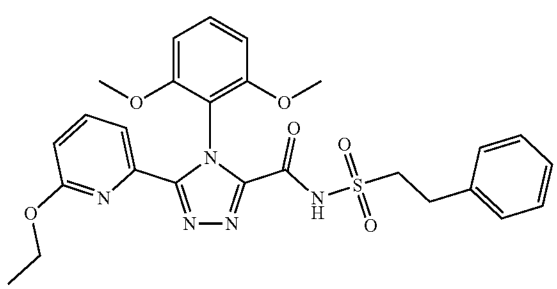 [SMILES: CCOc1cccc(-c2nnc(C(=O)NS(=O)(=O)CCc3ccccc3)n2-c2c(OC)cccc2OC)n1] | 4-(2,6-dimethoxyphenyl)-5-(6-ethoxypyridin-2-yl)-N-(phenethylsulfonyl)-4H-1,2,4-triazole-3-carboxamide |
| 17 | 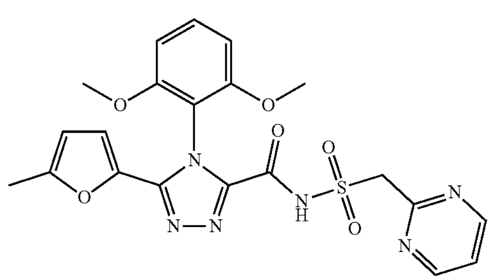 [SMILES: COc1cccc(OC)c1-n1c(C(=O)NS(=O)(=O)Cc2ncccn2)nnc1-c1ccc(C)o1] | 4-(2,6-Dimethoxyphenyl)-5-(5-methylfuran-2-yl)-N-((pyrimidin-2-ylmethyl)sulfonyl)-4H-1,2,4-triazole-3-carboxamide |

-continued

| Ex. number | Structure | IUPAC name |
|---|---|---|
| 20 | 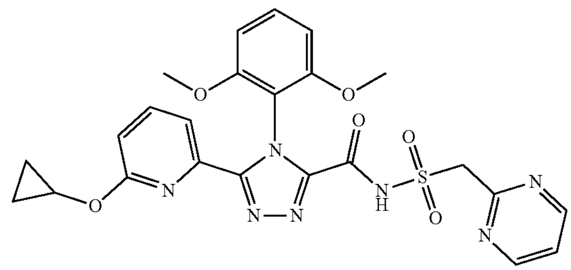 [SMILES: COc1cccc(OC)c1-n1c(C(=O)NS(=O)(=O)Cc2ncccn2)nnc1-c1cccc(OC2CC2)n1] | 5-(6-Cyclopropoxypyridin-2-yl)-4-(2,6-dimethoxyphenyl)-N-((pyrimidin-2-ylmethyl)sulfonyl)-4H-1,2,4-triazole-3-carboxamide |
| 34 | 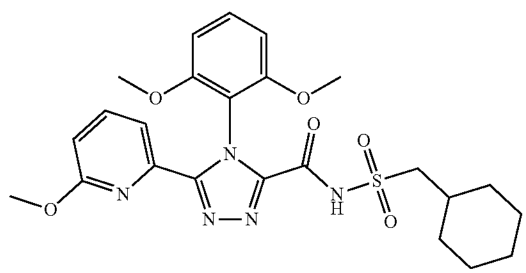 [SMILES: COc1cccc(-c2nnc(C(=O)NS(=O)(=O)CC3CCCCC3)n2-c2c(OC)cccc2OC)n1] | N-((cyclohexylmethyl)sulfonyl)-4-(2,6-dimethoxyphenyl)-5-(6-methoxypyridin-2-yl)-4H-1,2,4-triazole-3-carboxamide |
| 39 | 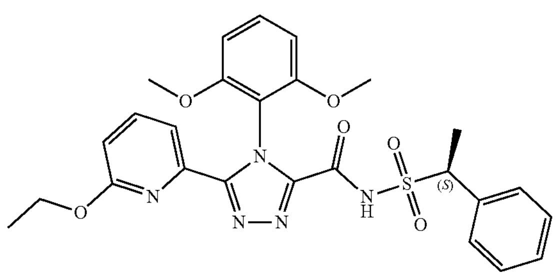 | (S)-4-(2,6-dimethoxyphenyl)-5-(6-ethoxypyridin-2-yl)-N-((1-phenylethyl)sulfonyl)-4H-1,2,4-triazole-3-carboxamide |
| 40 | 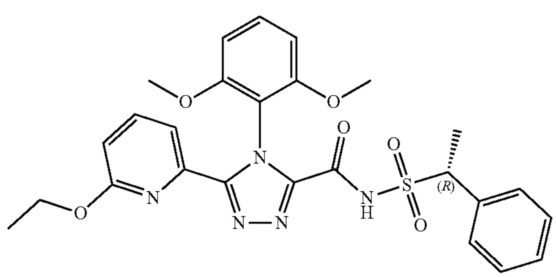 | (R)-4-(2,6-dimethoxyphenyl)-5-(6-ethoxypyridin-2-yl)-N-((1-phenylethyl)sulfonyl)-4H-1,2,4-triazole-3-carboxamide |
| 41 | 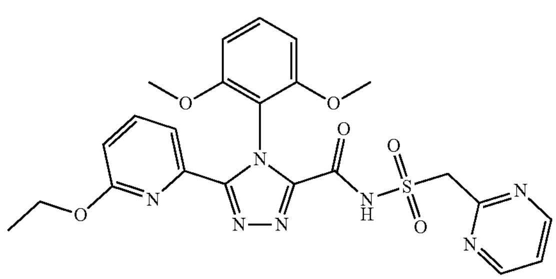 [SMILES: CCOc1cccc(-c2nnc(C(=O)NS(=O)(=O)Cc3ncccn3)n2-c2c(OC)cccc2OC)n1] | 4-(2,6-Dimethoxyphenyl)-5-(6-ethoxypyridin-2-yl)-N-((pyrimidin-2-ylmethyl)sulfonyl)-4H-1,2,4-triazole-3-carboxamide |

| Ex. number | Structure | IUPAC name |
|---|---|---|
| 47 | 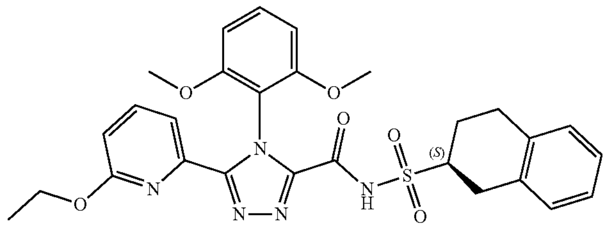 | (S)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide |
| 55 | 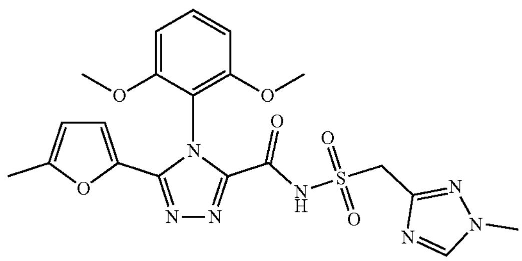 | 4-(2,6-Dimethoxyphenyl)-N-(((1-methyl-1H-1,2,4-triazol-3-yl)methyl)sulfonyl)-5-(5-methylfuran-2-yl)-4H-1,2,4-triazole-3-carboxamide |
| 57 | 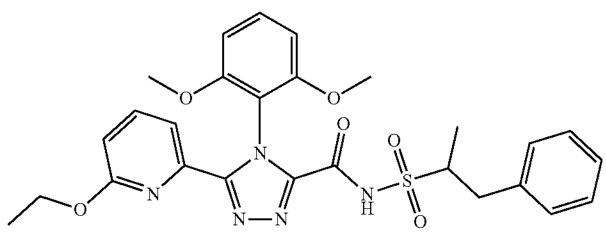 [SMILES: CCOc1cccc(-c2nnc(C(=O)NS(=O)(=O)C(C)Cc3ccccc3)n2-c2c(OC)cccc2OC)n1] | 4-(2,6-Dimethoxyphenyl)-5-(6-ethoxypyridin-2-yl)-N-((1-phenylpropan-2-yl)sulfonyl)-4H-1,2,4-triazole-3-carboxamide |

Embodiment 104. A pharmaceutical composition comprising a compound or salt as in any one of Embodiments 1-103 and one or more pharmaceutically acceptable excipients.

Embodiment 105. A method for modulating APJ receptor activity, the method comprising contacting the APJ receptor with a compound as in any one of Embodiments 1-103.

Embodiment 106. The method of Embodiment 105, wherein the modulating comprises agonizing the APJ receptor.

Embodiment 107. The method of Embodiment 105 or 106, which is carried out in vitro.

Embodiment 108. The method of Embodiment 105 or 106, which is carried out in vivo.

Embodiment 109. A method for modulating (e.g., decreasing) pulmonary vascular resistance in a subject in need of such modulating, the method comprising administering to the subject an effective amount of a compound as in any one of Embodiments 1-103.

Embodiment 110. A method for modulating (e.g., decreasing) right ventricular afterload in a subject in need of such modulating, the method comprising administering to the subject an effective amount of a compound as in any one of Embodiments 1-103.

Embodiment 111. A method for modulating (e.g., decreasing) mean pulmonary artery pressure in a subject in need of such modulating, the method comprising administering to the subject an effective amount of a compound as in any one of Embodiments 1-103.

Embodiment 112. The method of Embodiment 111, wherein the subject exhibits a mean pulmonary artery pressure of greater than 25 mmHg.

Embodiment 113. A method for reducing the risk of right ventricular failure in a subject in need of such reducing, the method comprising administering to the subject an effective amount of a compound as in any one of Embodiments 1-103.

Embodiment 114. A method for treating a disease, disorder, or condition, in which repressed or impaired APJ receptor signaling, or downregulation of endogenous apelin contributes to the pathology and/or symptoms and/or progression of the disease, disorder, or condition, the method comprising administering to the subject in need thereof an effective amount of a compound as in any one of Embodiments 1-103.

Embodiment 115. The method of Embodiment 114, wherein the disease, disorder, or condition is pulmonary arterial hypertension ("PAH").

Embodiment 116. The method of Embodiment 115, wherein the PAH is idiopathic.

Embodiment 117. The method of Embodiment 115, wherein the PAH is heritable PAH, toxin or drug-induced PAH; or a PAH associated with one or more of the following: congenital heart disease, connective tissue disorders (e.g., scleroderma, systemic lupus erythematosus, systemic sclerosis, Hashimoto's thyroiditis, Sjogren's Syndrome, and the antiphospholipid antibody syndrome), portal hypertension. BMPR2 mutations, Schistosomiasis, and HIV infection.

Embodiment 118. The method of any one of Embodiments 114-117, wherein the method further comprises identifying the subject.

Embodiment 119. The method of Embodiment 118, wherein identifying comprises determining the level of one or more of the following parameters in the subject: leukotriene B4 level, pulmonary vascular resistance, pulmonary arterial pressure, cardiac index, pulmonary capillary wedge pressure, right atrial pressure, six-minute walk distance, brain natriuretic peptide level, atrial natriuretic peptide level, and diffusion of lung capacity.

Embodiment 120. The method of any one of Embodiments 114-119, wherein the subject is a human.

Embodiment 121. The method of any one of Embodiments 114-120, which further comprises administering one or more additional therapeutic agents.

Embodiment 122. The method of any one of Embodiments 115-120, which further comprises treating one or more diseases, disorders, or conditions that are sequel a or comorbid with the PAH.

Non-Limiting Combinations [1]

In some embodiments:
$R^1$ is —$(Y^1)_n$—$Y^2$; and
$R^2$ is $C_{6-10}$ aryl, which is optionally substituted with from 1-4 $R^c$.
In certain of these embodiments, n is 0. In certain of these embodiments, $R^4$ is H.

In some embodiments:
$R^1$ is —$(Y^1)_n$—$Y^2$, in which $Y^2$ can be defined according to any one or more of Embodiments 6-19; or $R^1$ can be defined according to Embodiment 21 or 22; and
$R^2$ is $C_{6-10}$ aryl, which is optionally substituted with from 1-4 $R^c$.
In certain of these embodiments, n is 0 In certain of these embodiments, $R^4$ is H.

In some embodiments:
$R^1$ is —$(Y^1)_n$—$Y^2$, in which $Y^2$ can be defined according to any one or more of Embodiments 6-11, 13-15, and 18-19; or $R^1$ can be defined according to Embodiment 21; and
$R^2$ is $C_{6-10}$ aryl, which is optionally substituted with from 1-4 $R^c$.
In certain of these embodiments, n is 0. In certain of these embodiments, $R^4$ is H.

In certain of the foregoing embodiments of [1] $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy; and (xiv) —$C_{1-4}$ thioalkoxy. For example, each occurrence of $R^c$ is an independently selected $C_{1-4}$ alkoxy (e.g., —$OCH_3$).

In certain of the foregoing embodiments of [1], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and —$C_{1-4}$ thioalkoxy, e.g., each occurrence of $R^c$ is an independently selected $C_{1-4}$ alkoxy (e.g., —$OCH_3$). For example, $R^{2a}$ and $R^{2e}$ are each $OCH_3$.

In certain of the foregoing embodiments of [1], $R^2$ has formula (B).

Non-Limiting Combinations [2]

In some embodiments:
$R^1$ is —$Z^1$—$Z^2$—$Z^3$; and
$R^2$ is $C_{6-10}$ aryl, which is optionally substituted with from 1-4 $R^c$.
In certain of these embodiments, $R^4$ is H.

In some embodiments:
$R^1$ is —$Z^1$—$Z^2$—$Z^3$, in which $Z^1$—$Z^2$—$Z^3$ can be defined according to any one or more of Embodiments 24-27, or $R^1$ can be defined according to Embodiment 28; and
$R^2$ is $C_{6-10}$ aryl, which is optionally substituted with from 1-4 $R^c$.
In certain of these embodiments, $R^4$ is H.

In certain of the foregoing embodiments of [2], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy; and (xiv) —$C_{1-4}$ thioalkoxy. For example, each occurrence of $R^c$ is an independently selected $C_{1-4}$ alkoxy (e.g., —$OCH_3$).

In certain of the foregoing embodiments of [2], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy, and —$C_{1-4}$ thioalkoxy; e.g., each occurrence of $R^c$ is an independently selected $C_{1-4}$ alkoxy (e.g., —$OCH_3$). For example, $R^{2a}$ and $R^{2e}$ are each $OCH_3$.

In certain of the foregoing embodiments of [2], $R^2$ has formula (B).

Non-Limiting Combinations [3]

In some embodiments:
$R^2$ is $C_{6-10}$ aryl, which is optionally substituted with from 1-4 $R^c$; and
$R^3$ is —$(Y^3)_p$—$Y^4$; and
p is 1.
In certain of these embodiments, $R^4$ is H.

In some embodiments:
$R^2$ is $C_{6-10}$ aryl, which is optionally substituted with from 1-4 $R^c$; and
$R^3$ is —$(Y^3)_p$—$Y^4$, in which $Y^3$ can be defined according to Embodiment 38, 39, or 40 and/or $Y^4$ can be defined according to any one or more of Embodiments 42-52 and/or $R^3$ can be defined according to any one or more of Embodiments 55-56 and 58-59; and
p is 1.
In certain of these embodiments, $R^4$ is H.

In some embodiments:
$R^2$ is $C_{6-10}$ aryl, which is optionally substituted with from 1-4 $R^c$; and
$R^3$ is —$(Y^3)_p$—$Y^4$, in which $Y^3$ can be defined according to Embodiment 38, or 39 and/or $Y^4$ can be defined according to any one or more of Embodiments 42-44 and 47-48 and/or $R^3$ can be defined according to Embodiment 55; and
p is 1.
In certain of these embodiments, $R_4$ is H.

In some embodiments:
$R^2$ is $C_{6-10}$ aryl, which is optionally substituted with from 1-4 $R^c$; and
$R^3$ is —$(Y^3)_p$—$Y^4$, in which $Y_3$ can be defined according to Embodiment 38, 39, or 40 and/or $Y^4$ can be defined according to any one or more of Embodiments 61-64 and/or $R^3$ can be defined according to Embodiment 66; and
p is 1.
In certain of these embodiments, $R^4$ is H.

In some embodiments:
$R^2$ is $C_{6-10}$ aryl, which is optionally substituted with from 1-4 $R^c$; and
$R^3$ is $-(Y^3)_p-Y^4$; and
p is 0.
In certain of these embodiments, $R^4$ is H.
In some embodiments:
$R^2$ is $C_{6-10}$ aryl, which is optionally substituted with from 1-4 $R^c$; and
$R^3$ is $-(Y^3)_p-Y^4$, in which $Y^4$ can be defined according to any one or more of Embodiments 42-52 and/or $R^3$ can be defined according to Embodiment 57 or 60; and
p is 0.
In certain of these embodiments, $R^4$ is H.
In some embodiments:
$R^2$ is $C_{6-10}$ aryl, which is optionally substituted with from 1-4 $R^c$; and
$R^3$ is $-(Y^3)_p-Y^4$, in which $Y^4$ can be defined according to any one or more of Embodiments 42-44 and 47-48 and/or $R^3$ can be defined according to Embodiment 60; and
p is 0.
In certain of these embodiments, $R^4$ is H.
In some embodiments:
$R^2$ is $C_{6-10}$ aryl, which is optionally substituted with from 1-4 $R^c$; and
$R^3$ is $-(Y^3)_p-Y^4$, in which $Y^4$ can be defined according to any one or more of Embodiments 61-64; and
p is 0.
In certain of these embodiments, $R^4$ is H.
In certain of the foregoing embodiments of [3], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy; and (xiv) $-C_{1-4}$ thioalkoxy. For example, each occurrence of $R^c$ is an independently selected $C_{1-4}$ alkoxy (e.g., $-OCH_3$).
In certain of the foregoing embodiments of [3], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and $-C_{1-4}$ thioalkoxy; e.g., each occurrence of $R^c$ is an independently selected $C_{1-4}$ alkoxy (e g , $-OCH_3$). For example, $R^{2a}$ and $R^{2e}$ are each $OCH_3$.
In certain of the foregoing embodiments of [3], $R^2$ has formula (B).

Non-Limiting Combinations [4]

In some embodiments:
$R^2$ is $C_{6-10}$ aryl, which is optionally substituted with from 1-4 $R^c$; and
$R^3$ is $C_{1-10}$ alkyl, optionally substituted with from 1-6 independently selected $R^a$ (e.g., $R^3$ can be defined according to any one of Embodiments 45-48).
In certain of the foregoing embodiments of [4], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy; and (xiv) $-C_{1-4}$ thioalkoxy. For example, each occurrence of $R^c$ is an independently selected $C_{1-4}$ alkoxy (e.g., $-OCH_3$).
In certain of the foregoing embodiments of [4], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ and each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and $-C_{1-4}$ thioalkoxy; e.g., each occurrence of $R^c$ is an independently selected $C_{1-4}$ alkoxy (e.g., $-OCH_3$). For example, $R^{2a}$ and $R^{2e}$ are each $OCH_3$.
In certain of the foregoing embodiments of [4], $R^2$ has formula (B).

Non-Limiting Combinations [5]

In some embodiments:
$R^1$ is $-(Y^1)_n-Y^2$;
$R^2$ is $C_{6-10}$ aryl, which is optionally substituted with from 1-4 $R^c$; and
$R^3$ is $-(Y^3)_p-Y^4$.
In certain of these embodiments, n is 0.
In certain of these embodiments, p is 1.
In certain of these embodiments, n is 0, and p is 1.
In certain of these embodiments, $R^4$ is H.
In some embodiments:
$R^1$ is $-(Y_1)_n-Y^2$, in which $Y^2$ can be defined according to any one or more of Embodiments 6-19: or $R^1$ can be defined according to Embodiment 21 or 22;
$R^2$ is $C_{6-10}$ aryl, which is optionally substituted with from 1-4 $R^c$; and
$R^3$ is $-(Y^3)_p-Y^4$.
In certain of these embodiments, n is 0.
In certain of these embodiments, p is 1.
In certain of these embodiments, n is 0, and p is 1.
In certain of these embodiments, $R^4$ is H.
In some embodiments:
$R^1$ is $-(Y^1)_n-Y^2$, in which $Y^2$ can be defined according to any one or more of Embodiments 6-11, 13-15, and 18-19; or $R^1$ can be defined according to Embodiment 21:
$R^2$ is $C_{6-10}$ aryl, which is optionally substituted with from 1-4 $R^c$; and
$R^3$ is $-(Y^3)_p-Y^4$.
In certain of these embodiments, n is 0.
In certain of these embodiments, p is 1.
In certain of these embodiments, n is 0, and p is 1.
In certain of these embodiments, $R^4$ is H.
In some embodiments
$R^1$ is $-(Y^1)_n-Y^2$;
$R^2$ is $C_{6-10}$ aryl, which is optionally substituted with from 1-4 $R^c$; and
$R^3$ is $-(Y^3)_p-Y^4$, in which $Y^3$ can be defined according to Embodiment 38, 39, or 40 and/or $Y^4$ can be defined according to any one or more of Embodiments 42-52 and/or $R^3$ can be defined according to any one or more of Embodiments 55-60.
In certain of these embodiments, n is 0.
In certain of these embodiments, p is 1.
In certain of these embodiments, n is 0, and p is 1.
In certain of these embodiments, $R^4$ is H.

In some embodiments
$R^1$ is —$(Y^1)_n$—$Y^2$;
$R^2$ is $C_{6\text{-}10}$ aryl, which is optionally substituted with from 1-4 $R^c$; and
$R^3$ is —$(Y^3)_p$—$Y^4$, in which $Y^3$ can be defined according to Embodiment 38 or 39 and/or $Y^4$ can be defined according to any one or more of Embodiments 42-44 and 47-48 and/or $R^3$ can be defined according to Embodiment 55 or 60.
In certain of these embodiments, n is 0.
In certain of these embodiments, p is 1.
In certain of these embodiments, n is 0, and p is 1.
In certain of these embodiments, $R^4$ is H.

In some embodiments:
$R^1$ is —$(Y^1)_n$—$Y^2$;
$R^2$ is $C_{6\text{-}10}$ aryl, which is optionally substituted with from 1-4 $R^c$; and
$R^3$ is —$(Y^3)_p$—$Y^4$, in which $Y^3$ can be defined according to Embodiment 38, 39, or 40 and/or $Y^4$ can be defined according to any one or more of Embodiments 61-64 and/or $R^3$ can be defined according to Embodiment 66.
In certain of these embodiments, n is 0.
In certain of these embodiments, p is 1.
In certain of these embodiments, n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiments 6-19: or $R^1$ can be defined according to Embodiment 21 or 22;
$R^2$ is $C_{6\text{-}10}$ aryl, which is optionally substituted with from 1-4 $R^c$; and
$R^3$ is —$(Y^3)_p$—$Y^4$ in which $Y^3$ can be defined according to Embodiment 38, 39, or 40 and/or $Y^4$ can be defined according to any one or more of Embodiments 42-52 and/or $R^3$ can be defined according to any one or more of Embodiments 55-60.
In certain of these embodiments, n is 0.
In certain of these embodiments, p is 1.
In certain of these embodiments, n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiment 6-11, 13-15, and 18-19; or $R^1$ can be defined according to Embodiment 21;
$R^2$ is $C_{6\text{-}10}$ aryl, which is optionally substituted with from 1-4 $R^c$; and
$R^3$ is —$(Y^3)_p$—$Y^4$, in which $Y^3$ can be defined according to Embodiment 38 or 39 and/or $Y^4$ can be defined according to any one or more of Embodiments 42-44 and 47-48 and/or $R^3$ can be defined according to Embodiment 55 or 60.
In certain of these embodiments, n is 0.
In certain of these embodiments, p is 1.
In certain of these embodiments, n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiments 6-19; or $R^1$ can be defined according to Embodiment 21 or 22;
$R^2$ is $C_{6\text{-}10}$ aryl, which is optionally substituted with from 1-4 $R^c$; and
$R^3$ is —$(Y^3)_p$—$Y^4$, in which $Y^3$ can be defined according to Embodiment 38, 39, or 40 and/or $Y^4$ can be defined according to any one or more of Embodiments 61-64 and/or $R^3$ can be defined according to Embodiment 66.
In certain of these embodiments, n is 0.
In certain of these embodiments, p is 1.
In certain of these embodiments, n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiments 6-19; or $R^1$ can be defined according to Embodiment 21 or 22;
$R^2$ is $C_{6\text{-}10}$ aryl, which is optionally substituted with from 1-4 $R^c$;
$R^3$ is —$(Y^3)_p$—$Y^4$, in which $Y^3$ can be defined according to Embodiment 38, 39, or 40 and/or $Y^4$ can be defined according to any one or more of Embodiments 42-52 and/or $R^3$ can be defined according to any one or more of Embodiments 55-56 and 58-59; and
n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiments 6-11, 13-15, and 18-19; or $R^1$ can be defined according to Embodiment 21;
$R^2$ is $C_{6\text{-}10}$ aryl, which is optionally substituted with from 1-4 $R^c$;
$R^3$ is —$(Y^3)_p$—$Y^4$, in which $Y^3$ can be defined according to Embodiment 38 or 39 and/or $Y^4$ can be defined according to any one or more of Embodiments 42-44 and 47-48 and/or $R^3$ can be defined according to Embodiment 55; and
n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiments 6-19, or $R^1$ can be defined according to Embodiment 21 or 22;
$R^2$ is $C_{6\text{-}10}$ aryl, which is optionally substituted with from 1-4 $R^c$;
$R^3$ is —$(Y^3)_p$—$Y^4$, in which $Y^3$ can be defined according to Embodiment 38, 39, or 40 and/or $Y^4$ can be defined according to any one or more of Embodiments 61-64 and/or $R^3$ can be defined according to Embodiment 66; and
n is 0, and p is 1.
In certain of these embodiments, $R^4$ is H.

In some embodiments:
$R^1$ is —$(Y^1)_n$—$Y^2$, in which $Y^2$ can be defined according to any one or more of Embodiments 6-19; or $R^1$ can be defined according to Embodiment 21 or 22;
$R^2$ is $C_{6\text{-}10}$ aryl, which is optionally substituted with from 1-4 $R^c$;
$R^3$ is —$(Y^3)_p$—$Y^4$, in which $Y^4$ can be defined according to any one or more of Embodiments 42-52 and/or $R^3$ can be defined according to Embodiment 57 or Embodiment 60; and
n is 0, and p is 0.
In certain of these embodiments, $R^4$ is H.

In some embodiments:
$R^1$ is —$(Y^1)_n$—$Y^2$, which $Y^2$ can be defined according to any one or more of Embodiments 6-11, 13-15, and 18-19; or $R^1$ can be defined according to Embodiment 21;
$R^2$ is $C_{6\text{-}10}$ aryl, which is optionally substituted with from 1-4 $R^c$;
$R^3$ is —$(Y^3)_p$—$Y^4$ in which $Y^4$ can be defined according to any one or more of Embodiments 42-44 and 47-48 and/or $R^3$ can be defined according to Embodiment 60; and
n is 0, and p is 0.
In certain of these embodiments, $R^4$ is H.

In some embodiments:
$R^1$ is —$(Y^1)_n$—$Y^2$, in which $Y^2$ can be defined according to any one or more of Embodiments 6-19; or $R^1$ can be defined according to Embodiment 21 or 22;
$R^2$ is $C_{6\text{-}10}$ aryl, which is optionally substituted with from 1-4 $R^c$;
$R^3$ is —$(Y^3)_p$—$Y^4$, in which $Y^4$ can be defined according to any one or more of Embodiments 61-64; and
n is 0, and p is 0.
In certain of these embodiments, $R^4$ is H.

In certain of the foregoing embodiments of [5], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy; and (xiv) —$C_{1-4}$ thioalkoxy. For example, each occurrence of $R^c$ is an independently selected $C_{1-4}$ alkoxy (e.g., —$OCH_3$).

In certain of the foregoing embodiments of [5], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and —$C_{1-4}$ thioalkoxy; e.g., each occurrence of $R^c$ is an independently selected $C_{1-4}$ alkoxy (e.g., —$OCH_3$). For example, $R^{2a}$ and $R^{2e}$ are each $OCH_3$.

In certain of the foregoing embodiments of [5], $R^2$ has formula (B).

Non-Limiting Combinations [6]

In some embodiments:

$R^1$ is —$Z^1$—$Z^2$—$Z^3$ (e.g., in which $Z^1$—$Z^2$—$Z^3$ can be defined according to any one or more of Embodiments 24-27, or $R^1$ can be defined according to Embodiment 28);

$R^2$ is $C_{6-10}$ aryl, which is optionally substituted with from 1-4 $R^c$; and $R^3$ is —$(Y^3)_p$—$Y^4$.

In certain of these embodiments, p is 1.
In other embodiments, p is 0.
In certain of these embodiments, $R^4$ is H.

In some embodiments:

$R^1$ is —$Z^1$—$Z^2$—$Z^3$ (e.g., in which $Z^1$—$Z^2$—$Z^3$ can be defined according to any one or more of Embodiments 24-27, or $R^1$ can be defined according to Embodiment 28);

$R^2$ is $C_{6-10}$ aryl, which is optionally substituted with from 1-4 $R^c$; and $R^3$ is —$(Y^3)_p$—$Y^4$, in which $Y^3$ can be defined according to Embodiment 38, 39, or 40 and/or $Y^4$ can be defined according to any one or more of Embodiments 42-52 and/or $R^3$ can be defined according to any one or more of Embodiments 55-60.

In certain of these embodiments, p is 1.
In other embodiments, p is 0.
In certain of these embodiments, $R^4$ is H.

In some embodiments $R^1$ is —$Z^1$—$Z^2$—$Z^3$ (e g , in which $Z^1$—$Z^2$—$Z^3$ can be defined according to any one or more of Embodiments 24-27, or $R^1$ can be defined according to Embodiment 28);

$R^2$ is $C_{6-10}$ aryl, which is optionally substituted with from 1-4 $R^c$; and $R^3$ is —$(Y^3)_p$—$Y^4$, in which $Y^3$ can be defined according to Embodiment 38 or 39 and/or $Y^4$ can be defined according to any one or more of Embodiments 42-44 and 47-48 and/or $R^3$ can be defined according to Embodiment 55 or 60.

In certain of these embodiments, p is 1.
In other embodiments, p is 0.
In certain of these embodiments, $R^4$ is H.

In some embodiments:

$R^1$ is —$Z^1$—$Z^2$—$Z^3$ (e.g., in which $Z^1$—$Z^2$—$Z^3$ can be defined according to any one or more of Embodiments 24-27, or $R^1$ can be defined according to Embodiment 28);

$R^2$ is $C_{6-10}$ aryl, which is optionally substituted with from 1-4 $R^c$; and $R^3$ is —$(Y^3)_p$—$Y^4$, in which $Y^3$ can be defined according to Embodiment 38, 39, or 40 and/or $Y^4$ can be defined according to any one or more of Embodiments 61-64 and/or $R^3$ can be defined according to Embodiment 66.

In certain of these embodiments, p is 1.
In other embodiments, p is 0.
In certain of these embodiments, $R^4$ is H.

In certain of the foregoing embodiments of [6], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy, and (xiv) —$C_{1-4}$ thioalkoxy. For example, each occurrence of $R^c$ is an independently selected $C_{1-4}$ alkoxy (e.g., —$OCH_3$).

In certain of the foregoing embodiments of [6], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$(e.g., $C_{1-4}$ alkoxy; $C_{1-4}$ haloalkoxy; and —$C_{1-4}$ thioalkoxy, e.g., each occurrence of $R^c$ is an independently selected $C_{1-4}$ alkoxy (e g , —$OCH_3$). For example, $R^{2a}$ and $R^{2e}$ are each $OCH_3$.

In certain of the foregoing embodiments of [6], $R^2$ has formula (B).

Non-Limiting Combinations [7]

In some embodiments:

$R^1$ is —$(Y^1)_n$—$Y^2$;

$R^2$ is $C_{6-10}$ aryl, which is optionally substituted with from 1-4 $R^c$; and $R^3$ is $C_{1-10}$ alkyl, optionally substituted with from 1-6 independently selected $R^a$ (e.g., $R^3$ can be defined according to any one of Embodiments 67-70).

In certain of these embodiments, n is 0.
In certain of these embodiments, $R^4$ is H.

In some embodiments:

$R^1$ is —$(Y^1)_n$—$Y^2$, in which $Y^2$ can be defined according to any one or more of Embodiments 6-19; or $R^1$ can be defined according to Embodiment 21 or 22;

$R^2$ is $C_{6-10}$ aryl, which is optionally substituted with from 1-4 $R^c$; and $R^3$ is $C_{1-10}$ alkyl, optionally substituted with from 1-6 independently selected $R^a$ (e.g., $R^3$ can be defined according to any one of Embodiments 67-70)

In certain of these embodiments, n is 0.
In certain of these embodiments, $R^4$ is H.

In some embodiments:

$R^1$ is —$(Y^1)_n$—$Y^2$, in which $Y^2$ can be defined according to any one or more of Embodiments 6-11, 13-15, and 18-19; or $R^1$ can be defined according to Embodiment 21;

$R^2$ is $C_{6-10}$ aryl, which is optionally substituted with from 1-4 $R^c$; and $R^3$ is $C_{1-10}$ alkyl, optionally substituted with from 1-6 independently selected $R^a$ (e.g., $R^3$ can be defined according to any one of Embodiments 67-70).

In certain of these embodiments, n is 0.
In certain of these embodiments, $R^4$ is H.

In certain of the foregoing embodiments of [7], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of Re independently selected from the group consisting of: (vii) $C_{1-4}$ alkoxy; (viii) $C_{1-4}$ haloalkoxy; and (xiv) —$C_{1-4}$ thioalkoxy. For example, each occurrence of $R^c$ is an independently selected $C_{1-4}$ alkoxy (e g., —$OCH_3$).

In certain of the foregoing embodiments of [7], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and —$C_{1-4}$ thioalkoxy; e.g., each occurrence of $R^c$ is an independently selected $C_{1-4}$ alkoxy (e.g., —$OCH_3$). For example, $R^{2a}$ and $R^{2e}$ are each $OCH_3$.

In certain of the foregoing embodiments of [7], $R^2$ has formula (B).

Non-Limiting Combinations [8]

In some embodiments:

$R^1$ is —$Z^1$—$Z^2$—$Z^3$ (e.g., in which $Z^1$—$Z^2$—$Z^3$ can be defined according to any one or more of Embodiments 24-27, or $R^1$ can be defined according to Embodiment 28);

$R^2$ is $C_{6-10}$ aryl, which is optionally substituted with from 1-4 $R^c$; and $R^3$ is $C_{1-10}$ alkyl, optionally substituted with from 1-6 independently selected $R^a$ (e.g., $R^3$ can be defined according to any one Embodiments 67-70).

In certain of the foregoing embodiments of [8], $R^2$ is phenyl, which is optionally substituted with from 1-4 $R^c$. For example, $R^2$ can be phenyl, which is optionally substituted with from 1-2 $R^c$. In certain of the foregoing embodiments, each occurrence of $R^c$ is independently selected from the group consisting of: (vii) $C_{1-4}$ alkoxy; (viii) $C_{1-4}$ haloalkoxy; and (xiv) —$C_{1-4}$ thioalkoxy. For example, each occurrence of $R^c$ is an independently selected $C_{1-4}$ alkoxy (e.g., —$OCH_3$).

In certain of the foregoing embodiments of [8], $R^2$ has formula (A). In certain of these embodiments, four, three, or two of $R^{2a}$, $R^{2b}$, $R^{2c}$, $R^{2d}$, and $R^{2e}$ are each an independently selected $R^c$ and the other (s) is (are) H. In certain embodiments, two of $R^{2a}$, $R^{2b}$, $R^{2c}$, $R^{2d}$, and $R^{2e}$ are each an independently selected $R^c$, and the others are H. In certain of these embodiments, $R^{2a}$ and $R^{2e}$ are each an independently selected $R^c$ (e.g., $C_{1-4}$ alkoxy; $C_{1-4}$ haloalkoxy; and —$C_{1-4}$ thioalkoxy; e.g., each occurrence of $R^c$ is an independently selected $C_{1-4}$ alkoxy (e.g., —$OCH_3$). For example, $R^{2a}$ and $R^{2e}$ are each $OCH_3$.

In certain of the foregoing embodiments of [8], $R^2$ has formula (B).

Pharmaceutical Compositions and Administration

General

In some embodiments, a chemical entity (e.g., a compound or a pharmaceutically acceptable salt and/or hydrate and/or prodrug of the compound) that modulates (e.g., agonizes) the APJ receptor is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In general, the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules, sterility is not required. The USP/NF standard is usually sufficient.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Proper dosage for a particular situation can be determined by one skilled in the medical arts. In some cases, the total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped.

In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

This disclosure features methods for treating a subject (e.g., a human) having a disease, disorder, or condition in which a decrease in APJ receptor activity (e.g., repressed or impaired APJ receptor signaling; e.g., repressed or impaired apelin-APJ receptor signaling) or downregulation of endogenous apelin contributes to the pathology and/or symptoms and/or progression of the disease, disorder, or condition. In certain embodiments, the methods described herein can include or further include treating one or more conditions associated, co-morbid or sequela with any one or more of the conditions described herein.

In some embodiments, the method further comprises identifying the subject. In some embodiments, identifying comprises determining the level of one or more of the following parameters in the subject: leukotriene B4 level, pulmonary vascular resistance, pulmonary arterial pressure, cardiac index, pulmonary capillary wedge pressure, right atrial pressure, six-minute walk distance, brain natriuretic peptide level, atrial natriuretic peptide, and diffusion of lung capacity.

In certain embodiments, the chemical entities described herein modulate (e.g., decrease) pulmonary vascular resistance, modulate (e.g., decrease) right ventricular afterload, and modulate (e.g., decrease) mean pulmonary artery pressure. In certain embodiments, the chemical entities described herein reduce the risk of right ventricular failure.

In certain embodiments, the chemical entities described herein modulate vascular tone, modulate fluid homeostasis, modulate kidney function, modulate energy metabolism, modulate inflammatory response, and modulate thrombosis.

Indications

Pulmonary Hypertension

In some embodiments, the condition, disease or disorder is pulmonary arterial hypertension (PAH). Non-limiting examples of PAH and related conditions include idiopathic PAH, heritable PAH (e.g., $BMPR^2$ mutations and other mutations), drug-induced or toxin-induced PAH, and PAH associated with conditions including but not limited to connective tissue diseases (CTD) (e.g., scleroderma, systemic lupus erythematosus, systemic sclerosis, Hashimoto's thyroiditis, Sjogren's Syndrome, and the antiphospholipid antibody syndrome), HIV infection, portal hypertension, congenital heart disease, and schistosomiasis.

In some embodiments, the PAH is idiopathic.

In other embodiments, the PAH is heritable PAH, toxin or drug-induced PAH; or a PAH associated with one or more of the following: congenital heart disease, connective tissue disorders (e.g., scleroderma, systemic lupus erythematosus, systemic sclerosis, Hashimoto's thyroiditis, Sjogren's Syndrome, and the antiphospholipid antibody syndrome), portal hypertension, BMPR$^2$ mutations, Schistosomiasis, and HIV infection.

In some embodiments, the condition, disease or disorder is pulmonary hypertension other than PAH. Examples of such conditions include, without limitation, pulmonary hypertension due to left heart disease (e.g., left ventricular systolic dysfunction, left ventricular diastolic dysfunction, valvular heart disease, and congenital/acquired left heart inflow/outflow obstruction and congenital cardiomyopathies), pulmonary hypertension due to lung disease and/or hypoxia (e.g., choronic obstructive pulmonary disease, interstitial lung disease, other pulmonary disease with mixed restrictive and obstructive pattern, sleep-disordered breathing, alveolar hypoventilation disorders, chronic exposure to high altitude, developmental lung disease), chronic thromboembolic pulmonary hypertension and other pulmonary artery obstructions (e.g., chronic thromboembolic pulmonary hypertension, other pulmonary artery obstructions), and pulmonary hypertension with unclear multifactorial mechanisms (e.g., haematologic disorders, systemic disorders, metabolic disorders, and others).

Cardiovascular Conditions, Diseases or Disorders

In some embodiments, the condition, disease or disorder is a cardiovascular condition, disease or disorder. Non-limiting examples of cardiovascular condition, disease or disorder include coronary heart disease, acute coronary syndrome, peripheral vascular disease, angina, stroke, cerebrovascular accidents, transient ischemic attacks, heart failure, cardiomyopathy, myocardial infarction, myocardial remodeling after cardiac surgery, valvular heart disease, hypertension (e.g., systemic hypertension, essential hypertension, pulmonary hypertension, portal hypertension, systolic hypertension), aortic aneurysm (e.g., abdominal aortic aneurysm), atrial fibrillation, arrhythmia, atherosclerosis, Brugada syndrome, ischemic cardiovascular diseases, peripheral arterial disease, preeclampsia, ventricular tachycardia, and cardiac fibrosis.

In some embodiments, the cardiovascular condition, disease or disorder is heart failure. Non-limiting examples of heart failure include chronic heart failure, systolic heart failure, diastolic heart failure, diabetic heart failure, congestive heart failure, heart failure with preserved ejection fraction, heart failure with reduced ejection fraction, left ventricular dysfunction (e.g., left ventricular dysfunction after myocardial infarction), right ventricular dysfunction, cardiac hypertrophy, myocardial remodeling, and acute decompensated heart failure (ADHF).

In some embodiments, the cardiovascular condition, disease or disorder is a condition, disease or disorder with vascular pathology (e.g., with increased vascular permeability and nonfunctional blood vessels). Non-limiting examples of such condition, disease or disorder include vascular hypertrophy, vascular remodeling (e.g., vascular stiffness), atherosclerosis, peripheral arterial occlusive disease (PAOD), restenosis (e.g., angioplastic restenosis), thrombosis and vascular permeability disorders, and ischemia and/or reperfusion damage (e.g., ischemia and/or reperfusion damage of the heart, kidney and retina). In some embodiments, the conditions, disease or disorder is vein related. Non-limiting examples of such condition, disease or disorder include angioma, veinous insufficiency, stasis, or thrombosis.

In some embodiments, the chemical entities described herein can improve cardiac contractility (e.g., cardiac relaxation), ventricular arterial coupling, inotropic function, or luistropic function in a subject suffering from a cardiovascular condition. In some embodiments, the chemical entities described herein can increase ejection fraction in a subject suffering from a cardiovascular condition.

Metabolic and Homeostatic Dysfunction and Related Conditions, Diseases or Disorders In some embodiments, the condition, disease or disorder is associated with metabolic dysfunction. Non-limiting examples of such condition, disease or disorder include metabolic dysfunction, obesity, diabetes (e.g., type II diabetes mellitus, gestational diabetes), complications of diabetes (e.g., metabolic syndrome, insulin resistance, organ damages of micro- or macrovascular origins such as macro- and microvaculopathies, diabetic neuropathy, diabetic retinopathy, cardiac autonomic neuropathy), kidney disease (e.g., chronic kidney disease), edema, dyslipidemia, anorexia, hyperphagia, polyphagia, hypercholesterolemia, hyperglyceridemia, hyperlipemia, growth hormone disorder (e.g., gigantism, aromegaly), galactorrhea, and cardiac wasting.

In some embodiments, the condition, disease or disorder is associated with inappropriate vasopressin secretions (SIADH). Non-limiting examples of such condition, disease or disorder include neurogenic diabetes mellitus (e.g. diabetic complications such as diabetic nephropathy, diabetic neuropathy, diabetic retinopathy, etc.), lung cancer, septic shock, and thirst troubles.

In some embodiments, the condition, disease or disorder is associated with systemic inflammation. Non-limiting examples of such condition, disease or disorder include systemic inflammatory response syndrome (SIRs), sepsis (e.g., severe sepsis), and septic shock. In some embodiments, the condition, disease or disorder is associated with sepsis (e.g., a complication, co-morbidity, or sequela of sepsis). Non-limiting examples of conditions, diseases or disorders associated with sepsis include sepsis-induced myocardial dysfunction, sepsis-related inflammatory response (e.g., systemic inflammation), sepsis-related hemodynamic alterations, hypovolemia, sepsis-related organ failures (e.g., multi-organ failure, renal failure), acute kidney injury, vasoplegia, lung injury, inappropriate vasopressin secretions, persistent hypertension related to generalized vasodilation, refractory constrictive responsiveness, huge plasma capillary leak syndrome, coagulation/fibrinolysis imbalance, and metabolic disturbance highlighted by elevated blood-stream lactates. See. e.g., Coquerel et al. Critical Care (2018) 22:10.

In some embodiments, the chemical entities described herein can regulate arginine vasopressin (AVP) or angiotensin receptor.

In some embodiments, the condition, disease or disorder is associated with disturbed body's fluid homeostasis by CNS-dependent and -independent effects. Non-limiting examples of such condition, disease or disorder include renal failure (e.g., acute and chronic renal failure), renal perfusion, renal dysfunction (e.g., polycystic kidney disease), aquaresis, and diuresis.

Dementia and Related Conditions, Diseases or Disorders

In some embodiments, the condition, disease or disorder is dementia. Non-limiting examples of such condition, disease or disorder include senile dementia, cerebrovascular dementia, dementia due to genealogical denaturation degenerative diseases (e.g. Alzheimer's disease, Parkinson's disease, Pick's disease, Huntington's disease, etc.), dementia resulting from infectious diseases (e.g. delayed virus infections such as Creutzfeldt-Jakob disease), dementia associated with endocrine diseases, metabolic diseases, or poisoning (e.g. hypothyroidism, vitamin B12 deficiency, alcoholism, poisoning caused by various drugs, metals, or organic compounds), dementia caused by tumors (e.g. brain tumor), and dementia due to traumatic diseases (e.g. chronic subdural hematoma), depression, hyperactive child syndrome (microencephalopathy), disturbance of consciousness, anxiety disorder, schizophrenia, and phobia.

Other Conditions, Diseases or Disorders

In some embodiments, the condition, disease or disorder is a liver disease. Non-limiting examples of such condition, disease or disorder include alcoholic liver disease, toxicant-induced liver disease, viral induced liver disease, and liver cirrhosis.

In some embodiments, the condition, disease or disorder is a pulmonary disease. Non-limiting examples of such condition, disease or disorder include chronic obstructive pulmonary disease (COPD), asthma, acute respiratory dystress syndrome (ARDS), and amyotrophic lateral sclerosis. In some embodiments, the condition, disease or disorder is a retinal disease (e.g., macular degeneration).

In some embodiments, the condition, disease or disorder is HIV infection, HIV neurodegeneration, neurodegenerative disease, cancer (e.g., mammary cancer, lymphocytic leukemia, bladder cancer, ovary cancer, carcinoma of prostate, etc.), asthma, burn injuries (e.g., sun burn), traumatic brain injuries, pancreatitis, Turner's syndrome, neurosis, rheumatoid arthritis, spinal cord injury, immune function, inflammation, spinocerebellar degeneration, bone fracture, wounds, atopic dermatitis, osteoporosis, asthma, epilepsy, and sterility.

Activating Stem Cells

The chemical entities described herein can also be used to activate stem cells (e.g., cardiac stem cells such as endogenous cardiac stem cells). In some embodiments, the chemical entities described herein can be used in regrowing tissue, assisting functional recovery after transplanting cells (e.g., cells with bone marrow-derived mesenchymal stem cells), increasing cardiac stem cell proliferation (e.g., in patents that have suffered a myocardial infarction), reducing infarct size, promoting cardiac repair, activating stem cells and progenitors in postmyocardial infarction subjects, or reducing reperfusion injury (e.g., during surgeries such as heart bypass surgery or heart transplant procedures).

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the compound described herein can be administered in combination with one or more of additional therapeutic agents.

Representative additional therapeutic agents include, but are not limited to, therapeutic agents for PAH, pulmonary hypertension, heart failure (e.g., ADHF, chronic heart failure), hypertension (e.g., systemic hypertension), amyotrophic lateral sclerosis, arrhythmia, asthma, atherosclerosis, atrial fibrillation, Brugada syndrome, burn injuries (e.g., sunburn), cancer, cardiac fibrosis, cardiomyopathy, cerebrovascular accidents, diabetes (e.g., gestational diabetes), septic shock, sepsis, renal failure, dyslipidemia, HIV neurodegeneration, inflammation, ischemic cardiovascular disease, liver disease, metabolic disorder, neurodegenerative disease, obesity, peripheral arterial disease, preeclampsia, restenosis, transient ischemic attacks, traumatic brain injuries, ventricular tachycardia, edema, or immune function.

In some embodiments, the one or more additional therapeutic agents include those useful, e.g., as therapeutics for PAH. Non-limiting examples include:

prostacyclin analogues (e.g., Epoprostenol, Treprostinil, Iloprost);

prostacyclin IP receptor (e.g., Selexipag);

endothelin receptor antagonists (e.g., Bosentan, Ambrisentan, Macitentan);

PDE 5 inhibitors (e.g., Sildenafil, Tadalafil);

soluble guanylate cyclase stimulator (e.g., Riociguat);

therapeutics for mitochondria dysfunction (e.g., Bardoxolone methyl);

anti-inflammation agents (e.g., Rituximab, Tocilizumab, Ubenimex); and agents that modulate oxidative stress (e.g., dimethyl fumarate, intravenous iron).

In some embodiments, the one or more additional therapeutic agents include those useful, e.g., as therapeutics for heart failure or hypertension. Non-limiting examples include:

α-blockers (e.g., doxazosin, prazosin, tamsulosin, terazosin);

β-blockers (e.g., acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol);

calcium channel blockers including but not limited to dihydropyridines (DHPs) (e.g., amlodipine, felodipine, isradipine, lacidipine, nicardipine, nifedipine, nigulpidine, nilutipine, nimodiphine, nisoldipine, nitrendipine, nivaldipine, ryosidine) and non-DHPs (e.g., anipamil, diltiazem, fendiline, flunarizine, gallpamil, mibefradil, prenylamine, tiapamil, verapamil);

diuretics (e.g., thiazide derivatives such as, but not limited to, amiloride, chlorothalidon, chlorothiazide, hydrochlorthiazide, and methylchlorothiazide)

centrally acting hypertensive agents (e.g., clonidine, guanabenz, guanfacine, methyldopa);

angiotensin converting enzyme (ACE) inhibitors (alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril) and dual ACE/NEP inhibitors (e.g., omapatrilat, fasidotril, and fasidotrilat);

angiotensin receptor blockers (ARBs) (e.g., candesartan, eprosartan, irbesartan, losartan, olmesartan, tasosartan, telmisartan, valsartan) and dual ARB/NEP inhibitors (e.g., combinations of valsartan and sacubitril);

neutral endopeptidase (NEP) inhibitor (e.g., sacubitril);

aldosterone synthase inhibitors (e.g., anastrozole, fadrozole, exemestane);

endothelin antagonists (e.g., bosentan, enrasentan, atrasentan, darusentan, macitentan, sitaxentan, tezosentan);

inhibitors of funny current (e.g., ivabradine);

myosin activators (e.g., cardiac myosin activators);

natriuretic;

saluretic;

vasodilator/vasorelaxation agents (e.g., nitrates)

mineralocorticoid receptor antagonists;

renin inhibitors;

digitalis compounds;

inotropic agents and β-receptor agonists;

anti-hyperlipidemic agents;

plasma HDL-raising agents;

anti-hypercholesterolemic agents;

cholesterol biosynthesis inhibitors (e.g., HMG CoA reductase inhibitors)
LXR agonist;
probucol;
raloxifene;
nicotinic acid;
niacinamide;
cholesterol absorption inhibitors;
bile acid sequestrants (e.g., anion exchange resins, or quaternary amines such as cholestyramine or colestipol);
low density lipoprotein receptor inducers;
clofibrate;
fenofibrate;
bezafibrate;
ciprofibrate;
gemfibrizol;
vitamins (e.g., vitamin $B_6$, vitamin $B_{12}$, anti-oxidant vitamins);
platelet aggregation inhibitors;
fibrinogen receptor antagonists;
aspirin; and
fibric acid derivatives.

In some embodiments, the one or more additional therapeutic agents include those useful, e.g., for treating diabetes. Non-limiting examples include:
  sulfonylureas (e.g., chlorpropamide, tolbutamide, acetohexamide, tolazamide, glyburide, gliclazide, glynase, glimepiride, glipizide);
  biguanides (e.g., metformin);
  thiazolidinediones (e.g., ciglitazone, pioglitazone, troglitazone, rosiglitazone)
  insulin sensitizers related to the above (e.g., selective and non-selective activators of PPAR-alpha, PPAR-beta and PPAR-gamma);
  dehydroepiandrosterone (also referred to as DHEA or its conjugated sulfate ester, DHEA-$SO_4$);
  anti-glucocorticoids;
  TNF-alpha inhibitors;
  dipeptidyl peptidase IV (DPP4) inhibitors (e.g.; sitagliptin, saxagliptin);
  GLP-1 agonists or analogs (such as exenatide);
  alpha-glucosidase inhibitors (such as acarbose, miglitol, and voglibose);
  pramlintide (a synthetic analog of the human hormone amylin);
  other insulin secretagogues (such as repaglinide, gliquidone, and nateglinide); and
  insulin.

In some embodiments, the one or more additional therapeutic agents include those useful, e.g., for treating obesity. Non-limiting examples include phenylpropanolamine, phentermine, diethylpropion, mazindol, fenfluramine, dexfenfluramine, phentiramine, beta3-adrenergic receptor agonist agents, sibutramine, gastrointestinal lipase inhibitors (e.g., orlistat), leptins, neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin, and gamma amino butyric acid (GABA).

Other additional therapeutic agents include:
  anti-atherosclerotic agents;
  anti-dyslipidemic agents;
  antihyperinsulinemic agents;
  anti-thrombotic agents;
  anti-retinopathic agents;
  anti-neuropathic agents;
  anti-nephropathic agents;
  anti-ischemic agents;
  anti-hyperlipidemic agents;
  anti-hypertriglyceridemic agents;
  anti-hypercholesterolemic agents;
  anti-restenotic-agents;
  anti-pancreatic agents;
  anorectic agents;
  memory enhancing agents;
  antidementia agents;
  cognition promoting agents;
  appetite suppressants;
  agents for treating peripheral arterial disease;
  agents for treating malignant tumors;
  anti-inflammatory agents;
  aquaretics;
  digoxin;
  nitric oxide donors;
  hydralazines;
  ionotropes;
  vasopressin receptor antagonists;
  statins;
  anti-arrhythmics;
  phosphodiesterase inhibitors (e.g., PDE5 inhibitors); and
  nephro-protectives.

Non-limiting examples of additional therapeutic agents can also include those described in U.S. Pat. No. 9,156,796B2, which is incorporated herein by reference.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In some embodiments, intermediates useful for preparing the compounds described herein can be prepared using the chemistries delineated in any one or more of the following schemes and non-limiting examples.

Compound Preparation

For illustrative purposes, Schemes 1-3 show general methods for preparing the compounds provided herein as well as intermediates. For a more detailed description of the individual reaction steps, see the Synthetic Examples section below. Those skilled in the art will appreciate that other synthetic routes may be used to synthesize the inventive compounds. Although specific starting materials and reagents are depicted in the Scheme and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

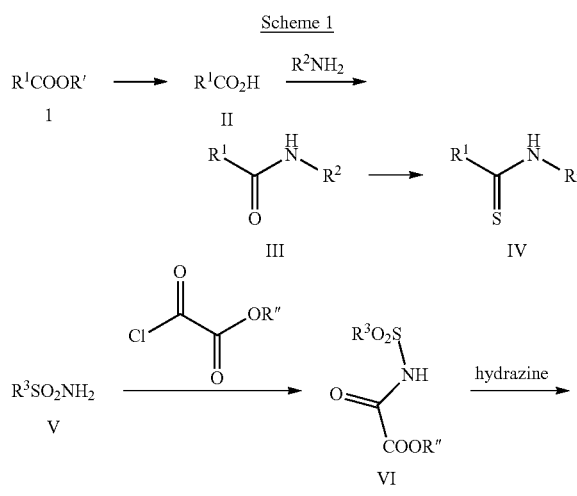

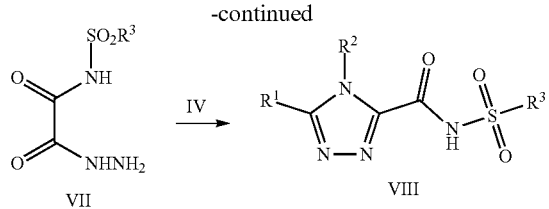

Referring to Scheme 1, a compound of Formula I (shown as VIII in Scheme 1) may be prepared from compound I and V wherein $R^1$, $R^2$, and $R^3$ are as defined herein. Ester I (e.g., ethyl ester wherein R' is ethyl), can be hydrolyzed to afford the corresponding carboxylic acid II under basic (e.g., with LiOH) or acidic conditions. Coupling between II and $R^2NH_2$ can afford amide III. The coupling reaction can be carried out in the presence of a carboxylic acid activating agent (e.g., HATU or EDCI). III can be treated with a thiation agent (e.g., the Lawesson's reagent) to provide IV.

Sulfonamide V can be coupled with an oxaloacetate electrophile (e.g., a 2-chloro-2-oxoacetate ester, such as ethyl ester wherein R" is ethyl) to provide compound VI. Reaction between VI and hydrazine or equivalent thereof (e.g., hydrazine hydrate) can provide compound VII.

Compound VIII can be obtained through the reaction between IV and VII (e.g., in the presence of silver (I) nitrate).

Scheme 2

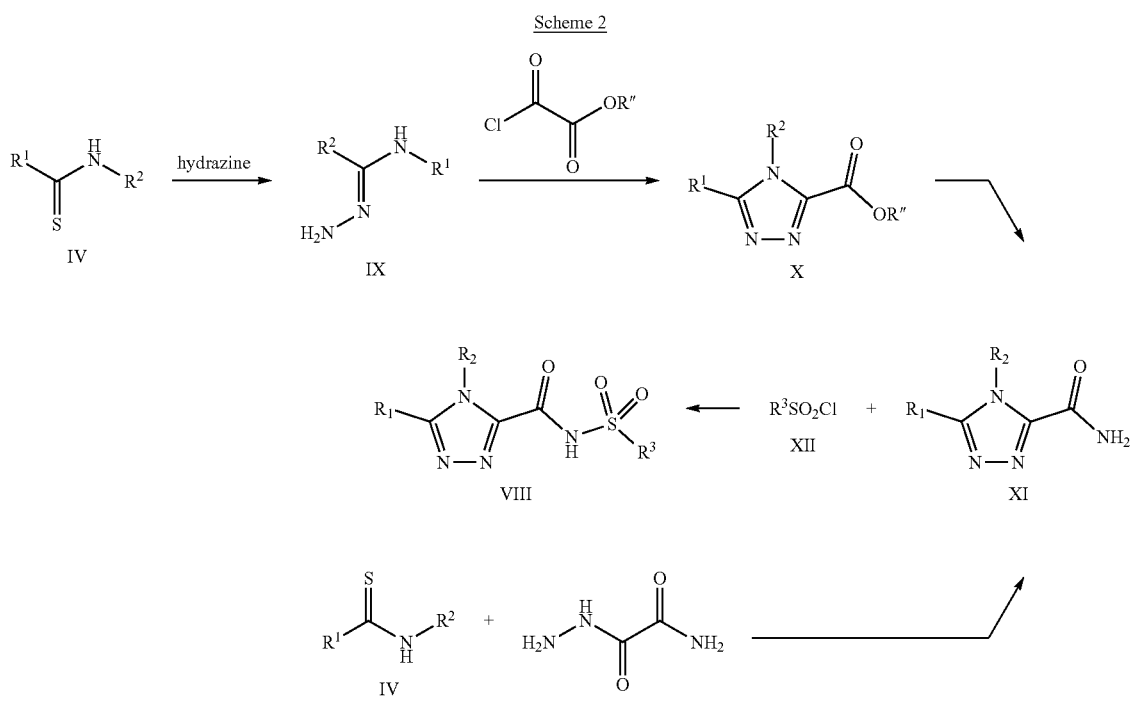

Scheme 2 depicts alternative approaches to prepare a compound of Formula I (shown as compound VIII in Scheme 2). Compound IV can be treated with hydrazine or equivalents thereof (e.g., hydrazine hydrate) to afford hydrazone IX (one approach to prepare compound IV is shown in Scheme 1). Reaction between X and an oxaloacetate electrophile (e.g., a 2-chloro-2-oxoacetate ester such as ethyl ester wherein R" is ethyl) can provide triazole X which can then be converted into carboxamide XI. Reaction between XI and an electrophilic sulfonyl source (e.g., a sulfonyl chloride such as compound XII) can afford VIII (a compound of Formula I). The sulfonylation of XI may be carried out in the presence of a base (e.g., sodium hydride).

Alternatively, as shown in Scheme 2, compound XI can be prepared from the reaction between IV and oxamic hydrazide (e.g., in the presence of a silver salt such as silver benzoate).

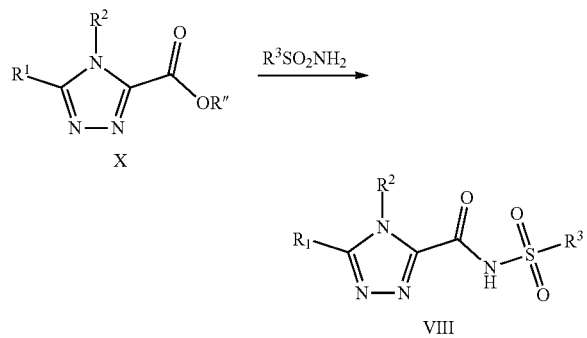

Scheme 3

Scheme 3 depicts alternative approaches to prepare a compound of Formula I (shown as compound VIII in Scheme 3). Compound X, wherein $R^1$ and $R^2$ can be as defined for Formula I anywhere herein; and R" is a $C_{1-6}$ alkyl (e.g., methyl or ethyl) can be subjected to reaction with a compound of formula $R^3SO_2NH_2$ wherein $R^3$ is as defined for Formula I anywhere herein (e.g., in the presence of $AlMe_3$ in a solvent such as toluene under heating (e.g., 60° C.)).

General Procedures

Reactions sensitive to moisture or air were performed under nitrogen or argon using anhydrous solvents and reagents. The progress of reactions was determined by either analytical thin layer chromatography (TLC) usually performed with Sanpont precoated TLC plates, silica gel GF-254, layer thickness 0.25 mm or liquid chromatography-mass spectrometry (LC-MS).

Typically, the analytical LC-MS system used consisted of an Agilent 6120 platform with electrospray ionization in positive ion detection mode with an Agilent 1260 series HPLC with autosampler. The column was usually an Agilent poroshell C18, 3.0×50 mm, 2.7 μm. The flow rate was 0.6 mL/min, and the injection volume was 5 μL. UV detection was in the range 190-400 nm. The mobile phase consisted of solvent A (water plus 0.1% TFA) and solvent B (acetonitrile plus 0.05% TFA) with a gradient of 90% solvent A changing to 95% solvent B over 1.7 min, maintained for 1.8 min, then reverting to 90% solvent A over 0.1 min and maintained for 1.4 mins.

Preparative HPLC purifications were usually performed Waters 2555-2767 system with a 2489 UV detector. The column was Welch C-18, 21.2×150 mm, 5 μm. The mobile phases consisted of mixtures of acetonitrile (5-95%) in water containing 0.05% TFA. Flow rates were maintained at 20 mL/min, the injection volume was 1800 μL, and the UV detector used two channels 254 nm and 280 nm. Mobile phase gradients were optimized for the individual compounds.

Reactions performed using microwave irradiation were normally carried out using an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (40-63 mM, 60 Å pore size) in pre-packed cartridges of the size noted. $^1H$ NMR spectra were acquired at 400 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions.

Abbreviations

Abbreviations used herein include: —C(O)CH$_3$ (Ac); acetic acid (AcOH); —OC(O)CH$_3$ (OAc); aqueous (aq); Cbz (benzyloxycarbonyl); N,N-diisopropylethylamine (DIEA); N;N-dimethylformamide (DMF); 1-ethyl-3-(3-dimethylaminopropyl)carbodiimide (EDCI); ethyl acetate (EtOAc); diethyl ether (ether or Et$_2$O); petroleum ether (PE); gram(s) (g); hour(s) (h or hr); 2-propanol (IPA); mass spectrum (ms or MS); microliter(s) (μL); milligram(s) (mg); milliliter(s) (mL); millimole (mmol); minute(s) (min); methyl t-butylether (MTBE); (benzotriazol-1-yloxy)tripyrrolidino-phosphonium hexafluorophosphate (PyBOP); retention time (R$_t$); room temperature (rt or RT); saturated aq sodium chloride solution (brine); trifluoroacetic acid (TFA); tetrahydrofuran (THF); flash chromatography (FC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); dichloromethane (DCM); dimethylacetamide (DMA or DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC); and petroleum ether (PE).

SYNTHETIC EXAMPLES

Example 1: 4-(2,6-dimethoxyphenyl)-5-(6-ethoxypyridin-2-yl)-N-(phenylsulfonyl)-4H-1,2,4-triazole-3-carboxamide

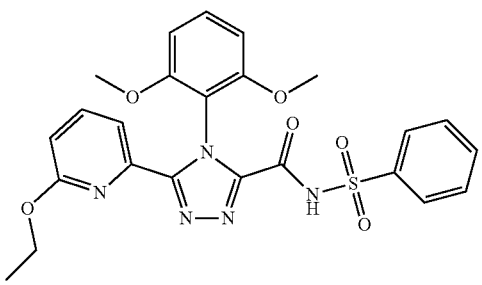 [SMILES: CCOc1cccc(-c2nnc(C(=O)NS(=O)(=O)c3ccccc3)n2-c2c(OC)cccc2OC)n1]

Step A: 6-ethoxypicolinic Acid

To a solution of ethyl 6-ethoxypicolinate (11 g) in THF (150 ml) was added a solution of LiOH hydrate (10 g, 238 mmol) in H$_2$O (50 ml) and the reaction mixture was stirred at 25° C. for 4 hr. Then pH value of the reaction was adjusted to 5.0 with 2 M HCl (aq.), and the mixture was filtered. The solid was dried in vacuo to give 6-ethoxypicolinic acid as a white solid. LCMS: m/z [M+H]$^+$ 168.4.

Step B: N-(2,6-dimethoxyphenyl)-6-ethoxypicolinamide

To a solution of 6-ethoxypicolinic acid (4.5 g, 26.95 mmol), 2,6-dimethoxyaniline (4.2 g, 27.45 mmol), HATU (12.6 g, 33.14 mmol) in THE (100 ml) was added DIPEA (7 g, 54.16 mmol), and the reaction mixture was stirred at 25° C. for 2 hr. Then the solvent was removed under reduced pressure, and the residue was dissolved in water (200 mL). The mixture was extracted with DCM (200 mL*3), and the collected organic layers were dried over Na$_2$SO$_4$, filtered, and concentrated in vacuo. The residue was purified by silica gel chromatography to give N-(2,6-dimethoxyphenyl)-6-ethoxypicolinamide as a white solid. LCMS: m/z [M+H]$^+$ 303.3.

Step C: N-(2,6-dimethoxyphenyl)-6-ethoxypyridine-2-carbothioamide

A mixture of N-(2,6-dimethoxyphenyl)-6-ethoxypicolinam (6.0 g, 19.87 mmol) and Lawesson's Reagent (8.4 g, 19.09 mmol) in toluene (100 ml) was stirred at 120° C. for 3 hr. The solvent was then removed under reduced pressure, and the residue was dissolved in water (200 mL). The mixture was extracted with EtOAc (200 mL*3), and the collected organic layers were dried over Na$_2$SO$_4$, filtered and concentrated in vacuo. The residue was purified by silica gel chromatography to give N-(2,6-dimethoxyphenyl)-6-ethoxypyridine-2-carbothioamide (1-4) as a yellow solid. LCMS: m/z [M+H]$^+$ 319.3.

Step D: Ethyl 2-oxo-2-(phenylsulfonamido)acetate

To a solution of phenyl sulfonamide (500 mg, 3.18 mmol) and TEA (643 mg, 6.37 mmol) in THE (6 ml) was added ethyl 2-chloro-2-oxoacetate (434 mg, 3.18 mmol), and the reaction mixture was stirred at 25° C. for 0.5 hr. The solvent was removed under reduced pressure to give ethyl 2-oxo-2-(phenylsulfonamido)acetate, which was used in the next step without further purification.

Step E: 2-hydrazineyl-2-oxo-N-(phenylsulfonyl)acetamide

To a solution of ethyl 2-oxo-2-(phenylsulfonamido)acetate (800 mg, crude) in EtOH (10 ml) was added hydrazine hydrate (3 ml) and the reaction mixture was stirred at 25° C. for 10 min. Then the solvent was removed in vacuo and the solid was used in the next step without further purification.

Step F: 4-(2,6-dimethoxyphenyl)-5-(6-ethoxypyridin-2-yl)-N-(phenylsulfonyl)-4H-1,2,4-triazole-3-carboxamide To a solution of 2-hydrazineyl-2-oxo-N-(phenylsulfonyl) acetamide (100 mg, crude) and N-(2,6-dimethoxyphenyl)-6-ethoxypyridine-2-carbothioamide (100 mg, 0.31 mmol) in CH$_3$CN (2 ml) was added AgNO$_3$ (160 mg, 0.94 mmol), and the reaction mixture was stirred at 25° C. for 13 hr. The mixture was filtered and the filtrate was concentrated in vacuo to give the residue, which was purified by prep-HPLC to give 4-(2,6-dimethoxyphenyl)-5-(6-ethoxypyridin-2-yl)-N-(phenylsulfonyl)-4H-1,2,4-triazole-3-carboxamide. LCMS: m/z [M+H]$^+$ 510.1.

Example 2: N-(benzylsulfonyl)-4-(2,6-dimethoxyphenyl)-5-(6-ethoxypyridin-2-yl)-4H-1,2,4-triazole-3-carboxamide

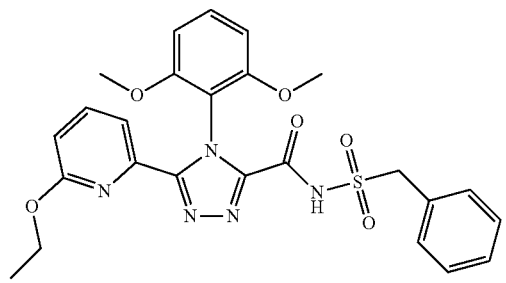 [SMILES: CCOc1cccc(-c2nnc(C(=O)NS(=O)(=O)Cc3ccccc3)n2-c2c(OC)cccc2OC)n1]

Step A: ethyl 2-oxo-2-((phenylmethyl)sulfonamido)acetate

To a solution of benzyl sulfonamide (300 mg, 1.75 mmol) and TEA (354 mg, 3.51 mmol) in THE (5 ml) was added ethyl 2-chloro-2-oxoacetate (273 mg, 1.75 mmol) dropwise, and the reaction mixture was stirred at 25° C. for 0.5 hr. The solvent was removed under reduced pressure to give ethyl 2-oxo-2-((phenylmethyl)sulfonamido)acetate, which was used in the next step without further purification.

Step B: N-(benzylsulfonyl)-2-hydrazineyl-2-oxoacetamide

To a solution of 2-oxo-2-((phenylmethyl)sulfonamido) acetate (300 mg, crude) in EtOH (5 ml) was added hydrazine hydrate (1 ml) and the reaction was stirred at 25° C. for 10 min. Then the solvent was removed in vacuum and the solid was used in the next step without further purification.

Step C: N-(benzylsulfonyl)-4-(2,6-dimethoxyphenyl)-5-(6-ethoxypyridin-2-yl)-4H-1,2,4-triazole-3-carboxamide To a solution of N-(benzylsulfonyl)-2-hydrazineyl-2-oxoacetamide (100 mg, crude) and N-(2,6-dimethoxyphenyl)-6-ethoxypyridine-2-carbothioamide (1-4) (100 mg, 0.31 mmol) in CH$_3$CN (2 ml) was added AgNO$_3$ (160 mg, 0.94 mmol). The mixture was filtered, and the filtrate was concentrated in vacuo to give a residue, which was purified by prep-HPLC to give N-(benzylsulfonyl)-4-(2,6-dimethoxyphenyl)-5-(6-ethoxypyridin-2-yl)-4H-1,2,4-triazole-3-carboxamide. LCMS: m/z [M+H]$^+$ 524.2.

Example 3: 4-(2,6-dimethoxyphenyl)-5-(6-ethoxy-pyridin-2-yl)-N-(phenethylsulfonyl)-4H-1,2,4-triazole-3-carboxamide

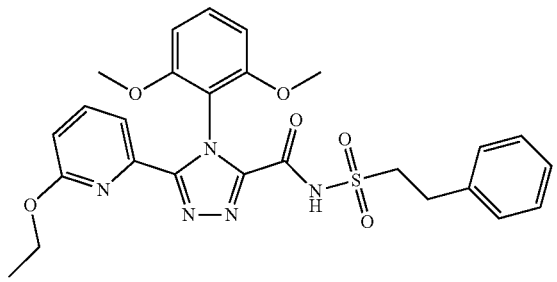 [SMILES: CCOc1cccc(-c2nnc(C(=O)NS(=O)(=O)CCc3ccccc3)n2-c2c(OC)cccc2OC)n1]

Example 4: N-(benzylsulfonyl)-4-(2,6-dimethoxyphenyl)-5-(1-methyl-1H-pyrazol-3-yl)-4H-1,2,4-triazole-3-carboxamide

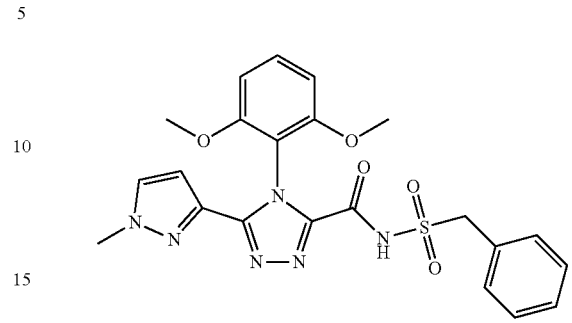

Step A: 2-phenylethane-1-sulfonamide

A solution of 2-phenylethane-1-sulfonyl chloride (200 mg, 0.98 mmol) in $NH_3 \cdot H_2O$ (4 ml) was stirred at 25° C. for 2 hr. The mixture was filtered and the solid was dried in vacuo to give crude 2-phenylethane-1-sulfonamide (240 mg, >100%), which was used for the next step directly.

Step B: Ethyl 2-oxo-2-((2-phenylethyl)sulfonamido)acetate

To a solution of 2-phenylethane-1-sulfonamide (240 mg, crude) and TEA (262 mg, 2.59 mmol) in THF (4 ml) was added ethyl 2-chloro-2-oxoacetate (177 mg, 1.30 mmol) dropwise, and the reaction mixture was stirred at 25° C. for 0.5 hr. The solvent was removed under reduced pressure to give ethyl 2-oxo-2-((2-phenylethyl)sulfonamido)acetate, which was used in the next step without further purification. LCMS: m/z [M+H]$^+$ 286.1.

Step C: 2-hydrazineyl-2-oxo-N-(phenethylsulfonyl)acetamide

To a solution of ethyl 2-oxo-2-((2-phenylethyl)sulfonamido)acetate (250 mg, crude) in EtOH (3 ml) was added hydrazine hydrate (1 ml) and the reaction was stirred at 25° C. for 10 min. Then the solvent was removed in vacuo, and the solid was used in the next step without further purification. LCMS: m/z [M+H]$^+$ 272.3.

Step D: 4-(2,6-dimethoxyphenyl)-5-(6-ethoxypyridin-2-yl)-N-(phenethylsulfonyl)-4H-1,2,4-triazole-3-carboxamide To a solution of 2-hydrazineyl-2-oxo-N-(phenethylsulfonyl)acetamide (100 mg, crude) and N-(2,6-dimethoxyphenyl)-6-ethoxypyridine-2-carbothioamide (1-4) (100 mg, 0.31 mmol) in $CH_3CN$ (2 ml) was added $AgNO_3$ (160 mg, 0.94 mmol). The mixture was filtered and the filtrate was concentrated in vacuo to give the residue, which was purified by prep-HPLC to give 4-(2,6-dimethoxyphenyl)-5-(6-ethoxypyridin-2-yl)-N-(phenethylsulfonyl)-4H-1,2,4-triazole-3-carboxamide as a white solid. LCMS: m/z [M+H]$^+$ 538.1.

Step A: N-(2,6-dimethoxyphenyl)-1-methyl-1H-pyrazole-3-carboxamide

To a solution of 1-methyl-1H-pyrazole-3-carboxylic acid (1.0 g, 7.93 mmol), 2,6-dimethoxyaniline (1.34 g, 8.72 mmol) and DMAP (48.4 mg, 0.40 mmol, 0.05 equiv) in DCM/DMF (20 mL/4 mL) was added EDCI (1.82 g, 9.52 mmol). The mixture was stirred at room temperature overnight. The mixture was then diluted with DCM (40 mL) and washed with $H_2O$ (20 mL). The water phase was extracted with DCM (2*40 mL). The combined organic phase was washed with HCl (1 mol/L, 20 mL) and brine, dried over anhydrous $Na_2SO_4$ and filtered through silica gel. The filtrate was concentrated in vacuo to afford the title compound as a brown solid.

$^1$H NMR (DMSO-d$_6$) δ: 8.68 (s, 1H), 7.80 (d, J=2.4 Hz, 1H), 7.22 (t, J=8.4 Hz, 1H), 6.69 (d, J=8.4 Hz, 2H), 6.67 (d, J=2.4 Hz, 1H), 3.93 (s, 3H), 3.72 (s, 6H).

LC-MS: m/z 262.1 (M+H)$^+$

Step B: N-(2,6-dimethoxyphenyl)-1-methyl-1H-pyrazole-3-carbothioamide

To a solution of N-(2,6-dimethoxyphenyl)-1-methyl-1H-pyrazole-3-carboxamide (800 mg, 3.07 mmol) in toluene (20 mL) was added Lawesson's reagent (869 mg, 2.15 mmol). The mixture was refluxed for 2 h under $N_2$ and cooled to room temperature. The precipitate was filtered off and rinsed by EtOAc (2*1 mL) to afford the title compound as a yellow solid.

$^1$H NMR (DMSO-d$_6$) δ: 10.48 (s, 1H), 7.75 (d, J=2.4 Hz, 1H), 7.27 (t, J=8.4 Hz, 1H), 6.81 (d, J=2.4 Hz, 1H), 6.71 (d, J=8.4 Hz, 2H), 3.93 (s, 3H), 3.71 (s, 6H).

LC-MS: m/z 278.1 (M+H)$^+$

Step C: N-(2,6-dimethoxyphenyl)-1-methyl-1-1H-pyrazole-3-carbohydrazonamide

To a suspension of N-(2,6-dimethoxyphenyl)-1-methyl-1H-pyrazole-3-carbothioamide (400 mg, 1.44 mmol) in 1,4-dioxane (15 mL) was added hydrazine hydrate (722 mg, 14.4 mmol). The mixture was stirred at 30° C. overnight under $N_2$. The mixture was lyophilized to afford the crude title compound as a yellow solid.

LC-MS: m/z 276.2 (M+H)$^+$

Step D: Ethyl 4-(2,6-dimethoxyphenyl)-5-(1-methyl-1H-pyrazol-3-yl)-4H-1,2,4-triazole-3-carboxylate To a solution of N-(2,6-dimethoxyphenyl)-1-methyl-1H-pyrazole-3-carbohydrazonamide (400 mg, 1.44 mmol) in THF (20 mL) was added a solution of ethyl 2-chloro-2-oxoacetate (177 mg, 1.30 mmol) in THF (1 mL) dropwise at −78° C. After the dropwise addition, diisopropylethylamine (DIPEA) (372 mg, 2.88 mmol) was added dropwise. The mixture was warmed to room temperature gradually and stirred at 50° C. overnight. The mixture was diluted with EtOAc and then washed successively with saturated NaHCO$_3$ (aq.) and brine. The organic phase was dried over anhydrous Na$_2$SO$_4$ and concentrated in vacuo. The resulting residue was purified by flash chromatography (MeOH/DCM, 0~1/20) to afford the title compound as a light yellow solid.

$^1$H NMR (DMSO-d$_6$) δ: 7.69 (d, J=2.4 Hz, 1H), 7.47 (t, J=8.4 Hz, 1H), 6.81 (d, J=8.4 Hz, 2H), 6.14 (d, J=2.4 Hz, 1H), 4.18 (d, J=7.2 Hz, 2H), 3.76 (s, 3H), 3.64 (s, 6H), 1.11 (t, J=7.2 Hz, 3H).
LC-MS: m/z 358.2 (M+H)$^+$

Step E: 4-(2,6-dimethoxyphenyl)-5-(1-methyl-1H-pyrazol-3-yl)-4H-1,2,4-triazole-3-carboxamide A solution of ethyl 4-(2,6-dimethoxyphenyl)-5-(1-methyl-1H-pyrazol-3-yl)-4H-1,2,4-triazole-3-carboxylate (190 mg, 0.53 mmol) in NH$_3$-MeOH (7 mol/L in MeOH, 4 mL, 28.0 mmol), was stirred at 60° C. in sealed tube overnight. The mixture was concentrated in vacuo to afford the title compound as a pale yellow solid.

$^1$H NMR (DMSO-d$_6$) δ: 8.14 (s, 1H), 7.65 (d, J=2.4 Hz, 1H), 7.57 (s, 1H), 7.40 (t, J=8.4 Hz, 1H), 6.76 (d, J=8.4 Hz, 2H), 6.00 (d, J=2.4 Hz, 1H), 3.76 (s, 3H), 3.62 (s, 6H).
LC-MS: m/z 329.2 (M+H)$^+$

Step F: N-(benzylsulfonyl)-4-(2,6-dimethoxyphenyl)-5-(1-methyl-1H-pyrazol-3-yl)-4H-1,2,4-triazole-3-carboxamide To a solution of 4-(2,6-dimethoxyphenyl)-5-(1-methyl-1H-pyrazol-3-yl)-4H-1,2,4-triazole-3-carboxamide (100 mg, 0.30 mmol) in DMF (5 mL) was added sodium hydride (60% in mineral oil, 24.4 mg, 0.61 mmol) at 0° C. After the mixture was stirred at 0° C. for 0.5 h, phenylmethanesulfonyl chloride (87 mg, 0.46 mmol) was added. The mixture was stirred at room temperature overnight. Another portion of sodium hydride (60% in mineral oil, 24.4 mg, 0.61 mmol) was added at 0° C. After the mixture was stirred at 0° C. for 0.5 h, phenylmethanesulfonyl chloride (87 mg, 0.46 mmol) was added. The mixture was stirred at room temperature for 5 h. The mixture was quenched with H$_2$O, diluted with EtOAc (30 mL) and was treated with HCl (1 mol/L) to adjust pH=5. The separated water phase was extracted with EtOAc (3*20 mL). The combined organic phase was washed with brine, dried over anhydrous Na$_2$SO$_4$ and concentrated in vacuo. Residue was purified by prep-TLC (MeOH/DCM, 1/10) to afford the title compound as a light yellow solid.

$^1$H NMR (DMSO-d$_6$) δ: 7.71 (d, J=2.4 Hz, 1H), 7.49 (t, J=8.4 Hz, 1H), 7.35-7.41 (m, 3H), 7.23-7.30 (m, 2H), 6.85 (d, J=8.4 Hz, 2H), 6.13 (d, J=2.4 Hz, 1H), 4.70 (s, 2H), 3.77 (s, 3H), 3.69 (s, 6H).
LC-MS: m/z 483.2 (M+H)$^+$

Example 5: N-(benzylsulfonyl)-4-(2,6-dimethoxyphenyl)-5-(1-ethyl-1H-pyrazol-3-yl)-4H-1,2,4-triazole-3-carboxamide

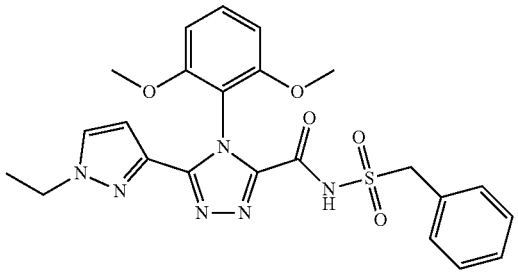 [SMILES: CCn1ccc(-c2nnc(C(=O)NS(=O)(=O)Cc3ccccc3)n2-c2c(OC)cccc2OC)n1]

Step A: N-(2,6-dimethoxyphenyl)-1-ethyl-1H-pyrazole-3-carboxamide

To a solution of 1-ethyl-1H-pyrazole-3-carboxylic acid (900 mg, 6.42 mmol), 2,6-dimethoxyaniline (1.08 g, 7.06 mmol) and DMAP (48.4 mg, 0.40 mmol) in DCM/DMF (20 mL/4 mL) was added EDCI (1.47 g, 7.68 mmol). The mixture was stirred at room temperature overnight. The mixture was then diluted with DCM (40 mL) and washed with H$_2$O (20 mL). The water phase was extracted with DCM (2*40 mL). The combined organic phase was washed with HCl (1 mol/L, 20 mL) and brine, dried over anhydrous Na$_2$SO$_4$ and filtered through silica gel. The filtrate was concentrated in vacuo to afford the title compound as a brown solid.

$^1$H NMR (DMSO-d$_6$) δ: 8.68 (s, 1H), 7.85 (d, J=2.4 Hz, 1H), 7.23 (t, J=8.4 Hz, 1H), 6.70 (d, J=8.4 Hz, 2H), 6.68 (d, J=2.4 Hz, 1H), 4.22 (q, J=7.2 Hz, 2H), 3.32 (s, 6H), 1.43 (t, J=7.2 Hz, 3H).
LC-MS: m/z 276.2 (M+H)$^+$

Step B: N-(2,6-dimethoxyphenyl)-1-ethyl-1H-pyrazole-3-carbothioamide

To a solution of N-(2,6-dimethoxyphenyl)-1-ethyl-1H-pyrazole-3-carboxamide (1.09 g, 3.96 mmol) in toluene (20 mL) was added Lawesson's reagent (1.12 g, 2.77 mmol). The mixture was refluxed for 2 h under N$_2$ and cooled to room temperature. The mixture was concentrated in vacuo and residue was purified by flash chromatography (MeOH/DCM, 0~1/20) to afford the title compound as a yellow solid.

$^1$H NMR (DMSO-d$_6$) δ: 10.47 (s, 1H), 7.80 (d, J=2.4 Hz, 1H), 7.27 (t, J=8.4 Hz, 1H), 6.81 (d, J=2.4 Hz, 1H), 6.71 (d, J=8.4 Hz, 2H), 4.22 (q, J=7.2 Hz, 2H), 3.72 (s, 6H), 1.44 (t, J=7.2 Hz, 3H).
LC-MS: m/z 292.1 (M+H)$^+$

Step C: N-(2,6-dimethoxyphenyl)-1-ethyl-1H-pyrazole-3-carbohydrazonamide

To a suspension of N-(2,6-dimethoxyphenyl)-1-ethyl-1H-pyrazole-3-carbothioamide (400 mg, 1.37 mmol) in 1,4-dioxane (15 mL) was added hydrazine hydrate (688 mg, 13.8 mmol). The mixture was stirred at 30° C. overnight under N$_2$. The mixture was lyophilized to afford the crude title compound as a yellow solid.
LC-MS: m/z 290.2 (M+H)$^+$

Step D: ethyl 4-(2,6-dimethoxyphenyl)-5-(1-ethyl-1H-pyrazol-3-yl)-4H-1,2,4-triazole-3-carboxylate To a solution of N-(2,6-dimethoxyphenyl)-1-ethyl-1H-pyrazole-3-carbohydrazonamide (400 mg, 1.37 mmol) in THF (20 mL) was added a solution of ethyl 2-chloro-2-oxoacetate (187 mg, 1.37 mmol) in THF (1 mL) dropwise at −78° C. After the dropwise addition, diisopropylethylamine (353 mg, 2.74 mmol) was added dropwise. The mixture was warmed to room temperature gradually and stirred at 50° C. overnight. The mixture was diluted with EtOAc and then washed successively with saturated NaHCO$_3$ (aq.) and brine. The organic phase was dried over anhydrous Na$_2$SO$_4$ and concentrated in vacuo. Residue was purified by flash chromatography (MeOH/DCM, 0~1/20) to afford the title compound as a light yellow solid.

$^1$H NMR (DMSO-d$_6$) δ: 7.74 (d, J=2.4 Hz, 1H), 7.45 (t, J=8.4 Hz, 1H), 6.80 (d, J=8.4 Hz, 2H), 6.26 (d, J=2.4 Hz, 1H), 4.19 (q, J=7.2 Hz, 2H), 4.02 (q, J=7.2 Hz, 2H), 3.62 (s, 6H), 1.21 (t, J=7.2 Hz, 4H), 1.11 (t, J=7.2 Hz, 3H).

LC-MS: m/z 372.2 (M+H)$^+$

Step E: 4-(2,6-dimethoxyphenyl)-5-(1-ethyl-1H-pyrazol-3-yl)-4H-1,2,4-triazole-3-carboxamide A solution of ethyl 4-(2,6-dimethoxyphenyl)-5-(1-ethyl-1H-pyrazol-3-yl)-4H-1,2,4-triazole-3-carboxylate (90 mg, 0.53 mmol) in NH$_3$-MeOH (7 mol/L in MeOH, 4 mL, 28.0 mmol), was stirred at 60° C. in sealed tube overnight. The mixture was concentrated in vacuo to afford the title compound as a pale yellow solid.

LC-MS: m/z 343.2 (M+H)$^+$

Step F: N-(benzylsulfonyl)-4-(2,6-dimethoxyphenyl)-5-(1-ethyl-1H-pyrazol-3-yl)-4H-1,2,4-triazole-3-carboxamide To a solution of 4-(2,6-dimethoxyphenyl)-5-(1-ethyl-1H-pyrazol-3-yl)-4H-1,2,4-triazole-3-carboxamide (83 mg, 0.24 mmol) in DMF (5 mL) was added sodium hydride (60% in mineral oil, 19.4 mg, 0.48 mmol) at 0° C. After the mixture was stirred at 0° C. for 0.5 h, phenylmethanesulfonyl chloride (69 mg, 0.36 mmol, 1.5 equiv) was added. The mixture was stirred at room temperature overnight. Another portion of sodium hydride (60% in mineral oil, 19.4 mg, 0.48 mmol) at 0° C. After the mixture was stirred at 0° C. for 0.5 h, phenylmethanesulfonyl chloride (69 mg, 0.36 mmol) was added. The mixture was stirred at room temperature for 5 h. The mixture was quenched with H$_2$O, diluted with EtOAc (30 mL) and was treated with HCl (1 mol/L) to adjust pH=5. The separated water phase was extracted with EtOAc (3*20 mL). The combined organic phase was washed brine, dried over anhydrous Na$_2$SO$_4$ and concentrated in vacuo. Residue was purified by prep-TLC (MeOH/DCM, 1/10) to afford the title compound as a light yellow solid.

$^1$H NMR (DMSO-d$_6$) δ: 7.66 (s, 1H), 7.37 (t, J=8.4 Hz, 1H), 7.17-7.28 (m, 5H), 6.75 (d, J=8.4 Hz, 2H), 6.06 (s, 1H), 4.21 (br. s., 2H), 4.01 (q, J=7.2 Hz, 2H), 3.62 (s, 6H), 1.22 (t, J=7.2 Hz, 3H).

LC-MS: m/z 497.2 (M+H)$^+$

Example 6: N-(benzylsulfonyl)-4-(2,6-dimethoxyphenyl)-5-(2-methoxythiazol-4-yl)-4H-1,2,4-triazole-3-carboxamide

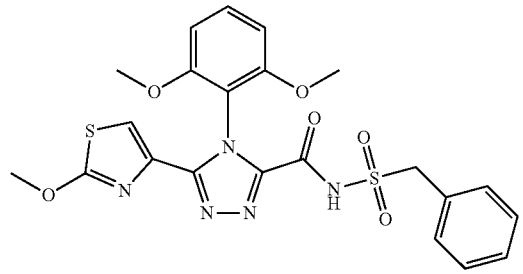 [SMILES: COc1nc(-c2nnc(C(=O)NS(=O)(=O)Cc3ccccc3)n2-c2c(OC)cccc2OC)cs1]

Step A: 2-bromo-N-(2,6-dimethoxyphenyl)thiazole-4-carboxamide

To a solution of 2-bromothiazole-4-carboxylic acid (2.5 g, 12.0 mmol) and 2,6-dimethoxyaniline (2.1 g, 13.2 mmol) in DCM (60 mL) was added DMAP (75 mg, 0.6 mmol) and EDCI (2.8 g, 14.4 mmol) at room temperature. The resulted mixture was stirred at room temperature overnight. The reaction solution was diluted with DCM (200 mL), washed with water (3*50 mL) and brine (100 mL), dried over anhydrous Na$_2$SO$_4$ and concentrated in vacuo. The residue was purified by flash chromatography eluting with PE/EtOAc (20/11/1) to afford the title compound as light yellow solid.

$^1$H NMR (400 MHz, DMSO-d$_6$) δ 9.21 (s, 1H), 8.35 (s, 1H), 7.25 (t, J=8.4 Hz, 1H), 6.71 (d, J=8.4 Hz, 2H), 3.73 (s, 6H).

LC-MS: m/z 342.9, 344.9 (M+H)$^+$

Step B: N-(2,6-dimethoxyphenyl)-2-methoxythiazole-4-carboxamide

A solution of 2-bromo-N-(2,6-dimethoxyphenyl)thiazole-4-carboxamide (2.7 g, 7.9 mmol) and sodium methoxide (468 mg, 8.7 mmol) in MeOH (50 mL) was refluxed at 70° C. for 24 h. The reaction mixture was diluted with water (100 mL) and extracted with DCM (3*50 mL). The combined organic phase was washed with brine (30 mL), dried over anhydrous Na$_2$SO$_4$, filtered and concentrated in vacuo. The residue was purified by flash chromatography on silica gel (PE/EtOAc, 20/1-1/1) to afford the title compound as light yellow solid.

LC-MS: m/z 295.0 (M+H)$^+$

Step C: N-(2,6-dimethoxyphenyl)-2-methoxythiazole-4-carbothioamide

A solution of N-(2,6-dimethoxyphenyl)-2-methoxythiazole-4-carboxamide (1.4 g, 4.7 mmol) and Lawesson's Reagent (1.3 g, 3.2 mmol) in toluene (30 mL) was stirred at 110° C. for 2 h under N$_2$ atmosphere. The reaction mixture was concentrated and residue was purified by flash chromatography on silica gel (PE/EtOAc, 20/1-1/1) to afford the title compound as a yellow solid.

LC-MS: m/z 311.0 (M+H)$^+$

Step D: 4-(2,6-dimethoxyphenyl)-5-(2-methoxythiazol-4-yl)-4H-1,2,4-triazole-3-carboxamide A solution of compound N-(2,6-dimethoxyphenyl)-2-methoxythiazole-4-carbothioamide (400 mg, 1.29 mmol), Oxamic hydrazide (264 mg, 2.58 mmol) and silver benzoate (592 mg, 2.58 mmol) in Acetic Acid (20 mL) was stirred at room temperature for 16 h and at 45° C. for 24 hours. Then the reaction mixture was diluted with water (30 mL) and extracted with EtOAc (3×50 mL). The combined organic phase was washed with brine (30 mL), dried over anhydrous $Na_2SO_4$, filtered and concentrated in vacuo. The residue was purified by flash chromatography on silica gel (DCM/MeOH=100/1) to afford the title compound as a yellow solid.

$^1$H NMR (400 MHz, DMSO-$d_6$) δ 8.17 (s, 1H), 7.61 (s, 1H), 8.35 (s, 1H), 7.38 (t, J=8.4 Hz, 1H), 6.75 (d, J=8.4 Hz, 2H), 3.68 (s, 3H), 3.63 (s, 6H).

LC-MS: m/z 362.0 (M+H)$^+$

Step E: N-(benzylsulfonyl)-4-(2,6-dimethoxyphenyl)-5-(2-methoxythiazol-4-yl)-4H-1,2,4-triazole-3-carboxamide A mixture of 4-(2,6-dimethoxyphenyl)-5-(2-methoxythiazol-4-yl)-4H-1,2,4-triazole-3-carboxamide (150 mg, 0.42 mmol) and DMF (8 mL) was treated with sodium hydride (60% in mineral oil, 33 mg, 0.83 mmol) and stirred for 20 min. Then Phenylmethanesulfonyl chloride (95 mg, 0.50 mmol) was added and the mixture was stirred at room temperature for 4 h. Another portion of sodium hydride (60% in mineral oil, 33 mg, 0.83 mmol) and Phenylmethanesulfonyl chloride (95 mg, 0.50 mmol) were added, and the mixture was stirred at room temperature for 24 h. The reaction was quenched with saturated aqueous solution of ammonium chloride. The mixture was extracted with DCM (3*30 mL). The combined organic layer was washed with brine and dried over anhydrous $Na_2SO_4$, filtered and concentrated in vacuo. The residue was purified by silica gel column chromatography (MeOH/DCM, 0~1/20) to afford the title compound as a pale yellow solid.

$^1$H NMR (400 MHz, DMSO-$d_6$) δ 7.35 (t, J=8.4 Hz, 1H), 7.15-7.29 (m, 6H), 6.75 (d, J=8.4 Hz, 2H), 4.16 (s, 2H), 3.70 (s, 3H), 3.65 (s, 6H).

LC-MS: m/z 516.0 (M+H)$^+$

Example 7: N-(benzylsulfonyl)-4-(2,6-dimethoxyphenyl)-5-(ethoxymethyl)-4H-1,2,4-triazole-3-carboxamide

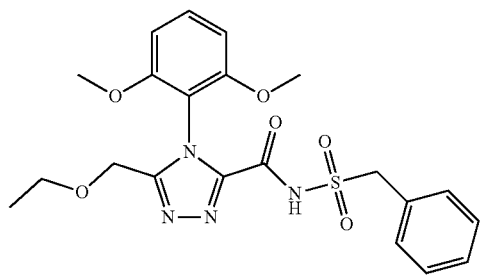 [SMILES: CCOCc1nnc(C(=O)NS(=O)(=O)Cc2ccccc2)n1-c1c(OC)cccc1OC]

Step A:
N-(2,6-dimethoxyphenyl)-2-ethoxyacetamide

To a solution of 2-ethoxyacetic acid (4.1 g, 39.2 mmol) and 2,6-dimethoxyaniline (5.0 g, 32.6 mmol) in DCM (100 mL) were added DMAP (200 mg, 1.6 mmol) and EDCI (7.5 g, 39.2 mmol) at room temperature. The resulted mixture was stirred at room temperature overnight. The mixture was diluted with EtOAc (500 mL), washed with water (3*100 mL) and brine (150 mL), dried over anhydrous $Na_2SO_4$ and concentrated in vacuo. The residue was purified by flash chromatography eluting with PE/EtOAc (20/1~1/1) to afford the title compound as a white solid.

$^1$H NMR (400 MHz, DMSO-$d_6$) δ: 8.53 (s, 1H), 7.21 (t, J=8.4 Hz, 1H), 6.68 (d, J=8.4 Hz, 2H), 3.95 (s, 2H), 3.72 (s, 6H), 3.57 (d, J=7.0 Hz, 2H), 1.19 (t, J=7.0 Hz, 3H).

LC-MS: m/z 240.1 (M+H)$^+$

Step B:
N-(2,6-dimethoxyphenyl)-2-ethoxyethanethioamide

A mixture of N-(2,6-dimethoxyphenyl)-2-ethoxyacetamide (1.0 g, 4.18 mmol) and $P_2S_5$ (930 mg, 4.18 mmol) in THF (30 mL) was stirred at 65° C. for 16 h under $N_2$ atmosphere. The mixture was cooled to room temperature, filtered and washed with THF. The filtrate was concentrated in vacuo and residue was purified by flash chromatography on silica gel PE/EtOAc (20/1-10/1) to afford the title compound as yellow solid.

$^1$H NMR (400 MHz, DMSO-$d_6$) δ 10.34 (s, 1H), 7.28 (t, J=8.4 Hz, 1H), 6.72 (d, J=8.4 Hz, 2H), 4.33 (s, 2H), 3.73 (s, 6H), 3.61 (q, J=7.0 Hz, 2H), 1.22 (t, J=7.0 Hz, 3H).

LC-MS: m/z 255.1 (M+H)$^+$

Step C: (E)-N-(2,6-dimethoxyphenyl)-2-ethoxyacetohydrazonamide

To a suspension of N-(2,6-dimethoxyphenyl)-2-ethoxyethanethioamide (741 mg, 2.9 mmol) in 1,4-dioxane (20 mL) was added hydrazine hydrate (1.45 g, 29 mmol). The mixture was stirred at 30° C. for 1 h under $N_2$. The mixture was lyophilized to afford the crude title compound as a yellow solid.

LC-MS: m/z 254.1 (M+H)$^+$

Step D: ethyl4-(2,6-dimethoxyphenyl)-5-(ethoxymethyl)-4H-1,2,4-triazole-3-carboxylate To a solution of (E)-N-(2,6-dimethoxyphenyl)-2-ethoxyacetohydrazonamide (735 mg, 2.9 mmol) in THF (20 mL) was added a solution of ethyl 2-chloro-2-oxoacetate (396 mg, 2.9 mmol) in THF (4 mL) dropwise at −78° C. After the dropwise addition, diisopropylethylamine (562 mg, 4.36 mmol) was added dropwise. The mixture was warmed to room temperature gradually and stirred at 50° C. overnight. The mixture was diluted with EtOAc and then washed successively with saturated NaHCO$_3$ (aq.) and brine. The organic phase was dried over anhydrous $Na_2SO_4$ and concentrated in vacuo. Residue was purified by flash chromatography (MeOH/DCM, 0~1/10) to afford the title compound as a light yellow solid.

$^1$H NMR (400 MHz, DMSO-$d_6$) δ 7.47 (t, J=10.0 Hz, 1H), 6.85 (d, J=8.0 Hz, 2H), 4.36 (s, 2H), 4.18 (q, J=7.2 Hz, 2H), 3.72 (s, 6H), 3.24 (q, J=7.0 Hz, 2H), 1.09 (t, J=7.2 Hz, 3H), 0.90 (t, J=7.0 Hz, 3H).

LC-MS: m/z 336.1 (M+H)$^+$

Step E: 4-(2,6-dimethoxyphenyl)-5-(ethoxymethyl)-4H-1,2,4-triazole-3-carboxamide A solution of ethyl4-(2,6-dimethoxyphenyl)-5-(ethoxymethyl)-4H-1,2,4-triazole-3-carboxylate (400 mg, 1.2 mmol)

in NH₃-MeOH (7 mol/L in MeOH, 10 mL, 70 mmol) was stirred at 60° C. in sealed tube overnight. The mixture was concentrated in vacuo to afford the title compound as a pale yellow solid.

¹H NMR (400 MHz, DMSO-d₆) δ 8.12 (s, 1H), 7.59 (s, 1H), 7.41 (t, J=8.4 Hz, 1H), 6.80 (d, J=8.4 Hz, 2H), 4.30 (s, 2H), 3.70 (s, 6H), 3.22 (q, J=7.0 Hz, 2H), 0.89 (t, J=7.0 Hz, 3H).

LC-MS: m/z 307.1 (M+H)⁺

Step F: N-(benzylsulfonyl)-4-(2,6-dimethoxyphenyl)-5-(ethoxymethyl)-4H-1,2,4-triazole-3-carboxamide A mixture of 4-(2,6-dimethoxyphenyl)-5-(ethoxymethyl)-4H-1,2,4-triazole-3-carboxamide (135 mg, 0.44 mmol) in N,N-Dimethylformamide (8 mL) was treated with sodium hydride (60% in mineral oil, 36 mg, 0.88 mmol) and stirred for 20 min. Then Phenylmethanesulfonyl chloride (100 mg, 0.53 mmol) was added and the mixture was stirred at room temperature for 4 h. The reaction was quenched with saturated aqueous solution of ammonium chloride. The mixture was extracted with DCM (3*30 mL). The combined organic layer was washed with brine and dried over anhydrous Na₂SO₄, filtered and concentrated in vacuo. The residue was purified by silica gel column chromatography to afford the title compound as a pale yellow solid.

¹H NMR (400 MHz, DMSO-d₆) δ 7.43 (t, J=8.8 Hz, 1H), 7.19-7.32 (m, 5H), 6.83 (d, J=8.4 Hz, 2H), 4.29 (s, 4H), 3.73 (s, 6H), 3.24 (q, J=7.0 Hz, 2H), 0.91 (t, J=7.0 Hz, 3H).

LC-MS: m/z 461.1 (M+H)⁺

Method A:

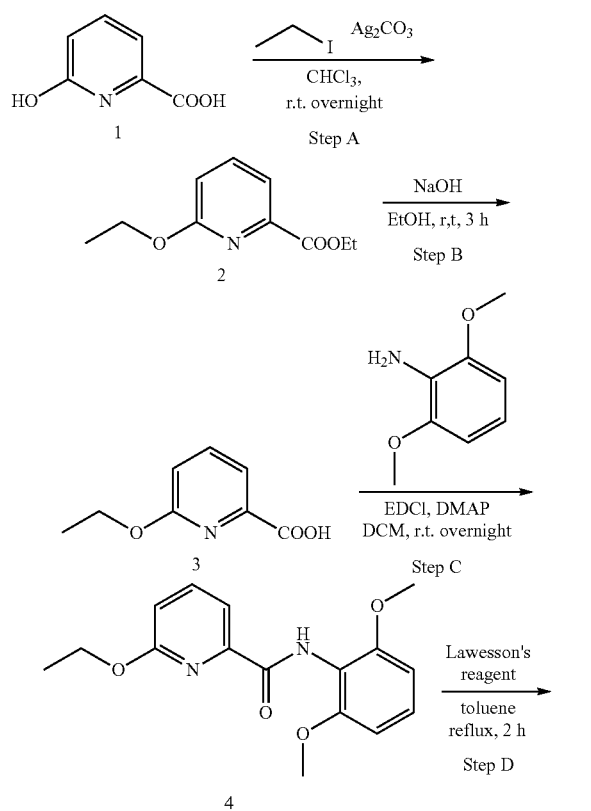

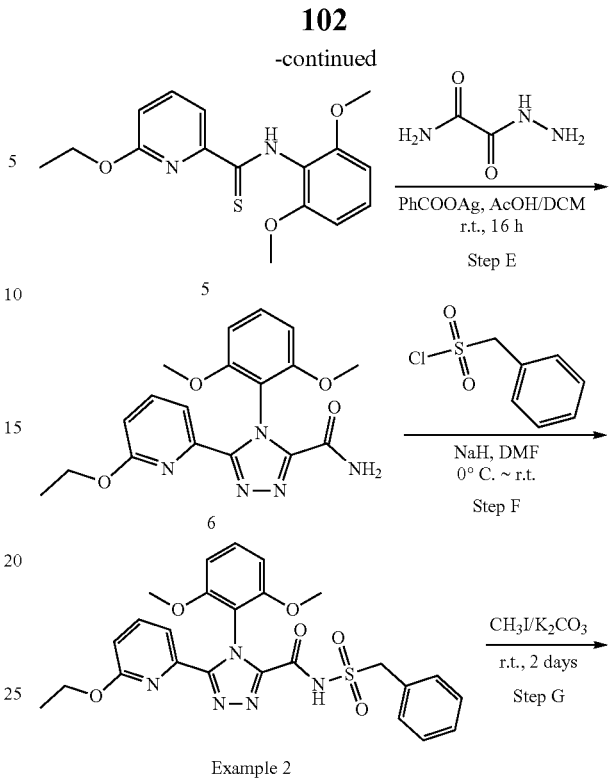

Example 2

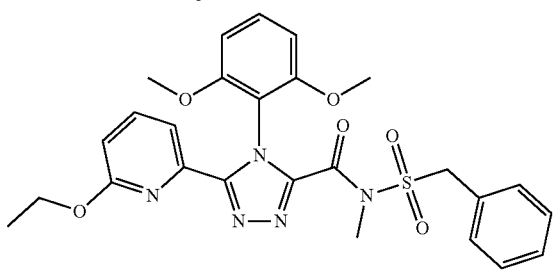

Example 8

Example 8: N-(benzylsulfonyl)-4-(2,6-dimethoxyphenyl)-5-(6-ethoxypyridin-2-yl)-N-methyl-4H-1,2,4-triazole-3-carboxamide Step A: ethyl 6-ethoxypicolinate

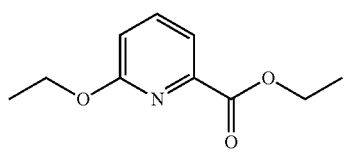

Ethyl iodide (22.4 g, 144 mmol, 4 equiv.) was added to a suspension of 6-hydroxy-pyridine-2-carboxylic acid (5.0 g, 36 mmol, 1 equiv) and silver(I) carbonate (20 g, 72 mmol, 2 equiv) in CHCl₃ (500 mL). The suspension was stirred at room temperature overnight. Insoluble material was removed by filtration and the solid was washed with CHCl₃. The filtrate was concentrated to afford the title compound ethyl 6-ethoxypicolinate as light yellow oil which was used in the next step without further purification (7 g, 100% yield).

LC-MS: m/z 196.0 (M+H)⁺

Step B: 6-ethoxypicolinic Acid

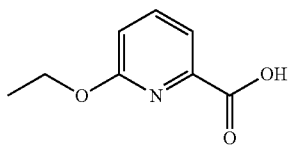

To a solution of ethyl 6-ethoxypicolinate (2.6 g, 13.3 mmol, 1 equiv) in EtOH (30 mL) was added sodium hydroxide solution (1 mol/L, 40 mL, 40 mmol, 3 equiv). The reaction mixture was stirred at room temperature for 3 h. The reaction mixture was diluted with 1 N HCl solution and ethyl acetate. The organic layer was separated and dried over anhydrous MgSO$_4$. The filtrate was concentrated in vacuo to afford the title compound 6-ethoxypicolinic acid as a white solid (2.2 g, 100% yield).

LC-MS: m/z 168.0 (M+H)$^+$

Step C: N-(2, 6-dimethoxyphenyl)-6-ethoxypicolinamide

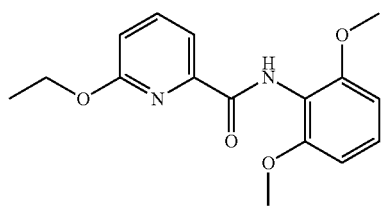 [SMILES: CCOc1cccc(C(=O)Nc2c(OC)cccc2OC)n1]

To a solution of 6-ethoxypicolinic acid (2.2 g, 13.2 mmol, 1 equiv) and 2,6-dimethoxyaniline (2.2 g, 14.5 mmol, 1.2 equiv) in DCM (40 mL) were added DMAP (80 mg, 0.6 mmol, 0.05 equiv) and EDCI (3.0 g, 15.8 mmol, 1.2 equiv) successively at room temperature. The resulting mixture was stirred at room temperature overnight. The reaction was diluted with EtOAc (300 mL) and water (3*100 mL). The organic layers were separated, washed with brine (100 mL), dried over anhydrous Na$_2$SO$_4$, and concentrated in vacuo. The residue was purified by flash column chromatography (eluted with PE/EtOAc=20/1~1/1) to afford the title compound N-(2,6-dimethoxyphenyl)-6-ethoxypicolinamide as a white solid (2.8 g, 70% yield).

$^1$H NMR (400 MHz, DMSO-d$_6$) δ 9.35 (s, 1H), 7.89 (t, J=7.6 Hz, 1H), 7.64 (d, J=7.2 Hz, 1H), 7.26 (d, J=8.4 Hz, 1H), 7.03 (d, J=8.0 Hz, 1H), 6.73 (d, J=8.4 Hz, 2H), 4.47 (q, J=7.2 Hz, 2H), 3.75 (s, 6H), 1.35 (t, J=7.2 Hz, 3H). LC-MS: m/z 303.1 (M+H)$^+$

Step D: N-(2, 6-dimethoxyphenyl)-6-ethoxypyridine-2-carbothioamide

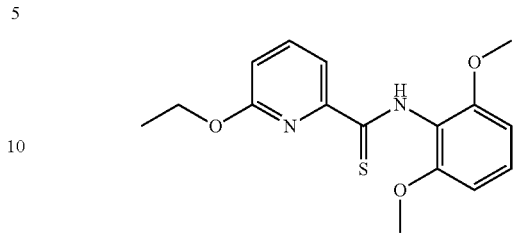

A solution of compound N-(2, 6-dimethoxyphenyl)-6-ethoxypicolinamide (5 g, 16.6 mmol, 1 equiv) and Lawesson's Reagent (4.7 g, 11.6 mmol, 0.7 equiv) in toluene (50 mL) was stirred at 110° C. for 2 h under N$_2$ atmosphere. The reaction mixture was concentrated and the residue was purified by flash column chromatography on silica gel to afford the title compound N-(2, 6-dimethoxyphenyl)-6-ethoxypyridine-2-carbothioamide as a yellow solid (3.5 g, 66% yield)

$^1$H NMR (400 MHz, DMSO-d$_6$) δ 11.14 (s, 1H), 8.11-8.13 (m, 1H), 7.87 (t, J=8.0 Hz, 1H), 7.32 (t, J=8.4 Hz, 1H), 7.03-7.05 (m, 1H), 6.76 (d, J=8.4 Hz, 2H), 4.49 (q, J=7.2 Hz, 2H), 3.74 (s, 6H), 1.34 (t, J=7.2 Hz, 3H). LC-MS: m/z 319.1 (M+H)$^+$

Step E: 4-(2,6-dimethoxyphenyl)-5-(6-ethoxypyridin-2-yl)-4H-1,2,4-triazole-3-carboxamide

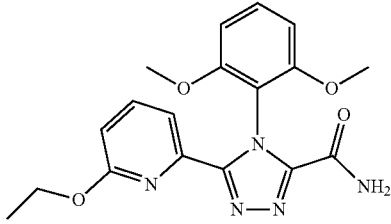 [SMILES: CCOc1cccc(-c2nnc(C(N)=O)n2-c2c(OC)cccc2OC)n1]

To a mixture of N-(2,6-dimethoxyphenyl)-6-ethoxypyridine-2-carbothioamide (1 g, 3.1 mmol, 1 equiv), 2-hydrazinyl-2-oxoacetamide (647 mg, 6.2 mmol, 2 equiv) in DCM (6 mL) was added silver benzoate (2.82 g, 12.4 mmol, 4 equiv). Then AcOH (30 mL) was added immediately, the mixture was stirred at room temperature for 16 h. The mixture was concentrated and the residue was dissolved in DMF (10 mL) and purified by reverse phase column chromatography (eluted with MeOH/H₂O=5%~95%) to afford the title compound 4-(2,6-dimethoxyphenyl)-5-(6-ethoxypyridin-2-yl)-4H-1,2,4-triazole-3-carboxamide as a white solid (600 mg, 52% yield).

¹H NMR (400 MHz, DMSO-d₆) δ: 8.18 (s, 1H), 7.75-7.85 (m, 1H), 7.70 (d, J=7.6 Hz, 1H), 7.62 (s, 1H), 7.34 (t, J=8.4 Hz, 1H), 6.67-6.81 (m, 3H), 3.58 (s, 6H), 3.42 (q, J=7.2 Hz, 2H), 1.02 (t, J=7.2 Hz, 3H). LC-MS: m/z 370.1 (M+H)⁺.

Step F: N-(benzylsulfonyl)-4-(2,6-dimethoxyphenyl)-5-(6-ethoxypyridin-2-yl)-4H-1,2,4-triazole-3-carboxamide (Example 2)

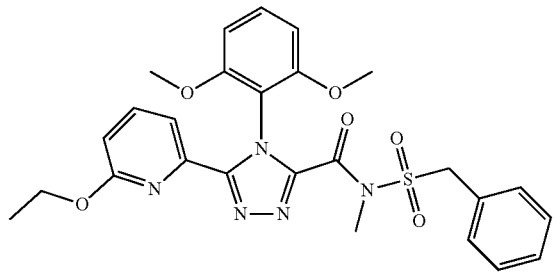 [SMILES: CCOc1cccc(-c2nnc(C(=O)N(C)S(=O)(=O)Cc3ccccc3)n2-c2c(OC)cccc2OC)n1]

A solution of 4-(2,6-dimethoxyphenyl)-5-(6-ethoxypyridin-2-yl)-4H-1,2,4-triazole-3-carboxamide (250 mg, 0.67 mmol, 1 equiv) in DMF (10 mL) was treated with sodium hydride (60% in mineral oil, 80 mg, 2 mmol, 3 equiv) at 0° C. The reaction was stirred at 0° C. for 1 hour. Phenylmethanesulfonyl chloride (386 mg, 2 mmol, 3 equiv) was added, and the mixture was stirred at room temperature for 24 hours. The reaction was quenched with saturated aqueous solution of ammonium chloride and extracted three times with dichloromethane. The combined organic layer were washed with brine, dried over anhydrous Na₂SO₄, filtered and concentrated under reduced pressure. The residue was purified by reverse phase column (eluted with MeOH/H₂O=5/95·95/5) to afford the title compound N-(benzylsulfonyl)-4-(2,6-dimethoxyphenyl)-5-(6-ethoxypyridin-2-yl)-4H-1,2,4-triazole-3-carboxamide as a white solid (80 mg, 22% yield).

¹H NMR (400 MHz, DMSO-d₆) δ: 7.83 (d, J=8.0 Hz, 1H), 7.74-7.78 (m, 1H), 7.37-7.42 (m, 4H), 7.25-7.30 (m, 2H), 6.80-6.86 (m, 3H), 4.71 (s, 2H), 3.64 (s, 6H), 3.43 (q, J=7.2 Hz, 2H), 1.03 (t, J=7.2 Hz, 3H). LC-MS: m/z 524.1 (M+H)⁺.

Step G: N-(benzylsulfonyl)-4-(2,6-dimethoxyphenyl)-5-(6-ethoxypyridin-2-yl)-N-methyl-4H-1,2,4-triazole-3-carboxamide (Example 8)

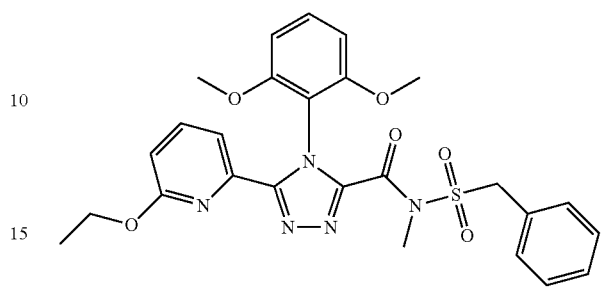

To a mixture of N-(benzylsulfonyl)-4-(2,6-dimethoxyphenyl)-5-(6-ethoxypyridin-2-yl)-4H-1,2,4-triazole-3-carboxamide (80 mg, 0.15 mmol, 1 equiv), K₂CO₃ (31 mg, 0.23 mmol, 1.5 equiv) in DMF (5 mL) was added CH₃I (43 mg, 0.3 mmol, 2 equiv). The resulting mixture was stirred at room temperature for 2 days. The mixture was directly purified by reverse phase column (eluted with MeOH/H₂O=5% 95%) to afford the title compound N-(benzylsulfonyl)-4-(2,6-dimethoxyphenyl)-5-(6-ethoxypyridin-2-yl)-N-methyl-4H-1,2,4-triazole-3-carboxamide as a white solid (40 mg, 49%).

¹H NMR (DMSO-d₆) δ: 7.84 (d, J=8.4 Hz, 1H), 6.83 (d, J=6.8 Hz, 1H), 7.40-7.50 (m, 4H), 7.33-7.40 (m, 2H), 6.82-6.84 (m, 3H), 5.13 (s, 2H), 3.60 (s, 6H), 3.41 (q, J=7.2 Hz, 2H), 1.01 (t, J=7.2 Hz, 3H). LC-MS: m/z 538.1 (M+H)⁺.

Example 9: 4-(2,6-Dimethoxyphenyl)-5-(6-ethoxypyridin-2-yl)-N-(methylsulfonyl)-4H-1,2,4-triazole-3-carboxamide

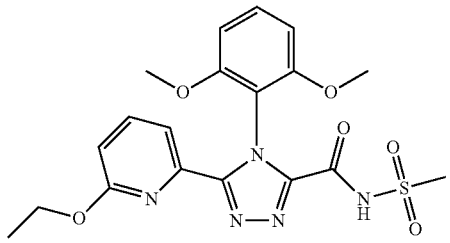 [SMILES: CCOc1cccc(-c2nnc(C(=O)NS(C)(=O)=O)n2-c2c(OC)cccc2OC)n1]

The title compound was prepared according to Method A, step F by using methanesulfonyl chloride.

¹H NMR (DMSO-d₆) δ: 7.75 (t, J=8.0 Hz, 1H), 7.64 (dd, J=7.6 Hz, 0.8 Hz, 1H), 7.27 (t, J=8.4 Hz, 1H), 6.66-6.74 (m, 3H), 3.56 (s, 6H), 3.41 (q, J=8.0 Hz, 2H), 2.59 (s, 3H), 1.01 (t, J=8.0 Hz, 3H). LC-MS: m/z 448.1 (M+H)⁺.

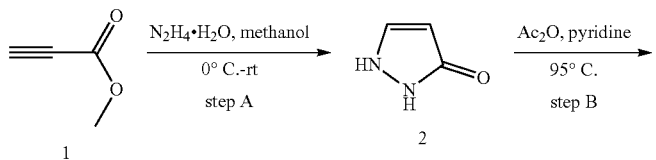

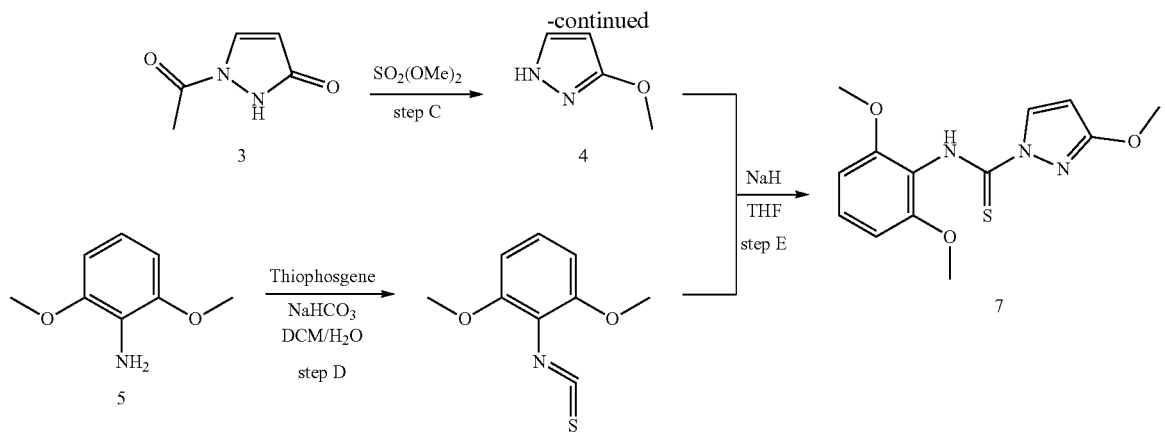

Step A: 1H-pyrazol-3(2H)-one

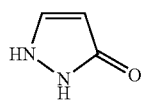

To a solution of methyl propiolate (4.2 mL, 47.58 mmol, 1 equiv) in methanol (40 mL) was added hydrazine hydrate (3.6 mL, 47.58 mmol, 1 equiv) dropwise at 0° C. The reaction mixture was allowed to be stirred at room temperature for 30 mins. Brine (10 mL) was added and then methanol was removed under vacuum. The remaining aqueous layer was extracted with EtOAc (4*75 mL). The combined organic phase was dried over anhydrous MgSO$_4$, filtered and concentrated in vacuo to afford the title compound 1H-pyrazol-3(2H)-one as a white solid (3.2 g, 78% yield).

$^1$H NMR (400 MHz, DMSO-d$_6$) δ: 10.68 (br. s., 2H), 7.40 (d, J=4.0 Hz, 1H), 5.50 (d, J=4.0 Hz, 1H).

Step B: 1-Acetyl-1H-pyrazol-3(2H)-one

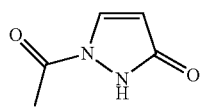

A mixture of 1H-pyrazol-3(2H)-one (2.5 g, 29.8 mmol, 1 equiv) in pyridine (20.4 mL) was heated to 95° C. and then charged with a solution of acetic anhydride (4.2 mL, 44.7 mmol, 1.5 equiv) in pyridine (9.6 mL) over a period of 15 mins. The resulting mixture was heated for an additional 1 hour at 95° C. Then the reaction mixture was concentrated and the residue was purified by flash column chromatography on silica gel (eluted with PE/EtOAc=2/1) to afford the title compound 1-acetyl-1H-pyrazol-3(2H)-one as a yellow solid (2.1 g, 56% yield).

$^1$H NMR (DMSO-d$_6$) δ: 10.95 (br. s., 1H), 8.13 (d, J=4.0 Hz, 1H), 6.01 (d, J=4.0 Hz, 1H), 2.48 (s, 3H). LC-MS: m/z 127.1 (M+H)$^+$

Step C: 3-Methoxy-1H-pyrazole

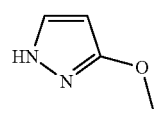

A mixture of 1-acetyl-1H-pyrazol-3(2H)-one (1.5 g, 11.9 mmol, 1 equiv) and potassium carbonate (1.64 g, 11.9 mmol, 1 equiv) in 2-butanone (36 mL) was charged with dimethyl sulfate (1.24 mL, 13.1 mmol, 1.1 equiv) and the resulting mixture was refluxed for 90 mins. An additional amount of dimethyl sulfate (0.23 mL, 2.4 mmol, 0.2 equiv) was added and the reaction mixture was refluxed for an additional 1 hour. The reaction mixture was cooled to room temperature and filtered through a fritted funnel and the filtrate was concentrated in vacuo resulting in dark yellow oil. The crude oil was charged with a 10 M NaOH (0.6 mL) and dissolved in a mixture of THF/MeOH (20 mL/20 mL). After being stirred at room temperature for 30 mins, the mixture was concentrated in vacuo and partitioned between EtOAc and brine. The organic phase was separated, dried over anhydrous Na$_2$SO$_4$, filtered and concentrated in vacuo to afford the title compound 3-methoxy-1H-pyrazole as orange oil (620 mg, 53% yield).

$^1$H NMR (400 MHz, DMSO-d$_6$) δ: 11.88 (br. s., 1H), 7.50 (d, J=4.0 Hz, 1H), 5.65 (d, J=4.0 Hz, 1H), 3.75 (s, 3H).

Step D: 2-Isothiocyanato-1,3-dimethoxybenzene

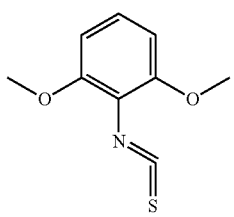

To a mixture of dichloromethane (50 mL) and water (50 mL) were added 2,6-dimethoxyaniline (4.6 g, 30 mmol, 1 equiv) and sodium bicarbonate (5.0 g, 60 mmol, 2 equiv).

Then thiophosgene (2.6 mL, 33 mmol, 1.1 equiv) was added in small portions with stirring at 0° C. After addition, the mixture was stirred for 10 mins at 0° C. and then at room temperature for 1 hour. The organic layer was separated and the aqueous layer was extracted with DCM (2*50 mL). The combined organic extracts were washed with brine (30 mL), dried over anhydrous Na$_2$SO$_4$, filtered and concentrated in vacuo. The residue was purified by flash column chromatography on silica gel (eluted with PE/EtOAc=200/1) to afford the title compound 2-isothiocyanato-1,3-dimethoxybenzene as an off-white solid (3.1 g, 53% yield).

$^1$H NMR (400 MHz, DMSO-d$_6$) δ: 7.29 (t, J=8.0 Hz, 1H), 6.76 (d, J=8.0 Hz, 2H), 3.86 (s, 6H). LC-MS: m/z 196.1 (M+H)$^+$

Step E: N-(2,6-dimethoxyphenyl)-3-methoxy-1H-pyrazole-1-carbothioamide

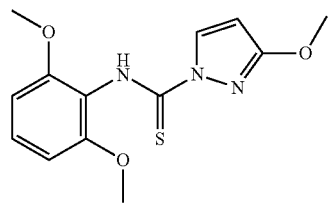 [SMILES: COc1ccn(C(=S)Nc2c(OC)cccc2OC)n1]

To a solution of 3-methoxy-1H-pyrazole (520 mg, 5.3 mmol, 1 equiv) in dry THF was added NaH (60% in mineral oil, 1.06 g, 26.5 mmol, 5 equiv) at 0° C. The reaction was stirred for 1 min at room temperature under nitrogen atmosphere. Then a solution of 2-isothiocyanato-1,3-dimethoxybenzene (1.56 g, 8 mmol, 1.5 equiv) in THF (5 mL) was added. The resulting mixture was stirred at room temperature for 4 hours. The reaction was quenched with H$_2$O (30 mL) and extracted with EtOAc (3*50 mL). The combined organic extracts were washed with brine (30 mL), dried over anhydrous Na$_2$SO$_4$, filtered and concentrated in vacuo. The residue was purified by flash column chromatography on silica gel (eluted with DCM/MeOH=100/1) to afford the title compound N-(2,6-dimethoxyphenyl)-3-methoxy-1H-pyrazole-1-carbothioamide as a white solid (1.1 g, 48% yield).

LC-MS: m/z 294.1 (M+H)$^+$

Example 10: N-(enzylsulfonyl)-4-(2,6-dimethoxyphenyl)-5-(3-methoxy-1H-pyrazol-1-yl)-4H-1,2,4-triazole-3-carboxamide

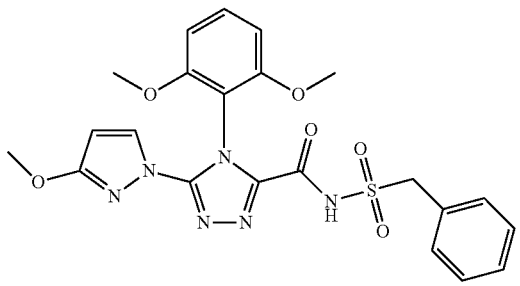 [SMILES: COc1ccn(-c2nnc(C(=O)NS(=O)(=O)Cc3ccccc3)n2-c2c(OC)cccc2OC)n1]

The title compound was prepared according to Method A, by using N-(2,6-dimethoxyphenyl)-3-methoxy-1H-pyrazole-1-carbothioamide in step E and phenylmethanesulfonyl chloride in step F.

$^1$H NMR (400 MHz, DMSO-d$_6$) δ: 7.96 (s, 1H), 7.35 (t, J=8.0 Hz, 1H), 7.24-7.30 (m, 3H), 7.20-7.22 (m, 2H), 6.72 (d, J=8.0 Hz, 2H), 5.95 (d, J=2.4 Hz, 1H), 4.26 (s, 2H), 3.67 (s, 6H), 3.50 (s, 3H). LC-MS: m/z 499.1 (M+H)$^+$

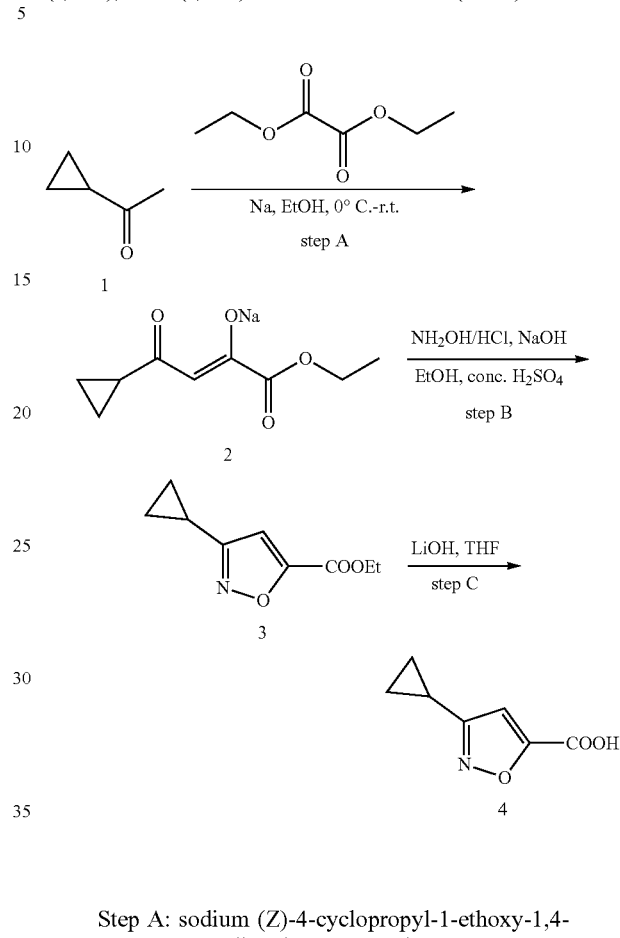

Step A: sodium (Z)-4-cyclopropyl-1-ethoxy-1,4-dioxobut-2-en-2-olate

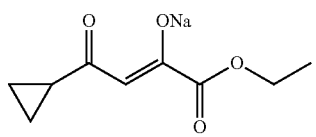

Sodium metal (1.4 g, 59.5 mmol, 1 equiv) was added into EtOH (10 mL) at room temperature under nitrogen atmosphere to form NaOEt solution. The solution was cooled to 0° C. and then diethyl oxalate (8.7 g, 59.5 mmol, 1 equiv) and 1-cyclopropylethan-1-one (5.0 g, 59.5 mmol, 1 equiv) were added dropwise over 20 mins. Then the mixture was allowed to warm to room temperature. After 15 mins, the white precipitate was filtered off and washed with ethanol. The filtrate was dried to afford the title compound sodium (Z)-4-cyclopropyl-1-ethoxy-1,4-dioxobut-2-en-2-olate as a white solid (6.1 g, 55.7% yield).

LC-MS: m/z 185.1 (M+H−Na)$^+$

Step B: ethyl 3-cyclopropylisoxazole-5-carboxylate

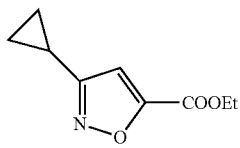 [SMILES: CCOC(=O)c1cc(C2CC2)no1]

To a 20% NaOH aqueous solution (10 mL) were added hydroxylamine hydrochloride (0.75 g, 10.9 mmol, 1 equiv) and sodium (Z)-4-cyclopropyl-1-ethoxy-1,4-dioxobut-2-en-2-olate (2.25 g, 10.9 mmol, 1 equiv) at room temperature. After stirred for 2 hours, the intermediate oxime was obtained via extraction with Et$_2$O. The crude oxime intermediate was dissolved in EtOH (15 mL) and concentrated H$_2$SO$_4$ (1.2 mL) was added gradually. The mixture was refluxed for 5 hours. The reaction mixture was cooled to room temperature and concentrated in vacuo. The residue was diluted with water and extracted with DCM (2*25 mL). The combined organic layers were washed with brine, dried over anhydrous Na$_2$SO$_4$, filtered and concentrated in vacuo. The residue was purified by flash column chromatography (eluted with PE/EtOAc=4/1) to afford the title compound ethyl 3-cyclopropylisoxazole-5-carboxylate as a yellow solid (1.4 g, 71% yield).

LC-MS: m/z 182.1 (M+H)$^+$

Step C: 3-cyclopropylisoxazole-5-carboxylic Acid

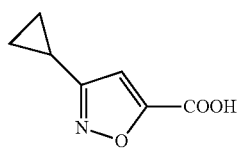 [SMILES: O=C(O)c1cc(C2CC2)no1]

To a solution of ethyl 3-cyclopropylisoxazole-5-carboxylate (320 mg, 1.8 mmol, 1 equiv) in THF (8 mL) was added a solution of lithium hydroxide monohydrate (110 mg, 2.7 mmol, 1.5 equiv) in H$_2$O (0.5 mL) dropwise at 0° C. After addition, the reaction mixture was stirred at room temperature for 1 hour and then THF was removed in vacuo. The aqueous solution was diluted with water (3 mL), adjusted to pH=2 with 1N HCl solution. The white precipitate was filtered off, washed with water, dried in vacuo to afford the title compound 3-cyclopropylisoxazole-5-carboxylic acid as a white solid (180 mg, 67% yield).

$^1$H NMR (400 MHz, CDCl$_3$) δ: 9.37 (s, 1H), 6.37 (s, 1H), 2.14-2.07 (m, 1H), 1.19-1.13 (m, 2H), 1.04-1.01 (m, 2H). LC-MS: m/z 154.1 (M+H)$^+$

Example 11: N-(benzylsulfonyl)-5-(3-cyclopropylisoxazol-5-yl)-4-(2,6-dimethoxyphenyl)-4H-1,2,4-triazole-3-carboxamide

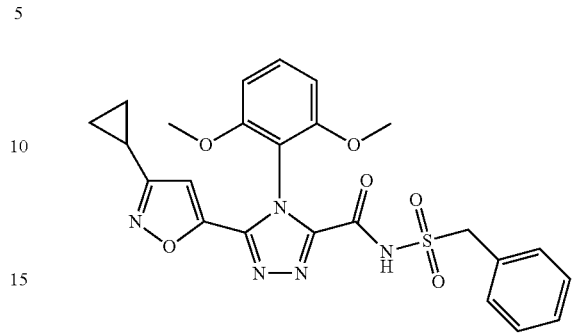

The title compound was prepared according to Method A, by using 3-cyclopropylisoxazole-5-carboxylic acid in step C and phenylmethanesulfonyl chloride in step F.

$^1$H NMR (400 MHz, DMSO-d$_6$) δ: 7.51 (t, J=8.0 Hz, 1H), 7.32-7.37 (m, 5H), 6.83 (d, J=12.0 Hz, 2H), 6.30 (s, 1H), 4.67 (s, 2H), 3.76 (s, 6H), 2.09-2.15 (m, 1H), 1.08-1.13 (m, 2H), 0.90-0.94 (m, 2H). LC-MS: m/z 510.2 (M+H)$^+$.

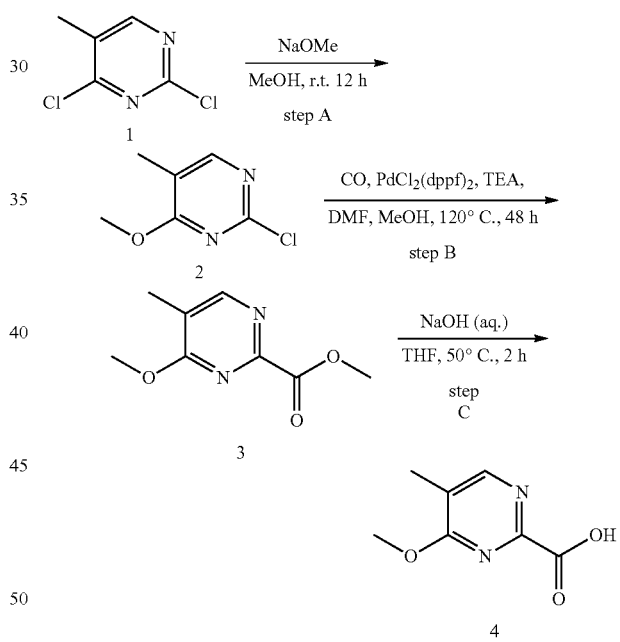

Step A: 2-chloro-4-methoxy-5-methylpyrimidine

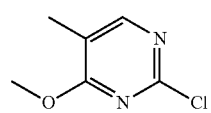

To a solution of 2,4-dichloro-5-methylpyrimidine (12.8 g, 80 mmol, 1 equiv) in MeOH (30 mL) was added NaOMe (5 mol/L in MeOH, 14.8 mL, 74 mmol, 0.9 equiv) dropwise. The reaction mixture was stirred at room temperature for 12 hours and concentrated. The residue was charged with H₂O (30 mL) and extracted with DCM (3*80 mL). The combined organic phase were washed with brine (30 mL), dried over anhydrous Na₂SO₄ and concentrated in vacuo. The residue was purified by flash column chromatography on silica gel (eluted with PE/EtOAc=100/1) to afford the title compound 2-chloro-4-methoxy-5-methylpyrimidine as a white solid (9.3 g, 74% yield).

LC-MS: m/z 159.1 (M+H)⁺

Step B: methyl 4-methoxy-5-methylpyrimidine-2-carboxylate

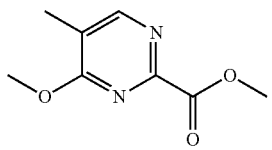

To a solution of 2-chloro-4-methoxy-5-methylpyrimidine (9.3 g, 58.6 mmol, 1 equiv) in MeOH (220 mL) and DMF (45 mL) were added Pd(dppf)Cl₂ (2.1 g, 2.9 mmol, 0.05 equiv) and triethylamine (17.8 g, 175.8 mmol, 3 equiv). The mixture was degassed and refilled with CO three times and then stirred at 120° C. under CO (50 Psi) for 48 hours. The reaction mixture was cooled to room temperature and concentrated in vacuo. The residue was purified by silica gel chromatography (eluted with PE/EtOAc=10/1) to afford the title compound methyl 6-(trifluoromethoxy)picolinate as yellow oil (5.0 g, 47% yield).

LC-MS: m/z 183.1 (M+H)⁺

Step C: 4-methoxy-5-methylpyrimidine-2-carboxylic Acid

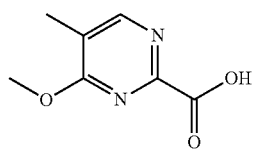

To a solution of methyl 4-methoxy-5-methylpyrimidine-2-carboxylate (1.8 g, 10 mmol, 1 equiv) in THF (30 mL) was added a solution of NaOH (1.2 g, 30 mmol, 3 equiv) in H₂O (6 mL) dropwise. The resulting mixture was stirred at 50° C. for 2 hours. Then the mixture was diluted with H₂O (50 mL) and washed with EtOAc (3*50 mL). The aqueous phase was adjusted to pH=4 with 1M HCl (aq.) and extracted with EtOAc (3*50 mL). The extracts were washed with brine (30 mL), dried over anhydrous Na₂SO₄, filtered and concentrated in vacuo to afford the title compound 4-methoxy-5-methylpyrimidine-2-carboxylic acid as a white solid (1.3 g, 77% yield).

LC-MS: m/z 169.1 (M+H)⁺

Example 12: N-(benzylsulfonyl)-4-(2,6-dimethoxyphenyl)-5-(4-methoxy-5-methylpyrimidin-2-yl)-4H-1,2,4-triazole-3-carboxamide

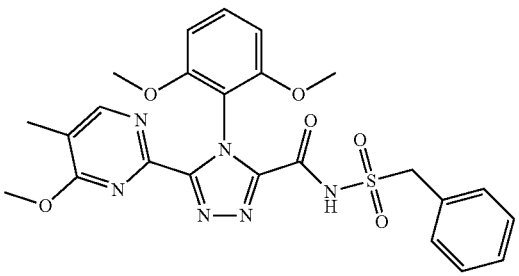 [SMILES: COc1cccc(OC)c1-n1c(C(=O)NS(=O)(=O)Cc2ccccc2)nnc1-c1ncc(C)c(OC)n1]

The title compound was prepared according to Method A, by using 4-methoxy-5-methylpyrimidine-2-carboxylic acid in step C and phenylmethanesulfonyl chloride in step F.

¹H NMR (400 MHz, DMSO-d₆) δ: 8.40 (s, 1H), 7.29 (t, J=8.0 Hz, 1H), 7.25-7.19 (m, 5H), 6.71 (d, J=8.0 Hz, 2H), 4.14 (s, 2H), 3.57 (s, 6H), 3.37 (s, 3H), 2.06 (s, 3H). LC-MS: m/z 525.1 (M+H)⁺

Example 13: N-(benzylsulfonyl)-4-(2,6-dimethoxyphenyl)-5-(6-methoxypyridin-2-yl)-4H-1,2,4-triazole-3-carboxamide

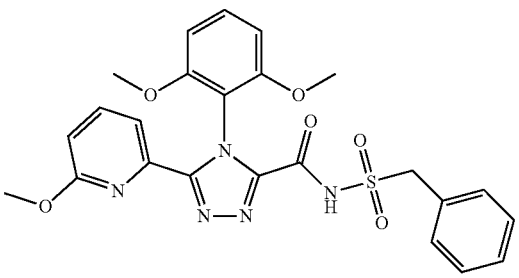 [SMILES: COc1cccc(-c2nnc(C(=O)NS(=O)(=O)Cc3ccccc3)n2-c2c(OC)cccc2OC)n1]

The title compound was prepared according to Method A, by using commercially available 6-methoxypicolinic acid in step C and phenylmethanesulfonyl chloride in step F.

¹H NMR (400 MHz, DMSO-d₆) δ 7.85 (t, J=7.6 Hz, 1H), 7.76 (d, J=7.2 Hz, 1H), 7.36-7.44 (m, 4H), 7.23=7.33 (m, 2H), 6.85 (d, J=8.0 Hz, 1H), 6.82 (d, J=8.4 Hz, 2H), 4.70 (s, 2H), 3.64 (s, 6H), 3.14 (s, 3H). LC-MS: m/z 510.1 (M+H)⁺

Example 14: N-(benzylsulfonyl)-4-(2,6-dimethoxyphenyl)-5-(6-methylpyridin-2-yl)-4H-1,2,4-triazole-3-carboxamide

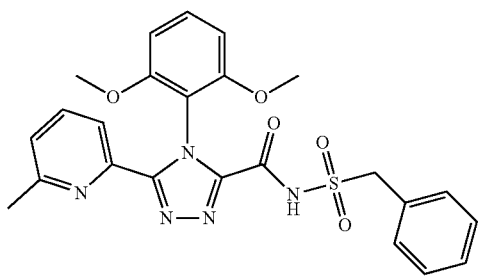 [SMILES: COc1cccc(OC)c1-n1c(C(=O)NS(=O)(=O)Cc2ccccc2)nnc1-c1cccc(C)n1]

The title compound was prepared according to Method A, by using commercially available 6-methylpicolinic acid in step C and phenylmethanesulfonyl chloride in step F.

$^1$H-NMR (400 MHz, DMSO-$d_6$) δ: 7.77-7.81 (m, 2H), 7.38-7.44 (m, 4H), 7.26-7.29 (m, 3H), 6.78 (d, J=8.4 Hz, 2H), 4.67 (s, 2H), 3.61 (s, 6H), 2.12 (s, 3H). LC-MS: m/z 494.1 (M+H)$^+$

Example 15: N-(benzylsulfonyl)-4-(2,6-dimethoxyphenyl)-5-(5-methylpyridin-2-yl)-4H-1,2,4-triazole-3-carboxamide

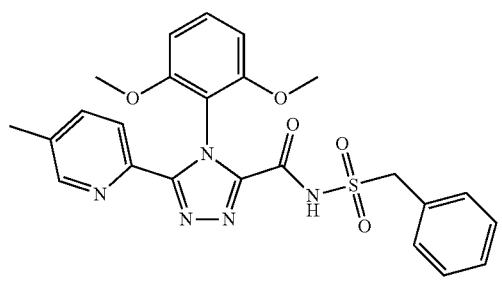 [SMILES: COc1cccc(OC)c1-n1c(C(=O)NS(=O)(=O)Cc2ccccc2)nnc1-c1ccc(C)cn1]

The title compound was prepared according to Method A, by using commercially available 5-methylpicolinic acid in step C and phenylmethanesulfonyl chloride in step F.

$^1$H NMR (400 MHz, DMSO-$d_6$) δ: 8.27 (s, 1H), 7.60-7.72 (m, 2H), 7.44 (t, J=8.4 Hz, 1H), 7.31-7.40 (m, 5H), 6.76 (d, J=8.4 Hz, 2H), 4.66 (s, 2H), 3.70 (s, 6H), 2.34 (s, 3H).

LC-MS: m/z 494.1 (M+H)$^+$

Method B:

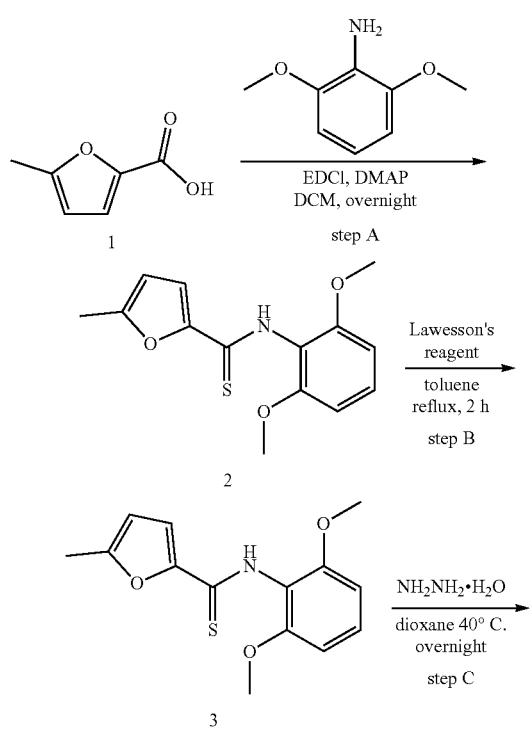

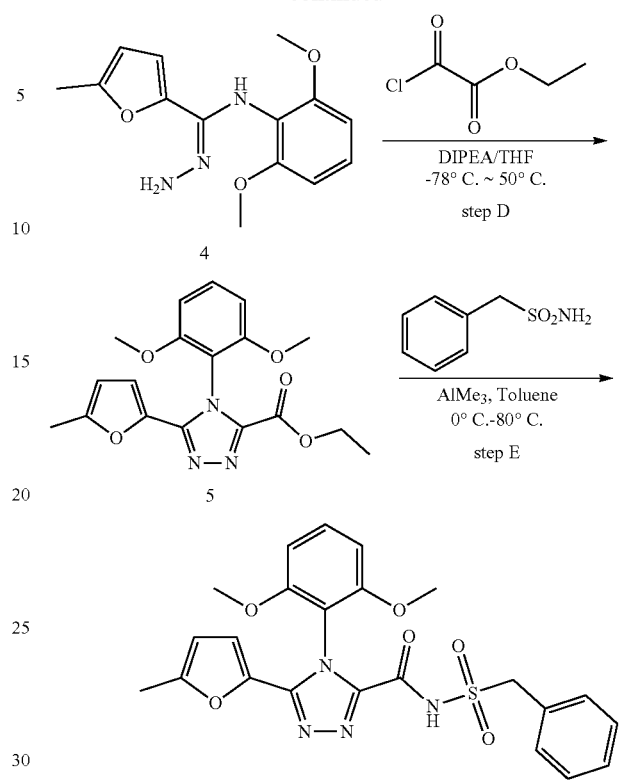

Step A: N-(2,6-dimethoxyphenyl)-5-methylfuran-2-carboxamide

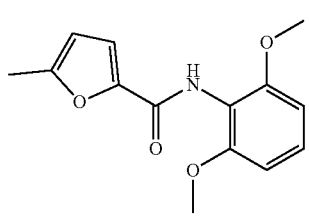

To a solution of 5-methylfuran-2-carboxylic acid (1.0 g, 8.0 mmol, 1 equiv) and 2,6-dimethoxyaniline (1.46 g, 9.5 mmol, 1.2 equiv) in DCM (10 mL) were added DMAP (44 mg, 0.4 mmol, 0.05 equiv) and EDCI (1.5 g, 9.6 mmol, 1.2 equiv) successively at room temperature. The resulting mixture was stirred at room temperature overnight. The reaction mixture was diluted with EtOAc (100 mL), washed with water (3*20 mL) and brine (50 mL), dried over anhydrous Na$_2$SO$_4$, and concentrated in vacuo. The residue was purified by flash column chromatography (eluted with PE/EtOAc=20/1~1/1) to afford the title compound N-(2,6-dimethoxyphenyl)-5-methylfuran-2-carboxamide as a white solid (1.23 g, 59% yield).

LC-MS: m/z 262.1 (M+H)$^+$

Step B: N-(2,6-dimethoxyphenyl)-5-methylfuran-2-carbothioamide

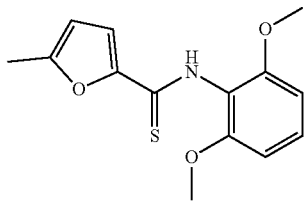

A solution of N-(2,6-dimethoxyphenyl)-5-methylfuran-2-carboxamide (1.0 g, 3.8 mmol, 1 equiv) and Lawesson's reagent (1.1 g, 2.7 mmol, 0.7 equiv) in toluene (50 mL) was stirred at 110° C. for 2 hours under $N_2$ atmosphere. The reaction mixture was concentrated and the residue was purified by flash column chromatography on silica gel (eluted with PE/EtOAc=5/1~1/1) to afford the title compound N-(2,6-dimethoxyphenyl)-5-methylfuran-2-carbothioamide as a yellow solid (880 mg, 83% yield).
LC-MS: m/z 278.1 (M+H)$^+$ Step C: N-(2,6-dimethoxyphenyl)-5-methylfuran-2-carbohydrazonamide

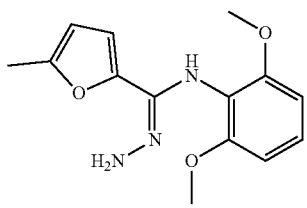 [SMILES: COc1cccc(OC)c1N/C(=N/N)c1ccc(C)o1]

To a suspension of N-(2,6-dimethoxyphenyl)-5-methylfuran-2-carbothioamide (200 mg, 0.72 mmol, 1 equiv) in 1,4-dioxane (5 mL) was added hydrazine hydrate (361 mg, 7.2 mmol, 10 equiv). The mixture was stirred at room temperature for 1 hour under $N_2$ atmosphere. The mixture was lyophilized to afford the crude title compound N-(2,6-dimethoxyphenyl)-5-methylfuran-2-carbohydrazonamide as a yellow solid (200 mg crude) which was used in next step directly.
LC-MS: m/z 276.1 (M+H)$^+$ Step D: ethyl 4-(2,6-dimethoxyphenyl)-5-(5-methylfuran-2-yl)-4H-1,2,4-triazole-3-carboxylate

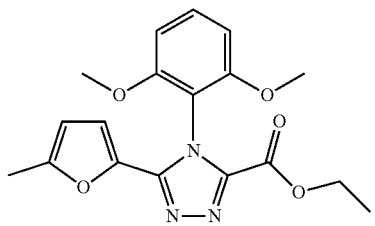 [SMILES: CCOC(=O)c1nnc(-c2ccc(C)o2)n1-c1c(OC)cccc1OC]

To a solution of N-(2,6-dimethoxyphenyl)-5-methylfuran-2-carbohydrazonamide (200 mg crude, 0.72 mmol, 1 equiv) in THF (10 mL) was added a solution of ethyl 2-chloro-2-oxoacetate (100 mg, 0.73 mmol, 1 equiv) in THF dropwise at −78° C. After addition, diisopropylethylamine (141 mg, 1.1 mmol, 1.5 equiv) was added dropwise. The mixture was warmed to room temperature gradually and stirred at 50° C. overnight. The mixture was diluted with EtOAc (30 mL) and then washed with water (15 mL). The organic phase was dried over anhydrous $Na_2SO_4$ and concentrated in vacuo. The residue was purified by flash column chromatography (eluted with PE/EtOAc=20/1~5/1) to afford the title compound ethyl 4-(2,6-dimethoxyphenyl)-5-(5-methylfuran-2-yl)-4H-1,2,4-triazole-3-carboxylate as a light yellow solid (130 mg, 50% yield in two steps).
LC-MS: m/z 358.1 (M+H)$^+$ Step E: N-(benzylsulfonyl)-4-(2,6-dimethoxyphenyl)-5-(5-methylfuran-2-yl)-4H-1,2,4-triazole-3-carboxamide (Example 16)

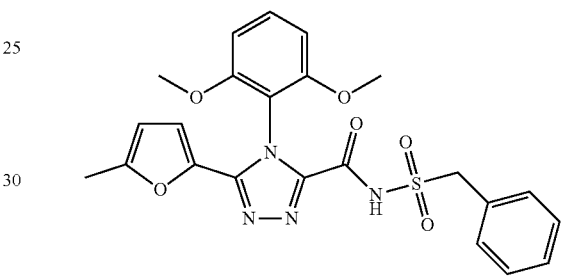

To a solution of phenylmethanesulfonamide (48 mg, 0.28 mmol, 2 equiv) in dry toluene (1 mL) was added $AlMe_3$ (1.6 mol/L in toluene, 0.35 mL, 0.56 mmol, 4 equiv) dropwise at 0° C. Then the mixture was stirred at 50° C. for 30 mins. Ethyl 4-(2,6-dimethoxyphenyl)-5-(5-methylfuran-2-yl)-4H-1,2,4-triazole-3-carboxylate (50 mg, 0.14 mmol, 1 equiv) was added and the mixture was stirred at 80° C. for 2 hours. The reaction mixture was quenched with water (10 mL), followed by extraction with EtOAc (3*10 mL). The combined organic layers were washed with brine (10 mL), dried over anhydrous $Na_2SO_4$ and concentrated in vacuo. The residue was purified by flash column chromatography (eluted with PE/EtOAc=20/1~5/1) to afford the title compound N-(benzylsulfonyl)-4-(2,6-dimethoxyphenyl)-5-(5-methylfuran-2-yl)-4H-1,2,4-triazole-3-carboxamide as a yellow solid (22 mg, 33% yield).
$^1$H NMR (400 MHz, DMSO-d$_6$) δ: 7.56 (t, J=8.4 Hz, 1H), 7.37-7.38 (m, 3H), 7.24-7.26 (m, 2H), 6.92 (d, J=8.4 Hz, 2H), 6.18 (dd, J=3.6 Hz, 1.2 Hz, 1H), 5.97 (d, J=3.2 Hz, 1H), 4.68 (s, 2H), 3.73 (s, 6H), 2.27 (s, 3H). LC-MS: m/z 483.1 (M+H)$^+$ Method C:

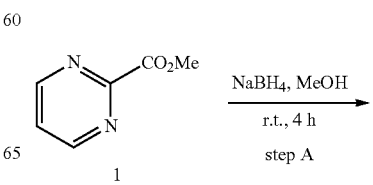

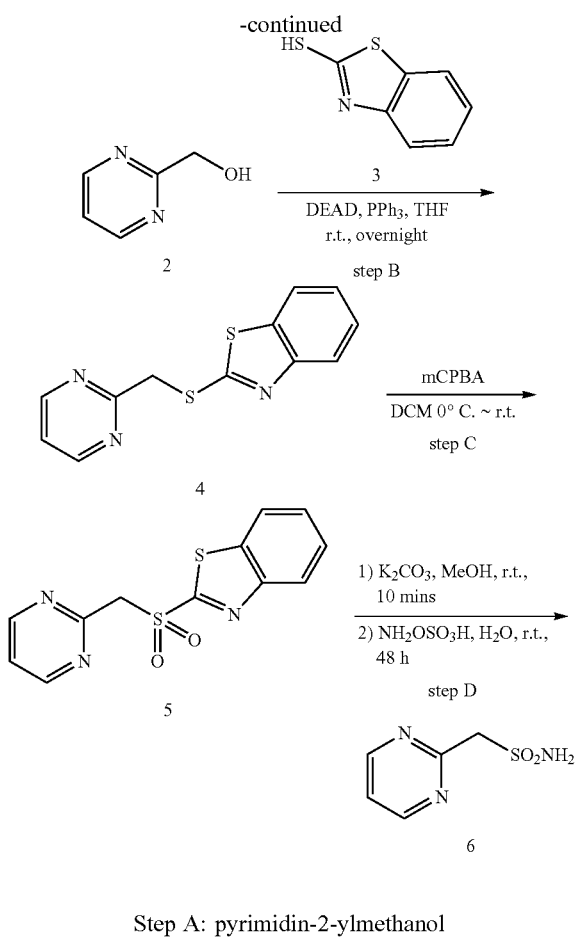

Step A: pyrimidin-2-ylmethanol

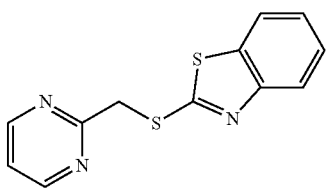 [SMILES: c1cnc(CSc2nc3ccccc3s2)nc1]

To a solution of methyl pyrimidine-2-carboxylate (25 g, 181 mmol, 1 equiv) in MeOH (500 mL) was added NaBH$_4$ (8.2 g, 217 mmol, 1.2 equiv) at 0° C. The reaction mixture was stirred at room temperature for 4 hours. The reaction mixture was quenched with H$_2$O (20 mL), concentrated in vacuo and the residue was purified by flash column chromatography (eluted with PE/EtOAc=1/1) to afford the title compound pyrimidin-2-ylmethanol as a yellow oil (16 g, 80% yield).

LC-MS: m/z 111.0 (M+H)$^+$

Step B: 2-((pyrimidin-2-ylmethyl)thio)benzo[d]thiazole

To a solution of pyrimidin-2-ylmethanol (16.6 g, 151 mmol, 1 equiv), benzo[d]thiazole-2-thiol (30 g, 181 mmol, 1.2 equiv) and PPh$_3$ (47.4 g, 181 mmol, 1.2 equiv) in THF (500 mL) was added DEAD (36.6 g, 181 mmol, 1.2 equiv) at 0° C. The mixture was stirred at room temperature for 16 hours. The reaction mixture was treated with HCl solution in dioxane and the white precipitate was collected via filtration. The solid was charged with 1N Na$_2$CO$_3$ aqueous solution (100 mL) and extracted with EtOAc (3*200 mL). The combined organic phase were concentrated in vacuo to afford the title compound 2-((pyrimidin-2-ylmethyl)thio)benzo[d]thiazole as a yellow solid (27 g, 77% yield).

LC-MS: m/z 260.0 (M+H)$^+$

Step C: 2-((pyrimidin-2-ylmethyl)sulfonyl)benzo[d]thiazole

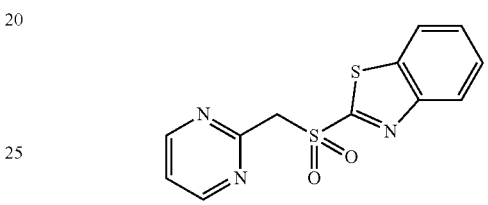

To a solution of 2-((pyrimidin-2-ylmethyl)thio)benzo[d]thiazole (27 g, 104 mmol, 1 equiv) in DCM (500 mL) was added m-CPBA (51 g, 249 mmol, 2.4 equiv). The mixture was stirred at room temperature for 16 hours. After the reaction completed, the solution was washed with 1N Na$_2$SO$_3$ aqueous solution, saturated Na$_2$CO$_3$ solution, brine, dried over anhydrous Na$_2$SO$_4$, filtered and concentrated in vacuo. The residue was purified by flash column chromatography (eluted with PE/EtOAc=5/1) to afford the title compound 2-((pyrimidin-2-ylmethyl)sulfonyl)benzo[d]thiazole as a white solid (17 g, 80% yield).

LC-MS: m/z 292.0 (M+H)$^+$

Step D: pyrimidin-2-ylmethanesulfonamide

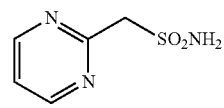

To a solution of 2-((pyrimidin-2-ylmethyl)sulfonyl)benzo[d]thiazole (500 mg, 1.7 mmol, 1 equiv) in MeOH (10 mL) was added K$_2$CO$_3$ (1.2 g, 8.5 mmol, 5 equiv). After the mixture was stirred at room temperature for 10 mins, NH$_2$OSO$_3$H (250 mg, 2.0 mmol, 1.2 equiv) in H$_2$O (1 mL) was added. The mixture was stirred at room temperature for 15 mins and another NH$_2$OSO$_3$H (250 mg, 2.0 mmol, 1.2 equiv) in H$_2$O (1 mL) was added. The resulting mixture was stirred at room temperature for 60 hours. The mixture was concentrated and the residue was purified by flash column chromatography (DCM/MeOH=50/1) to afford the title compound pyrimidin-2-ylmethanesulfonamide as a white solid (100 mg, 34% yield).

$^1$H NMR (400 MHz, DMSO-d$_6$) δ: 8.83 (d, J=4.8 Hz, 2H), 7.49 (t, J=4.8 Hz, 1H), 7.01 (s, 2H), 4.55 (s, 2H). LC-MS: m/z 174.0 (M+H)$^+$

Example 17: 4-(2,6-Dimethoxyphenyl)-5-(5-methyl-furan-2-yl)-N-((pyrimidin-2-ylmethyl)sulfonyl)-4H-1,2,4-triazole-3-carboxamide

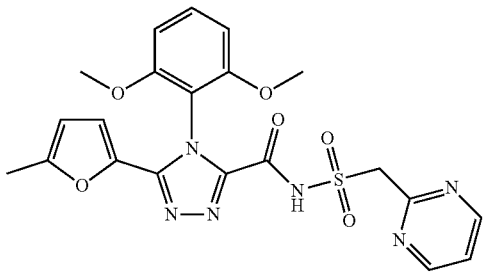 [SMILES: COc1cccc(OC)c1-n1c(C(=O)NS(=O)(=O)Cc2ncccn2)nnc1-c1ccc(C)o1]

The title compound was prepared according to Method B, by using pyrimidin-2-ylmethanesulfonamide in step E.

$^1$H NMR (400 MHz, CDCl$_3$) δ: 8.73 (d, J=4.8 Hz, 2H), 7.46 (t, J=8.4 Hz, 1H), 7.29 (t, J=4.8 Hz, 1H), 6.69 (d, J=8.4 Hz, 2H), 6.04 (d, J=3.6 Hz, 1H), 5.97 (d, J=3.6 Hz, 1H), 4.98 (s, 2H), 3.72 (s, 6H), 2.32 (s, 3H). LC-MS: m/z 485.1 (M+H)$^+$

Example 18: N-(benzylsulfonyl)-5-(6-cyclobutoxy-pyridin-2-yl)-4-(2,6-dimethoxyphenyl)-4H-1,2,4-triazole-3-carboxamide

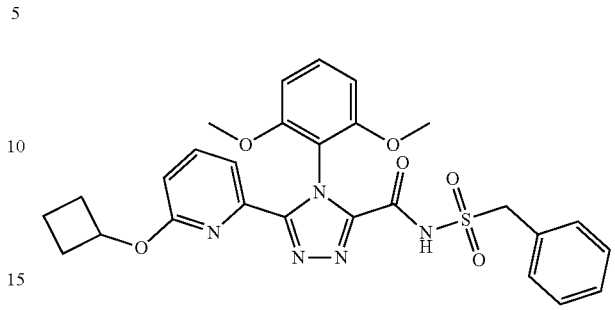

The title compound was prepared according to Method B, by using 6-cyclobutoxypicolinic acid in step A and phenyl-methanesulfonamide in step E.

$^1$H NMR (DMSO-d$_6$) δ: 7.84 (d, J=8.0 Hz, 1H), 7.72 (dd, J=7.2 Hz, 0.4 Hz 1H), 7.50 (t, J=8.4 Hz, 1H), 7.42-7.38 (m, 3H), 7.32-7.28 (m, 2H), 6.88 (d, J=8.0 Hz, 2H), 6.80 (dd, J=7.6 Hz, 0.4 Hz, 1H), 4.71 (s, 2H), 4.00-3.92 (m, 1H), 3.62 (s, 6H), 1.90-1.92 (m, 2H), 1.78-1.82 (m, 2H), 1.61-1.65 (m, 1H), 1.41-1.48 (m, 1H). LC-MS: m/z 550.2 (M+H)$^+$

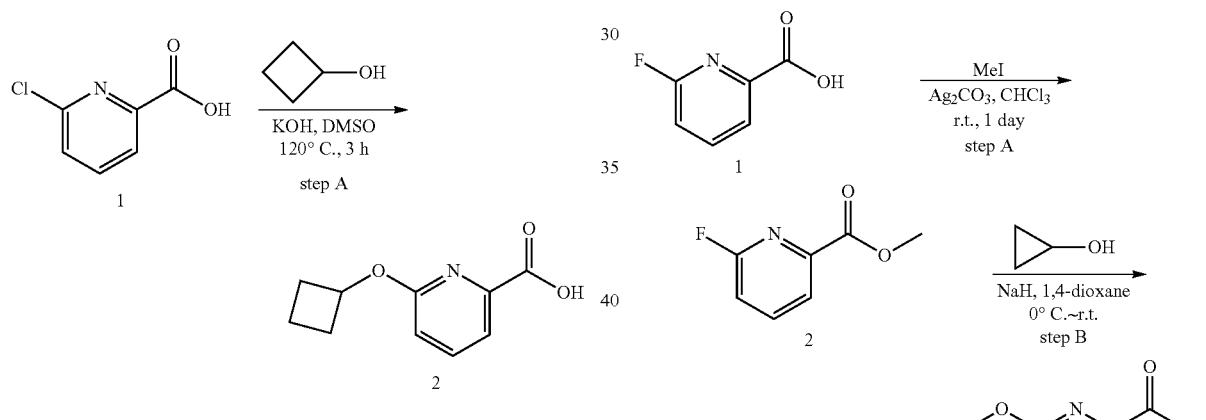

Step A: 6-cyclobutoxypicolinic Acid

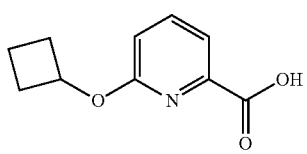 [SMILES: O=C(O)c1cccc(OC2CCC2)n1]

To a solution of 6-chloropicolinic acid (3.2 g, 20 mmol, 1 equiv) and cyclobutanol (1.9 g, 26 mmol, 1.3 equiv) in DMSO (30 mL) was added KOH (3.4 g, 60 mmol, 3 equiv). The resulting mixture was stirred at 120° C. for 3 hours. The reaction mixture was neutralized with 1 N HCl (aq.). The precipitate was collected, washed with water, dried in vacuo to afford the title compound 6-cyclobutoxypicolinic acid as a yellow solid (2.1 g, 48% yield).

LC-MS: m/z 194.0 (M+H)$^+$

Step A: methyl 6-fluoropicolinate

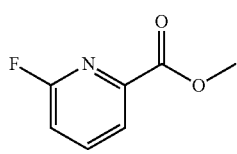

Methyl iodide (20 g, 142 mmol, 2 equiv) was added to a suspension of 6-fluoropicolinic acid (10.0 g, 71 mmol, 1 equiv) and silver(I) carbonate (19.5 g, 71 mmol, 1 equiv) in CHCl$_3$ (100 mL). The suspension was stirred at r.t. for 1 day. Insoluble material was removed by filtration and the filter cake was washed with CHCl₃. The filtrate was concentrated in vacuo to afford the title compound methyl 6-fluoropicolinate as a light yellow solid which was used in the next step without further purification (9.0 g, 82% yield).

LC-MS: m/z 156.0 (M+H)⁺

Step B: 6-cyclopropoxypicolinic Acid

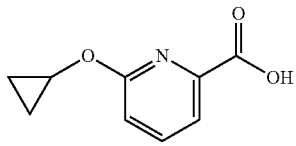 [SMILES: O=C(O)c1cccc(OC2CC2)n1]

To a mixture of cyclopropanol (1.5 g, 25.8 mmol, 3 equiv) in dry dioxane (20 mL) was added NaH (1.03 g, 25.8 mmol, 3 equiv) at 0° C. The mixture was stirred at 0° C. for 30 mins. Then methyl 6-fluoropicolinate (2.0 g, 12.9 mmol, 1 equiv) was added and the resulting mixture was stirred at room temperature for 2 hours. The reaction mixture was quenched with saturated aqueous NH₄Cl solution and washed with EtOAc three times. The aqueous phase was acidified with concentrated hydrochloric acid to pH=6 and extracted with DCM (3*30 mL). The extracts were washed with brine, dried over anhydrous Na₂SO₄ and concentrated in vacuo. The residue was purified by column chromatography on silica gel (eluted with DCM/MeOH=50/1~10/1) to afford the title compound 6-cyclopropoxypicolinic acid as a white solid (600 mg, 13% yield).

LC-MS: m/z 180.0 (M+H)⁺

Example 19: N-(benzylsulfonyl)-5-(6-cyclopropoxypyridin-2-yl)-4-(2,6-dimethoxyphenyl)-4H-1,2,4-triazole-3-carboxamide

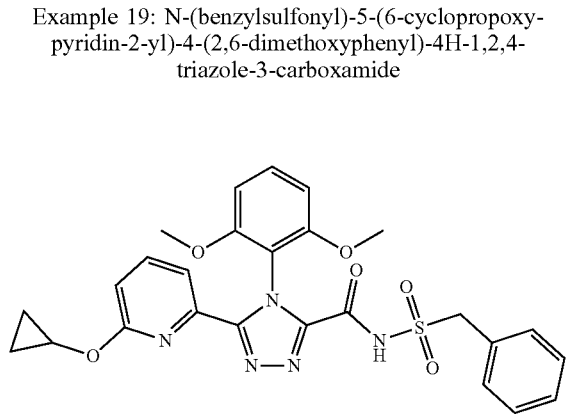

The title compound was prepared according to Method B, by using 6-cyclopropoxypicolinic acid in step A and phenylmethanesulfonamide in step E.

¹H NMR (400 MHz, DMSO-d₆) δ: 7.85 (t, J=8.0 Hz, 1H), 7.77 (d, J=4.0 Hz, 1H), 7.38-7.40 (m, 4H), 7.26-7.28 (m, 2H), 6.80-6.83 (m, 3H), 4.70 (s, 2H), 3.62 (s, 6H), 3.26-3.28 (m, 1H), 0.39-0.46 (m, 4H). LC-MS: m/z 536.1 (M+H)⁺

Example 20: 5-(6-Cyclopropoxypyridin-2-yl)-4-(2,6-dimethoxyphenyl)-N-((pyrimidin-2-ylmethyl)sulfonyl)-4H-1,2,4-triazole-3-carboxamide

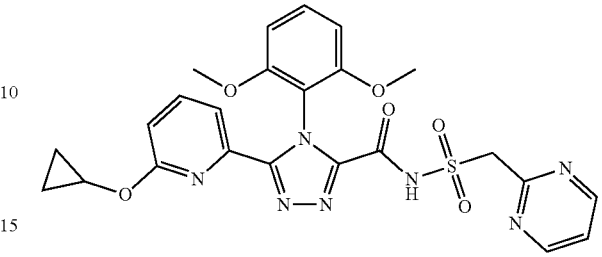

The title compound was prepared according to Method B, by using 6-cyclopropoxypicolinic acid in step A and pyrimidin-2-ylmethanesulfonamide in step E.

¹H NMR (400 MHz, DMSO-d₆) δ: 8.73 (d, J=4.8 Hz, 2H), 8.14 (s, 1H), 7.75 (t, J=8.0 Hz, 1H), 7.69 (d, J=7.2 Hz, 1H), 7.36 (t, J=4.8 Hz, 1H), 7.22 (t, J=8.4 Hz, 1H), 6.71 (d, J=8.0 Hz, 1H), 6.68 (d, J=8.4 Hz, 2H), 4.42 (s, 2H), 3.57 (s, 6H), 3.27-3.29 (m, 1H), 0.42-0.44 (m, 2H), 0.35-0.39 (m, 2H). LC-MS: m/z 538.1 (M+H)⁺

Example 21: N-(benzylsulfonyl)-5-(6-(difluoromethoxy)pyridin-2-yl)-4-(2,6-dimethoxyphenyl)-4H-1,2,4-triazole-3-carboxamide

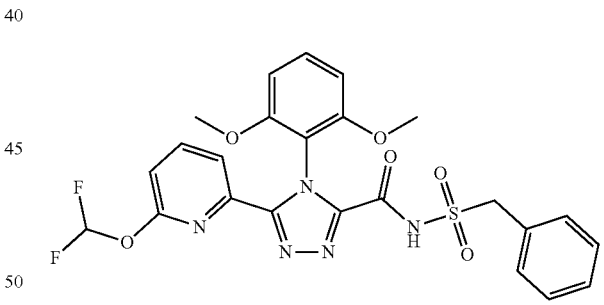

The title compound was prepared according to Method B, by using commercially available 6-(difluoromethoxy)picolinic acid in step A and phenylmethanesulfonamide in step E.

¹H NMR (400 MHz, DMSO-d₆) δ: 8.01-8.10 (m, 2H), 7.45 (t, J=8.4 Hz, 1H), 7.31-7.35 (m, 3H), 7.21-7.26 (m, 2H), 7.13 (d, J=8.0 Hz, 1H), 6.85 (dd, J=8.4 Hz, 0.8 Hz, 2H), 6.13 (t, J=72.8 Hz, 1H), 4.49 (s, 2H), 3.62 (s, 6H). LC-MS: m/z 546.1 (M+H)⁺

Example 22: 5-(6-(Difluoromethoxy)pyridin-2-yl)-4-(2,6-dimethoxyphenyl)-N-((pyrimidin-2-ylmethyl)sulfonyl)-4H-1,2,4-triazole-3-carboxamide

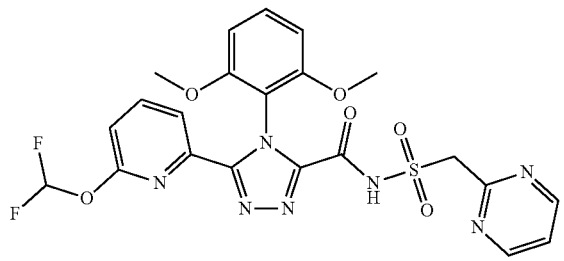

The title compound was prepared according to Method B, by using commercially available 6-(difluoromethoxy)picolinic acid in step A and pyrimidin-2-ylmethanesulfonamide in step E.

$^1$H NMR (400 MHz, DMSO-$d_6$) δ: 8.80 (d, J=4.8 Hz, 2H), 8.04-8.12 (m, 2H), 7.46-7.50 (m, 2H), 7.15 (d, J=8.0 Hz, 1H), 6.84 (d, J=8.4 Hz, 2H), 6.14 (t, J=72.8 Hz, 1H), 4.83 (s, 2H), 3.63 (s, 6H). LC-MS: m/z 548.1 (M+H)$^+$

Example 23: 4-(2,6-Dimethoxyphenyl)-5-(5-fluoro-6-methoxypyridin-2-yl)-N-((pyrimidin-2-ylmethyl)sulfonyl)-4H-1,2,4-triazole-3-carboxamide

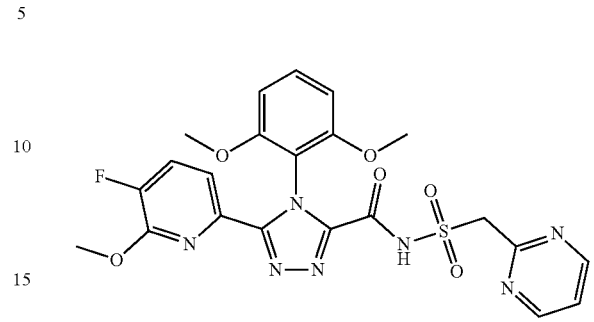

The title compound was prepared according to Method B, by using 5-fluoro-6-methoxypicolinic acid in step A and pyrimidin-2-ylmethanesulfonamide in step E.

$^1$H NMR (400 MHz, DMSO-$d_6$) δ: 8.81 (d, J=5.2 Hz, 2H), 7.77-7.87 (m, 2H), 7.50 (t, J=5.2 Hz, 1H), 7.39 (t, J=8.4 Hz, 1H), 6.80 (d, J=8.4 Hz, 2H), 4.86 (s, 2H), 3.63 (s, 6H), 3.23 (s, 3H). LC-MS: m/z 530.1 (M+H)$^+$.

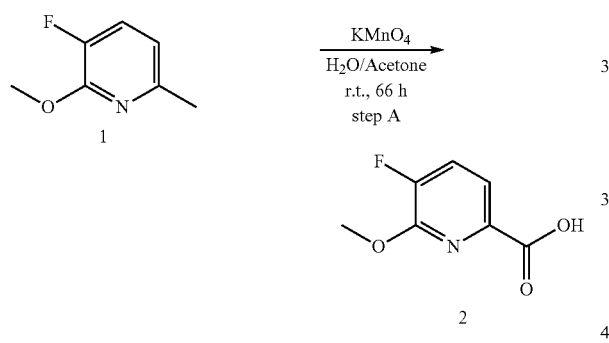

Step A: 5-fluoro-6-methoxypicolinic Acid

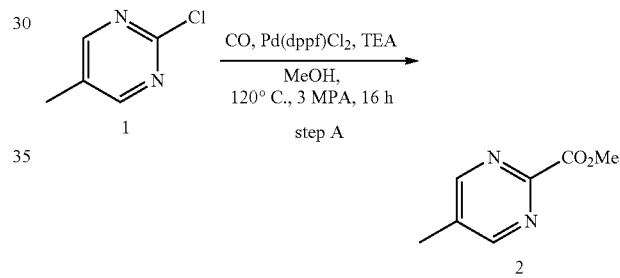

Step A: methyl 5-methylpyrimidine-2-carboxylate

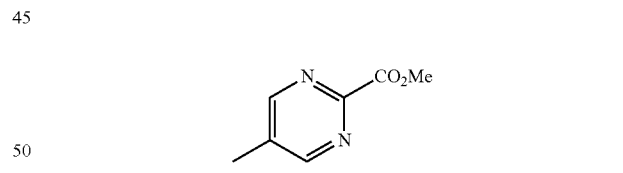

To a mixture of 3-fluoro-2-methoxy-6-methylpyridine (5 g, 35.46 mmol, 1 equiv) in acetone (140 mL) and water (80 mL) was added potassium permanganate (33.6 g, 212.8 mmol, 6 equiv) at room temperature. The resulting mixture was stirred at room temperature for 66 hours under $N_2$ atmosphere. Then the mixture was filtered. The filtrate was adjusted with 3 mol/L HCl solution to pH=4. Acetone was evaporated and the aqueous phase was extracted with ethyl acetate (3*60 mL). The combined organic layer were dried over anhydrous $Na_2SO_4$ and concentrated in vacuo to afford the title compound 5-fluoro-6-methoxypicolinic acid as a white solid (980 mg, 16% yield).

$^1$H NMR (400 MHz, DMSO-$d_6$) δ: 13.16 (br.s, 1H), 7.82-7.69 (m, 2H), 3.99 (s, 3H).

To a solution of 2-chloro-5-methyl-pyrimidine (10.0 g, 77.8 mmol, 1 equiv) in MeOH (200 mL) and DMF (40 mL) were added triethylamine (23.6 g, 233.4 mmol, 32.4 mL, 3 equiv) and Pd(dppf)Cl$_2$ (8.5 g, 11.7 mmol, 0.15 equiv). The suspension was degassed and purged with CO several times. The mixture was stirred under CO (3 Mpa) at 120° C. for 72 hours. The reaction mixture was filtered and the filtrate was concentrated. The residue was purified by column chromatography (eluted with PE/EtOAc=20/1~10/1) to afford the title compound methyl 5-methylpyrimidine-2-carboxylate as a light yellow solid (6.7 g, 57% yield).

LCMS: m/z: 153.1 (M+H)$^+$.

(5-Methylpyrimidin-2-yl)methanesulfonamide

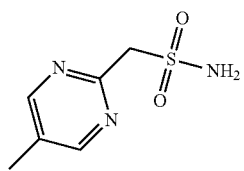

(5-Methylpyrimidin-2-yl)methanesulfonamide was prepared according to Method C, by using methyl 5-methylpyrimidine-2-carboxylate in step A.
LCMS: m/z 188.1 (M+H)+.

Example 24: 4-(2,6-Dimethoxyphenyl)-5-(5-methylpyridin-2-yl)-N-(((5-methylpyrimidin-2-yl)methyl)sulfonyl)-4H-1,2,4-triazole-3-carboxamide

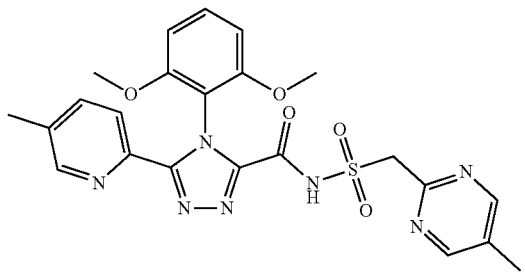

The title compound was prepared according to Method B, by using 5-methylpicolinic acid in step A and (5-methylpyrimidin-2-yl)methanesulfonamide in step E.
¹HNMR (400 MHz, DMSO-d₆) δ: 8.67 (s, 2H), 8.20 (s, 1H), 7.86 (d, J=8.0 Hz, 1H), 7.74 (d, J=8.0 Hz, 1H), 7.37 (t, J=8.4 Hz, 1H), 6.75 (d, J=8.4 Hz, 2H), 4.88 (s, 2H), 3.60 (s, 6H), 2.30 (s, 6H). LC-MS: m/z 510.1 (M+H)+

Example 25: 4-(2,6-Dimethoxyphenyl)-5-(4-methylpyridin-2-yl)-N-((pyrimidin-2-ylmethyl)sulfonyl)-4H-1,2,4-triazole-3-carboxamide

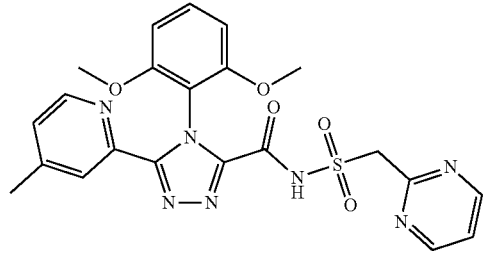 [SMILES: COc1cccc(OC)c1-n1c(C(=O)NS(=O)(=O)Cc2ncccn2)nnc1-c1cc(C)ccn1]

The title compound was prepared according to Method B, by using 4-methylpicolinic acid in step A and pyrimidin-2-ylmethanesulfonamide in step E.
¹H NMR (400 MHz, DMSO) δ: 8.15 (d, J=4.8 Hz, 2H), 8.18 (d, J=4.8 Hz, 1H), 7.84 (s, 1H), 7.50 (t, J=4.8 Hz, 1H), 7.36 (t, J=8.4 Hz, 1H), 7.24 (d, J=4.8 Hz, 1H), 6.73 (d, J=8.4 Hz, 2H), 4.86 (s, 2H), 3.58 (s, 6H), 2.38 (s, 3H). LC-MS: m/z 496.1 (M+H)+

Method D:

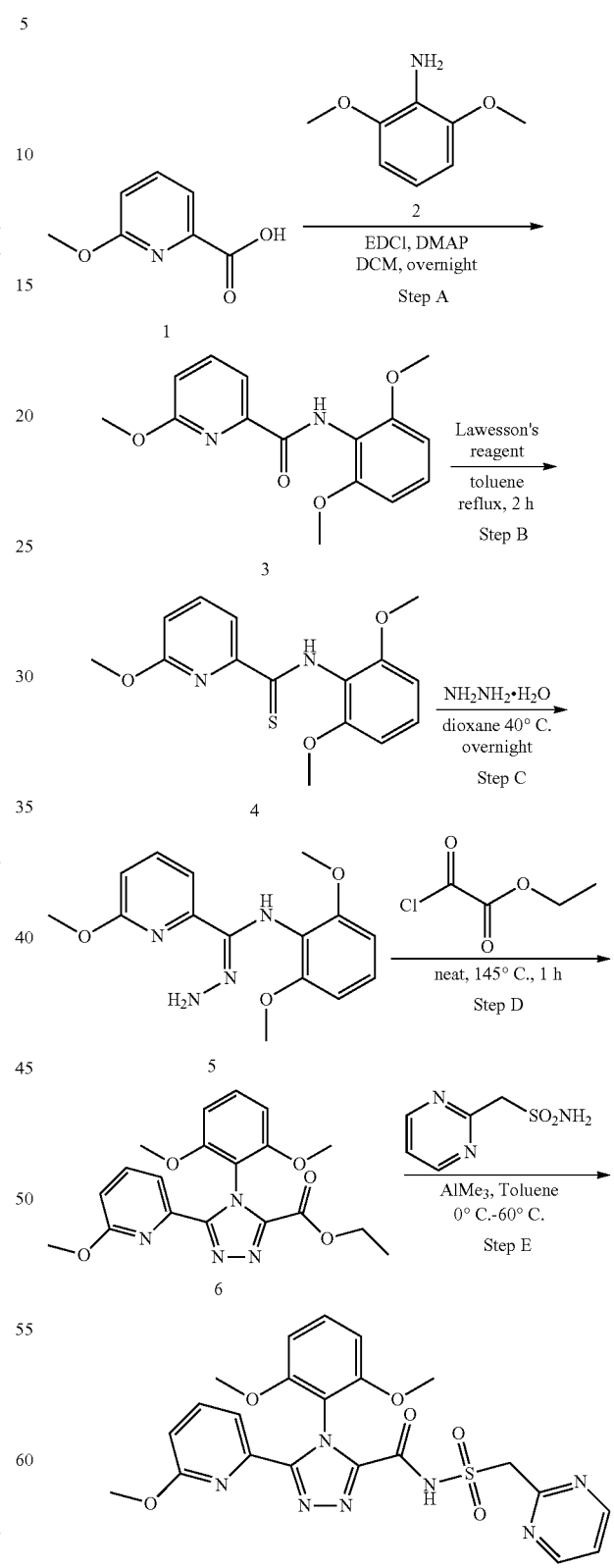

Example 26

Step A:
N-(2,6-dimethoxyphenyl)-6-methoxypicolinamide

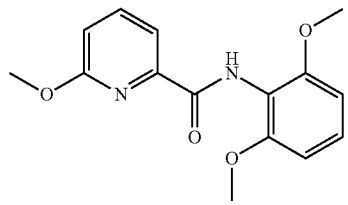

To a solution of 6-methoxypicolinic acid (15.0 g, 98.0 mmol, 1 equiv) and 2,6-dimethoxyaniline (16.5 g, 107.8 mmol, 1.1 equiv) in DCM (40 mL) was added DMAP (598 mg, 4.9 mmol, 0.05 equiv) and EDCI (22.5 g, 117.6 mmol, 1.2 equiv) successively at room temperature. The resulting mixture was stirred at room temperature overnight. The reaction solution was diluted with DCM (300 mL) and washed with water (3*100 mL). The organic layer was washed with brine (100 mL), dried over anhydrous $Na_2SO_4$ and concentrated in vacuo. The residue was purified by flash column chromatography eluted with PE/EtOAc (20/1-1/1) to afford the title N-(2,6-dimethoxyphenyl)-6-methoxypicolinamide as a solid (20 g, 71% yield).
LC-MS: m/z 289.1 (M+H)$^+$

Step B: N-(2, 6-dimethoxyphenyl)-6-ethoxypyridine-2-carbothioamide

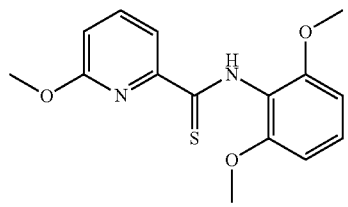

A mixture of N-(2,6-dimethoxyphenyl)-6-methoxypicolinamide (20 g, 69.4 mmol, 1 equiv) and Lawesson's Reagent (19.6 g, 48.5 mmol, 0.7 equiv) in toluene (30 mL) was stirred at 110° C. for 2 h under $N_2$ atmosphere. The reaction mixture was cooled to room temperature. The precipitate was collected and washed with EtOAc to afford the title compound N-(2, 6-dimethoxyphenyl)-6-ethoxypyridine-2-carbothioamide as a yellow solid (16 g, 76% yield).
LC-MS: m/z 305.1 (M+H)$^+$

Step C: N-(2,6-dimethoxyphenyl)-6-methoxypicolinohydrazonamide

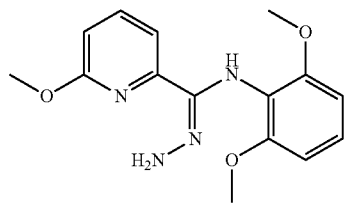 [SMILES: COc1cccc(/C(=N\N)Nc2c(OC)cccc2OC)n1]

To a suspension of N-(2, 6-dimethoxyphenyl)-6-ethoxypyridine-2-carbothioamide (16 g, 52.6 mmol, 1 equiv) in 1,4-dioxane (30 mL) was added hydrazine hydrate (26.0 g, 526 mmol, 10 equiv). The mixture was stirred at 40° C. overnight under $N_2$. Then the mixture was diluted with DCM (300 mL), washed with water (3*100 mL) and brine (100 mL) successively, dried over anhydrous $Na_2SO_4$ and concentrated in vacuo to afford the crude title compound N-(2,6-dimethoxyphenyl)-6-methoxypicolinohydrazonamide as a yellow solid which was used directly in the next step without further purification (16.0 g crude).
LC-MS: m/z 303.1 (M+H)$^+$

Step D: ethyl 4-(2,6-dimethoxyphenyl)-5-(6-methoxypyridin-2-yl)-4H-1,2,4-triazole-3-carboxylate

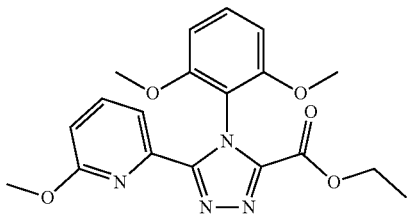 [SMILES: CCOC(=O)c1nnc(-c2cccc(OC)n2)n1-c1c(OC)cccc1OC]

A solution of N-(2,6-dimethoxyphenyl)-6-methoxypicolinohydrazonamide (16.0 g, 52.6 mmol, 1 equiv) in ethyl 2-chloro-2-oxoacetate (25 mL) was refluxed for 1 hour. The mixture was then concentrated in vacuo. The residue was purified by re-slurrying in EtOAc followed by flash column chromatography purification (eluted with EtOAc/DCM=1/10~1/1) to afford the title compound ethyl 4-(2,6-dimethoxyphenyl)-5-(6-methoxypyridin-2-yl)-4H-1,2,4-triazole-3-carboxylate as a light yellow solid (7.0 g, 35% yield in two steps).
LC-MS: m/z 385.1 (M+H)$^+$

Step E: 4-(2,6-dimethoxyphenyl)-5-(6-methoxypyridin-2-yl)-N-((pyrimidin-2-ylmethyl)sulfonyl)-4H-1,2,4-triazole-3-carboxamide (Example 26)

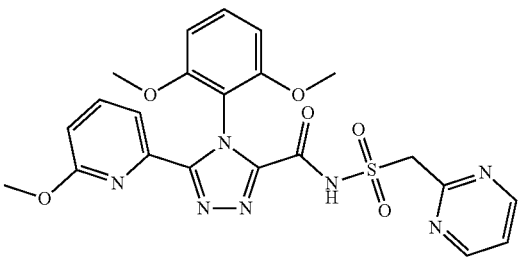

To a mixture of pyrimidin-2-ylmethanesulfonamide (108 mg, 0.624 mmol, 1.2 equiv) in toluene (2 mL) was added AlMe$_3$ (1.6 mol/L in toluene, 0.8 mL, 1.25 mmol, 2.4 equiv) dropwise at 0° C. The mixture was stirred at 0° C. for 0.5 hour. Then ethyl 4-(2,6-dimethoxyphenyl)-5-(6-methoxypyridin-2-yl)-4H-1,2,4-triazole-3-carboxylate (200 mg, 0.52 mmol, 1 equiv) was added. The resulting mixture was stirred at 60° C. for 18 hours. The mixture was cooled to 0° C. and formic acid solution (5% in water, 1 mL) was added carefully to quench the reaction. The mixture was extracted with DCM (3*20 mL). The combined organic layers were washed with brine, dried over anhydrous Na$_2$SO$_4$ and concentrated in vacuo. The residue was purified by reverse phase HPLC (eluted with MeOH/H$_2$O=5/95~95/5) to afford the title compound 4-(2,6-dimethoxyphenyl)-5-(6-methoxypyridin-2-yl)-N-((pyrimidin-2-ylmethyl)sulfonyl)-4H-1,2,4-triazole-3-carboxamide as a light yellow solid (105 mg, 40% yield).

$^1$HNMR (400 MHz, DMSO-d$_6$) δ: 8.12 (d, J=4.8 Hz, 2H), 7.83 (t, J=7.6 Hz, 1H), 7.75 (d, J=7.2 Hz, 1H), 7.50 (t, J=4.8 Hz, 1H), 7.37 (t, J=8.4 Hz, 1H), 6.84 (d, J=8.0 Hz, 1H), 6.78 (d, J=8.4 Hz, 2H), 4.89 (s, 2H), 3.62 (s, 6H), 3.13 (s, 3H). LC-MS: m/z 512.2 (M+H)$^+$

Example 27: 4-(2,6-Dimethoxyphenyl)-5-(6-methoxypyridin-2-yl)-N-(((5-methylpyrimidin-2-yl)methyl)sulfonyl)-4H-1,2,4-triazole-3-carboxamide

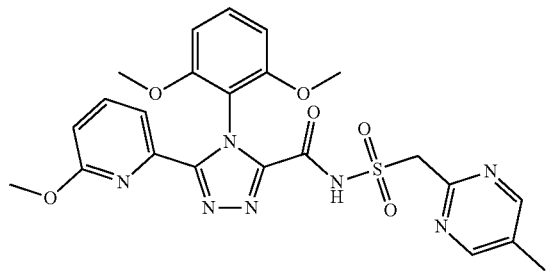

The title compound was prepared according to Method D, by using (5-methylpyrimidin-2-yl)methanesulfonamide in step E.

$^1$H NMR (400 MHz, CDCl$_3$) δ: 8.56 (s, 2H), 7.88 (d, J=8.4 Hz, 1H), 7.67 (t, J=8.4 Hz, 1H), 7.33 (t, J=8.4 Hz, 1H), 6.72 (d, J=8.0 Hz, 1H), 6.62 (d, J=8.4 Hz, 2H), 4.95 (s, 2H), 3.67 (s, 6H), 3.18 (s, 3H), 2.32 (s, 3H). LC-MS: m/z 526.1 (M+H)$^+$

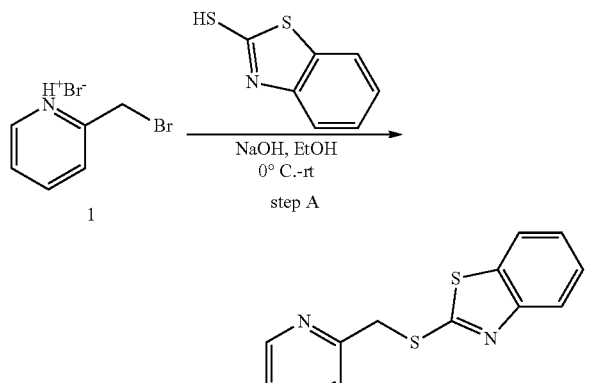

Step A: 2-((pyridin-2-ylmethyl)thio)benzo[d]thiazole

To a solution of NaOH (7.9 g, 197.8 mmol, 2.5 equiv) in EtOH (200 mL) was added benzo[d]thiazole-2-thiol (13.2 g, 79.1 mmol, 1 equiv) at 0° C. Then 2-(bromomethyl)pyridin-1-ium bromide (20 g, 79.1 mmol, 1 equiv) was added in portions. The mixture was stirred at room temperature overnight. The reaction solution was diluted with water (100 mL). EtOH was removed under reduced pressure. The aqueous phase was extracted with EtOAc (3*100 mL). The combined organic layer was washed with brine, dried over anhydrous Na$_2$SO$_4$ and concentrated in vacuo. The residue was purified by flash column chromatography (eluted with PE/EtOAc=10/1~1/1) to afford the title compound 2-((pyridin-2-ylmethyl)thio)benzo[d]thiazole as an off-white solid (16.9 g, 83% yield).

LC-MS: m/z 259.0 (M+H)$^+$

Pyridin-2-ylmethanesulfonamide

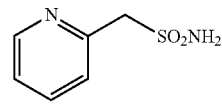 [SMILES: NS(=O)(=O)Cc1ccccn1]

Pyridin-2-ylmethanesulfonamide was prepared according to the preparation of pyrimidin-2-ylmethanesulfonamide in Method C, by using 2-((pyridin-2-ylmethyl)thio)benzo[d]thiazole in step C.

LC-MS: m/z 173.0 (M+H)$^+$

Example 28: 4-(2,6-Dimethoxyphenyl)-5-(6-methoxypyridin-2-yl)-N-((pyridin-2-ylmethyl)sulfonyl)-4H-1,2,4-triazole-3-carboxamide

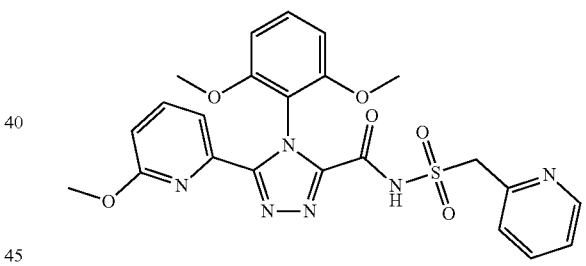

The title compound was prepared according to Method D, by using pyridin-2-ylmethanesulfonamide in step E.

$^1$HNMR (400 MHz, DMSO-d$_6$) δ: 8.55 (d, J=4.8 Hz, 2H), 7.84-7.89 (m, 2H), 7.75 (d, J=7.2 Hz, 1H), 7.38-7.47 (m, 3H), 6.85 (d, J=8.0 Hz, 1H), 6.80 (d, J=8.8 Hz, 2H), 4.83 (s, 2H), 3.63 (s, 6H), 3.14 (s, 3H). LC-MS: m/z 511.0 (M+H)$^+$

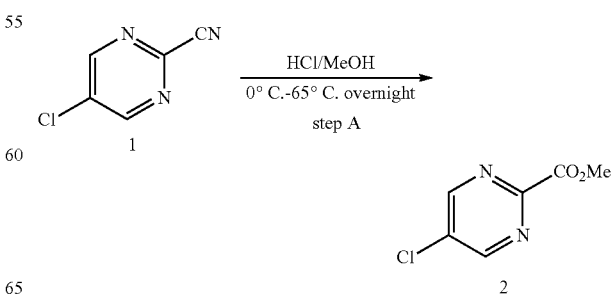

Step A: methyl 5-chloropyrimidine-2-carboxylate

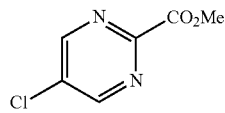 [SMILES: COC(=O)c1ncc(Cl)cn1]

A solution of 5-chloropyrimidine-2-carbonitrile (4.9 g, 35.5 mmol, 1 equiv) in MeOH (10 mL) was added HCl/MeOH (4 mol/L, 155 mL, 620.0 mmol, 17.5 equiv) at 0° C. The mixture was stirred at 65° C. overnight. The reaction mixture was concentrated and the residue was charged with $Na_2CO_3$ (10% aq., 50 mL), extracted with DCM (3*50 mL). The combined organic phase was washed with brine, dried over anhydrous $Na_2SO_4$ and concentrated in vacuo. The residue was purified by reverse phase HPLC (eluted with MeOH/$H_2O$=5/95~95/5) to afford the title compound methyl 5-chloropyrimidine-2-carboxylate as a white solid (3.0 g, 49.0% yield).

$^1$H NMR (400 MHz, DMSO-$d_6$) δ: 9.12 (s, 2H), 3.92 (s, 3H). LC-MS: m/z 173.0 (M+H)$^+$ (5-Chloropyrimidin-2-yl)methanesulfonamide

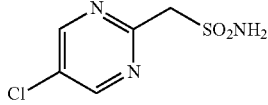 [SMILES: NS(=O)(=O)Cc1ncc(Cl)cn1]

(5-Chloropyrimidin-2-yl)methanesulfonamide was prepared according to the preparation of pyrimidin-2-ylmethanesulfonamide in Method C, by using methyl 5-chloropyrimidine-2-carboxylate in step A.

LC-MS: m/z 208.0 (M+H)$^+$

Example 29: N-(((5-chloropyrimidin-2-yl)methyl)sulfonyl)-4-(2,6-dimethoxyphenyl)-5-(6-methoxypyridin-2-yl)-4H-1,2,4-triazole-3-carboxamide

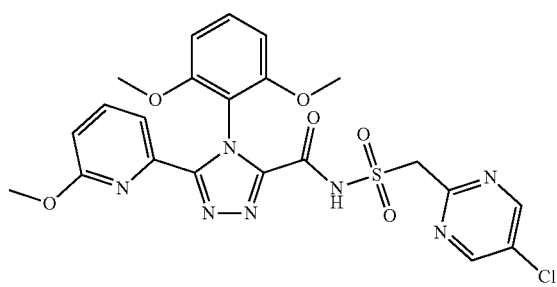 [SMILES: COc1cccc(-c2nnc(C(=O)NS(=O)(=O)Cc3ncc(Cl)cn3)n2-c2c(OC)cccc2OC)n1]

The title compound was prepared according to Method D, by using (5-chloropyrimidin-2-yl)methanesulfonamide in step E.

$^1$H NMR (400 MHz, DMSO-$d_6$) δ: 8.94 (s, 2H), 7.84 (t, J=8.0 Hz, 1H), 7.75 (d, J=7.2 Hz, 1H), 7.37 (t, J=8.4 Hz, 1H), 6.85 (d, J=8.0 Hz, 1H), 6.78 (d, J=8.4 Hz, 2H), 4.86 (s, 2H), 3.61 (s, 6H), 3.13 (s, 3H). LC-MS: m/z 545.8 (M+H)$^+$

(3-Fluorophenyl)methanesulfonamide

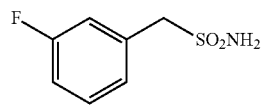

(3-Fluorophenyl)methanesulfonamide was prepared according to the preparation of pyrimidin-2-ylmethanesulfonamide in Method C, by using (3-fluorophenyl)methanol in step B.

$^1$HNMR (400 MHz, DMSO-$d_6$) δ: 7.41-7.43 (m, 1H), 7.18-7.22 (m, 3H), 6.92 (br.s, 2H), 4.31 (s, 2H). LC-MS: m/z 190.0 (M+H)$^+$

Example 30: 4-(2,6-Dimethoxyphenyl)-N-((3-fluorobenzyl)sulfonyl)-5-(6-methoxypyridin-2-yl)-4H-1,2,4-triazole-3-carboxamide

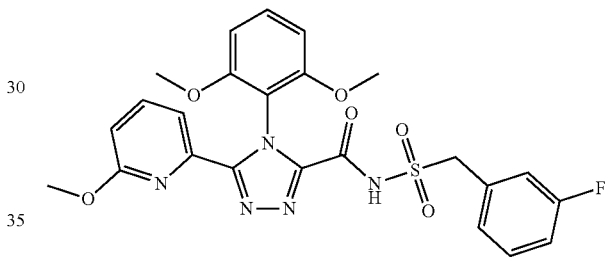

The title compound was prepared according to Method D, by using (3-fluorophenyl)methanesulfonamide in step E.

$^1$H NMR (400 MHz, CDCl$_3$) δ: 7.84 (t, J=4.0 Hz, 1H), 7.52 (d, J=4.0 Hz, 1H), 7.39-7.46 (m, 2H), 7.20-7.25 (m, 1H), 7.09-7.12 (m, 2H), 6.84 (d, J=4.0 Hz, 1H), 6.80 (d, J=4.0 Hz, 2H), 4.69 (s, 2H), 3.62 (s, 6H), 3.14 (s, 3H). LC-MS: m/z 528.1 (M+H)$^+$

(4-Fluorophenyl)methanesulfonamide

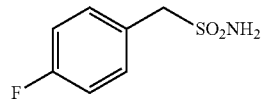

(4-Fluorophenyl)methanesulfonamide was prepared according to the preparation of pyrimidin-2-ylmethanesulfonamide in Method C, by using (4-fluorophenyl)methanol in step B.

$^1$H NMR (400 MHz, DMSO) δ: 7.38-7.41 (m, 2H), 7.18-7.23 (m, 2H), 6.82 (s, 2H), 4.26 (s, 2H). LC-MS: m/z 190.0 (M+H)$^+$

Example 31: 4-(2,6-Dimethoxyphenyl)-N-((4-fluorobenzyl)sulfonyl)-5-(6-methoxypyridin-2-yl)-4H-1,2,4-triazole-3-carboxamide

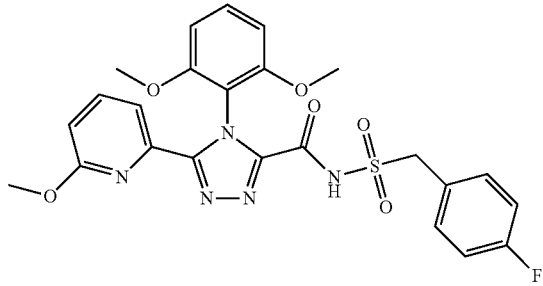 [SMILES: COc1cccc(-c2nnc(C(=O)NS(=O)(=O)Cc3ccc(F)cc3)n2-c2c(OC)cccc2OC)n1]

The title compound was prepared according to Method D, by using (4-fluorophenyl)methanesulfonamide in step E.

$^1$H NMR (400 MHz, DMSO-d$_6$) δ 7.85 (t, J=7.6 Hz, 1H), 7.75 (d, J=7.6 Hz, 1H), 7.40 (t, J=8.4 Hz, 1H), 7.28-7.34 (m, 2H), 7.24 (t, J=8.8 Hz, 2H), 6.80-6.86 (m, 3H), 4.69 (s, 2H), 3.63 (s, 6H), 3.14 (s, 3H). LC-MS: m/z 528.1 (M+H)$^+$

1-Phenylethanesulfonamide

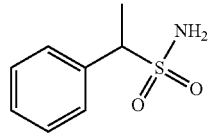

1-Phenylethanesulfonamide was prepared according to the preparation of pyrimidin-2-ylmethanesulfonamide in Method C, by using 1-phenylethanol in step B.

LC-MS: m/z 186.0 (M+H)$^+$

Example 32: (S)-4-(2,6-Dimethoxyphenyl)-5-(6-methoxypyridin-2-yl)-N-((1-phenylethyl)sulfonyl)-4H-1,2,4-triazole-3-carboxamide

Example 33: (R)-4-(2,6-Dimethoxyphenyl)-5-(6-methoxypyridin-2-yl)-N-((1-phenylethyl)sulfonyl)-4H-1,2,4-triazole-3-carboxamide

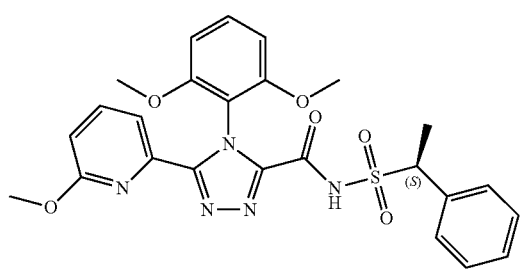

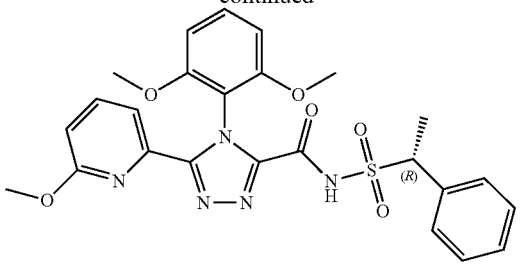

The title compounds were prepared according to Method D, by using 1-phenylethanesulfonamide in step E. The racemate was separated by chiral separation and chirality of the two enantiomers was assigned arbitrarily.

$^1$H-NMR (400 MHz, DMSO-d$_6$) δ 7.85 (t, J=8.0 Hz, 1H), 7.75 (d, J=7.2 Hz, 1H), 7.33-7.43 (m, 6H), 6.79-6.86 (m, 3H), 4.75 (q, J=7.2 Hz, 1H), 3.62 (d, J=4.0 Hz, 6H), 3.13 (s, 3H), 1.66 (d, J=7.2 Hz, 3H). LC-MS: m/z 524.0 (M+H)$^+$

Cyclohexylmethanesulfonamide

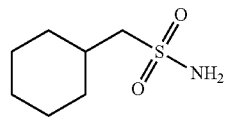 [SMILES: NS(=O)(=O)CC1CCCCC1]

Cyclohexylmethanesulfonamide was prepared according to the preparation of 2-(pyridin-3-yl)ethanesulfonamide in Method F, by using (bromomethyl)cyclohexane in step D.

$^1$H NMR (400 MHz, DMSO-d$_6$) δ: 6.74 (s, 2H), 2.86 (d, J=4.0 Hz, 2H), 1.63-1.87 (m, 6H), 1.02-1.26 (m, 5H).

Example 34: N-((cyclohexylmethyl)sulfonyl)-4-(2,6-dimethoxyphenyl)-5-(6-methoxypyridin-2-yl)-4H-1,2,4-triazole-3-carboxamide

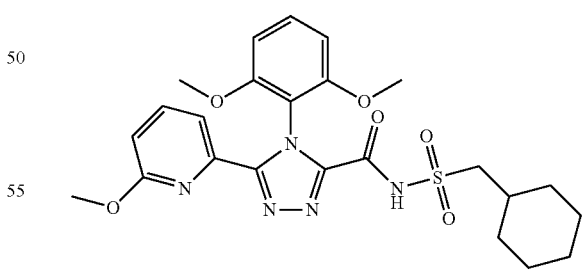

The title compound was prepared according to Method D, by using cyclohexylmethanesulfonamide in step E.

$^1$H NMR (400 MHz, DMSO-d$_6$) δ: 7.82 (t, J=8.0 Hz, 1H), 7.71 (d, J=8.0 Hz, 1H), 7.34 (t, J=8.0 Hz, 1H), 6.81 (d, J=8.0 Hz, 1H), 6.75 (d, J=8.0 Hz, 2H), 3.58 (s, 6H), 3.13 (s, 3H), 3.02 (s, 2H), 1.58-1.80 (m, 6H), 0.95-1.26 (m, 5H). LC-MS: m/z 516.1 (M+H)$^+$

Example 35: N-((cyclopropylmethyl)sulfonyl)-4-(2,6-dimethoxyphenyl)-5-(6-methoxypyridin-2-yl)-4H-1,2,4-triazole-3-carboxamide

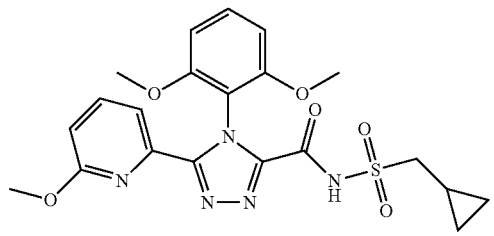 [SMILES: COc1cccc(-c2nnc(C(=O)NS(=O)(=O)CC3CC3)n2-c2c(OC)cccc2OC)n1]

The title compound was prepared according to Method D, by using commercially available cyclopropylmethanesulfonamide in step E.

¹H NMR (400 MHz, DMSO-d₆) δ: 7.85 (t, J=8.0 Hz, 1H), 7.77 (d, J=7.2 Hz, 1H), 7.38 (t, J=8.4 Hz, 1H), 6.85 (d, J=8.4 Hz, 1H), 6.78 (d, J=8.8 Hz, 2H), 3.59 (s, 6H), 3.31 (d, J=6.8 Hz, 2H), 3.12 (s, 3H), 0.95-1.04 (m, 1H), 0.53-0.61 (m, 2H), 0.29 (dt, J=9.2 Hz, 4.4 Hz, 2H). LC-MS: m/z 474.1 (M+H)⁺

Pyrimidin-5-ylmethanesulfonamide

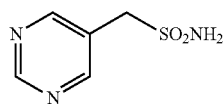

Pyrimidin-5-ylmethanesulfonamide was prepared according to the preparation of pyrimidin-2-ylmethanesulfonamide in Method C, by using pyrimidin-5-ylmethanol in step B.

¹H NMR (400 MHz, DMSO-d₆) δ: 9.16 (s, 1H), 8.77 (s, 2H), 7.03 (s, 2H), 4.38 (s, 2H). LC-MS: m/z 174.0 (M+H)⁺

Example 36: 4-(2,6-Dimethoxyphenyl)-5-(6-methoxypyridin-2-yl)-N-((pyrimidin-5-ylmethyl)sulfonyl)-4H-1,2,4-triazole-3-carboxamide

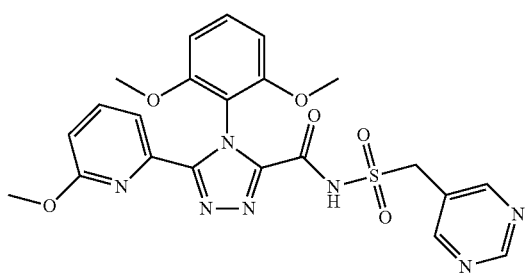 [SMILES: COc1cccc(-c2nnc(C(=O)NS(=O)(=O)Cc3cncnc3)n2-c2c(OC)cccc2OC)n1]

The title compound was prepared according to Method D, by using pyrimidin-5-ylmethanesulfonamide in step E.

¹H NMR (400 MHz, CDCl₃) δ: 9.20 (s, 1H), 8.72 (s, 2H), 7.88 (d, J=7.2 Hz, 1H), 7.66 (t, J=8.0 Hz, 1H), 7.38 (t, J=8.4 Hz, 1H), 6.73 (d, J=8.4 Hz, 1H), 6.66 (d, J=8.4 Hz, 2H), 4.68 (s, 2H), 3.72 (s, 6H), 3.18 (s, 3H). LC-MS: 512.2 (M+H)⁺.

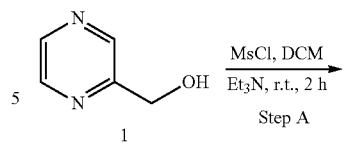

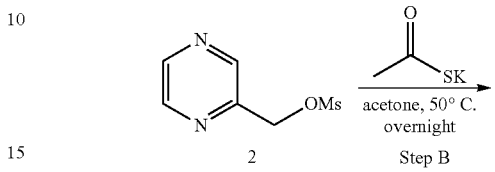

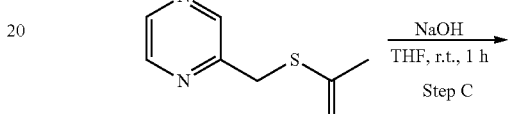

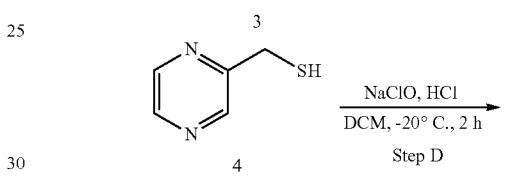

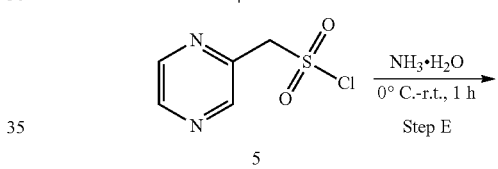

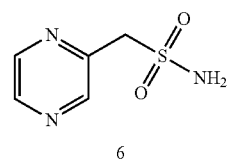

Step A: pyrazin-2-ylmethyl Methanesulfonate

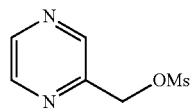

To a solution of pyrazin-2-ylmethanol (550 mg, 5 mmol, 1 equiv) and triethylamine (1.52 mL, 11 mmol, 2.2 equiv) in DCM (15 mL) was added MsCl (1.26 g, 11 mmol, 2.2 equiv) dropwise. The resulting mixture was stirred at room temperature for 2 hours. The reaction mixture was diluted with water and extracted with DCM (3*50 mL). The combined organic phase were dried over MgSO₄ and concentrated in vacuo to afford the title compound pyrazin-2-ylmethyl methanesulfonate as a yellow solid which was used for the next step without any further purification (940 mg crude).

LC-MS: m/z 189.0 (M+H)⁺

Step B: S-(pyrazin-2-ylmethyl) Ethanethioate

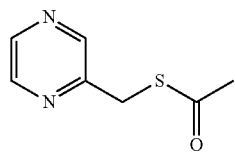

To the solution of pyrazin-2-ylmethyl methanesulfonate (940 mg crude, 5 mmol, 1 equiv) in acetone (30 mL) was added potassium ethanethioate (857 mg, 7.5 mmol, 1.5 equiv). The resulting mixture was stirred at 50° C. overnight. The mixture was filtered and the filtrate was concentrated in vacuo. The residue was purified by column chromatography (PE/EtOAc=10/1) to afford the title compound S-(pyrazin-2-ylmethyl) ethanethioate as a yellow solid (240 mg, 29% yield in two steps).

LC-MS: m/z 169.0 (M+H)$^+$

Step C: pyrazin-2-ylmethanethiol

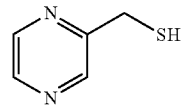

To a solution of S-(pyrazin-2-ylmethyl) ethanethioate (1.0 g, 5.95 mmol, 1 equiv) in THF (15 mL) was added KOH (1.0 g, 17.8 mmol, 3 equiv) in water (5 mL) at room temperature. The mixture was then stirred at room temperature for 1 hour. The reaction mixture was adjusted to pH=6 with 1 mol/L HCl aqueous solution and extracted with DCM (3*15 mL). The combined organic phase was washed with brine (10 mL), dried over anhydrous Na$_2$SO$_4$, filtered and concentrated in vacuo to afford the title compound pyrazin-2-ylmethanethiol as a yellow oil which was used directly in the next step without purification (750 mg crude).

Step D: pyrazin-2-ylmethanesulfonyl Chloride

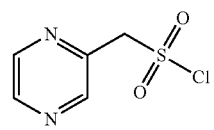 [SMILES: O=S(=O)(Cl)Cc1cnccn1]

Sodium hypochlorite solution (26.6 mL, 35.7 mmol, 6 equiv) was added dropwise to a rapidly stirring solution of pyrazin-2-ylmethanethiol (750 mg crude, 5.95 mmol, 1 equiv) in DCM (36 mL) and 1N HCl (35.7 mL, 35.7 mmol, 6 equiv) at −20° C. After addition, the mixture was stirred at −20° C. for 2 hours. The organic layer was separated and used directly in the next step.

Step E: pyrazin-2-ylmethanesulfonamide

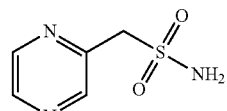

The solution of pyrimidine-2-sulfonyl chloride in DCM (36 mL) was added to NH$_4$OH (aq., 34%, 60 mL) at 0° C. The mixture was allowed to warm to room temperature slowly and stirred for 1 hour. The mixture was concentrated under vacuum and the residue was purified by silica gel chromatography (eluted with DCM/MeOH=20/1) to afford the title compound pyrazin-2-ylmethanesulfonamide as a brown solid (180 mg, 1.0 mmol, 17% yield in three steps).

LC-MS: m/z 174.0 (M+H)$^+$

Example 37: 4-(2,6-Dimethoxyphenyl)-5-(6-methoxypyridin-2-yl)-N-((pyrazin-2-ylmethyl)sulfonyl)-4H-1,2,4-triazole-3-carboxamide

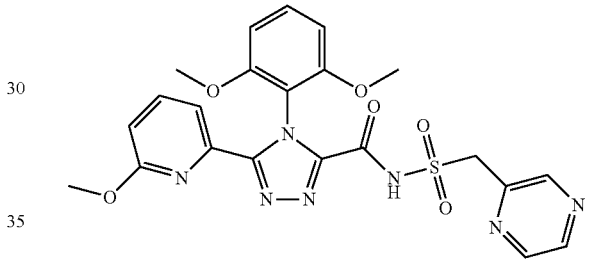

The title compound was prepared according to Method D, by using pyrazin-2-ylmethanesulfonamide in step E.

$^1$H NMR (400 MHz, DMSO-d$_6$) δ: 8.55 (dd, J=1.6 Hz, 1.2 Hz, 1H), 8.50 (d, J=2.0 Hz, 2H), 7.78 (dd, J=8.4 Hz, 7.6 Hz, 1H), 7.67 (dd, J=7.2 Hz, 0.8 Hz, 1H), 7.28 (t, J=8.4 Hz, 1H), 6.75 (dd, J=8.4 Hz, 0.8 Hz, 1H), 6.71 (d, J=8.4 Hz, 2H), 4.38 (s, 2H), 3.59 (s, 6H), 3.13 (s, 3H). LC-MS: m/z 512.1 (M+H)$^+$

Example 38: 4-(2,6-Dimethoxyphenyl)-5-(6-ethoxypyridin-2-yl)-N-(((5-methylpyrimidin-2-yl)methyl)sulfonyl)-4H-1,2,4-triazole-3-carboxamide

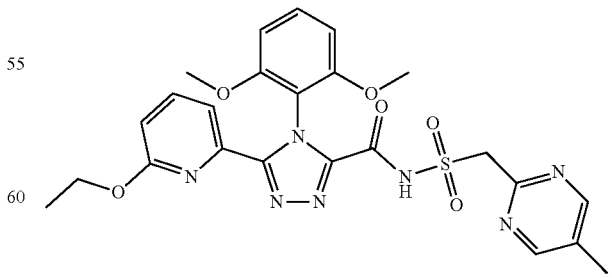

The title compound was prepared according to Method D, by using 6-ethoxypicolinic acid in step A and (5-methylpyrimidin-2-yl)methanesulfonamide in step E.

¹HNMR (400 MHz, DMSO-d₆) δ: 8.66 (s, 2H), 7.84 (t, J=7.2 Hz, 1H), 7.75 (d, J=6.8 Hz, 1H), 7.40 (t, J=8.4 Hz, 1H), 6.79-6.83 (m, 3H), 4.84 (s, 2H), 3.63 (s, 6H), 3.41 (q, J=7.2 Hz, 2H), 2.29 (s, 3H), 1.02 (t, J=7.2 Hz, 3H). LC-MS: m/z 540.0 (M+H)⁺

Example 39: (S)-4-(2,6-dimethoxyphenyl)-5-(6-ethoxypyridin-2-yl)-N-((1-phenylethyl)sulfonyl)-4H-1,2,4-triazole-3-carboxamide Example 40: (R)-4-(2,6-dimethoxyphenyl)-5-(6-ethoxypyridin-2-yl)-N-((1-phenylethyl)sulfonyl)-4H-1,2,4-triazole-3-carboxamide

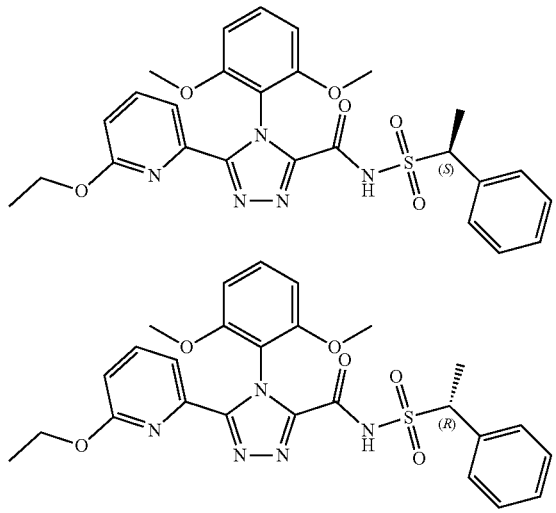

The title compounds were prepared according to Method D, by using 6-ethoxypicolinic acid in step A and 1-phenylethanesulfonamide in step E. The racemate was separated by chiral separation and chiral center arbitrarily assigned.

¹H-NMR (400 MHz, DMSO-d₆) δ 7.75 (t, J=8.0 Hz, 1H), 7.65 (d, J=7.2 Hz, 1H), 7.28 (t, J=12.0 Hz, 1H), 7.22-7.25 (m, 5H), 6.70-6.74 (m, 3H), 4.38-4.43 (m, 1H), 3.58 (d, J=11.6 Hz, 6H), 3.43 (q, J=7.2 Hz, 2H), 1.34 (d, J=7.2 Hz, 3H), 1.03 (t, J=7.2 Hz, 3H). LC-MS: m/z 538.2 (M+H)⁺

Example 41: 4-(2,6-Dimethoxyphenyl)-5-(6-ethoxypyridin-2-yl)-N-((pyrimidin-2-ylmethyl)sulfonyl)-4H-1,2,4-triazole-3-carboxamide

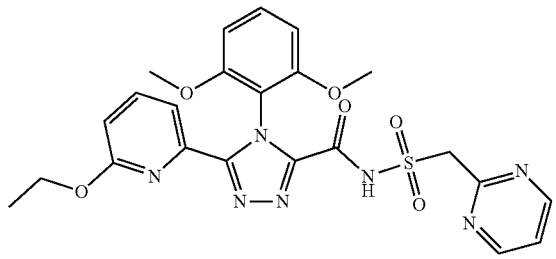 [SMILES: CCOc1cccc(-c2nnc(C(=O)NS(=O)(=O)Cc3ncccn3)n2-c2c(OC)cccc2OC)n1]

The title compound was prepared according to Method D, by using 6-ethoxypicolinic acid in step A and pyrimidin-2-ylmethanesulfonamide in step E.

¹H NMR (DMSO-d₆) δ: 8.80 (d, J=5.2 Hz, 2H), 7.82 (t, J=7.6 Hz, 1H), 7.74 (d, J=7.2 Hz, 1H), 7.48 (t, J=4.8 Hz, 1H), 7.38 (t, J=8.4 Hz, 1H), 6.77-6.81 (m, 3H), 4.81 (s, 2H), 3.62 (s, 6H), 3.43 (q, J=6.8 Hz, 2H), 1.02 (t, J=6.8 Hz, 3H). LC-MS: m/z 526.5 (M+H)⁺

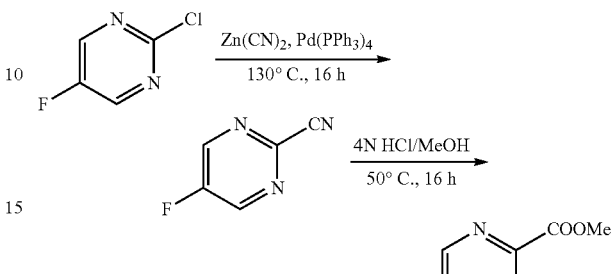

5-Fluoropyrimidine-2-carbonitrile

2-Chloro-5-fluoropyrimidine (30 g, 227 mmol, 1 equiv), Zn(CN)₂ (53 g, 454 mmol, 2 equiv), Pd(PPh₃)₄ (13.1 g, 11.35 mmol, 0.05 equiv) and DMF were charged into round bottom flask The mixture was degassed and refilled with N₂ three times. Then the mixture was stirred at 130° C. overnight. The suspension was filtered. The filtrate was diluted with water and extracted with EtOAc three times. The organic layers were washed with brine, dried over anhydrous Na₂SO₄, and filtered. The filtrate was adjusted to PH=4 with 4 mol/L HCl/MeOH solution. Then the solution was concentrated to give crude 5-fluoropyrimidine-2-carbonitrile as brown oil which was used in next step without further purification.

LC-MS: m/z 124.0 (M+H)⁺

Methyl 5-fluoropyrimidine-2-carboxylate

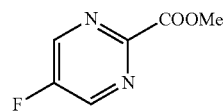

5-Fluoropyrimidine-2-carbonitrile obtained above was dissolved in 4 mol/L HCl/MeOH. The solution was stirred in sealed tube at 50° C. overnight. After the reaction was completed, the mixture was concentrated and the residue was basified with sat. NaHCO₃ solution. The mixture was extracted with EtOAc three times. The combined organic layers were washed with brine, dried over anhydrous Na₂SO₄, and filtered. The filtrate was concentrated and the residue was purified via silica gel chromatography to give methyl 5-fluoropyrimidine-2-carboxylate (20 g, 56.5% yield for two steps).

LC-MS: m/z 157.0 (M+H)⁺

(5-Fluoropyrimidin-2-yl)methanesulfonamide

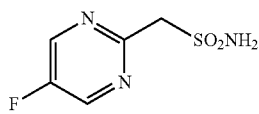

(5-Fluoropyrimidin-2-yl)methanesulfonamide was prepared according to the preparation of pyrimidin-2-ylmethanesulfonamide in Method C, by using methyl 5-fluoropyrimidine-2-carboxylate in step A.

$^1$H NMR (DMSO-d$_6$) δ: 8.93 (d, J=0.8 Hz, 2H), 7.02 (s, 2H), 4.57 (s, 2H).

Example 42: 4-(2,6-Dimethoxyphenyl)-5-(6-ethoxypyridin-2-yl)-N-(((5-fluoropyrimidin-2-yl)methyl)sulfonyl)-4H-1,2,4-triazole-3-carboxamide

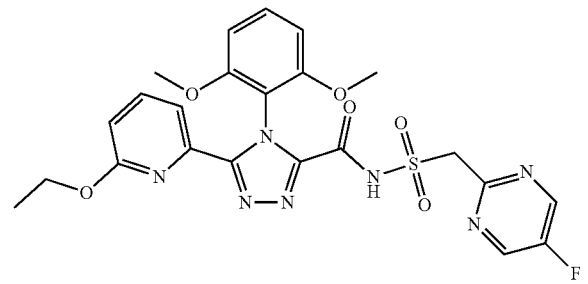 [SMILES: CCOc1cccc(-c2nnc(C(=O)NS(=O)(=O)Cc3ncc(F)cn3)n2-c2c(OC)cccc2OC)n1]

The title compound was prepared according to Method D, by using 6-ethoxypicolinic acid in step A and (5-fluoropyrimidin-2-yl)methanesulfonamide in step E.

$^1$H NMR (DMSO-d$_6$) δ: 8.82 (s, 2H), 7.76 (d, J=8.0 Hz, 1H), 7.64-7.68 (m, 1H), 7.27 (d, J=8.0 Hz, 1H), 6.68-6.72 (m, 3H), 4.44 (s, 2H), 3.58 (s, 6H), 3.38-3.46 (m, 2H), 1.02 (d, J=8.0 Hz, 3H). LC-MS: m/z 544.5 (M+H)$^+$

Example 43: N-(((5-chloropyrimidin-2-yl)methyl)sulfonyl)-4-(2,6-dimethoxyphenyl)-5-(6-ethoxypyridin-2-yl)-4H-1,2,4-triazole-3-carboxamide

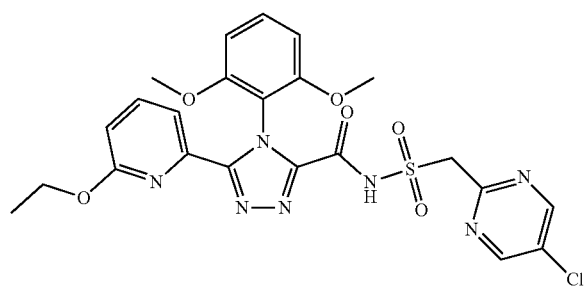 [SMILES: CCOc1cccc(-c2nnc(C(=O)NS(=O)(=O)Cc3ncc(Cl)cn3)n2-c2c(OC)cccc2OC)n1]

The title compound was prepared according to Method D, by using 6-ethoxypicolinic acid in step A and (5-chloropyrimidin-2-yl)methanesulfonamide in step E.

$^1$H NMR (400 MHz, DMSO-d$_6$) δ: 8.95 (s, 2H), 7.81 (t, J=8.0 Hz, 1H), 7.75 (d, J=7.2 Hz, 1H), 7.39 (t, J=8.4 Hz, 1H), 6.78-6.82 (m, 3H), 4.89 (s, 2H), 3.62 (s, 6H), 3.42 (q, J=6.8 Hz, 2H), 1.03 (t, J=7.2 Hz, 3H). LC-MS: m/z 559.9 (M+H)$^+$

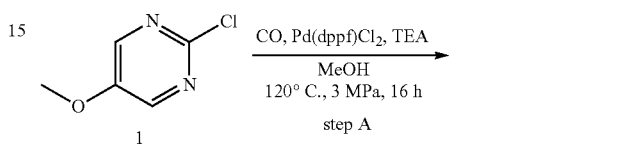

Step A: methyl 5-methoxypyrimidine-2-carboxylate

To a solution of 2-chloro-5-methoxypyrimidine (5.0 g, 34.6 mmol, 1.0 equiv) in MeOH (100 mL) and DMF (20 mL) were added triethylamine (10.5 g, 103.8 mmol, 3.0 equiv) and Pd(dppf)Cl$_2$ (3.8 g, 5.2 mmol, 0.15 equiv). The suspension was degassed and purged with CO several times. The mixture was stirred under CO (3 Mpa) at 120° C. for 72 hours. The reaction mixture was filtered and the filtrate was concentrated. The residue was purified by column chromatography (eluted with PE/EtOAc=20/1~10/1) to afford the title compound methyl 5-methoxypyrimidine-2-carboxylate as a light yellow solid (3.3 g, 57% yield).

LCMS: m/z: 169.0 (M+H)$^+$ (5-Methoxypyrimidin-2-yl)methanesulfonamide

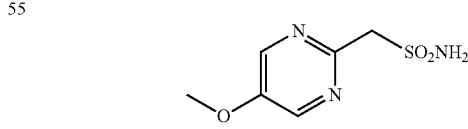

(5-Methoxypyrimidin-2-yl)methanesulfonamide was prepared according to the preparation of pyrimidin-2-ylmethanesulfonamide in Method C, by using methyl 5-methoxypyrimidine-2-carboxylate in step A.

$^1$H NMR (400 MHz, DMSO-d$_6$) δ: 8.56 (s, 2H), 6.93 (s, 2H), 4.48 (s, 2H), 3.32 (s, 3H).

Example 44: 4-(2,6-Dimethoxyphenyl)-5-(6-ethoxy-pyridin-2-yl)-N-(((5-methoxypyrimidin-2-yl)methyl)sulfonyl)-4H-1,2,4-triazole-3-carboxamide

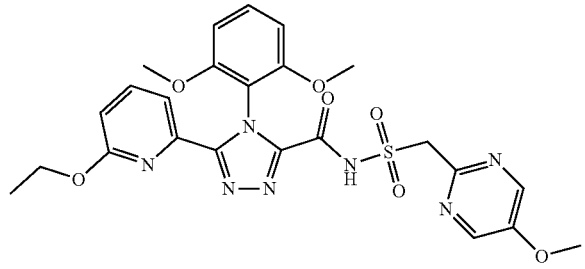 [SMILES: CCOc1cccc(-c2nnc(C(=O)NS(=O)(=O)Cc3ncc(OC)cn3)n2-c2c(OC)cccc2OC)n1]

The title compound was prepared according to Method D, by using 6-ethoxypicolinic acid in step A and (5-methoxy-pyrimidin-2-yl)methanesulfonamide in step E.

$^1$H NMR (400 MHz, DMSO) δ: 8.54 (s, 2H), 7.83 (t, J=8.0 Hz, 1H), 7.75 (d, J=6.8 Hz, 1H), 7.40 (t, J=8.0 Hz, 1H), 6.79-6.83 (m, 3H), 4.83 (s, 2H), 3.92 (s, 3H), 3.62 (s, 6H), 3.43 (q, J=7.2 Hz, 2H), 1.03 (t, J=7.2 Hz, 3H). LC-MS: m/z 556.3 (M+H)$^+$

2-Phenylpropane-1-sulfonamide

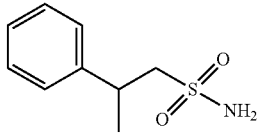

2-Phenylpropane-1-sulfonamide was prepared according to the preparation of pyrimidin-2-ylmethanesulfonamide in Method C, by using 2-phenylpropan-1-ol in step B.
LC-MS: m/z 200.0 (M+H)$^+$ Example 45: (S)-4-(2,6-Dimethoxyphenyl)-5-(6-ethoxypyridin-2-yl)-N-((2-phenylpropyl)sulfonyl)-4H-1,2,4-triazole-3-carboxamide Example 46: (R)-4-(2,6-Dimethoxyphenyl)-5-(6-ethoxypyridin-2-yl)-N-((2-phenylpropyl)sulfonyl)-4H-1,2,4-triazole-3-carboxamide

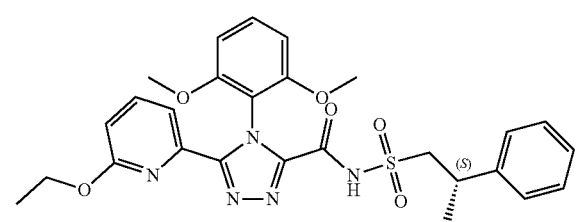

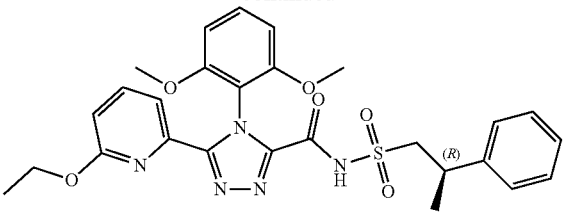

The title compounds prepared according to Method D, by using 6-ethoxypicolinic acid in step A and 2-phenylpropane-1-sulfonamide in step E. The racemate was separated by chiral separation and chiral center arbitrarily assigned.

$^1$H-NMR (400 MHz, DMSO-d$_6$) δ 7.84 (t, J=8.0 Hz, 1H), 7.76 (d, J=8.8 Hz, 1H), 7.39 (t, J=8.4 Hz, 1H), 7.26-7.32 (m, 2H), 7.17-7.25 (m, 3H), 6.82 (dd, J=8.0 Hz, 0.8 Hz, 1H), 6.78 (d, J=8.4 Hz, 2H), 3.62-3.66 (m, 1H), 3.58 (s, 3H), 3.56 (s, 3H), 3.41 (q, J=7.2 Hz, 2H), 3.21-3.26 (m, 2H), 1.36 (d, J=6.8 Hz, 3H), 1.01 (t, J=7.2 Hz, 3H). LC-MS: m/z 552.2 (M+H)$^+$

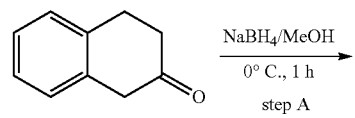

Step A: 1,2,3,4-tetrahydronaphthalen-2-ol

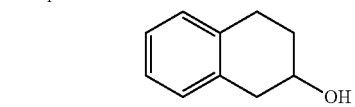

3,4-Dihydronaphthalen-2(1H)-one (2 g, 13.7 mmol) in MeOH (25 mL) was cooled to 0° C. and NaBH$_4$ (1.3 g, 34.2 mmol) was added. The reaction was stirred at 0° C. for 1 hour. Then ice water was added and the resulting mixture was extracted with EtOAc (3*10 mL). The combined organic layers were dried over anhydrous Na$_2$SO$_4$ and concentrated in vacuo. The residue was purified by silica gel chromatography (PE/EtOAc=3/1) to afford the title compound 1,2,3,4-tetrahydronaphthalen-2-ol as a yellow oil (1.7 g, 85%).

$^1$H NMR (400 MHz, METHANOL-d4) δ: 6.95-7.11 (m, 4H), 3.96-4.08 (m, 1H), 2.68-3.01 (m, 4H), 2.00-2.02 (m, 1H), 1.68-1.78 (m, 1H).

1,2,3,4-Tetrahydronaphthalene-2-sulfonamide

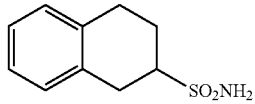

1,2,3,4-Tetrahydronaphthalene-2-sulfonamide was prepared according to the preparation of pyrimidin-2-ylmethanesulfonamide in Method C, by using 1,2,3,4-tetrahydronaphthalen-2-ol in step B.

$^1$H NMR (400 MHz, DMSO-$d_6$) δ: 7.13 (dd, J=4.0 Hz, 9.2 Hz, 4H), 6.85 (s, 2H), 3.18-3.29 (m, 1H), 3.07-3.16 (m, 1H), 2.76-2.99 (m, 3H), 2.24-2.36 (m, 1H), 1.62-1.78 (m, 1H).

Example 47: (S)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide

Example 48: (R)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide

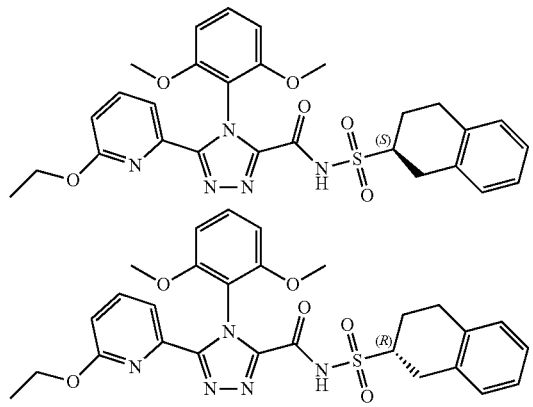

The title compounds were prepared according to Method D, by using 6-ethoxypicolinic acid in step A and 1,2,3,4-tetrahydronaphthalene-2-sulfonamide in step E. The racemates were separated by chiral separation and the chiral centers were assigned arbitrarily.

$^1$H NMR (400 MHz, DMSO-$d_6$) δ: 7.84 (t, J=8.0 Hz, 1H), 7.75 (d, J=6.8 Hz, 1H), 7.36 (t, J=8.4 Hz, 1H), 7.03-7.21 (m, 4H), 6.81 (d, J=7.6 Hz, 1H), 6.75 (t, J=8.4 Hz, 2H), 3.71-3.82 (m, 1H), 3.57 (s, 3H), 3.55 (s, 3H), 3.40 (q, J=7.2 Hz, 2H), 3.04 (d, J=8.0 Hz, 2H), 2.89-2.97 (m, 1H), 2.79-2.82 (m, 1H), 2.18-2.31 (m, 1H), 1.78-1.89 (m, 1H), 1.01 (t, J=7.2 Hz, 3H). LC-MS: m/z 563.7 (M+H)$^+$.

Method E

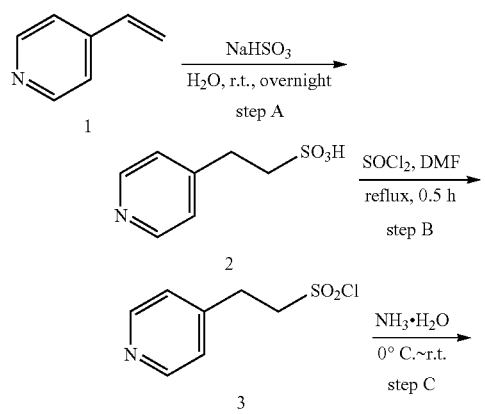

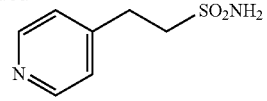

Step A: 2-(pyridin-4-yl)ethanesulfonic Acid

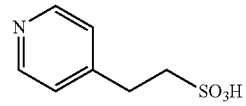

To a solution of NaHSO$_3$ (10 g, 95.2 mmol, 1 equiv) in water (50 mL) was added 4-vinylpyridine (10 g, 95.1 mmol, 1 equiv). The resulting mixture was stirred at room temperature overnight. The mixture was adjusted with 1 mol/L HCl solution to pH=5. Then the mixture was concentrated to give the crude product. The crude product was stirred in hot CH$_3$OH (200 mL) for 0.5 hour and filtered. The filtrate was concentrated in vacuo to afford the title compound 2-(pyridin-4-yl)ethanesulfonic acid as a white solid (16 g, 90% yield).

LC-MS: m/z 188.0 (M+H)$^+$

Step B: 2-(pyridin-4-yl)ethanesulfonyl Chloride

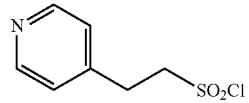

To a mixture of 2-(pyridin-4-yl)ethanesulfonic acid (5 g, 26.7 mmol, 1 equiv) in SOCl$_2$ (25 mL) was added several drops of DMF. The resulting mixture was refluxed for 0.5 hour and concentrated in vacuo. The residue was used directly for next step without purification (5.5 g crude).

Step C: 2-(pyridin-4-yl)ethanesulfonamide

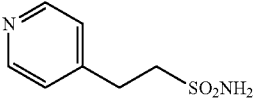 [SMILES: NS(=O)(=O)CCc1ccncc1]

A solution of 2-(pyridin-4-yl)ethanesulfonyl chloride (5.5 g crude, 26.7 mmol, 1 equiv) in DCM was added to aqueous NH$_4$OH solution (150 mL) at 0° C. The resulting mixture was allowed to be slowly warmed to room temperature and stirred for 12 hours. The mixture was concentrated under vacuum and the residue was purified by silica gel chromatography (eluted with DCM/MeOH=20/1) to afford the title compound 2-(pyridin-4-yl)ethanesulfonamide as a white solid (2.6 g, 52% yield in two steps).

$^1$H NMR (400 MHz, DMSO) δ: 8.48 (dd, J=4.4 Hz, 1.6 Hz, 2H), 7.31 (dd, J=4.4 Hz, 1.6 Hz, 2H), 6.91 (s, 2H), 3.29-3.31 (m, 2H), 3.01-3.05 (m, 2H). LC-MS: m/z 187.0 (M+H)$^+$

Example 49: 4-(2,6-Dimethoxyphenyl)-5-(6-ethoxy-pyridin-2-yl)-N-((2-(pyridin-4-yl)ethyl)sulfonyl)-4H-1,2,4-triazole-3-carboxamide

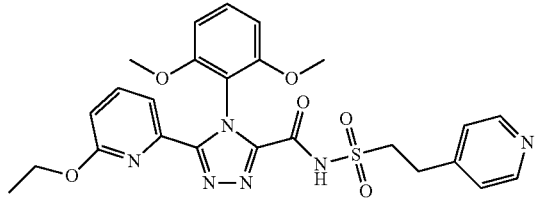 [SMILES: CCOc1cccc(-c2nnc(C(=O)NS(=O)(=O)CCc3ccncc3)n2-c2c(OC)cccc2OC)n1]

The title compound was prepared according to Method D, by using 6-ethoxypicolinic acid in step A and 2-(pyridin-4-yl)ethanesulfonamide in step E.

$^1$H NMR (400 MHz, DMSO-$d_6$) δ: 8.62-8.70 (m, 2H), 7.84 (t, J=8.0 Hz, 1H), 7.75 (d, J=6.8 Hz, 1H), 7.57-7.71 (m, 2H), 7.39 (t, J=8.4 Hz, 1H), 6.82 (d, J=8.0 Hz, 1H), 6.78 (d, J=8.4 Hz, 2H), 3.77-3.83 (m, 2H), 3.58 (s, 6H), 3.41 (q, J=7.2 Hz, 2H), 3.13-3.21 (m, 2H), 1.01 (t, J=7.2 Hz, 3H). LC-MS: m/z 539.2 (M+H)$^+$

Method F

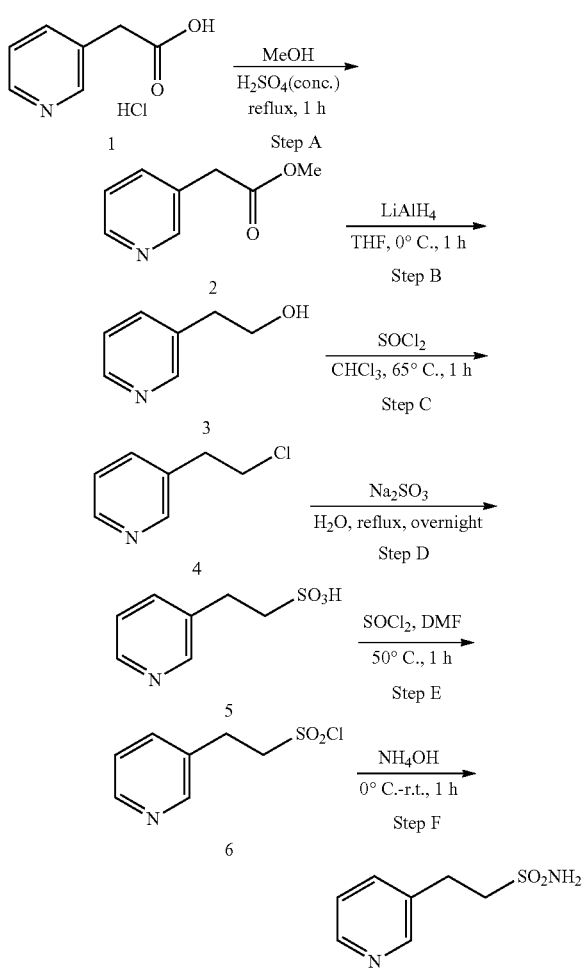

Step A: methyl 2-(pyridin-3-yl)acetate

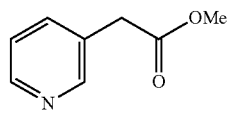 [SMILES: COC(=O)Cc1cccnc1]

To a solution of 2-(pyridin-3-yl)acetic acid hydrochloride (17.3 g, 100 mmol, 1 equiv) in MeOH (80 mL) was added concentrated H$_2$SO$_4$ (6.4 mL, 120 mmol, 1.2 equiv) dropwise at room temperature and the resulting mixture was refluxed for 1 hour. The reaction mixture was poured into saturated NaHCO$_3$ solution and extracted with DCM (3*100 mL). The combined organic phase were washed with brine (30 mL), dried over anhydrous Na$_2$SO$_4$, filtered and concentrated in vacuo to afford the title compound methyl 2-(pyridin-3-yl)acetate as yellow solid (15 g, 98% yield).

LC-MS: m/z 152.1 (M+H)$^+$

Step B: 2-(pyridin-3-yl)ethanol

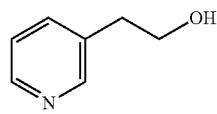

To a solution of methyl 2-(pyridin-3-yl)acetate (15.1 g, 100 mmol, 1 equiv) in anhydrous THF (180 mL) was added LiAlH$_4$ (4.18 g, 110 mmol, 1.1 equiv) in portions at 0° C. The reaction mixture was stirred at 0° C. for 1 hour. Then the reaction was quenched carefully with 10% NaOH (aq.), filtered, and extracted with DCM (3*150 mL). The combined organic phase were washed with brine (30 mL), dried over anhydrous Na$_2$SO$_4$, filtered and concentrated in vacuo to afford the title compound 2-(pyridin-3-yl)ethanol as a yellow oil (6.1 g, 51% yield).

LC-MS: m/z 124.1 (M+H)$^+$

Step C: 3-(2-chloroethyl)pyridine

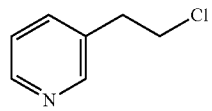

To a solution of 2-(pyridin-3-yl)ethanol (4.8 g, 39 mmol, 1 equiv) and DMF (1 mL) in CHCl$_3$ (50 mL) was added SOCl$_2$ (3.1 mL, 43 mmol, 1.1 equiv) dropwise at room temperature under N$_2$ atmosphere and then the reaction mixture was stirred at 65° C. for 1 hour. The reaction mixture was poured into saturated NaHCO$_3$ solution and extracted with DCM (3*100 mL). The combined organic phase were washed with brine (30 mL), dried over anhydrous Na$_2$SO$_4$, filtered and concentrated to afford the title compound 3-(2-chloroethyl)pyridine as a red oil (5 g, 80% yield).

LC-MS: m/z 142.1 (M+H)$^+$

Step D: 2-(pyridin-3-yl)ethanesulfonic Acid

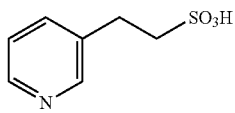 [SMILES: O=S(=O)(O)CCc1cccnc1]

A mixture of 3-(2-chloroethyl)pyridine (2.8 g, 20 mmol, 1 equiv) and Na$_2$SO$_3$ (6.3 g, 50 mmol, 2.5 equiv) in water (30 mL) was refluxed overnight. The reaction mixture was adjusted with HCl (aq., 1 mol/L) to pH=5 and concentrated in vacuo. The residue was charged with CH$_3$OH and the mixture was stirred at 60° C. for 0.5 hour. Then the mixture was filtered and the filtrate was concentrated in vacuo to afford the title compound 2-(pyridin-3-yl)ethanesulfonic acid as a white solid (4.2 g, crude).

LC-MS: m/z 188.0 (M+H)$^+$

Step E: 2-(pyridin-3-yl)ethanesulfonyl Chloride

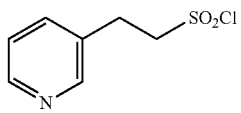 [SMILES: O=S(=O)(Cl)CCc1cccnc1]

A mixture of 2-(pyridin-3-yl)ethanesulfonic acid (4.2 g crude, 20 mmol, 1 equiv) and DMF (1 mL) in SOCl$_2$ (30 mL) was stirred at 50° C. for 1 hour under N$_2$ atmosphere. The reaction mixture was concentrated in vacuo to afford the title compound 2-(pyridin-3-yl)ethanesulfonyl chloride as a yellow solid, which was used directly for next step without purification (4.6 g crude).

Step F: 2-(pyridin-3-yl)ethanesulfonamide

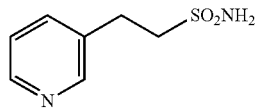

To a mixture of 2-(pyridin-3-yl)ethanesulfonyl chloride (4.6 g crude, 20 mmol, 1 equiv) in DCM (20 mL) was added NH$_3$.H$_2$O (aq., 34%, 10 mL, 200 mmol, 10 equiv) dropwise at 0° C. The reaction mixture was stirred at room temperature for 1 hour. The reaction mixture was concentrated and residue was purified by flash column chromatography on silica gel (eluted with DCM/MeOH=20/1) to afford the title compound 2-(pyridin-3-yl)ethanesulfonamide as a white solid (1.0 g, 27% yield for three steps).

LC-MS: m/z 187.1 (M+H)$^+$

Example 50: 4-(2,6-Dimethoxyphenyl)-5-(6-ethoxypyridin-2-yl)-N-((2-(pyridin-3-yl)ethyl)sulfonyl)-4H-1,2,4-triazole-3-carboxamide

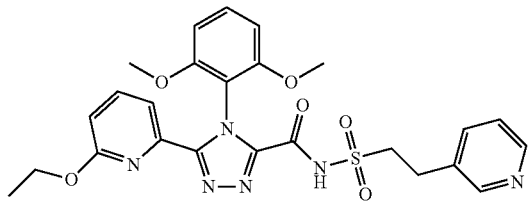

The title compound was prepared according to Method D, by using 6-ethoxypicolinic acid in step A and 2-(pyridin-3-yl)ethanesulfonamide in step E.

$^1$H NMR (400 MHz, DMSO-d$_6$) δ: 8.41 (dd, J=4.8 Hz, 1.2 Hz, 1H), 8.35 (d, J=1.6 Hz, 1H), 7.77 (t, J=8.0 Hz, 1H), 7.67 (dd, J=8.0 Hz, 0.8 Hz, 1H), 7.51-7.54 (m, 1H), 7.31 (dd, J=8.0 Hz, 4.0 Hz, 1H), 7.25 (t, J=8.4 Hz, 1H), 6.72 (dd, J=8.0 Hz, 0.8 Hz, 1H), 6.68 (d, J=8.4 Hz, 2H), 3.55 (s, 6H), 3.41 (q, J=7.2 Hz, 2H), 3.03-3.07 (m, 2H), 2.67-2.71 (m, 2H), 1.01 (t, J=7.2 Hz, 3H). LC-MS: m/z 539.2 (M+H)$^+$ 2-(Pyridin-2-yl)ethanesulfonamide

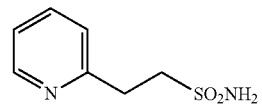

2-(Pyridin-2-yl)ethanesulfonamide was prepared according to the preparation of 2-(pyridin-4-yl)ethanesulfonamide in Method E, by using 2-vinylpyridine in step A.

$^1$H NMR (400 MHz, DMSO-d$_6$) δ: 8.50 (dd, J=4.8 Hz, 0.8 Hz, 1H), 7.73 (td, J=7.7 Hz, 1.8 Hz, 1H), 7.35 (d, J=7.8 Hz, 1H), 7.27-7.22 (m, 1H), 6.89 (s, 2H), 3.42-3.36 (m, 2H), 3.20-3.13 (m, 2H). LC-MS: m/z 187.0 (M+H)$^+$

Example 51: 4-(2,6-Dimethoxyphenyl)-5-(6-ethoxypyridin-2-yl)-N-((2-(pyridin-2-yl)ethyl)sulfonyl)-4H-1,2,4-triazole-3-carboxamide

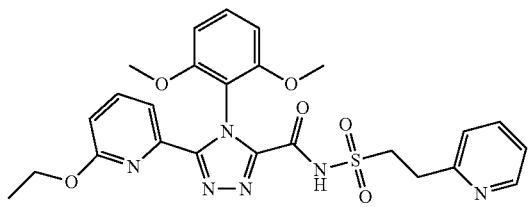 [SMILES: CCOc1cccc(-c2nnc(C(=O)NS(=O)(=O)CCc3ccccn3)n2-c2c(OC)cccc2OC)n1]

The title compound was prepared according to Method D, by using 6-ethoxypicolinic acid in step A and 2-(pyridin-2-yl)ethanesulfonamide in step E.

$^1$H NMR (400 MHz, DMSO-d$_6$) δ: 8.51 (dd, J=4.8 Hz, 0.8 Hz, 1H), 7.74-7.85 (m, 3H), 7.35-7.41 (m, 2H), 7.25-7.33 (m, 1H), 6.81 (dd, J=8.0 Hz, 0.8 Hz, 1H), 6.77 (d, J=8.4 Hz, 2H), 3.76-3.82 (m, 2H), 3.57 (s, 6H), 3.41 (q, J=7.2 Hz, 2H), 3.15-3.21 (m, 2H), 1.01 (t, J=7.2 Hz, 3H). LC-MS: m/z 539.2 (M+H)$^+$

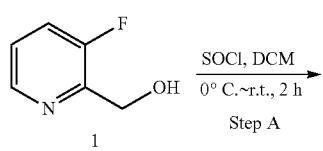

Step B: S-((3-fluoropyridin-2-yl)methyl) Ethanethioate

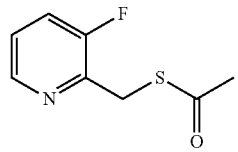

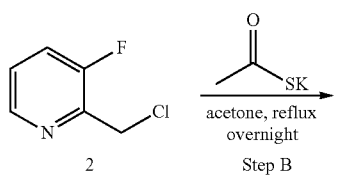

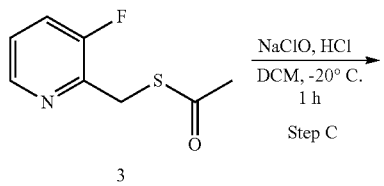

To a solution of 2-(chloromethyl)-3-fluoropyridine (1.0 g, 6.7 mmol, 1 equiv) in acetone (20 mL) was added potassium ethanethioate (918 mg, 8.0 mmol, 1.2 equiv) in one portion. The resulting mixture was refluxed overnight. The reaction mixture was filtered through a plug of silica gel. The filtrate was concentrated in vacuo and the residue was purified by column chromatography (eluted with PE/EtOAc=5/1) to afford the title compound S-((3-fluoropyridin-2-yl)methyl) ethanethioate (1.0 g, 81% yield).

LC-MS: m/z 186.0 (M+H)$^+$

Step C: (3-fluoropyridin-2-yl)methanesulfonyl Chloride

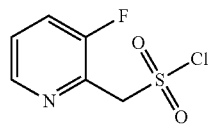

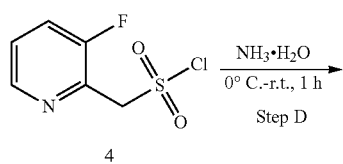

Sodium hypochlorite solution (12.0 mL, 16.2 mmol, 6 equiv) was added dropwise to a vigorously stirred solution of S-((3-fluoropyridin-2-yl)methyl) ethanethioate (500 mg, 2.7 mmol, 1 equiv) in DCM (17 mL) and HCl solution (aq. 1 mol/L, 16.2 mL, 16.2 mmol, 6 equiv) at −20° C. After the completion of addition, the mixture was stirred at −20° C. for 1 hour. The organic layer was separated and used directly for next step.

Step D: (3-fluoropyridin-2-yl)methanesulfonamide

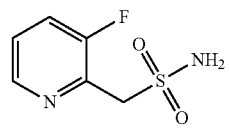 [SMILES: NS(=O)(=O)Cc1ncccc1F]

Step A: 2-(chloromethyl)-3-fluoropyridine

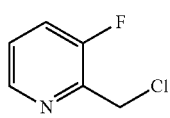

To a solution of (3-fluoropyridin-2-yl)methanol (1.8 g, 13.8 mmol, 1 equiv) in DCM (20 mL) was added SOCl$_2$ (2.5 mL, 35 mmol, 2.5 equiv) dropwise at 0° C. The resulting mixture was stirred at room temperature for 2 hours. The reaction mixture was quenched with saturated aqueous NaHCO$_3$ solution and extracted with DCM (3*20 mL). The combined organic layers were dried over anhydrous Na$_2$SO$_4$ and concentrated in vacuo. The residue was purified by column chromatography (eluted with PE/EtOAc=5/1) to afford the title compound 2-(chloromethyl)-3-fluoropyridine (1.33 g, 66.5% yield).

LC-MS: m/z 146.0, 148.0 (M+H)$^+$

A solution of (3-fluoropyridin-2-yl)methanesulfonyl chloride in DCM (17 mL) was added to NH$_4$OH (aq., 34%, 60 mL) at 0° C. The mixture was allowed to be slowly warmed to room temperature and stirred for 1 hour. The mixture was concentrated under vacuum. The residue was purified by silica gel chromatography (eluted with DCM/MeOH=25/1) to afford the title compound (3-fluoropyridin-2-yl)methanesulfonamide as a white solid (142 mg, 28% yield for two steps).

LC-MS: m/z 191.0 (M+H)$^+$

Example 52: 4-(2,6-Dimethoxyphenyl)-5-(6-ethoxy-pyridin-2-yl)-N-(((3-fluoropyridin-2-yl)methyl)sulfonyl)-4H-1,2,4-triazole-3-carboxamide

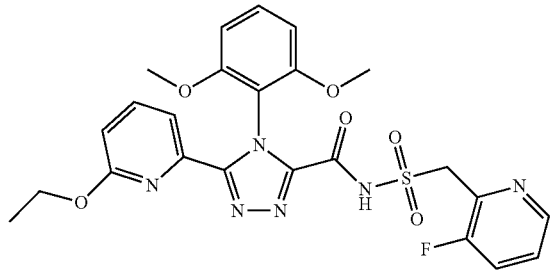 [SMILES: CCOc1cccc(-c2nnc(C(=O)NS(=O)(=O)Cc3ncccc3F)n2-c2c(OC)cccc2OC)n1]

The title compound was prepared according to Method D, by using 6-ethoxypicolinic acid in step A and (3-fluoropyridin-2-yl)methanesulfonamide in step E.
$^1$H NMR (400 MHz, DMSO-d$_6$) δ: 8.44 (d, J=4.8 Hz, 1H), 7.69-7.91 (m, 3H), 7.54 (s, 1H), 7.42 (t, J=8.4 Hz, 1H), 6.80-6.84 (m, 3H), 4.88 (s, 2H), 3.65 (s, 6H), 3.44 (q, J=7.2 Hz, 2H), 1.04 (t, J=7.2 Hz, 3H). LC-MS: m/z 543.1 (M+H)$^+$ (2-Fluorophenyl)methanesulfonamide

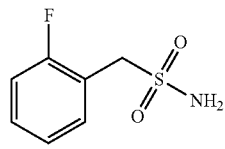 [SMILES: NS(=O)(=O)Cc1ccccc1F]

(2-Fluorophenyl)methanesulfonamide was prepared according to the preparation of pyrimidin-2-ylmethanesulfonamide in Method C, by using (2-fluorophenyl)methanol in step B.
$^1$H NMR (400 MHz, DMSO-d$_6$) δ: 7.38-7.46 (m, 2H), 7.20-7.25 (m, 2H), 7.00 (s, 2H), 4.31 (s, 2H)

Example 53: 4-(2,6-Dimethoxyphenyl)-5-(6-ethoxy-pyridin-2-yl)-N-((2-fluorobenzyl)sulfonyl)-4H-1,2,4-triazole-3-carboxamide

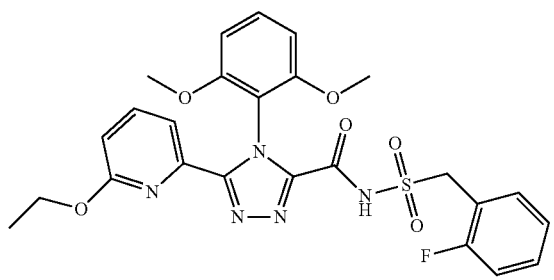

Molecular Weight: 541.55

The title compound was prepared according to Method D, by using 6-ethoxypicolinic acid in step A and (2-fluorophenyl)methanesulfonamide in step E.
$^1$H NMR (400 MHz, DMSO-d$_6$) δ: 7.83 (t, J=8.0 Hz, 1H), 7.76 (d, J=6.8 Hz, 1H), 7.36-7.48 (m, 3H), 7.23-7.28 (m, 2H), 6.80-6.83 (m, 3H), 4.74 (s, 2H), 3.63 (s, 6H), 3.43 (q, J=7.2 Hz, 2H), 1.03 (t, J=7.2 Hz, 3H). LC-MS: m/z 542.0 (M+H)$^+$ (1-Methyl-1H-1,2,4-triazol-3-yl)methanesulfonamide

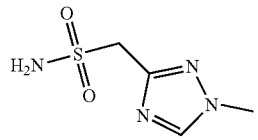

(1-Methyl-1H-1,2,4-triazol-3-yl)methanesulfonamide was prepared according to the preparation of pyrimidin-2-ylmethanesulfonamide in Method C, by using (1-methyl-1H-1,2,4-triazol-3-yl)methanol in step B.
$^1$H NMR (400 MHz, DMSO-d$_6$) δ: 8.44 (s, 1H), 6.90 (s, 2H), 4.32 (s, 2H), 3.85 (s, 3H).

Example 54: 4-(2,6-Dimethoxyphenyl)-5-(6-ethoxy-pyridin-2-yl)-N-(((1-methyl-1H-1,2,4-triazol-3-yl)methyl)sulfonyl)-4H-1,2,4-triazole-3-carboxamide

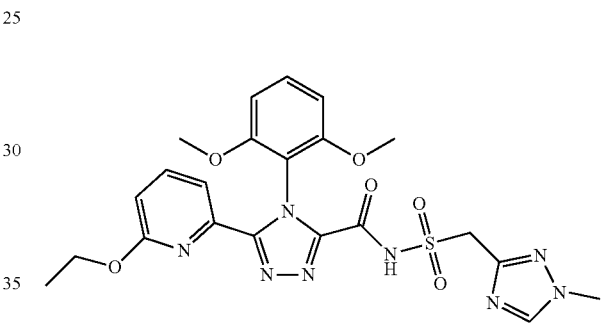

The title compound was prepared according to Method D, by using 6-ethoxypicolinic acid in step A and (1-methyl-1H-1,2,4-triazol-3-yl)methanesulfonamide in step E.
$^1$H NMR (400 MHz, DMSO-d$_6$) δ: 8.44 (s, 1H), 7.82 (t, J=7.6 Hz, 1H), 7.74 (d, J=7.2 Hz, 1H), 7.38 (t, J=8.4 Hz, 1H), 6.77-6.81 (m, 3H), 4.63 (s, 2H), 3.84 (s, 3H), 3.61 (s, 6H), 3.43 (q, J=7.2 Hz, 2H), 1.02 (t, J=7.2 Hz, 3H). LC-MS: m/z 529.1 (M+H)$^+$ Example 55: 4-(2,6-Dimethoxyphenyl)-N-(((1-methyl-1H-1,2,4-triazol-3-yl)methyl)sulfonyl)-5-(5-methylfuran-2-yl)-4H-1,2,4-triazole-3-carboxamide

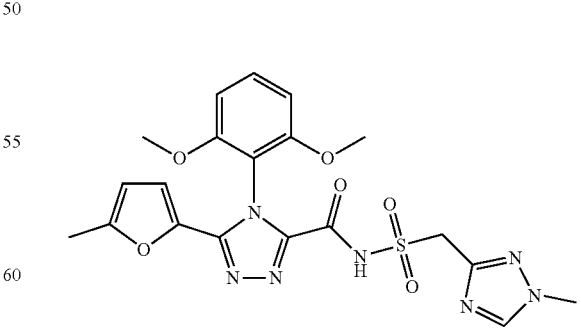

The title compound was prepared according to Method D, by using 5-methylfuran-2-carboxylic acid in step A and (1-methyl-1H-1,2,4-triazol-3-yl)methanesulfonamide in step E.

¹H NMR (400 MHz, DMSO-d₆) δ: 8.03 (s, 1H), 7.46 (t, J=8.4 Hz, 1H), 6.69 (d, J=8.4 Hz, 2H), 6.03 (d, J=3.2 Hz, 1H), 5.96 (dd, J=3.6 Hz, 0.9 Hz, 1H), 4.82 (s, 2H), 3.88 (s, 3H), 3.71 (s, 6H), 2.32 (s, 3H). LC-MS: m/z 488.1 (M+H)⁺

Pyridin-3-ylmethanesulfonamide

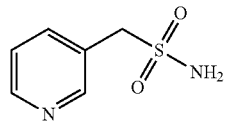 [SMILES: NS(=O)(=O)Cc1cccnc1]

Pyridin-3-ylmethanesulfonamide was prepared according to the preparation of 2-(pyridin-3-yl)ethanesulfonamide in Method F, by using 3-(chloromethyl)pyridine hydrochloride in step D.

¹H NMR (400 MHz, DMSO-d₆) δ: 8.52-8.56 (m, 2H), 7.76-7.79 (m, 1H), 7.40-7.43 (m, 1H), 6.93 (s, 2H), 4.32 (s, 2H).

Example 56: 4-(2,6-Dimethoxyphenyl)-5-(6-ethoxy-pyridin-2-yl)-N-((pyridin-3-ylmethyl)sulfonyl)-4H-1,2,4-triazole-3-carboxamide

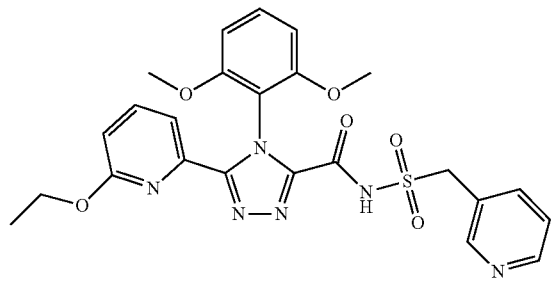 [SMILES: CCOc1cccc(-c2nnc(C(=O)NS(=O)(=O)Cc3cccnc3)n2-c2c(OC)cccc2OC)n1]

The title compound was prepared according to Method D, by using 6-ethoxypicolinic acid in step A and pyridin-3-ylmethanesulfonamide in step E.

¹H NMR (400 MHz, DMSO-d₆) δ: 8.58 (dd, J=4.8 Hz, 1.6 Hz, 1H), 8.43 (d, J=1.6 Hz, 1H), 7.83 (t, J=8.0 Hz, 1H), 7.70-7.77 (m, 2H), 7.44-7.50 (m, 1H), 7.41 (t, J=8.4 Hz, 1H), 6.77-6.84 (m, 3H), 4.72 (s, 2H), 3.64 (s, 6H), 3.43 (q, J=6.8 Hz, 2H), 1.03 (t, J=6.8 Hz, 3H). LC-MS: m/z 525.0 (M+H)⁺

1-Phenylpropane-2-sulfonamide

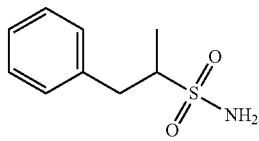

1-Phenylpropane-2-sulfonamide was prepared according to the preparation of pyrimidin-2-ylmethanesulfonamide in Method C, by using 1-phenylpropan-2-ol in step B.

LC-MS: m/z 200.0 (M+H)⁺

Example 57: 4-(2,6-Dimethoxyphenyl)-5-(6-ethoxy-pyridin-2-yl)-N-((1-phenylpropan-2-yl)sulfonyl)-4H-1,2,4-triazole-3-carboxamide

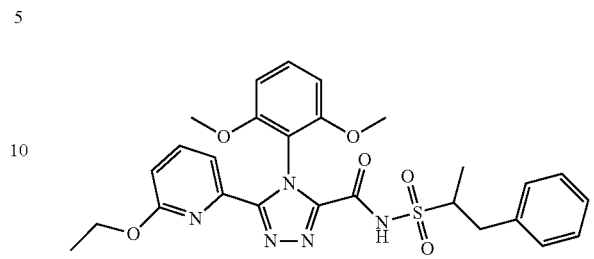

The title compound was prepared according to Method D, by using 6-ethoxypicolinic acid in step A and 1-phenylpropane-2-sulfonamide in step E.

¹H NMR (400 MHz, DMSO-d₆) δ: 7.78 (t, J=8.0 Hz, 1H), 7.69 (d, J=8.0 Hz, 1H), 7.27-7.32 (m, 3H), 7.19-7.22 (m, 1H), 7.07 (d, J=8.0 Hz, 2H), 6.69-6.75 (m, 3H), 3.55 (s, 3H), 3.54 (s, 3H), 3.46-3.52 (m, 1H), 3.41 (q, J=7.2 Hz, 2H), 3.14-3.20 (m, 2H), 1.08 (br.s, 3H), 1.02 (t, J=7.2 Hz, 3H). LC-MS: m/z 552.1 (M+H)⁺

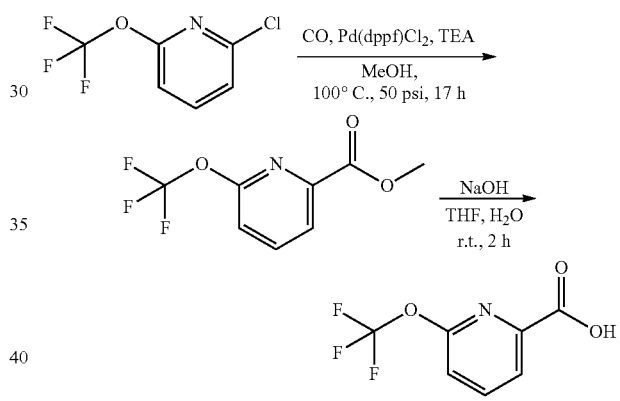

Step A: methyl 6-(trifluoromethoxy)picolinate

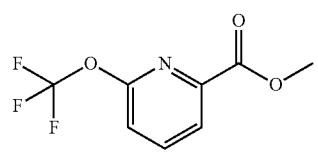

To a solution of 2-chloro-6-(trifluoromethoxy)pyridine (5.0 g, 25.3 mmol, 1 equiv) in MeOH (120 mL) was added triethylamine (7.7 g, 75.9 mmol, 10.5 mL, 3.00 eq) and Pd(dppf)Cl₂ (930 mg, 1.27 mmol, 0.05 equiv). The suspension was degassed and purged with CO several times. The mixture was stirred at 100° C. under CO (50 Psi) for 48 hours. The reaction mixture was cooled to 20° C. and concentrated in vacuo. The residue was purified by silica gel chromatography (eluted with PE/EtOAc=10/1) to afford the title compound methyl 6-(trifluoromethoxy)picolinate as a yellow oil (3.85 g, 68% yield).

LC-MS: m/z 222.0 (M+H)⁺

Step B: 6-(trifluoromethoxy)picolinic Acid

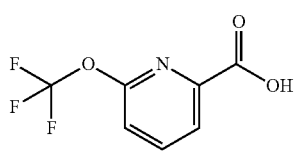 [SMILES: O=C(O)c1cccc(OC(F)(F)F)n1]

To a solution of 6-(trifluoromethoxy)picolinate (2.49 g, 11.27 mmol) in THF (30 mL) and H$_2$O (6 mL) was added NaOH (33.8 mmol, 1.35 g). The reaction mixture was stirred at room temperature for 2 hours. The reaction mixture was diluted with H$_2$O (50 mL) and washed with EtOAc (3*50 mL). The water phase was adjusted with 1M HCl aqueous solution to pH=4, followed by extraction with EtOAc (3*50 mL). The combined organic phase were washed with brine (30 mL), dried over anhydrous Na$_2$SO$_4$ and concentrated in vacuo to afford the title 6-(trifluoromethoxy)picolinic acid as white solid (2.88 g, 85% yield).

LC-MS: m/z 208.0 (M+H)$^+$

Example 58: 4-(2,6-Dimethoxyphenyl)-N-((pyrimidin-2-ylmethyl)sulfonyl)-5-(6-(trifluoromethoxy)pyridin-2-yl)-4H-1,2,4-triazole-3-carboxamide

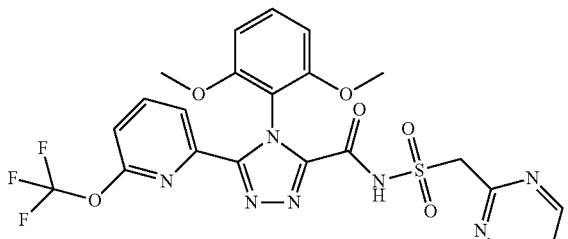

The title compound was prepared according to Method D, by using 6-(trifluoromethoxy)picolinic acid in step A and pyrimidin-2-ylmethanesulfonamide in step E.

$^1$H NMR (400 MHz, CDCl$_3$) δ: 8.75 (d, J=4.0 Hz, 2H), 8.21 (d, J=8.0 Hz, 1H), 7.91 (t, J=8.0 Hz, 1H), 7.37 (t, J=8.0 Hz, 1H), 7.30 (t, J=4.0 Hz, 1H), 6.91 (d, J=8.0 Hz, 1H), 6.61 (d, J=8.0 Hz, 2H), 4.99 (s, 2H), 3.65 (s, 6H). LC-MS: m/z 566.1 (M+H)$^+$

Example 59: 4-(2,6-Dimethoxyphenyl)-5-(5-methylpyridin-3-yl)-N-((pyrimidin-2-ylmethyl)sulfonyl)-4H-1,2,4-triazole-3-carboxamide

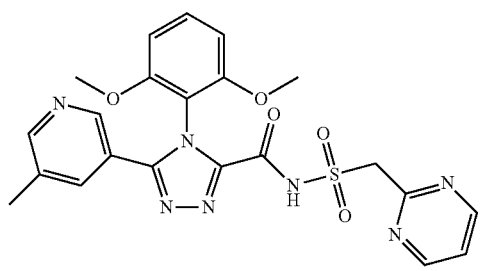 [SMILES: COc1cccc(OC)c1-n1c(C(=O)NS(=O)(=O)Cc2ncccn2)nnc1-c1cncc(C)c1]

The title compound was prepared according to Method D, by using 5-methylnicotinic acid in step A and pyrimidin-2-ylmethanesulfonamide in step E.

$^1$H NMR (400 MHz, CDCl$_3$) δ: 8.76 (d, J=4.8 Hz, 2H), 8.48 (s, 1H), 8.40 (s, 1H), 7.87 (s, 1H), 7.42 (t, J=8.4 Hz, 1H), 7.31 (t, J=4.8 Hz, 1H), 6.64 (d, J=8.4 Hz, 2H), 5.00 (s, 2H), 3.70 (s, 6H), 2.35 (s, 3H). LC-MS: m/z 496.1 (M+H)$^+$

Method G:

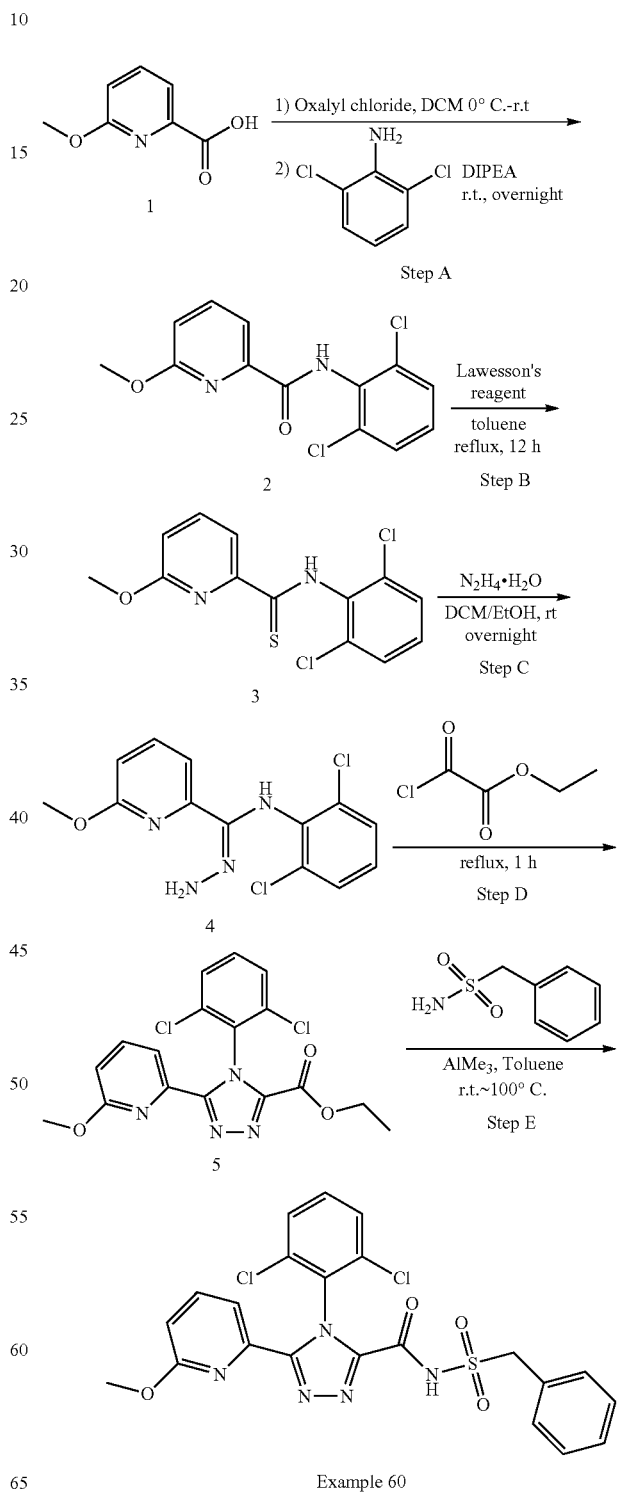

Example 60

Step A: N-(2,6-dichlorophenyl)-6-methoxypicolinamide

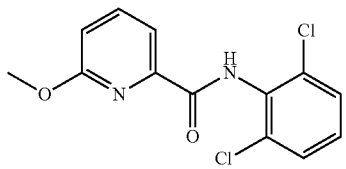 [SMILES: COc1cccc(C(=O)Nc2c(Cl)cccc2Cl)n1]

To a solution of 6-methoxypicolinic acid (2.0 g, 13.0 mmol, 1 equiv) in DCM (50 mL) was added oxalyl dichloride (2.5 g, 19.6 mmol, 1.5 equiv) and DMF (0.5 mL) dropwise at 0° C. The reaction mixture was stirred at room temperature for 2 hours and then concentrated. The residue was dissolved in DCM (100 mL). DIPEA (26 mmol, 3.25 g) and 2,6-dichloroaniline (14.3 mmol, 2.32 g) was added. The resulting mixture was stirred at room temperature for 16 hours. The reaction mixture was washed with water (30 mL), dried over anhydrous $Na_2SO_4$, filtered and concentrated in vacuo. The residue was purified by flash column chromatography on silica gel (eluted with PE/EtOAc=2/1) to afford the title compound N-(2,6-dichlorophenyl)-6-methoxypicolinamide as a white solid (1.9 g, 50% yield).
LC-MS: m/z 297.0 $(M+H)^+$

Step B: N-(2,6-dichlorophenyl)-6-methoxypyridine-2-carbothioamide

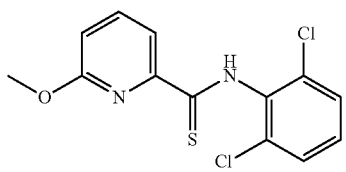 [SMILES: COc1cccc(C(=S)Nc2c(Cl)cccc2Cl)n1]

A solution of N-(2,6-dichlorophenyl)-6-methoxypicolinamide (1.7 g, 5.7 mmol, 1 equiv) and Lawesson's reagent (2.3 g, 5.7 mmol, 1 equiv) in toluene (20 mL) was refluxed for 12 hours. The reaction mixture was concentrated and the residue was purified by flash column chromatography on silica gel (eluted with PE/EtOAc=5/1) to afford the title compound N-(2,6-dichlorophenyl)-6-methoxypyridine-2-carbothioamide as a yellow solid (1.4 g, 78% yield).
LC-MS: m/z 313.0 $(M+H)^+$

Step C: N-(2,6-dichlorophenyl)-6-methoxypicolinohydrazonamide

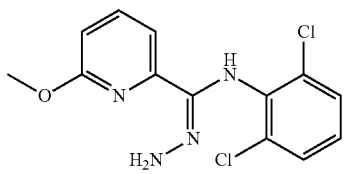 [SMILES: COc1cccc(/C(=N\N)Nc2c(Cl)cccc2Cl)n1]

To a solution of N-(2,6-dichlorophenyl)-6-methoxypyridine-2-carbothioamide (1 g, 3.2 mmol, 1 equiv) in EtOH/DCM (10 mL/10 mL) was added $N_2H_4 \cdot H_2O$ (480 mg, 3.6 mmol, 1.1 equiv) at room temperature. The mixture was stirred at r.t. for 12 hours under $N_2$ atmosphere. The reaction mixture was concentrated to afford the crude title compound N-(2,6-dichlorophenyl)-6-methoxypicolinohydrazonamide as a yellow solid, which was used directly for next step without purification (1 g crude).
LC-MS: m/z 311.0 $(M+H)^+$

Step D: ethyl 4-(2,6-dichlorophenyl)-5-(6-methoxypyridin-2-yl)-4H-1,2,4-triazole-3-carboxylate

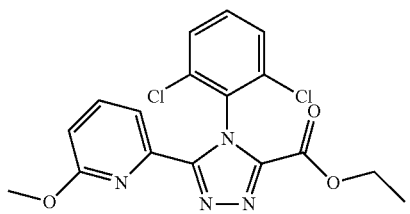 [SMILES: CCOC(=O)c1nnc(-c2cccc(OC)n2)n1-c1c(Cl)cccc1Cl]

A mixture of N-(2,6-dichlorophenyl)-6-methoxypicolinohydrazonamide (1 g crude, 3.2 mmol, 1 equiv) in ethyl 2-chloro-2-oxoacetate (15 mL) was refluxed for 1 hour under $N_2$ atmosphere. The reaction mixture was concentrated and the residue was purified by flash column chromatography on silica gel (eluted with PE/EtOAc=5/1) to afford the title compound ethyl 4-(2,6-dichlorophenyl)-5-(6-methoxypyridin-2-yl)-4H-1,2,4-triazole-3-carboxylate as a yellow solid (850 mg, 68% yield for two steps).
LC-MS: m/z 393.0 $(M+H)^+$

Step E: N-(benzylsulfonyl)-4-(2,6-dichlorophenyl)-5-(6-methoxypyridin-2-yl)-4H-1,2,4-triazole-3-carboxamide (Example 60)

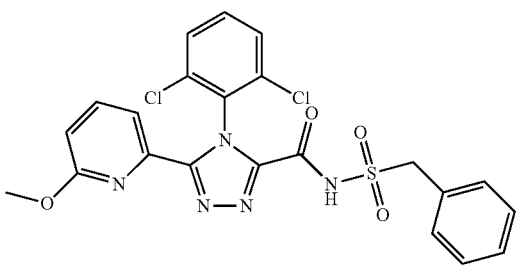

To a solution of phenylmethanesulfonamide (75 mg, 0.44 mmol, 1 equiv) in anhydrous toluene (10 mL) was added dropwise $AlMe_3$ (1.6 mol/L in toluene, 0.55 mL, 0.88 mmol, 2 equiv) at room temperature under $N_2$ atmosphere. The mixture was stirred at 50° C. for 0.5 hour. Then ethyl 4-(2,6-dichlorophenyl)-5-(6-methoxypyridin-2-yl)-4H-1,2,4-triazole-3-carboxylate (173 mg, 0.44 mmol, 1 equiv) in anhydrous toluene (5 mL) was added. The resulting mixture was stirred at 100° C. for 2 hours. The reaction mixture was acidified with HCOOH (aq., 1 mol/L) to pH=5, and extracted with DCM (3*20 mL). The combined organic phase was dried over anhydrous $Na_2SO_4$ and concentrated in vacuo. The residue was purified by flash column chromatography on silica gel (eluted with DCM/MeOH=100/1) to afford the title compound N-(benzylsulfonyl)-4-(2,6-dichlorophenyl)-5-(6-methoxypyridin-2-yl)-4H-1,2,4-triazole-3-carboxamide as a white solid (35 mg, 17% yield).

$^1$H NMR (400 MHz, DMSO-$d_6$) δ: 8.40 (d, J=4.0 Hz, 1H), 7.77 (t, J=8.0 Hz, 1H), 7.52-7.57 (m, 2H), 7.42-7.46 (m, 1H), 7.32-7.32 (m, 2H), 7.26-7.28 (m, 3H), 6.79 (d, J=8.0 Hz, 1H), 4.39 (s, 2H), 3.21 (s, 3H). LC-MS: m/z 518.0 (M+H)$^+$

Example 61: N-(benzylsulfonyl)-4-(2,6-difluorophenyl)-5-(6-methoxypyridin-2-yl)-4H-1,2,4-triazole-3-carboxamide

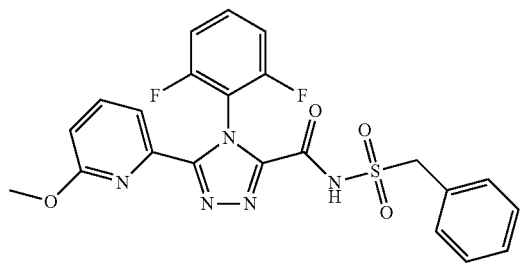 [SMILES: COc1cccc(-c2nnc(C(=O)NS(=O)(=O)Cc3ccccc3)n2-c2c(F)cccc2F)n1]

The title compound was prepared according to Method G, by using 2,6-difluoroaniline in step A.

$^1$H NMR (400 MHz, DMSO-$d_6$) δ: 7.82-7.91 (m, 2H), 7.55-7.61 (m, 1H), 7.27-7.36 (m, 5H), 7.18-7.20 (m, 2H), 6.88 (dd, J=7.2 Hz, 1.6 Hz, 1H), 4.35 (s, 2H), 3.17 (s, 3H). LC-MS: m/z 486.1 (M+H)$^+$

Example 62: N-(benzylsulfonyl)-4-(2-methoxy-6-(trifluoromethyl)phenyl)-5-(6-methoxypyridin-2-yl)-4H-1,2,4-triazole-3-carboxamide

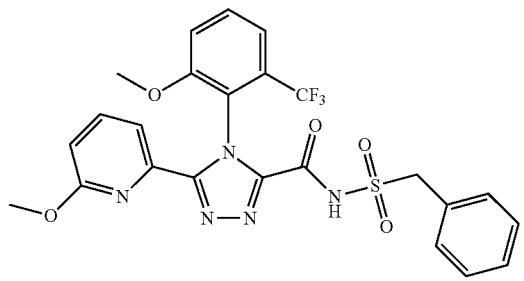 [SMILES: COc1cccc(-c2nnc(C(=O)NS(=O)(=O)Cc3ccccc3)n2-c2c(OC)cccc2C(F)(F)F)n1]

The title compound was prepared according to Method G, by using 2-methoxy-6-(trifluoromethyl)aniline in step A.

$^1$H NMR (400 MHz, DMSO-$d_6$) δ: 7.92 (dd, J=7.6 Hz, 1.2 Hz, 1H), 7.86 (t, J=7.6 Hz, 1H), 7.74 (t, J=8.0 Hz, 1H), 7.63 (d, J=8.4 Hz, 1H), 7.50 (d, J=7.6 Hz, 1H), 7.34-7.39 (m, 3H), 7.20-7.27 (m, 2H), 6.88 (dd, J=8.0 Hz, 1.2 Hz, 1H), 4.63 (s, 2H), 3.79 (s, 3H), 3.01 (s, 3H). LC-MS: m/z 548.1 (M+H)$^+$

Example 63: N-(benzylsulfonyl)-4-(2-fluoro-6-methoxyphenyl)-5-(6-methoxypyridin-2-yl)-4H-1,2,4-triazole-3-carboxamide

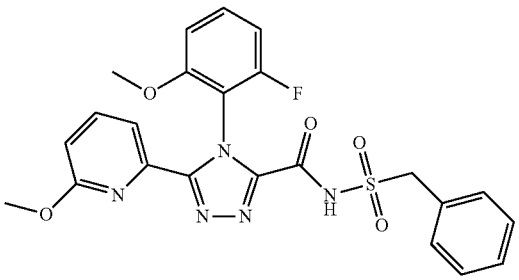 [SMILES: COc1cccc(-c2nnc(C(=O)NS(=O)(=O)Cc3ccccc3)n2-c2c(F)cccc2OC)n1]

The title compound was prepared according to Method G, by using 2-fluoro-6-methoxyaniline in step A.

$^1$H-NMR (400 MHz, DMSO-$d_6$) δ: 7.83-7.90 (m, 2H), 7.48-7.57 (m, 1H), 7.37-7.39 (m, 3H), 7.24-7.26 (m, 2H), 7.05-7.10 (m, 2H), 6.90 (dd, J=8.0 Hz, 1.2 Hz, 1H), 4.68 (s, 2H), 3.70 (s, 3H), 3.16 (s, 3H). LC-MS: m/z 498.0 (M+H)$^+$

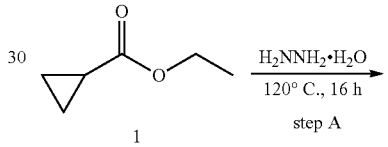

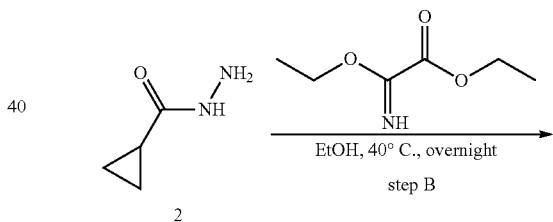

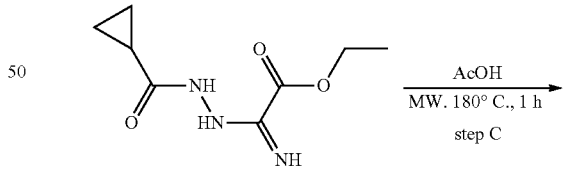

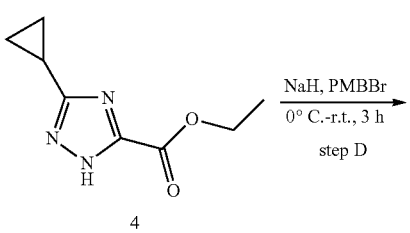

-continued

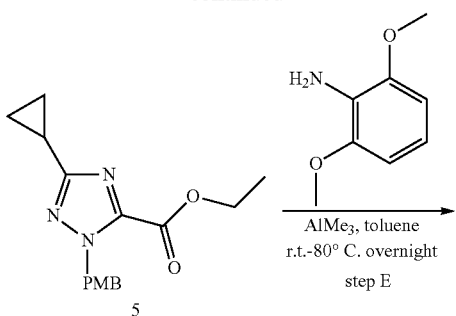

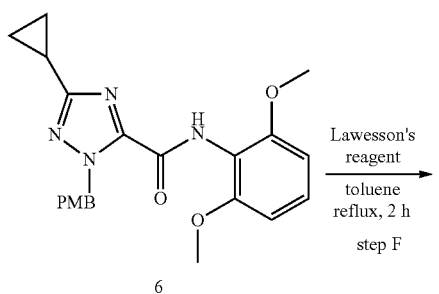

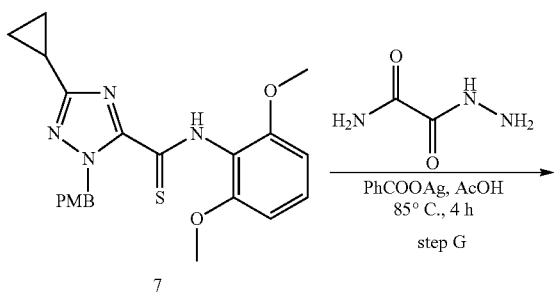

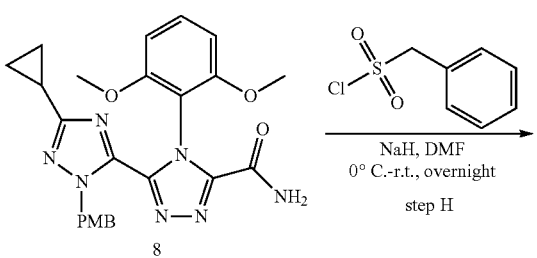

-continued

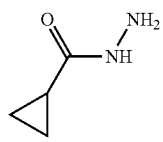

Step A: Cyclopropanecarbohydrazide

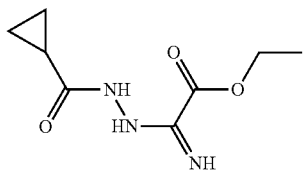

20 g (200 mmol, 1 equiv) ethyl cyclopropanecarboxylate and 20 g (400 mmol, 2 equiv) hydrazine hydrate (99%) were charged into round bottom flask. The solution was stirred at 120° C. for 16 h. After that, the reaction mixture was concentrated. The residue was suspended in toluene and the mixture was stirred at r.t. for 1 h. The mixture was filtered and the filter cake was dried to give cyclopropanecarbohydrazide (20 g, 100% yield) as a white solid.

LC-MS: m/z 101.0 (M+H)$^+$

Step B: ethyl 2-(2-(cyclopropanecarbonyl)hydrazinyl)-2-iminoacetate

To a solution of cyclopropanecarbohydrazide (6.9 g, 69 mmol, 1 equiv) in ethanol (20 mL) was added ethyl 2-ethoxy-2-iminoacetate (10 g, 69 mmol, 1 equiv). The mixture was stirred at 40° C. overnight. The resulting solid was filtered and the filter cake was washed with cool ethanol to afford ethyl 2-(2-(cyclopropanecarbonyl)hydrazinyl)-2-iminoacetate as a white solid, which was used for next step without further purification (5.8 g, 42.7% yield).

LC-MS: m/z 200.1 (M+H)$^+$

Step C: ethyl 3-cyclopropyl-1H-1,2,4-triazole-5-carboxylate

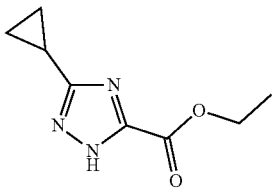

A solution of ethyl 2-(2-(cyclopropanecarbonyl)hydrazinyl)-2-iminoacetate (1.0 g, 5.0 mmol, 1 equiv) in AcOH (10 mL) was stirred at 180° C. under microwave irradiation for 1 hour. The mixture was concentrated in vacuo. The residue was purified by column chromatography (eluted with EtOAc/PE=1/1) to afford the title compound ethyl 3-cyclopropyl-1H-1,2,4-triazole-5-carboxylate as a white solid (750 mg, 83% yield).
LC-MS: m/z 182.1 (M+H)$^+$

Step D: ethyl 3-cyclopropyl-1-(4-methoxybenzyl)-1H-1,2,4-triazole-5-carboxylate

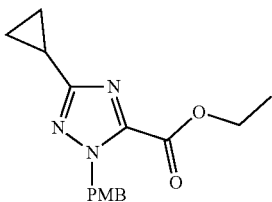

To a solution of ethyl 3-cyclopropyl-1H-1,2,4-triazole-5-carboxylate (1.0 g, 5.5 mmol, 1 equiv) in DMF (10 mL) was added NaH (60% in mineral oil, 267 mg, 6.6 mmol, 1.2 equiv) at 0° C. The reaction was stirred at 0° C. for 1 hour. PMBBr (1.33 g, 6.6 mmol, 1.2 equiv) was added to the above mixture. The resulting mixture was stirred at room temperature for 3 hours. The reaction mixture was quenched with water (30 mL) and extracted with EtOAc (3*50 mL). The combined organic layers were dried over anhydrous Na$_2$SO$_4$ and concentrated in vacuo. The residue was purified by column chromatography (eluted with PE/EtOAc=1/1) to afford the title compound ethyl 3-cyclopropyl-1-(4-methoxybenzyl)-1H-1,2,4-triazole-5-carboxylate as a white solid (400 mg, 24% yield).
LC-MS: m/z 302.1 (M+H)$^+$

Step E: 3-cyclopropyl-N-(2,6-dimethoxyphenyl)-1-(4-methoxybenzyl)-1H-1,2,4-triazole-5-carboxamide

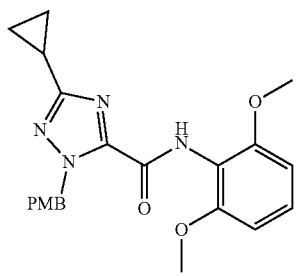

To a solution of 2,6-dimethoxyaniline (100 mg, 0.65 mmol, 2 equiv) in toluene (10 mL) was added AlMe$_3$ (1.6 mol/L in toluene, 0.4 mL, 0.65 mmol, 2 equiv) dropwise at room temperature. The mixture was stirred at room temperature for 0.5 hour. Then ethyl 3-cyclopropyl-1-(4-methoxybenzyl)-1H-1,2,4-triazole-5-carboxylate (100 mg, 0.33 mmol, 1 equiv) was added in one portion. The resulting mixture was stirred at 80° C. overnight. The mixture was quenched with water and extracted with EtOAc (3*20 mL). The combined organic layers were dried over anhydrous Na$_2$SO$_4$ and concentrated in vacuo. The residue was purified by column chromatography (eluted with PE/EtOAc=2/1) to afford the title compound 3-cyclopropyl-N-(2,6-dimethoxyphenyl)-1-(4-methoxybenzyl)-1H-1,2,4-triazole-5-carboxamide as an off-white solid (45 mg, 33% yield).
LC-MS: m/z 409.2 (M+H)$^+$

Step F: 3-cyclopropyl-N-(2,6-dimethoxyphenyl)-1-(4-methoxybenzyl)-1H-1,2,4-triazole-5-carbothioamide

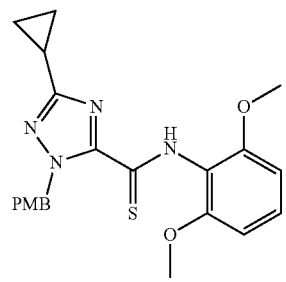

To a solution of 3-cyclopropyl-N-(2,6-dimethoxyphenyl)-1-(4-methoxybenzyl)-1H-1,2,4-triazole-5-carboxamide (4.9 g, 12 mmol, 1 equiv) in toluene (30 mL) was added Lawesson's reagent (3.15 g, 7.8 mmol, 0.7 equiv) under argon atmosphere. The resulting mixture was refluxed for 2 hours. The mixture was concentrated in vacuo and the residue was purified by column chromatography (eluted with DCM/methanol=1/1) to afford the title compound 3-cyclopropyl-N-(2,6-dimethoxyphenyl)-1-(4-methoxybenzyl)-1H-1,2,4-triazole-5-carbothioamide as a yellow solid (2.3 g, 45% yield).
LC-MS: m/z 425.2 (M+H)$^+$

Step G: 5-cyclopropyl-4'-(2,6-dimethoxyphenyl)-2-(4-methoxybenzyl)-2H,4'H-[3,3'-bi(1,2,4-triazole)]-5'-carboxamide

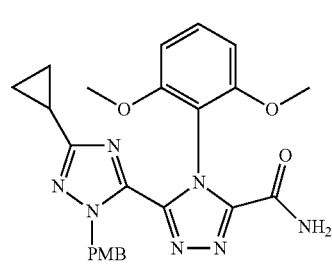

A suspension of 3-cyclopropyl-N-(2,6-dimethoxyphenyl)-1-(4-methoxybenzyl)-1H-1,2,4-triazole-5-carbothioamide (2.3 g, 5.4 mmol, 1 equiv), silver benzoate (3.7 g, 16.2 mmol, 3 equiv) and oxamic hydrazide (1.7 g, 16.2 mmol, 3 equiv) in acetic acid (20 mL) was stirred at 85° C. for 4 hours. The mixture was filtered and the filtrate was concentrated in vacuo. The residue was purified by column chromatography (eluted with DCM/MeOH=1/20) to afford the title compound 5-cyclopropyl-4'-(2,6-dimethoxyphenyl)-2-(4-methoxybenzyl)-2H,4'H-[3,3'-bi(1,2,4-triazole)]-5'-carboxamide as a white solid (1.74 g, 67% yield).

LC-MS: m/z 476.2 (M+H)$^+$

Step H: N-(benzylsulfonyl)-5-cyclopropyl-4'-(2,6-dimethoxyphenyl)-2-(4-methoxybenzyl)-2H,4'H-[3,3'-bi(1,2,4-triazole)]-5'-carboxamide (Example 64)

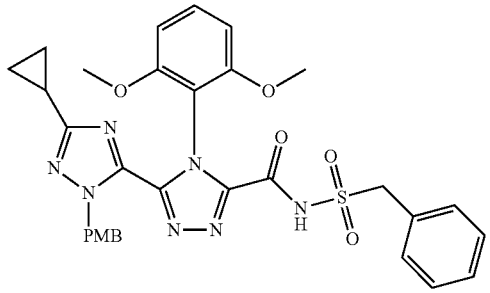

To a solution of 5-cyclopropyl-4'-(2,6-dimethoxyphenyl)-2-(4-methoxybenzyl)-2H,4'H-[3,3'-bi(1,2,4-triazole)]-5'-carboxamide (1.2 g, 2.5 mmol, 1 equiv) in DMF (20 mL) was added NaH (60% in mineral oil, 0.5 g, 12.6 mmol, 5 equiv) at 0° C. The mixture was stirred at 0° C. for 0.5 hour. Then phenylmethanesulfonyl chloride (2.4 g, 12.6 mmol, 5 equiv) was added. The resulting mixture was stirred at r.t. overnight. The mixture was quenched with water (60 mL) and extracted with EtOAc (3*100 mL). The combined organic layers were dried over anhydrous Na$_2$SO$_4$ and concentrated in vacuo. The residue was purified by reverse phase column chromatography (eluted with MeOH/H$_2$O=5/95~95/5) to afford the title compound N-(benzylsulfonyl)-5-cyclopropyl-4'-(2,6-dimethoxyphenyl)-2-(4-methoxybenzyl)-2H,4'H-[3,3'-bi(1,2,4-triazole)]-5'-carboxamide as a white solid (260 mg, 16% yield).

$^1$H-NMR (400 MHz, DMSO-d$_6$) δ 7.33-7.38 (m, 1H), 7.14-7.29 (m, 5H), 7.06 (d, J=8.4 Hz, 2H), 6.88 (d, J=8.4 Hz, 2H), 6.71 (d, J=8.4 Hz, 2H), 5.26 (s, 2H), 4.14 (s, 2H), 3.74 (s, 3H), 3.55 (s, 6H), 2.15-2.25 (m, 1H), 0.90-1.00 (m, 2H), 0.63-0.75 (m, 2H).

LC-MS: m/z 630.1 (M+H)$^+$

Step I: N-(benzylsulfonyl)-5-cyclopropyl-4'-(2,6-dimethoxyphenyl)-2H,4'H-[3,3'-bi(1,2,4-triazole)]-5'-carboxamide (Example 65)

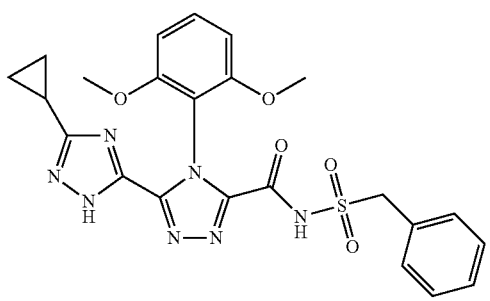 [SMILES: COc1cccc(OC)c1-n1c(C(=O)NS(=O)(=O)Cc2ccccc2)nnc1-c1nc(C2CC2)n[nH]1]

A suspension of N-(benzylsulfonyl)-5-cyclopropyl-4'-(2,6-dimethoxyphenyl)-2-(4-methoxybenzyl)-2H,4'H-[3,3'-bi(1,2,4-triazole)]-5'-carboxamide (90 mg, 0.14 mmol, 1 equiv) in TFA (10 mL) was stirred at 110° C. under argon atmosphere under microwave irradiation for 1 hour. The mixture was concentrated in vacuo and the residue was purified by prep-HPLC (eluted with MeOH/H$_2$O=5/95~95/5) to afford the title compound N-(benzylsulfonyl)-5-cyclopropyl-4'-(2,6-dimethoxyphenyl)-2H,4'H-[3,3'-bi(1,2,4-triazole)]-5'-carboxamide as a white solid (34 mg, 48% yield).

$^1$H NMR (400 MHz, DMSO-d$_6$) δ 14.07 (br.s, 1H), 7.43 (t, J=8.4 Hz, 1H), 7.35-7.41 (m, 3H), 7.22-7.32 (m, 2H), 6.80 (d, J=8.4 Hz, 2H), 4.70 (s, 2H), 3.65 (s, 6H), 1.95-1.98 (m, 1H), 0.91-1.03 (m, 2H), 0.67-0.82 (m, 2H). LC-MS: m/z 510.0 (M+H)$^+$

Methods for Evaluating Compounds:

Activation of APJ receptor is known to inhibit forskolin-stimulated cyclic AMP (cAMP) production in cells in a pertussis toxin-sensitive manner which indicates primary coupling to the G$_{αi}$ subunit of the G protein heterotrimeric complex. In addition to signaling through G protein and inhibition of cAMP, APJ receptor activation also results in β-arrestin recruitment, receptor internalization and activation of extracellular-regulated kinases (ERKs). Evidence suggests signaling through Gi induced cAMP inhibition elicits the desired inotropic and vasodilatory pharmacological response whereas arrestin recruitment results in receptor internalization, downregulation and ultimately cardiac hypertrophy.

In order to optimize functional activity directed toward Gi coupling we utilized a CHO-K1 cell line developed by DiscoverX stably expressing the APJ Receptor. Cells expressing APJR receptor were plated in a 384-well microtiter plates and incubated overnight at 37° C. with 5% CO$_2$ to allow the cells to attach and grow. Media was then aspirated from the cells and replaced with 15 uL 2:1 Hanks Balanced Salt Solution (HBSS)/10 mM Hepes. cAMP XS+ Ab reagent. Five microliters (5 uL) of previously generated compound sample stocks at 4× final concentration in assay buffer containing 4×EC80 forskolin were then added to the cells and allowed to incubate at 37° C. for 30 minutes.

After incubation the assay signal was generated using a technology termed enzyme fragment complementation (EFC). In EFC the enzyme B-galactosidase is split into two complementary portions (EA and ED). The fragment ED is fused to cAMP and in the assay format competes with endogenous cAMP for binding to a cAMP specific antibody. Activated B-Gal is formed when exogenous EA fragment binds to free ED-cAMP (not bound to cAMP specific antibody). Activated enzyme levels are detected through conversion of B-gal chemiluminescent substrate which generates a detectable luminescence signal and read on standard microtiter plate.

The methodology for detection of cAMP using EFC requires incubation with 20 uL of cAMP XS+ ED/CL lysis cocktail for one hour followed by incubation with 20 uL cAMP XS+ EA reagent for three hours at room temperature. Microplates were read following signal generation with a PerkinElmer Envision instrument utilizing chemiluminescent signal detection.

Compound activity was analyzed using CBIS data analysis suite (ChemInnovation, CA).

Percentage activity was calculated using the following formula:

% Activity=10000×(1−(mean RLU of test sample−mean RLU of Max control)/(mean RLU of vehicle control−mean RLU of Max control))

The biological activity of the exemplified compounds of this invention determined by the assay described above is shown in Table 1. The APJ cAMP $EC_{50}$ potency ranges are as follows: A: $EC_{50}<1$ nM; B: $1\leq EC_{50}<100$ nM; and C: $100\leq EC_{50}<10,000$ nM.

TABLE 1

Example compounds and their potency range

| Ex. number | Structure | IUPAC name | Potency range |
|---|---|---|---|
| 1 | 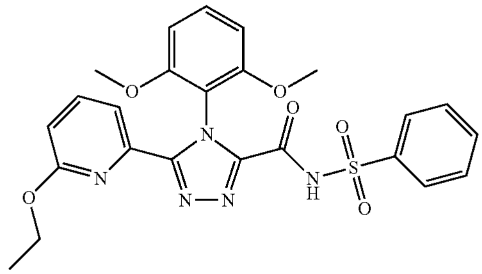 [SMILES: CCOc1cccc(-c2nnc(C(=O)NS(=O)(=O)c3ccccc3)n2-c2c(OC)cccc2OC)n1] | 4-(2,6-dimethoxyphenyl)-5-(6-ethoxypyridin-2-yl)-N-(phenylsulfonyl)-4H-1,2,4-triazole-3-carboxamide | A |
| 2 | 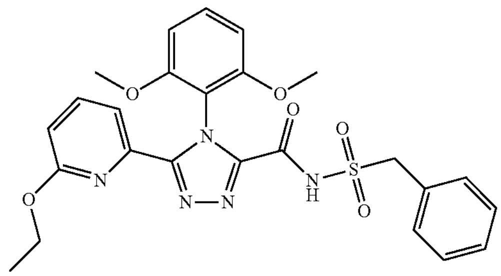 [SMILES: CCOc1cccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(6-ethoxypyridin-2-yl)-4H-1,2,4-triazole-3-carboxamide | A |
| 3 | 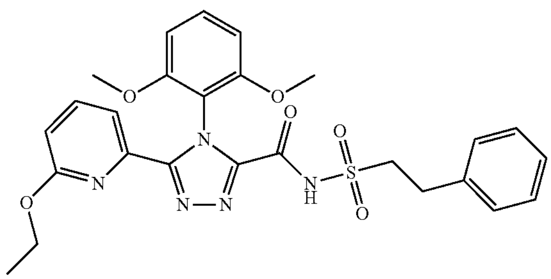 [SMILES: CCOc1cccc(-c2nnc(C(=O)NS(=O)(=O)CCc3ccccc3)n2-c2c(OC)cccc2OC)n1] | 4-(2,6-dimethoxyphenyl)-5-(6-ethoxypyridin-2-yl)-N-(phenethylsulfonyl)-4H-1,2,4-triazole-3-carboxamide | A |
| 4 | 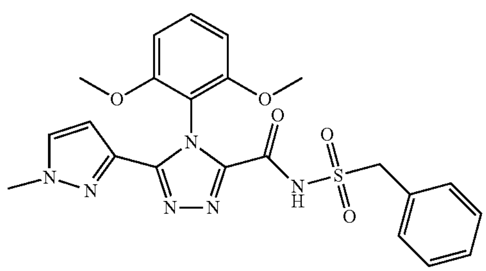 [SMILES: COc1cccc(OC)c1-n1c(C(=O)NS(=O)(=O)Cc2ccccc2)nnc1-c1ccn(C)n1] | N-(benzylsulfonyl)-4-(2,6-dimethoxyphenyl)-5-(1-methyl-1H-pyrazol-3-yl)-4H-1,2,4-triazole-3-carboxamide | B |
| 5 | 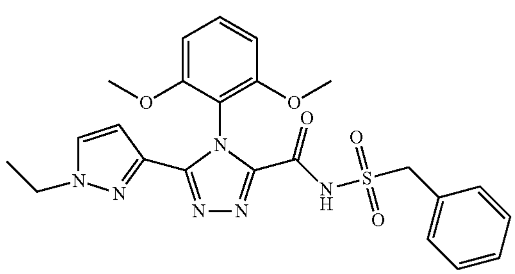 [SMILES: CCn1ccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(1-ethyl-1H-pyrazol-3-yl)-4H-1,2,4-triazole-3-carboxamide | B |

TABLE 1-continued

Example compounds and their potency range

| Ex. number | Structure | IUPAC name | Potency range |
|---|---|---|---|
| 6 | 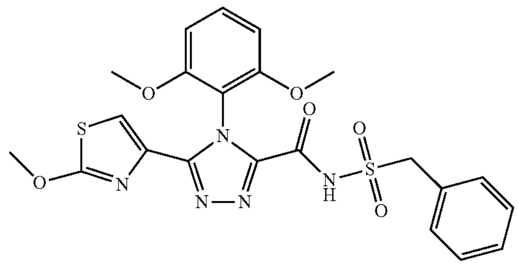 [SMILES: COc1nc(-c2nnc(C(=O)NS(=O)(=O)Cc3ccccc3)n2-c2c(OC)cccc2OC)cs1] | N-(benzylsulfonyl)-4-(2,6-dimethoxyphenyl)-5-(2-methoxythiazol-4-yl)-4H-1,2,4-triazole-3-carboxamide | B |
| 7 | 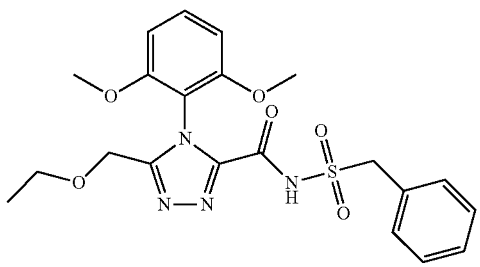 [SMILES: CCOCc1nnc(C(=O)NS(=O)(=O)Cc2ccccc2)n1-c1c(OC)cccc1OC] | N-(benzylsulfonyl)-4-(2,6-dimethoxyphenyl)-5-(ethoxymethyl)-4H-1,2,4-triazole-3-carboxamide | C |
| 8 | 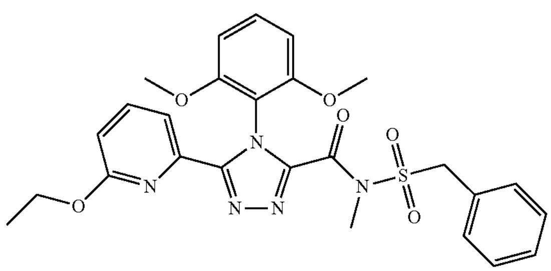 [SMILES: CCOc1cccc(-c2nnc(C(=O)N(C)S(=O)(=O)Cc3ccccc3)n2-c2c(OC)cccc2OC)n1] | N-(benzylsulfonyl)-4-(2,6-dimethoxyphenyl)-5-(6-ethoxypyridin-2-yl)-N-methyl-4H-1,2,4-triazole-3-carboxamide | B |
| 9 | 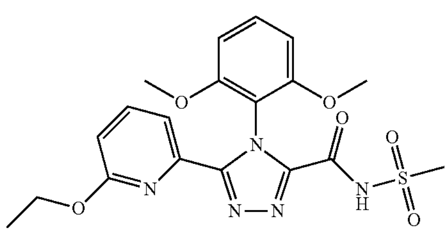 [SMILES: CCOc1cccc(-c2nnc(C(=O)NS(C)(=O)=O)n2-c2c(OC)cccc2OC)n1] | 4-(2,6-Dimethoxyphenyl)-5-(6-ethoxypyridin-2-yl)-N-(methylsulfonyl)-4H-1,2,4-triazole-3-carboxamide | B |
| 10 | 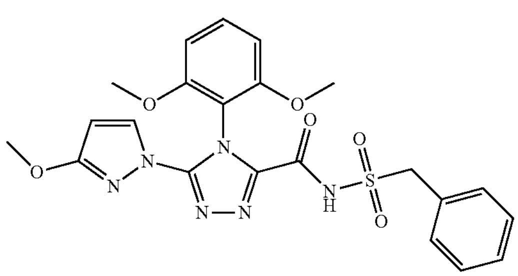 [SMILES: COc1ccn(-c2nnc(C(=O)NS(=O)(=O)Cc3ccccc3)n2-c2c(OC)cccc2OC)n1] | N-(enzylsulfonyl)-4-(2,6-dimethoxyphenyl)-5-(3-methoxy-1H-pyrazol-1-yl)-4H-1,2,4-triazole-3-carboxamide | C |

TABLE 1-continued

Example compounds and their potency range

| Ex. number | Structure | IUPAC name | Potency range |
|---|---|---|---|
| 11 | 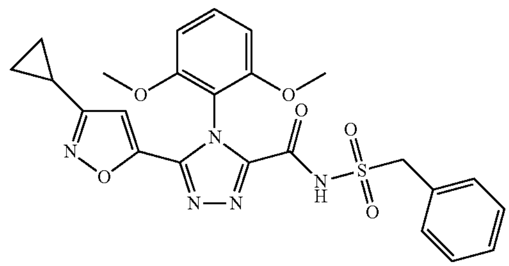 [SMILES: COc1cccc(OC)c1-n1c(C(=O)NS(=O)(=O)Cc2ccccc2)nnc1-c1cc(C2CC2)no1] | N-(benzylsulfonyl)-5-(3-cyclopropylisoxazol-5-yl)-4-(2,6-dimethoxyphenyl)-4H-1,2,4-triazole-3-carboxamide | C |
| 12 | 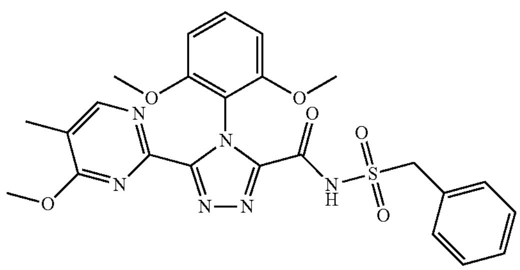 [SMILES: COc1cccc(OC)c1-n1c(C(=O)NS(=O)(=O)Cc2ccccc2)nnc1-c1ncc(C)c(OC)n1] | N-(benzylsulfonyl)-4-(2,6-dimethoxyphenyl)-5-(4-methoxy-5-methylpyrimidin-2-yl)-4H-1,2,4-triazole-3-carboxamide | C |
| 13 | 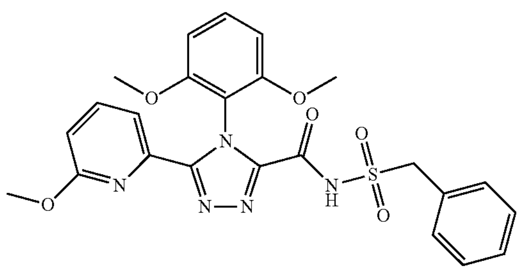 [SMILES: COc1cccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(6-methoxypyridin-2-yl)-4H-1,2,4-triazole-3-carboxamide | B |
| 14 | 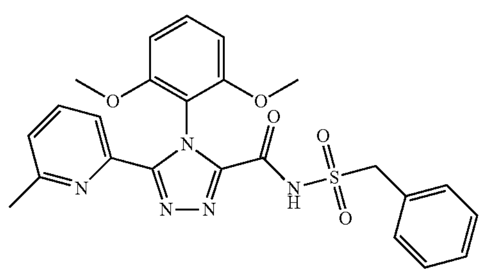 [SMILES: COc1cccc(OC)c1-n1c(C(=O)NS(=O)(=O)Cc2ccccc2)nnc1-c1cccc(C)n1] | N-(benzylsulfonyl)-4-(2,6-dimethoxyphenyl)-5-(6-methylpyridin-2-yl)-4H-1,2,4-triazole-3-carboxamide | B |
| 15 | 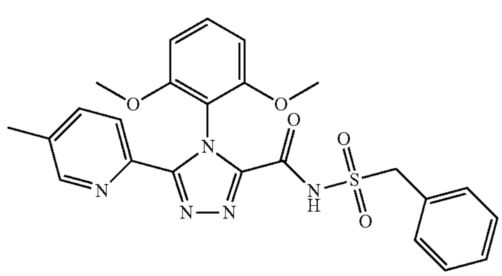 [SMILES: COc1cccc(OC)c1-n1c(C(=O)NS(=O)(=O)Cc2ccccc2)nnc1-c1ccc(C)cn1] | N-(benzylsulfonyl)-4-(2,6-dimethoxyphenyl)-5-(5-methylpyridin-2-yl)-4H-1,2,4-triazole-3-carboxamide | B |

TABLE 1-continued

Example compounds and their potency range

| Ex. number | Structure | IUPAC name | Potency range |
|---|---|---|---|
| 16 | 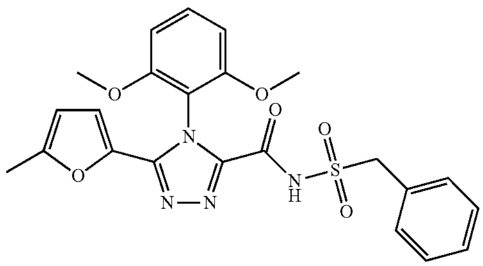 [SMILES: COc1cccc(OC)c1-n1c(C(=O)NS(=O)(=O)Cc2ccccc2)nnc1-c1ccc(C)o1] | N-(benzylsulfonyl)-4-(2,6-dimethoxyphenyl)-5-(5-methylfuran-2-yl)-4H-1,2,4-triazole-3-carboxamide | B |
| 17 | 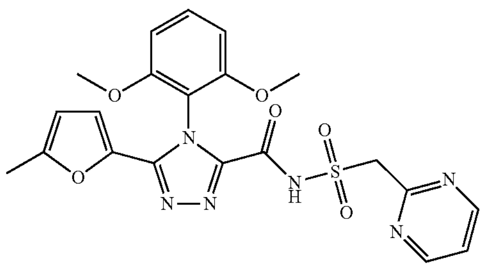 [SMILES: COc1cccc(OC)c1-n1c(C(=O)NS(=O)(=O)Cc2ncccn2)nnc1-c1ccc(C)o1] | 4-(2,6-Dimethoxyphenyl)-5-(5-methylfuran-2-yl)-N-((pyrimidin-2-ylmethyl)sulfonyl)-4H-1,2,4-triazole-3-carboxamide | A |
| 18 | 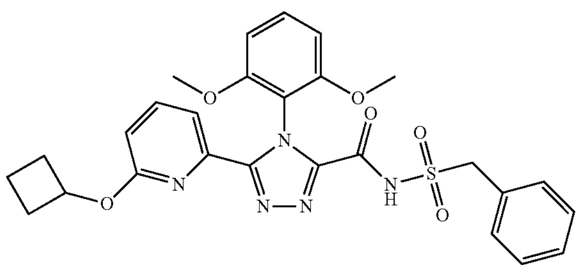 [SMILES: COc1cccc(OC)c1-n1c(C(=O)NS(=O)(=O)Cc2ccccc2)nnc1-c1cccc(OC2CCC2)n1] | N-(benzylsulfonyl)-5-(6-cyclobutoxypyridin-2-yl)-4-(2,6-dimethoxyphenyl)-4H-1,2,4-triazole-3-carboxamide | B |
| 19 | 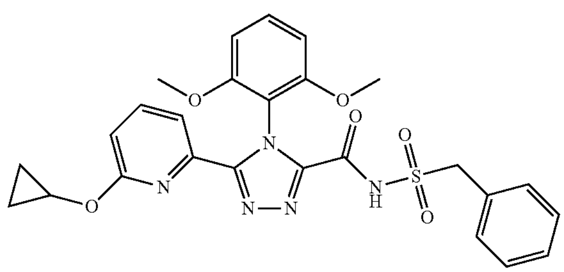 [SMILES: COc1cccc(OC)c1-n1c(C(=O)NS(=O)(=O)Cc2ccccc2)nnc1-c1cccc(OC2CC2)n1] | N-(benzylsulfonyl)-5-(6-cyclopropoxypyridin-2-yl)-4-(2,6-dimethoxyphenyl)-4H-1,2,4-triazole-3-carboxamide | A |
| 20 | 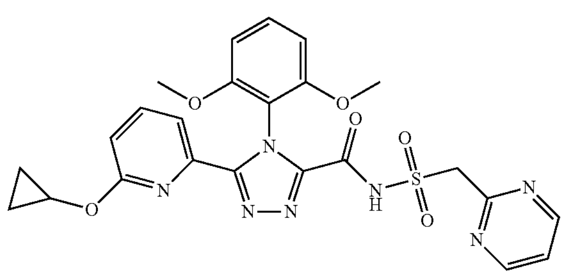 [SMILES: COc1cccc(OC)c1-n1c(C(=O)NS(=O)(=O)Cc2ncccn2)nnc1-c1cccc(OC2CC2)n1] | 5-(6-Cyclopropoxypyridin-2-yl)-4-(2,6-dimethoxyphenyl)-N-((pyrimidin-2-ylmethyl)sulfonyl)-4H-1,2,4-triazole-3-carboxamide | A |

TABLE 1-continued

Example compounds and their potency range

| Ex. number | Structure | IUPAC name | Potency range |
|---|---|---|---|
| 21 | 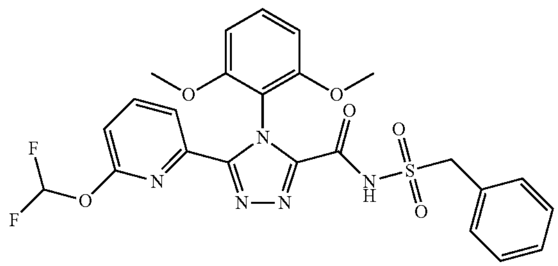 [SMILES: COc1cccc(OC)c1-n1c(C(=O)NS(=O)(=O)Cc2ccccc2)nnc1-c1cccc(OC(F)F)n1] | N-(benzylsulfonyl)-5-(6-(difluoromethoxy)pyridin-2-yl)-4-(2,6-dimethoxyphenyl)-4H-1,2,4-triazole-3-carboxamide | B |
| 22 | 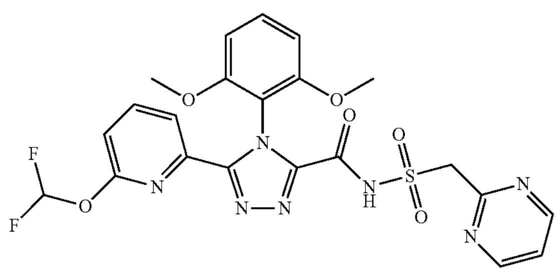 [SMILES: COc1cccc(OC)c1-n1c(C(=O)NS(=O)(=O)Cc2ncccn2)nnc1-c1cccc(OC(F)F)n1] | 5-(6-(Difluoromethoxy)pyridin-2-yl)-4-(2,6-dimethoxyphenyl)-N-((pyrimidin-2-ylmethyl)sulfonyl)-4H-1,2,4-triazole-3-carboxamide | B |
| 23 | 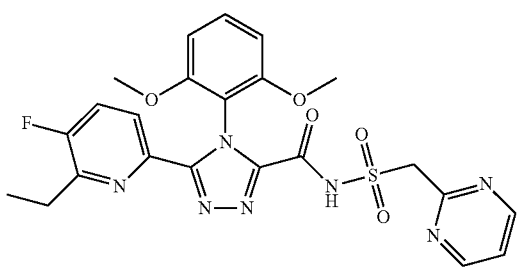 [SMILES: CCc1nc(-c2nnc(C(=O)NS(=O)(=O)Cc3ncccn3)n2-c2c(OC)cccc2OC)ccc1F] | 4-(2,6-Dimethoxyphenyl)-5-(5-fluoro-6-methoxypyridin-2-yl)-N-((pyrimidin-2-ylmethyl)sulfonyl)-4H-1,2,4-triazole-3-carboxamide | C |
| 24 | 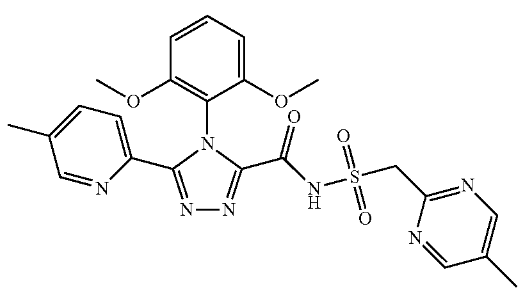 | 4-(2,6-Dimethoxyphenyl)-5-(5-methylpyridin-2-yl)-N-(((5-methylpyrimidin-2-yl)methyl)sulfonyl)-4H-1,2,4-triazole-3-carboxamide | C |
| 25 | 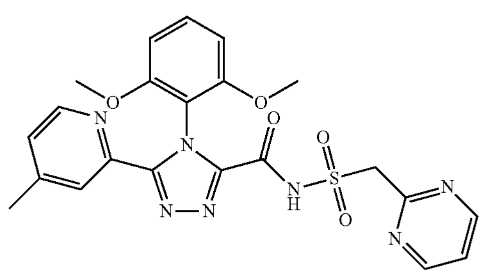 [SMILES: COc1cccc(OC)c1-n1c(C(=O)NS(=O)(=O)Cc2ncccn2)nnc1-c1cc(C)ccn1] | 4-(2,6-Dimethoxyphenyl)-5-(4-methylpyridin-2-yl)-N-((pyrimidin-2-ylmethyl)sulfonyl)-4H-1,2,4-triazole-3-carboxamide | C |

TABLE 1-continued

Example compounds and their potency range

| Ex. number | Structure | IUPAC name | Potency range |
|---|---|---|---|
| 26 | 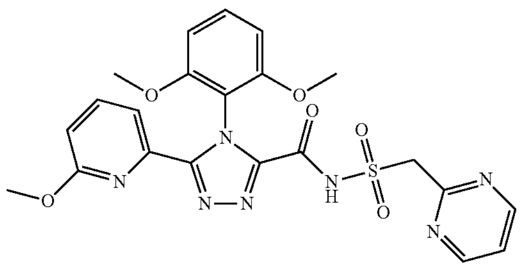 [SMILES: COc1cccc(-c2nnc(C(=O)NS(=O)(=O)Cc3ncccn3)n2-c2c(OC)cccc2OC)n1] | 4-(2,6-dimethoxyphenyl)-5-(6-methoxypyridin-2-yl)-N-((pyrimidin-2-ylmethyl)sulfonyl)-4H-1,2,4-triazole-3-carboxamide | A |
| 27 | 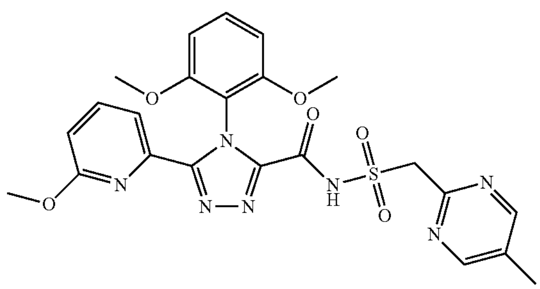 | 4-(2,6-Dimethoxyphenyl)-5-(6-methoxypyridin-2-yl)-N-(((5-methylpyrimidin-2-yl)methyl)sulfonyl)-4H-1,2,4-triazole-3-carboxamide | A |
| 28 | 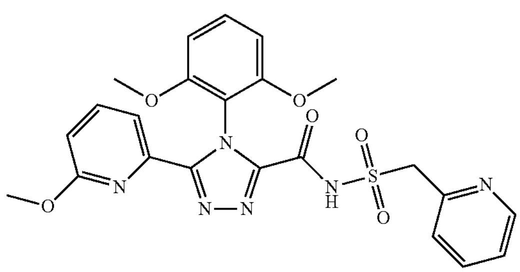 [SMILES: COc1cccc(-c2nnc(C(=O)NS(=O)(=O)Cc3ccccn3)n2-c2c(OC)cccc2OC)n1] | 4-(2,6-Dimethoxyphenyl)-5-(6-methoxypyridin-2-yl)-N-((pyridin-2-ylmethyl)sulfonyl)-4H-1,2,4-triazole-3-carboxamide | A |
| 29 | 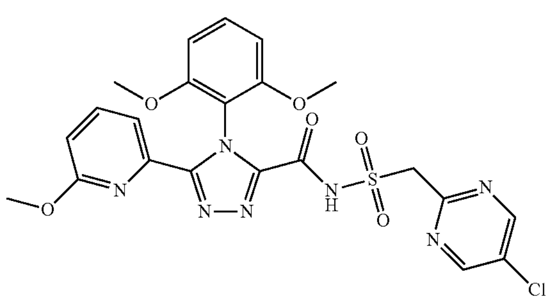 [SMILES: COc1cccc(-c2nnc(C(=O)NS(=O)(=O)Cc3ncc(Cl)cn3)n2-c2c(OC)cccc2OC)n1] | N-(((5-chloropyrimidin-2-yl)methyl)sulfonyl)-4-(2,6-dimethoxyphenyl)-5-(6-methoxypyridin-2-yl)-4H-1,2,4-triazole-3-carboxamide | A |
| 30 | 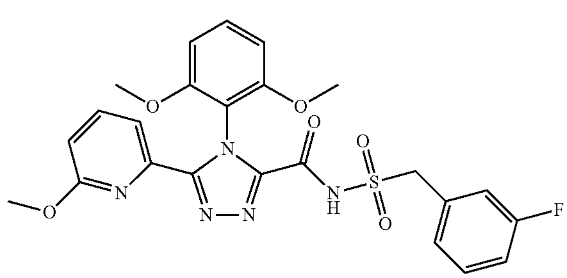 [SMILES: COc1cccc(-c2nnc(C(=O)NS(=O)(=O)Cc3cccc(F)c3)n2-c2c(OC)cccc2OC)n1] | 4-(2,6-Dimethoxyphenyl)-N-((3-fluorobenzyl)sulfonyl)-5-(6-methoxypyridin-2-yl)-4H-1,2,4-triazole-3-carboxamide | B |

TABLE 1-continued

Example compounds and their potency range

| Ex. number | Structure | IUPAC name | Potency range |
|---|---|---|---|
| 31 | 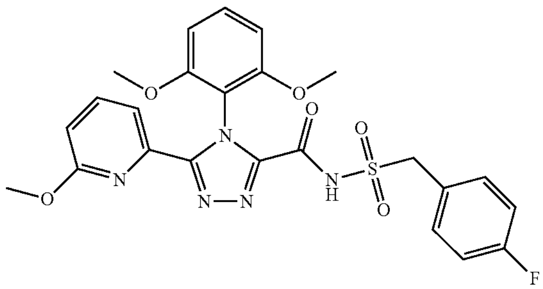 [SMILES: COc1cccc(-c2nnc(C(=O)NS(=O)(=O)Cc3ccc(F)cc3)n2-c2c(OC)cccc2OC)n1] | 4-(2,6-Dimethoxyphenyl)-N-((4-fluorobenzyl)sulfonyl)-5-(6-methoxypyridin-2-yl)-4H-1,2,4-triazole-3-carboxamide | A |
| 32 | 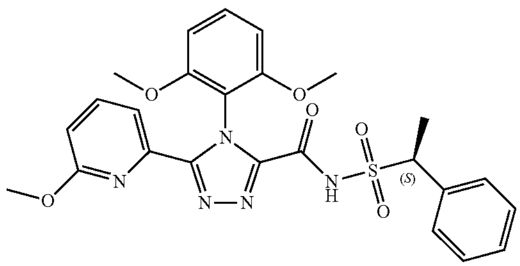 | (S)-4-(2,6-Dimethoxyphenyl)-5-(6-methoxypyridin-2-yl)-N-((1-phenylethyl)sulfonyl)-4H-1,2,4-triazole-3-carboxamide | B |
| 33 | 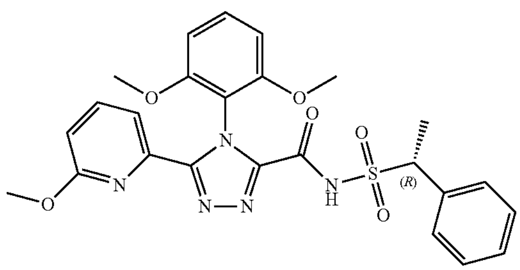 | (R)-4-(2,6-Dimethoxyphenyl)-5-(6-methoxypyridin-2-yl)-N-((1-phenylethyl)sulfonyl)-4H-1,2,4-triazole-3-carboxamide | B |
| 34 | 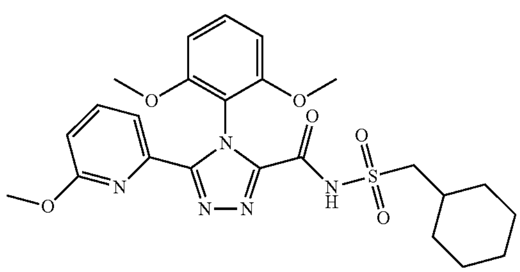 [SMILES: COc1cccc(-c2nnc(C(=O)NS(=O)(=O)CC3CCCCC3)n2-c2c(OC)cccc2OC)n1] | N-((cyclohexylmethyl)sulfonyl)-4-(2,6-dimethoxyphenyl)-5-(6-methoxypyridin-2-yl)-4H-1,2,4-triazole-3-carboxamide | A |
| 35 | 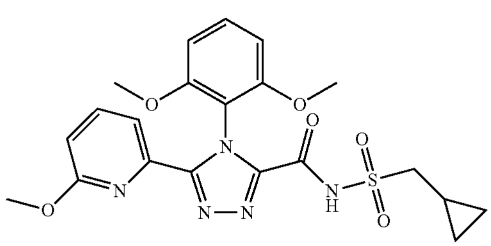 [SMILES: COc1cccc(-c2nnc(C(=O)NS(=O)(=O)CC3CC3)n2-c2c(OC)cccc2OC)n1] | N-((cyclopropylmethyl)sulfonyl)-4-(2,6-dimethoxyphenyl)-5-(6-methoxypyridin-2-yl)-4H-1,2,4-triazole-3-carboxamide | B |

TABLE 1-continued

Example compounds and their potency range

| Ex. number | Structure | IUPAC name | Potency range |
|---|---|---|---|
| 36 | 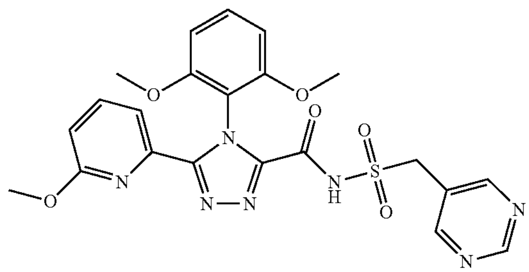 [SMILES: COc1cccc(-c2nnc(C(=O)NS(=O)(=O)Cc3cncnc3)n2-c2c(OC)cccc2OC)n1] | 4-(2,6-Dimethoxyphenyl)-5-(6-methoxypyridin-2-yl)-N-((pyrimidin-5-ylmethyl)sulfonyl)-4H-1,2,4-triazole-3-carboxamide | B |
| 37 | 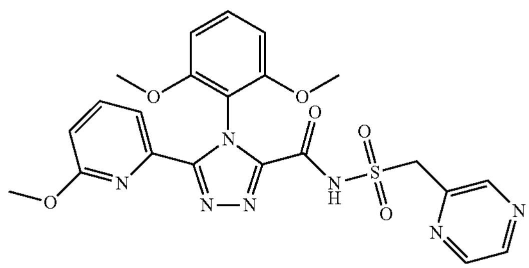 [SMILES: COc1cccc(-c2nnc(C(=O)NS(=O)(=O)Cc3cnccn3)n2-c2c(OC)cccc2OC)n1] | 4-(2,6-Dimethoxyphenyl)-5-(6-methoxypyridin-2-yl)-N-((pyrazin-2-ylmethyl)sulfonyl)-4H-1,2,4-triazole-3-carboxamide | B |
| 38 | 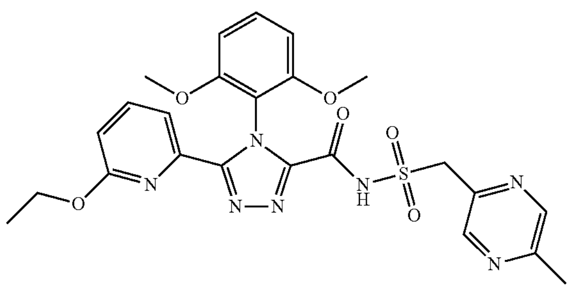 [SMILES: CCOc1cccc(-c2nnc(C(=O)NS(=O)(=O)Cc3cnc(C)cn3)n2-c2c(OC)cccc2OC)n1] | 4-(2,6-Dimethoxyphenyl)-5-(6-ethoxypyridin-2-yl)-N-(((5-methylpyrimidin-2-yl)methyl)sulfonyl)-4H-1,2,4-triazole-3-carboxamide | A |
| 39 | 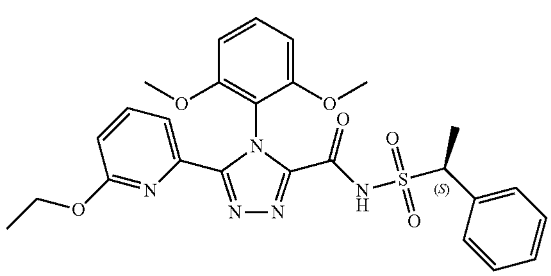 | (S)-4-(2,6-dimethoxyphenyl)-5-(6-ethoxypyridin-2-yl)-N-((1-phenylethyl)sulfonyl)-4H-1,2,4-triazole-3-carboxamide | A |
| 40 | 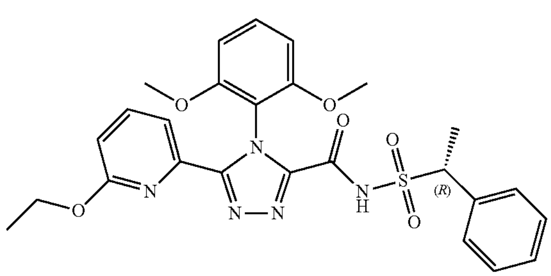 | (R)-4-(2,6-dimethoxyphenyl)-5-(6-ethoxypyridin-2-yl)-N-((1-phenylethyl)sulfonyl)-4H-1,2,4-triazole-3-carboxamide | A |

TABLE 1-continued

Example compounds and their potency range

| Ex. number | Structure | IUPAC name | Potency range |
|---|---|---|---|
| 41 | 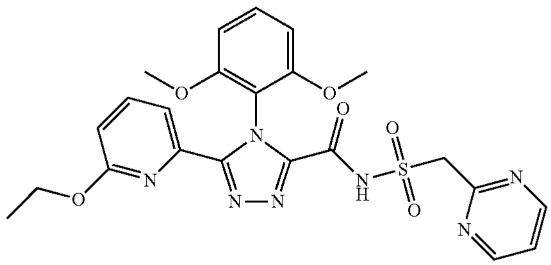 [SMILES: CCOc1cccc(-c2nnc(C(=O)NS(=O)(=O)Cc3ncccn3)n2-c2c(OC)cccc2OC)n1] | 4-(2,6-Dimethoxyphenyl)-5-(6-ethoxypyridin-2-yl)-N-((pyrimidin-2-ylmethyl)sulfonyl)-4H-1,2,4-triazole-3-carboxamide | A |
| 42 | 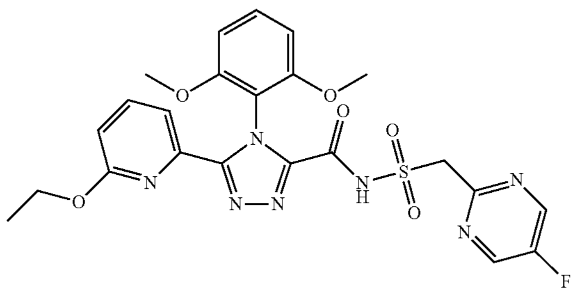 [SMILES: CCOc1cccc(-c2nnc(C(=O)NS(=O)(=O)Cc3ncc(F)cn3)n2-c2c(OC)cccc2OC)n1] | 4-(2,6-Dimethoxyphenyl)-5-(6-ethoxypyridin-2-yl)-N-(((5-fluoropyrimidin-2-yl)methyl)sulfonyl)-4H-1,2,4-triazole-3-carboxamide | A |
| 43 | 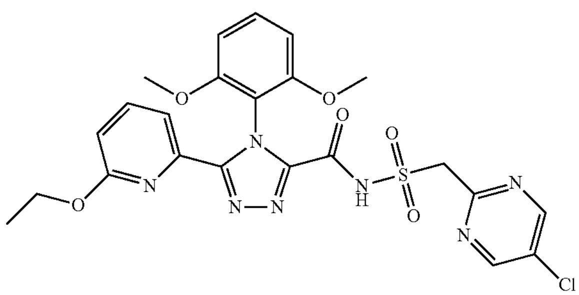 [SMILES: CCOc1cccc(-c2nnc(C(=O)NS(=O)(=O)Cc3ncc(Cl)cn3)n2-c2c(OC)cccc2OC)n1] | N-(((5-chloropyrimidin-2-yl)methyl)sulfonyl)-4-(2,6-dimethoxyphenyl)-5-(6-ethoxypyridin-2-yl)-4H-1,2,4-triazole-3-carboxamide | A |
| 44 | 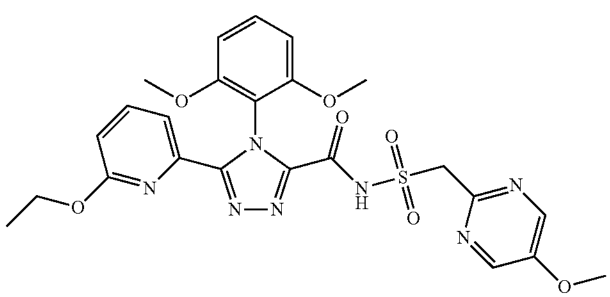 [SMILES: CCOc1cccc(-c2nnc(C(=O)NS(=O)(=O)Cc3ncc(OC)cn3)n2-c2c(OC)cccc2OC)n1] | 4-(2,6-Dimethoxyphenyl)-5-(6-ethoxypyridin-2-yl)-N-(((5-methoxypyrimidin-2-yl)methyl)sulfonyl)-4H-1,2,4-triazole-3-carboxamide | A |
| 45 | 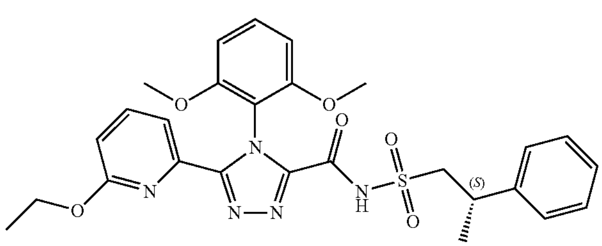 | (S)-4-(2,6-Dimethoxyphenyl)-5-(6-ethoxypyridin-2-yl)-N-((2-phenylpropyl)sulfonyl)-4H-1,2,4-triazole-3-carboxamide | A |

TABLE 1-continued

Example compounds and their potency range

| Ex. number | Structure | IUPAC name | Potency range |
|---|---|---|---|
| 46 | 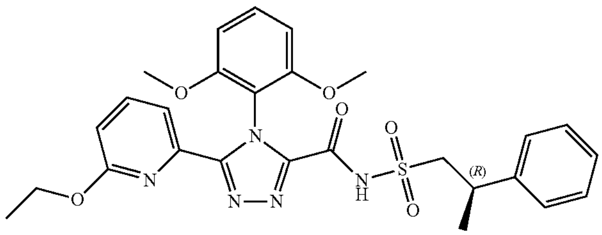 | (R)-4-(2,6-Dimethoxyphenyl)-5-(6-ethoxypyridin-2-yl)-N-((2-phenylpropyl)sulfonyl)-4H-1,2,4-triazole-3-carboxamide | A |
| 47 | 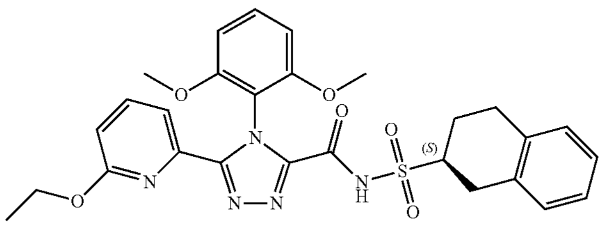 | (S)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide | A |
| 48 | 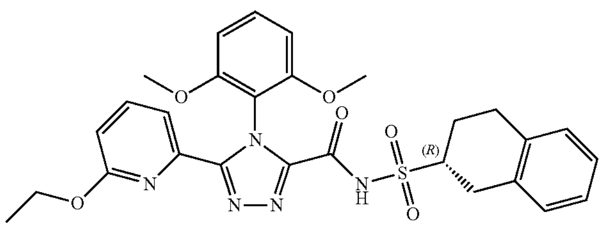 | (R)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide | A |
| 49 | 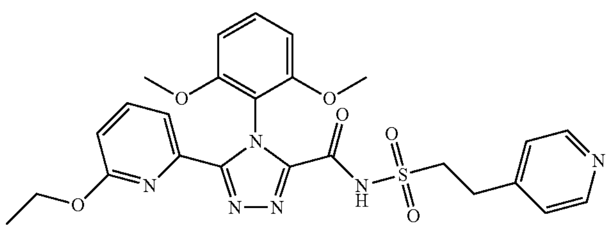 [SMILES: CCOc1cccc(-c2nnc(C(=O)NS(=O)(=O)CCc3ccncc3)n2-c2c(OC)cccc2OC)n1] | 4-(2,6-Dimethoxyphenyl)-5-(6-ethoxypyridin-2-yl)-N-((2-(pyridin-4-yl)ethyl)sulfonyl)-4H-1,2,4-triazole-3-carboxamide | A |
| 50 | 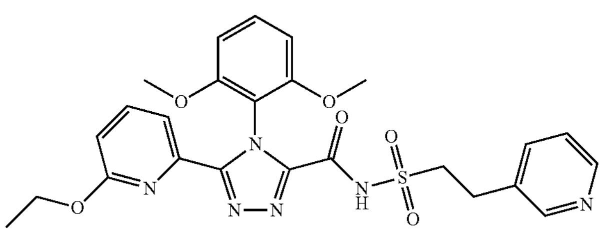 [SMILES: CCOc1cccc(-c2nnc(C(=O)NS(=O)(=O)CCc3cccnc3)n2-c2c(OC)cccc2OC)n1] | 4-(2,6-Dimethoxyphenyl)-5-(6-ethoxypyridin-2-yl)-N-((2-(pyridin-3-yl)ethyl)sulfonyl)-4H-1,2,4-triazole-3-carboxamide | A |
| 51 | 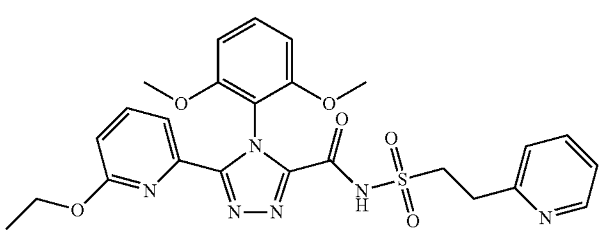 [SMILES: CCOc1cccc(-c2nnc(C(=O)NS(=O)(=O)CCc3ccccn3)n2-c2c(OC)cccc2OC)n1] | 4-(2,6-Dimethoxyphenyl)-5-(6-ethoxypyridin-2-yl)-N-((2-(pyridin-2-yl)ethyl)sulfonyl)-4H-1,2,4-triazole-3-carboxamide | A |

TABLE 1-continued

Example compounds and their potency range

| Ex. number | Structure | IUPAC name | Potency range |
|---|---|---|---|
| 52 | 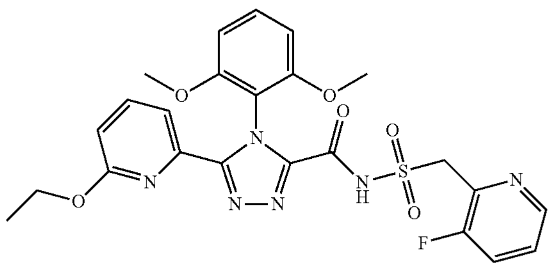 [SMILES: CCOc1cccc(-c2nnc(C(=O)NS(=O)(=O)Cc3ncccc3F)n2-c2c(OC)cccc2OC)n1] | 4-(2,6-Dimethoxyphenyl)-5-(6-ethoxypyridin-2-yl)-N-(((3-fluoropyridin-2-yl)methyl)sulfonyl)-4H-1,2,4-triazole-3-carboxamide | A |
| 53 | 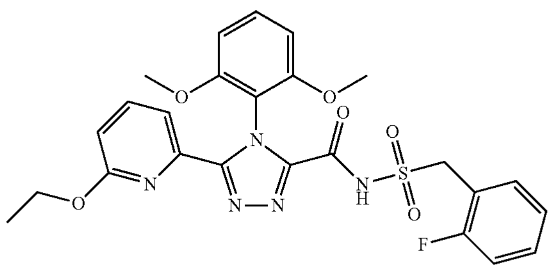 [SMILES: CCOc1cccc(-c2nnc(C(=O)NS(=O)(=O)Cc3ccccc3F)n2-c2c(OC)cccc2OC)n1] | 4-(2,6-Dimethoxyphenyl)-5-(6-ethoxypyridin-2-yl)-N-((2-fluorobenzyl)sulfonyl)-4H-1,2,4-triazole-3-carboxamide | A |
| 54 | 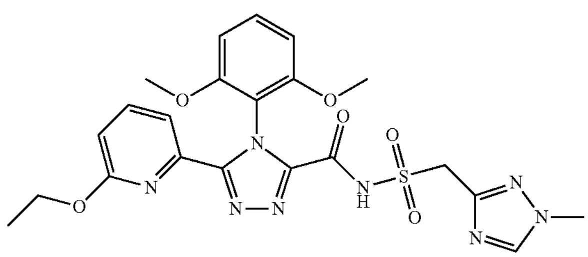 [SMILES: CCOc1cccc(-c2nnc(C(=O)NS(=O)(=O)Cc3ncn(C)n3)n2-c2c(OC)cccc2OC)n1] | 4-(2,6-Dimethoxyphenyl)-5-(6-ethoxypyridin-2-yl)-N-(((1-methyl-1H-1,2,4-triazol-3-yl)methyl)sulfonyl)-4H-1,2,4-triazole-3-carboxamide | A |
| 55 | 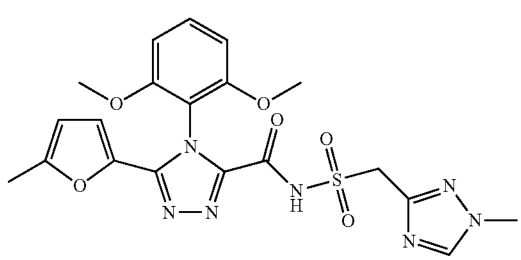 | 4-(2,6-Dimethoxyphenyl)-N-(((1-methyl-1H-1,2,4-triazol-3-yl)methyl)sulfonyl)-5-(5-methylfuran-2-yl)-4H-1,2,4-triazole-3-carboxamide | A |
| 56 | 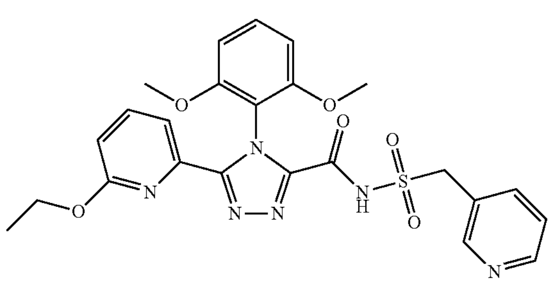 [SMILES: CCOc1cccc(-c2nnc(C(=O)NS(=O)(=O)Cc3cccnc3)n2-c2c(OC)cccc2OC)n1] | 4-(2,6-Dimethoxyphenyl)-5-(6-ethoxypyridin-2-yl)-N-((pyridin-3-ylmethyl)sulfonyl)-4H-1,2,4-triazole-3-carboxamide | A |

TABLE 1-continued

Example compounds and their potency range

| Ex. number | Structure | IUPAC name | Potency range |
|---|---|---|---|
| 57 | 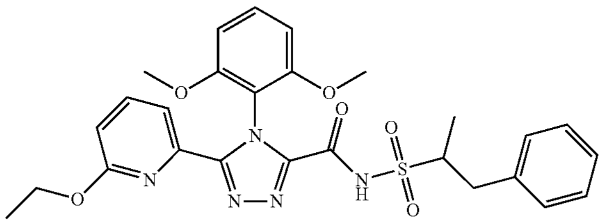 [SMILES: CCOc1cccc(-c2nnc(C(=O)NS(=O)(=O)C(C)Cc3ccccc3)n2-c2c(OC)cccc2OC)n1] | 4-(2,6-Dimethoxyphenyl)-5-(6-ethoxypyridin-2-yl)-N-((1-phenylpropan-2-yl)sulfonyl)-4H-1,2,4-triazole-3-carboxamide | A |
| 58 | 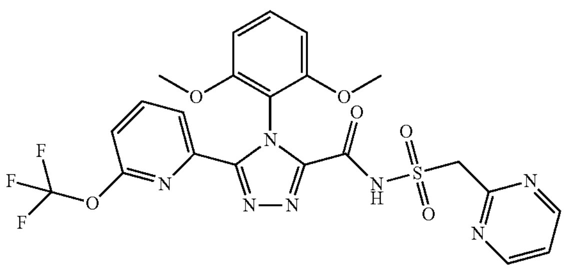 [SMILES: COc1cccc(OC)c1-n1c(C(=O)NS(=O)(=O)Cc2ncccn2)nnc1-c1cccc(OC(F)(F)F)n1] | 4-(2,6-Dimethoxyphenyl)-N-((pyrimidin-2-ylmethyl)sulfonyl)-5-(6-(trifluoromethoxy)pyridin-2-yl)-4H-1,2,4-triazole-3-carboxamide | B |
| 59 | 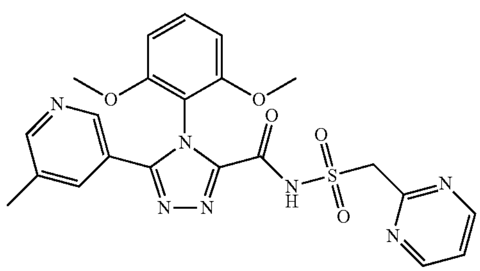 [SMILES: COc1cccc(OC)c1-n1c(C(=O)NS(=O)(=O)Cc2ncccn2)nnc1-c1cncc(C)c1] | 4-(2,6-Dimethoxyphenyll)-5-(5-methylpyridin-3-yl)-N-((pyrimidin-2-ylmethyl)sulfonyl)-4H-1,2,4-triazole-3-carboxamide | C |
| 60 | 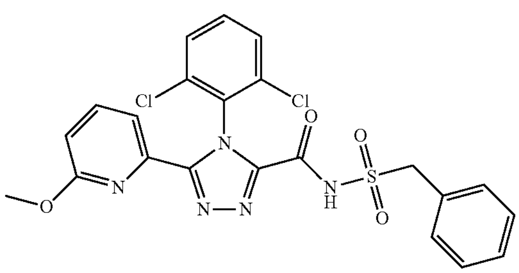 [SMILES: COc1cccc(-c2nnc(C(=O)NS(=O)(=O)Cc3ccccc3)n2-c2c(Cl)cccc2Cl)n1] | N-(benzylsulfonyl)-4-(2,6-dichlorophenyl)-5-(6-methoxypyridin-2-yl)-4H-1,2,4-triazole-3-carboxamide | C |
| 61 | 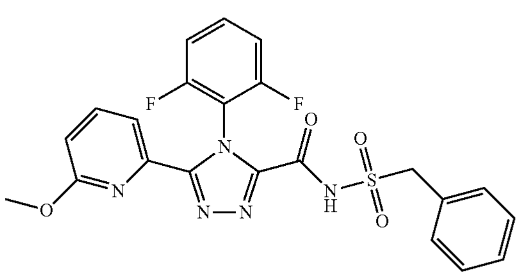 [SMILES: COc1cccc(-c2nnc(C(=O)NS(=O)(=O)Cc3ccccc3)n2-c2c(F)cccc2F)n1] | N-(benzylsulfonyl)-4-(2,6-difluorophenyl)-5-(6-methoxypyridin-2-yl)-2H-1,2,4-triazole-3-carboxamide | C |

TABLE 1-continued

Example compounds and their potency range

| Ex. number | Structure | IUPAC name | Potency range |
|---|---|---|---|
| 62 | 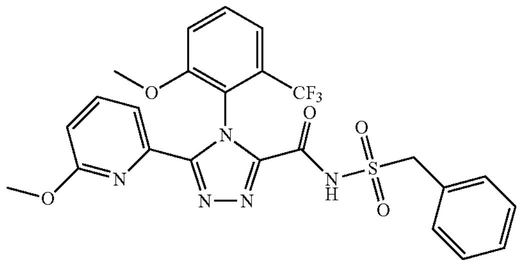 [SMILES: COc1cccc(-c2nnc(C(=O)NS(=O)(=O)Cc3ccccc3)n2-c2c(OC)cccc2C(F)(F)F)n1] | N-(benzylsulfonyl)-4-(2-methoxy-6-(trifluoromethyl)phenyl)-5-(6-methoxypyridin-2-yl)-4H-1,2,4-triazole-3-carobxamide | B |
| 63 | 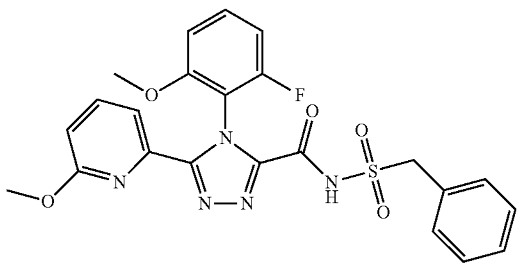 [SMILES: COc1cccc(-c2nnc(C(=O)NS(=O)(=O)Cc3ccccc3)n2-c2c(F)cccc2OC)n1] | N-(benzylsulfonyl)-4-(2-fluoro-6-methoxyphenyl)-5-(6-methoxypyridin-2-yl)-4H-1,2,4-triazole-3-carboxamide | B |
| 64 | 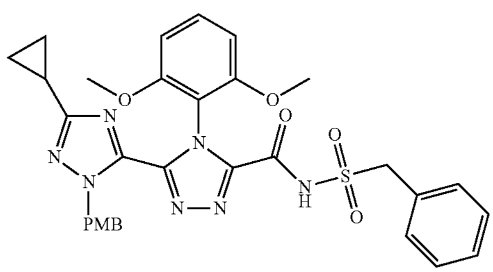 | N-(benzylsulfonyl)-5-cyclopropyl-4'-(2,6-dimethoxyphenyl)-2-(4-methoxybenzyl)-2H,4'H-[3,3'-bi(1,2,4-triazole)]-5'-carboxamide | C |
| 65 | 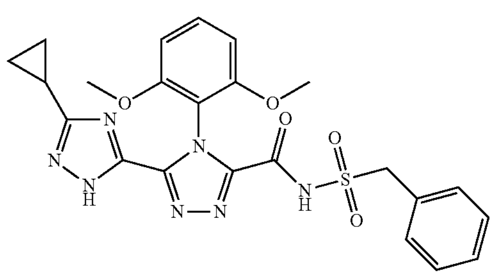 [SMILES: COc1cccc(OC)c1-n1c(C(=O)NS(=O)(=O)Cc2ccccc2)nnc1-c1nc(C2CC2)n[nH]1] | N-(benzylsulfonyl)-5-cylcopropyl-4'-(2,6-dimethoxyphenyl)-2H,4'H-[3,3'-bi(1,2,4-triazole)]-5'-carboxamide | C |

A number of embodiments of the invention have been described. Nevertheless, it will be understood that various modifications may be made without departing from the spirit and scope of the invention. Accordingly, other embodiments are within the scope of the following claims

What is claimed is:

1. A compound having formula (I):

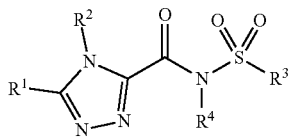

or a pharmaceutically acceptable salt thereof;
wherein:
$R^1$ is heteroaryl including from 5-6 ring atoms, wherein from 1-3 ring atoms are heteroatoms, each independently selected from the group consisting of N, N(H), $N(R^d)$, O, and S, and wherein one or more of the heteroaryl ring carbon atoms are optionally substituted with from 1-4 independently selected $R^c$,
$R^2$ is

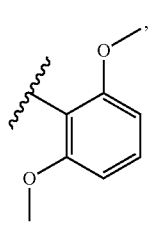

$R^3$ is:
(i) —$(Y^3)_p$—$Y^4$, wherein:
  p is 0 or 1;
  $Y^3$ is $C_{1-6}$ alkylene, which is optionally substituted with from 1-6 independently selected $R^a$; and
  $Y^4$ is:
   (a) $C_{3-6}$ cycloalkyl, which is optionally substituted with from 1-4 independently selected $R^b$;
   (b) $C_{6-10}$ aryl, which is optionally further substituted with from 1-4 independently selected $R^c$;
   (c) heteroaryl including from 5-10 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-4 independently selected $R^c$,
OR
(ii) $C_{1-10}$ alkyl, optionally substituted with from 1-6 independently selected $R^a$;
OR
(iii) —$Z^7$—$Z^8$—$Z^9$—$Y^4$ wherein:
  $Z^7$ is a bond or $C_{1-3}$ alkylene, which is optionally substituted with from 1-4 independently selected $R^a$;
  $Z^8$ is —N(H)— or —$N(R^d)$—;
  $Z^9$ is a bond or $C_{1-4}$ alkylene, which is optionally substituted with from 1-4 independently selected $R^a$; and
  $Y^4$ is as defined above;
$R^4$ is H or $C_{1-3}$ alkyl;

each occurrence of $R^a$ is independently selected from the group consisting of: —OH; —F; —Cl; —Br; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano, and $C_{3-6}$ cycloalkyl optionally substituted with from 1-4 independently selected $C_{1-4}$ alkyl;

each occurrence of $R^b$ is independently selected from the group consisting of: $C_{1-6}$ alkyl; $C_{1-4}$ haloalkyl; —OH; oxo; —F; —Cl; —Br; —$NR^eR^f$; $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —S(O)$_{1-2}$(NR'R''); —S(O)$_{1-2}$($C_{1-4}$ alkyl); cyano; and $C_{3-6}$ cycloalkyl optionally substituted with from 1-4 independently selected $C_{1-4}$ alkyl;

each occurrence of $R^c$ is independently selected from the group consisting of:
(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —S(O)$_{1-2}$($C_{1-4}$ alkyl);
(xi) —$NR^eR^f$;
(xii) —OH;
(xiii) —S(O)$_{1-2}$(NR'R'');
(xiv) —$C_{1-4}$ thioalkoxy;
(xv) —NO$_2$;
(xvi) —C(=O)($C_{1-4}$ alkyl);
(xvii) —C(=O)O($C_{1-4}$ alkyl);
(xviii) —C(=O)OH;
(xix) —C(=O)N(R')(R''); and
(xx) $C_{3-6}$ cycloalkoxy, $R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; $C_{1-4}$ alkoxy; and —($C_{0-3}$ alkylene)-$C_{6-10}$ aryl optionally substituted with from 1-4 independently selected $C_{1-4}$ alkyl, $C_{1-4}$ alkoxy, $C_{1-4}$ haloalkyl, or $C_{1-4}$ haloalkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —C(O)N(R')(R''); —S(O)$_{1-2}$(NR'R''); —S(O)$_{1-2}$($C_{1-4}$ alkyl); —OH; and $C_{1-4}$ alkoxy; or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of O, S, N($C_{1-6}$ alkyl), N($C_{3-6}$ cycloalkyl), N(C(O)($C_{1-4}$ alkyl)), N(C(O)O ($C_{1-4}$ alkyl)), N(CON(R')(R'')), N(S(O)$_{1-2}$(NR'R'')), N(S(O)$_{1-2}$($C_{1-4}$ alkyl)), N(OH), N($C_{1-4}$ alkoxy), and N(($C_{0-3}$ alkylene)-$C_{6-10}$ aryl) optionally substituted with from 1-4 independently selected $C_{1-4}$ alkyl, $C_{1-4}$ alkoxy, $C_{1-4}$ haloalkyl, or $C_{1-4}$ haloalkoxy; and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms.

2. The compound of claim 1, wherein $R^1$ is pyridyl, wherein one or more of the ring carbon atoms are optionally substituted with from 1-4 independently selected $R^c$.

3. The compound of claim 1, wherein each occurrence of $R^c$ is independently selected from the group consisting of:
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —$(C_{0-3}$ alkylene)-$C_{3-6}$ cycloalkyl optionally substituted with from 1-4 independently selected $C_{1-4}$ alkyl;
(xiv) —$C_{1-4}$ thioalkoxy; and
(xx) $C_{3-6}$ cycloalkoxy.

4. The compound of claim 1, wherein $R^1$ is selected from the group consisting of:

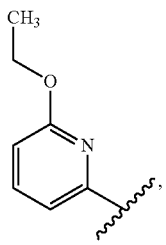 , 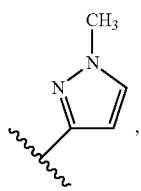 ,

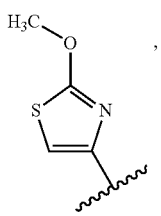 , 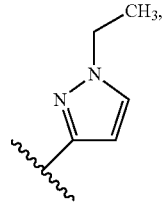 ,

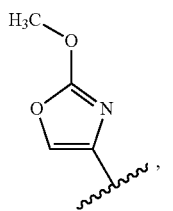 , 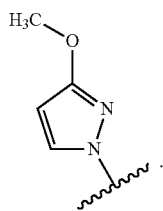 and .

5. The compound of claim 1, wherein $R^1$ is selected from the group consisting of:

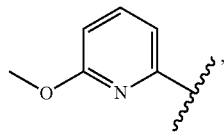 , 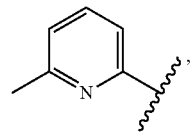 ,

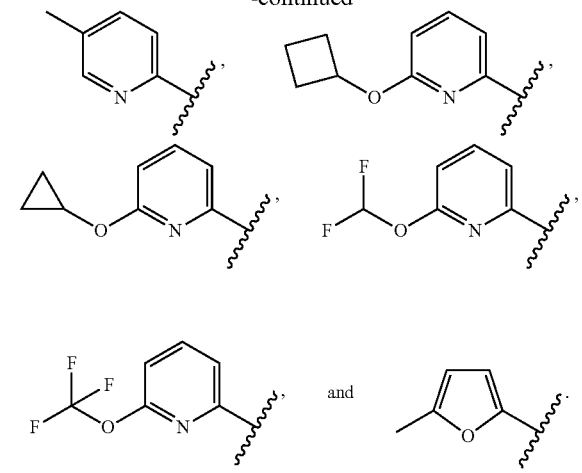

6. The compound of claim 1, wherein p is 1.
7. The compound of claim 1, wherein $Y^3$ is $C_{1-3}$ alkylene.
8. The compound of claim 1, wherein $Y^4$ is $C_{6-10}$ aryl, which is optionally substituted with from 1-4 independently selected $R^c$.
9. The compound of claim 1, wherein $Y^4$ is phenyl, which is optionally substituted with from 1-4 independently selected $R^c$.
10. The compound of claim 1, wherein $Y^4$ is unsubstituted phenyl.
11. The compound of claim 8, wherein p is 1.
12. The compound of claim 1, wherein $R^3$ is selected from the group consisting of:

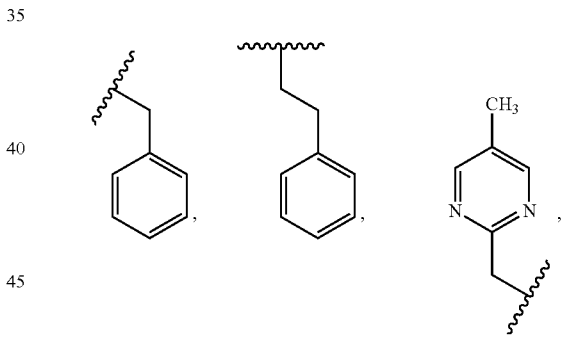

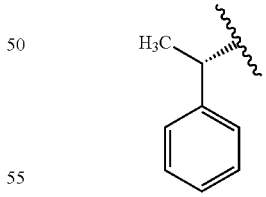 , and .

13. The compound of claim 1, wherein $R^3$ is selected from the group consisting of:

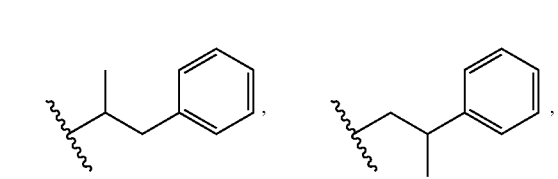

-continued

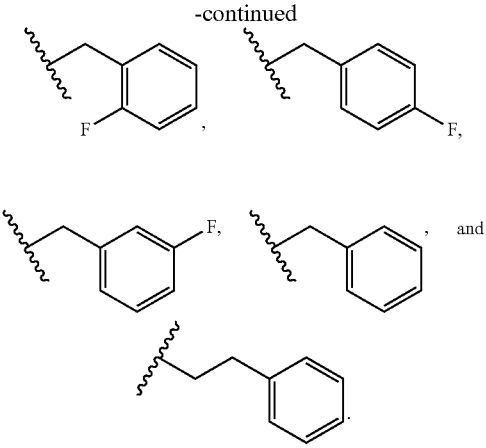

14. The compound of claim 1, wherein R³ is:

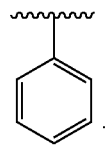

15. The compound of claim 1, wherein Y⁴ is $C_{3-6}$ cycloalkyl, which is optionally substituted with from 1-4 independently selected $R^b$.

16. The compound of claim 15, wherein p is 1.

17. The compound of claim 1, wherein R³ is $C_{1-10}$ alkyl, optionally substituted with from 1-6 independently selected $R^a$.

18. A compound selected from the group consisting of:

| | | |
|---|---|---|
| 1 | 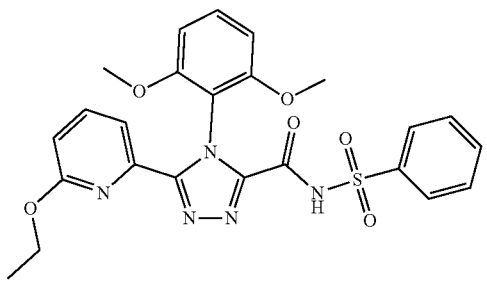 [SMILES: CCOc1cccc(-c2nnc(C(=O)NS(=O)(=O)c3ccccc3)n2-c2c(OC)cccc2OC)n1] | 4-(2,6-dimethoxyphenyl)-5-(6-ethoxypyridin-2-yl)-N-(phenylsulfonyl)-4H-1,2,4-triazole-3-carboxamide, |
| 2 | 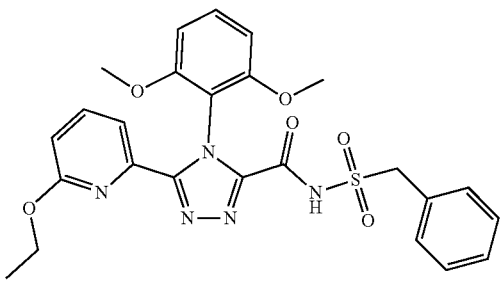 [SMILES: CCOc1cccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(6-ethoxypyridin-2-yl)-4H-1,2,4-triazole-3-carboxamide, |
| 3 | 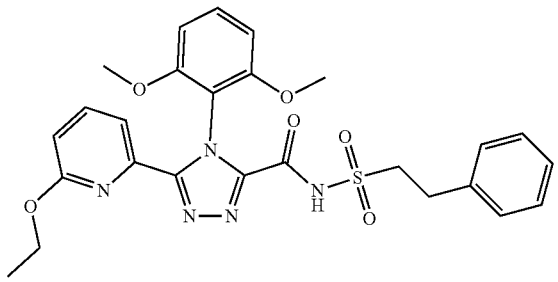 [SMILES: CCOc1cccc(-c2nnc(C(=O)NS(=O)(=O)CCc3ccccc3)n2-c2c(OC)cccc2OC)n1] | 4-(2,6-dimethoxyphenyl)-5-(6-ethoxypyridin-2-yl)-N-(phenethylsulfonyl)-4H-1,2,4-triazole-3-carboxamide, |
| 4 | 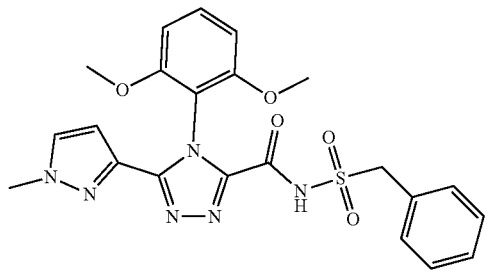 [SMILES: COc1cccc(OC)c1-n1c(C(=O)NS(=O)(=O)Cc2ccccc2)nnc1-c1ccn(C)n1] | N-(benzylsulfonyl)-4-(2,6-dimethoxyphenyl)-5-(1-methyl-1H-pyrazol-3-yl)-4H-1,2,4-triazole-3-carboxamide, |

| 5 | 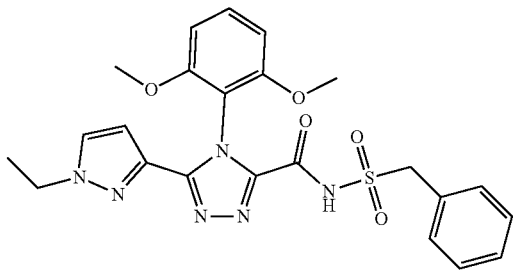 [SMILES: CCn1ccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(1-ethyl-1H-pyrazol-3-yl)-4H-1,2,4-triazole-3-carboxamide, |
|---|---|---|
| 6 | 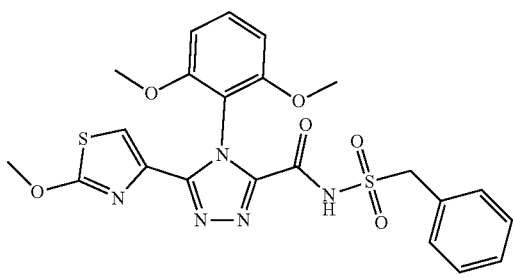 [SMILES: COc1nc(-c2nnc(C(=O)NS(=O)(=O)Cc3ccccc3)n2-c2c(OC)cccc2OC)cs1] | N-(benzylsulfonyl)-4-(2,6-dimethoxyphenyl)-5-(2-methoxythiazol-4-yl)-4H-1,2,4-triazole-3-carboxamide, |
| 8 | 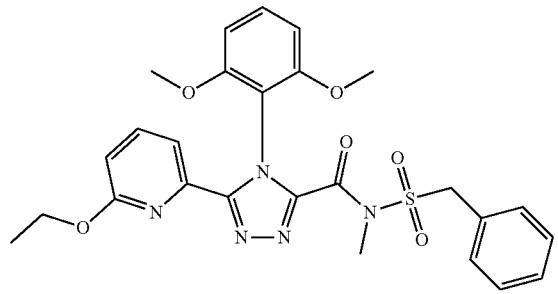 [SMILES: CCOc1cccc(-c2nnc(C(=O)N(C)S(=O)(=O)Cc3ccccc3)n2-c2c(OC)cccc2OC)n1] | N-(benzylsulfonyl)-4-(2,6-dimethoxyphenyl)-5-(6-ethoxypyridin-2-yl)-N-methyl-4H-1,2,4-triazole-3-carboxamide, |
| 9 | 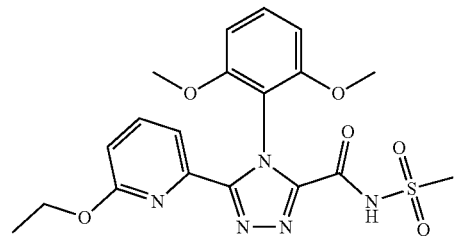 [SMILES: CCOc1cccc(-c2nnc(C(=O)NS(C)(=O)=O)n2-c2c(OC)cccc2OC)n1] | 4-(2,6-Dimethoxyphenyl)-5-(6-ethoxypyridin-2-yl)-N-(methylsulfonyl)-4H-1,2,4-triazole-3-carboxamide, |
| 10 | 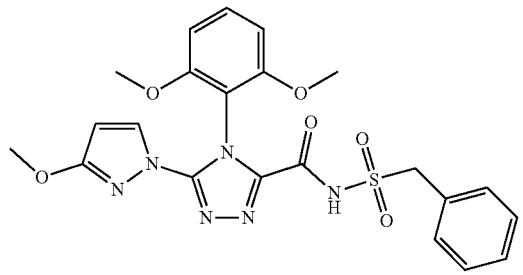 [SMILES: COc1ccn(-c2nnc(C(=O)NS(=O)(=O)Cc3ccccc3)n2-c2c(OC)cccc2OC)n1] | N-(enzylsulfonyl)-4-(2,6-dimethoxyphenyl)-5-(3-methoxy-1H-pyrazol-1-yl)-4H-1,2,4-triazole-3-carboxamide, |

| | | |
|---|---|---|
| 11 | 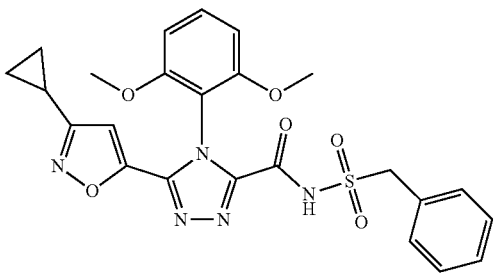 [SMILES: COc1cccc(OC)c1-n1c(C(=O)NS(=O)(=O)Cc2ccccc2)nnc1-c1cc(C2CC2)no1] | N-(benzylsulfonyl)-5-(3-cyclopropylisoxazol-5-yl)-4-(2,6-dimethoxyphenyl)-4H-1,2,4-triazole-3-carboxamide, |
| 12 | 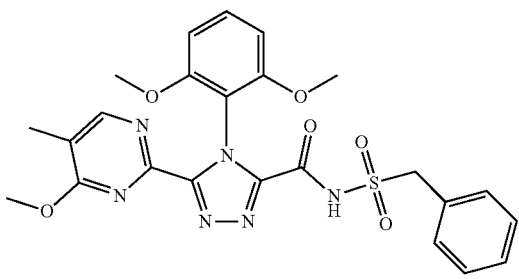 [SMILES: COc1cccc(OC)c1-n1c(C(=O)NS(=O)(=O)Cc2ccccc2)nnc1-c1ncc(C)c(OC)n1] | N-(benzylsulfonyl)-4-(2,6-dimethoxyphenyl)-5-(4-methoxy-5-methylpyrimidin-2-yl)-4H-1,2,4-triazole-3-carboxamide, |
| 13 | 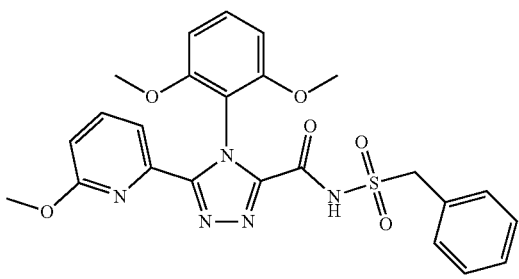 [SMILES: COc1cccc(-c2nnc(C(=O)NS(=O)(=O)Cc3ccccc3)n2-c2c(OC)cccc2OC)n1] | N-(benzylsulfonyl)-4-(2,6-dimethoxyphenyl)-5-(6-methoxypyridin-2-yl)-4H-1,2,4-triazole-3-carboxamide, |
| 14 | 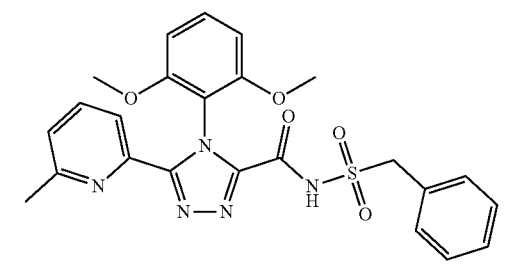 [SMILES: COc1cccc(OC)c1-n1c(C(=O)NS(=O)(=O)Cc2ccccc2)nnc1-c1cccc(C)n1] | N-(benzylsulfonyl)-4-(2,6-dimethoxyphenyl)-5-(6-methylpyridin-2-yl)-4H-1,2,4-triazole-3-carboxamide, |
| 15 | 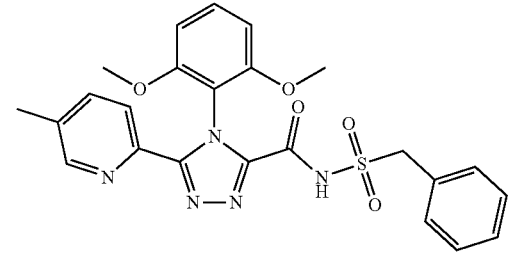 [SMILES: COc1cccc(OC)c1-n1c(C(=O)NS(=O)(=O)Cc2ccccc2)nnc1-c1ccc(C)cn1] | N-(benzylsulfonyl)-4-(2,6-dimethoxyphenyl)-5-(5-methylpyridin-2-yl)-4H-1,2,4-triazole-3-carboxamide, |
| 16 | 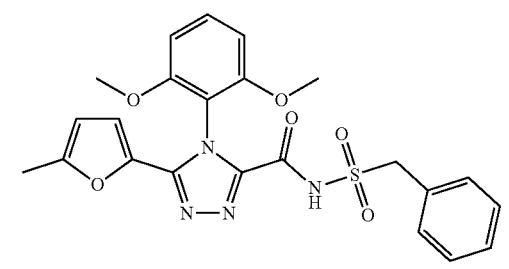 [SMILES: COc1cccc(OC)c1-n1c(C(=O)NS(=O)(=O)Cc2ccccc2)nnc1-c1ccc(C)o1] | N-(benzylsulfonyl)-4-(2,6-dimethoxyphenyl)-5-(5-methylfuran-2-yl)-4H-1,2,4-triazole-3-carboxamide, |

| | | |
|---|---|---|
| 17 | 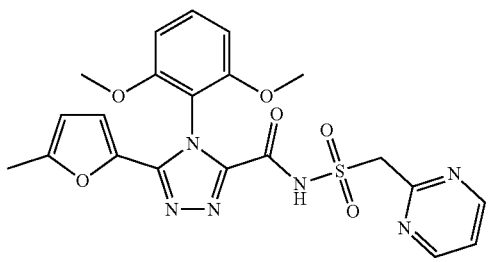 [SMILES: COc1cccc(OC)c1-n1c(C(=O)NS(=O)(=O)Cc2ncccn2)nnc1-c1ccc(C)o1] | 4-(2,6-Dimethoxyphenyl)-5-(5-methylfuran-2-yl)-N-((pyrimidin-2-ylmethyl)sulfonyl)-4H-1,2,4-triazole-3-carboxamide, |
| 18 | 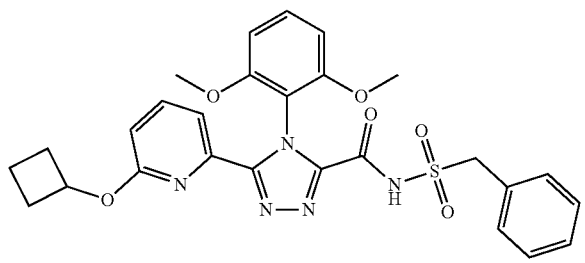 [SMILES: COc1cccc(OC)c1-n1c(C(=O)NS(=O)(=O)Cc2ccccc2)nnc1-c1cccc(OC2CCC2)n1] | N-(benzylsulfonyl)-5-(6-cyclobutoxypyridin-2-yl)-4-(2,6-dimethoxyphenyl)-4H-1,2,4-triazole-3-carboxamide, |
| 19 | 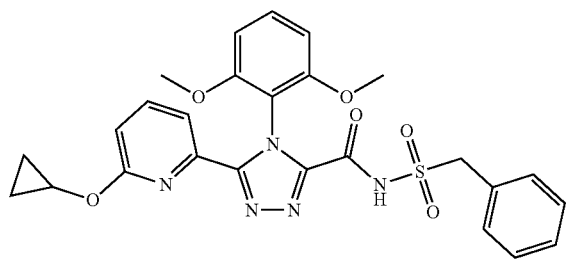 [SMILES: COc1cccc(OC)c1-n1c(C(=O)NS(=O)(=O)Cc2ccccc2)nnc1-c1cccc(OC2CC2)n1] | N-(benzylsulfonyl)-5-(6-cyclopropoxypyridin-2-yl)-4-(2,6-dimethoxyphenyl)-4H-1,2,4-triazole-3-carboxamide, |
| 20 | 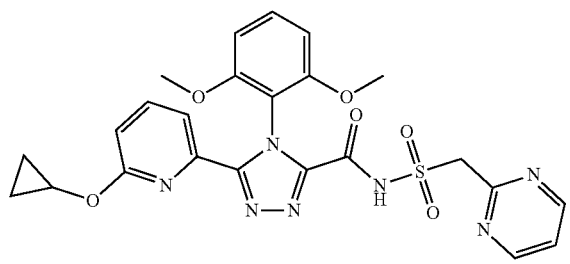 [SMILES: COc1cccc(OC)c1-n1c(C(=O)NS(=O)(=O)Cc2ncccn2)nnc1-c1cccc(OC2CC2)n1] | 5-(6-Cyclopropoxypyridin-2-yl)-4-(2,6-dimethoxyphenyl)-N-((pyrimidin-2-ylmethyl)sulfonyl)-4H-1,2,4-triazole-3-carboxamide, |
| 21 | 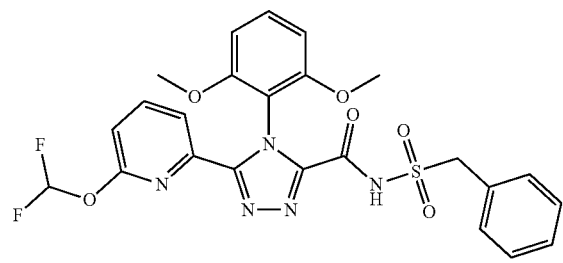 [SMILES: COc1cccc(OC)c1-n1c(C(=O)NS(=O)(=O)Cc2ccccc2)nnc1-c1cccc(OC(F)F)n1] | N-(benzylsulfonyl)-5-(6-(difluoromethoxy)pyridin-2-yl)-4-(2,6-dimethoxyphenyl)-4H-1,2,4-triazole-3-carboxamide, |
| 22 | 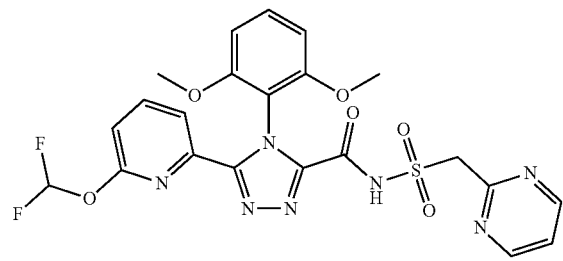 [SMILES: COc1cccc(OC)c1-n1c(C(=O)NS(=O)(=O)Cc2ncccn2)nnc1-c1cccc(OC(F)F)n1] | 5-(6-(Difluoromethoxy)pyridin-2-yl)-4-(2,6-dimethoxyphenyl)-N-((pyrimidin-2-ylmethyl)sulfonyl)-4H-1,2,4-triazole-3-carboxamide, |

| | | |
|---|---|---|
| 23 | 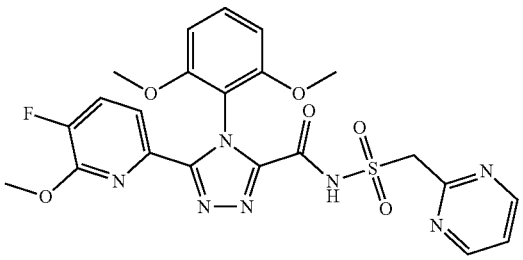 [SMILES: COc1cccc(OC)c1-n1c(C(=O)NS(=O)(=O)Cc2ncccn2)nnc1-c1ccc(F)c(OC)n1] | 4-(2,6-Dimethoxyphenyl)-5-(5-fluoro-6-methoxypyridin-2-yl)-N-((pyrimidin-2-ylmethyl)sulfonyl)-4H-1,2,4-triazole-3-carboxamide, |
| 24 | 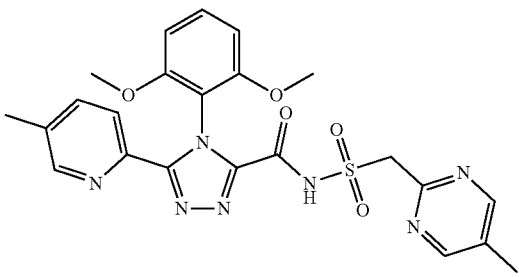 | 4-(2,6-Dimethoxyphenyl)-5-(5-methylpyridin-2-yl)-N-(((5-methylpyrimidin-2-yl)methyl)sulfonyl)-4H-1,2,4-triazole-3-carboxamide, |
| 25 | 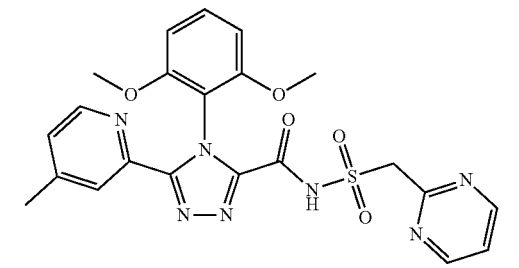 [SMILES: COc1cccc(OC)c1-n1c(C(=O)NS(=O)(=O)Cc2ncccn2)nnc1-c1cc(C)ccn1] | 4-(2,6-Dimethoxyphenyl)-5-(4-methylpyridin-2-yl)-N-((pyrimidin-2-ylmethyl)sulfonyl)-4H-1,2,4-triazole-3-carboxamide, |
| 26 | 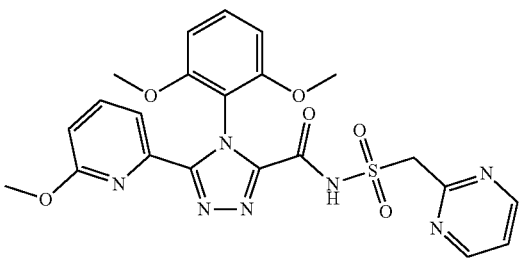 [SMILES: COc1cccc(-c2nnc(C(=O)NS(=O)(=O)Cc3ncccn3)n2-c2c(OC)cccc2OC)n1] | 4-(2,6-dimethoxyphenyl)-5-(6-methoxypyridin-2-yl)-N-((pyrimidin-2-ylmethyl)sulfonyl)-4H-1,2,4-triazole-3-carboxamide, |
| 27 | 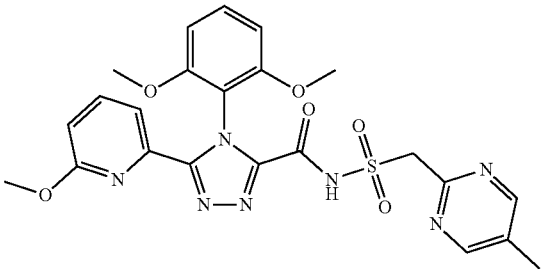 | 4-(2,6-Dimethoxyphenyl)-5-(6-methoxypyridin-2-yl)-N-(((5-methylpyrimidin-2-yl)methyl)sulfonyl)-4H-1,2,4-triazole-3-carboxamide, |
| 28 | 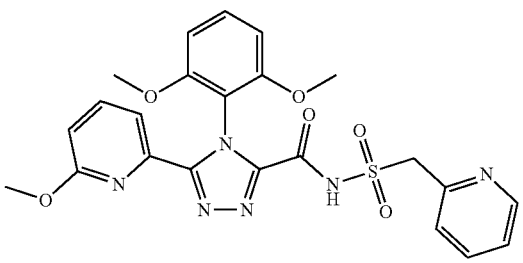 [SMILES: COc1cccc(-c2nnc(C(=O)NS(=O)(=O)Cc3ccccn3)n2-c2c(OC)cccc2OC)n1] | 4-(2,6-Dimethoxyphenyl)-5-(6-methoxypyridin-2-yl)-N-((pyridin-2-ylmethyl)sulfonyl)-4H-1,2,4-triazole-3-carboxamide, |

| # | Structure | Name |
|---|---|---|
| 29 | 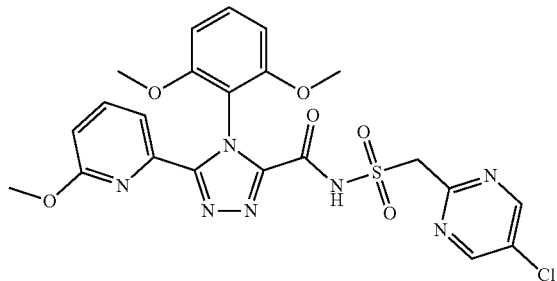 [SMILES: COc1cccc(-c2nnc(C(=O)NS(=O)(=O)Cc3ncc(Cl)cn3)n2-c2c(OC)cccc2OC)n1] | N-(((5-chloropyrimidin-2-yl)methyl)sulfonyl)-4-(2,6-dimethoxyphenyl)-5-(6-methoxypyridin-2-yl)-4H-1,2,4-triazole-3-carboxamide, |
| 30 | 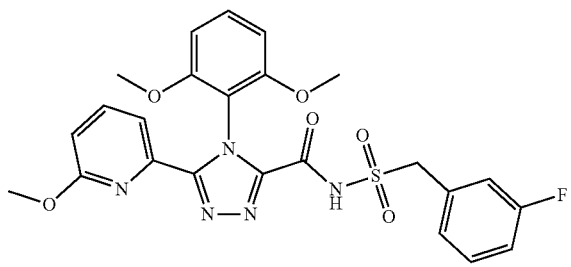 [SMILES: COc1cccc(-c2nnc(C(=O)NS(=O)(=O)Cc3cccc(F)c3)n2-c2c(OC)cccc2OC)n1] | 4-(2,6-Dimethoxyphenyl)-N-((3-fluorobenzyl)sulfonyl)-5-(6-methoxypyridin-2-yl)-4H-1,2,4-triazole-3-carboxamide, |
| 31 | 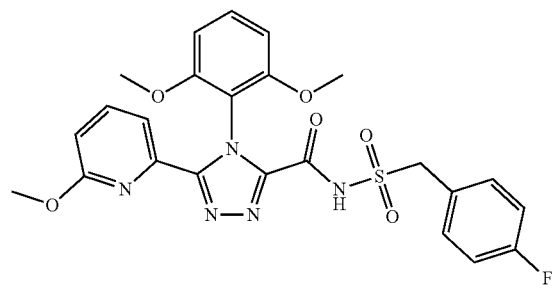 [SMILES: COc1cccc(-c2nnc(C(=O)NS(=O)(=O)Cc3ccc(F)cc3)n2-c2c(OC)cccc2OC)n1] | 4-(2,6-Dimethoxyphenyl)-N-((4-fluorobenzyl)sulfonyl)-5-(6-methoxypyridin-2-yl)-4H-1,2,4-triazole-3-carboxamide, |
| 32 | 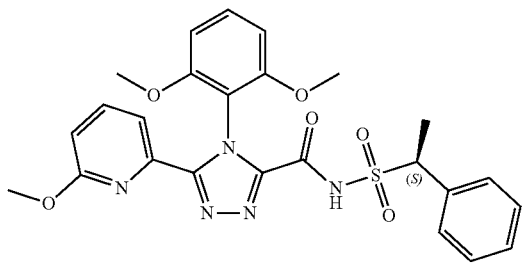 | (S)-4-(2,6-Dimethoxyphenyl)-5-(6-methoxypyridin-2-yl)-N-((1-phenylethyl)sulfonyl)-4H-1,2,4-triazole-3-carboxamide, |
| 33 | 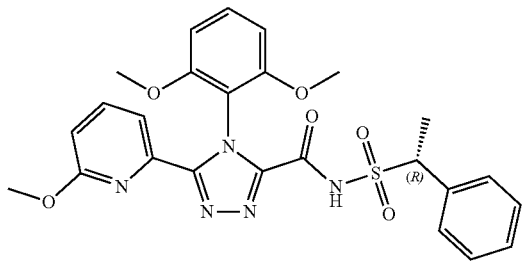 | (R)-4-(2,6-Dimethoxyphenyl)-5-(6-methoxypyridin-2-yl)-N-((1-phenylethyl)sulfonyl)-4H-1,2,4-triazole-3-carboxamide, |
| 34 | 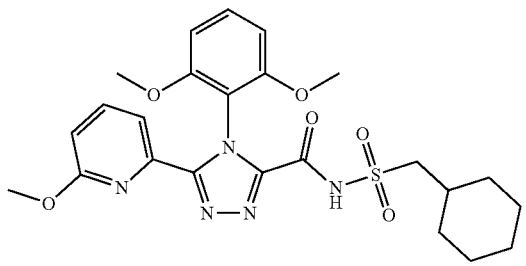 [SMILES: COc1cccc(-c2nnc(C(=O)NS(=O)(=O)CC3CCCCC3)n2-c2c(OC)cccc2OC)n1] | N-((cyclohexylmethyl)sulfonyl)-4-(2,6-dimethoxyphenyl)-5-(6-methoxypyridin-2-yl)-4H-1,2,4-triazole-3-carboxamide, |

| | | |
|---|---|---|
| 35 | 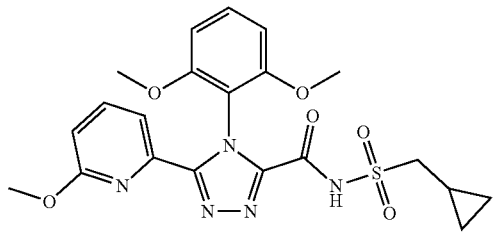 [SMILES: COc1cccc(-c2nnc(C(=O)NS(=O)(=O)CC3CC3)n2-c2c(OC)cccc2OC)n1] | N-((cyclopropylmethyl)sulfonyl)-4-(2,6-dimethoxyphenyl)-5-(6-methoxypyridin-2-yl)-4H-1,2,4-triazole-3-carboxamide, |
| 36 | 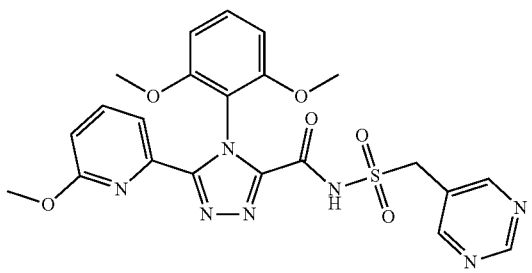 [SMILES: COc1cccc(-c2nnc(C(=O)NS(=O)(=O)Cc3cncnc3)n2-c2c(OC)cccc2OC)n1] | 4-(2,6-Dimethoxyphenyl)-5-(6-methoxypyridin-2-yl)-N-((pyrimidin-5-ylmethyl)sulfonyl)-4H-1,2,4-triazole-3-carboxamide, |
| 37 | 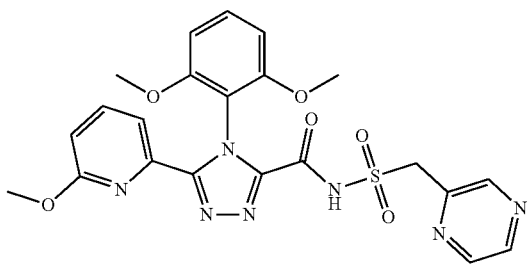 [SMILES: COc1cccc(-c2nnc(C(=O)NS(=O)(=O)Cc3cnccn3)n2-c2c(OC)cccc2OC)n1] | 4-(2,6-Dimethoxyphenyl)-5-(6-methoxypyridin-2-yl)-N-((pyrazin-2-ylmethyl)sulfonyl)-4H-1,2,4-triazole-3-carboxamide, |
| 38 | 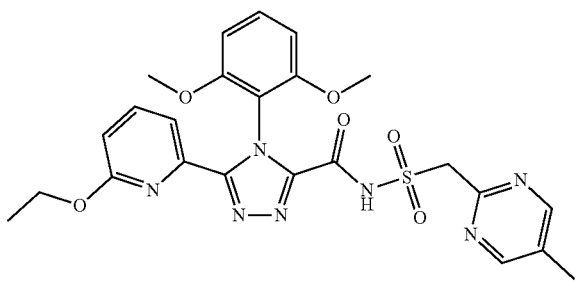 [SMILES: CCOc1cccc(-c2nnc(C(=O)NS(=O)(=O)Cc3ncc(C)cn3)n2-c2c(OC)cccc2OC)n1] | 4-(2,6-Dimethoxyphenyl)-5-(6-ethoxypyridin-2-yl)-N-(((5-methylpyrimidin-2-yl)methyl)sulfonyl)-4H-1,2,4-triazole-3-carboxamide, |
| 39 | 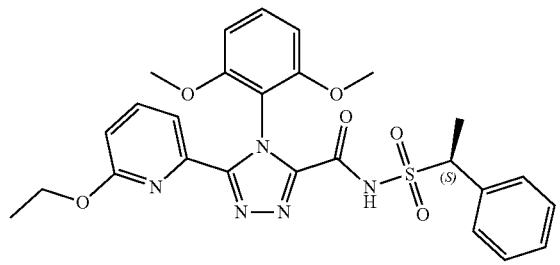 | (S)-4-(2,6-dimethoxyphenyl)-5-(6-ethoxypyridin-2-yl)-N-((1-phenylethyl)sulfonyl)-4H-1,2,4-triazole-3-carboxamide, |
| 40 | 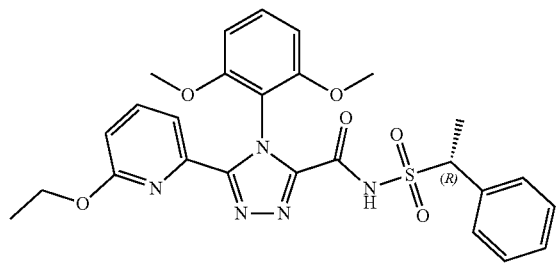 | (R)-4-(2,6-dimethoxyphenyl)-5-(6-ethoxypyridin-2-yl)-N-((1-phenylethyl)sulfonyl)-4H-1,2,4-triazole-3-carboxamide, |

| # | | |
|---|---|---|
| 41 | 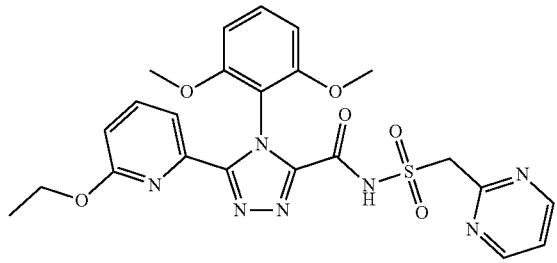 [SMILES: CCOc1cccc(-c2nnc(C(=O)NS(=O)(=O)Cc3ncccn3)n2-c2c(OC)cccc2OC)n1] | 4-(2,6-Dimethoxyphenyl)-5-(6-ethoxypyridin-2-yl)-N-((pyrimidin-2-ylmethyl)sulfonyl)-4H-1,2,4-triazole-3-carboxamide, |
| 42 | 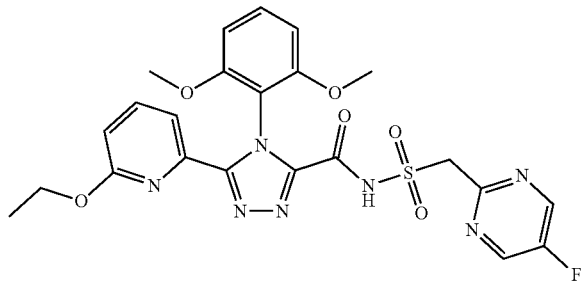 [SMILES: CCOc1cccc(-c2nnc(C(=O)NS(=O)(=O)Cc3ncc(F)cn3)n2-c2c(OC)cccc2OC)n1] | 4-(2,6-Dimethoxyphenyl)-5-(6-ethoxypyridin-2-yl)-N-(((5-fluoropyrimidin-2-yl)methyl)sulfonyl)-4H-1,2,4-triazole-3-carboxamide, |
| 43 | 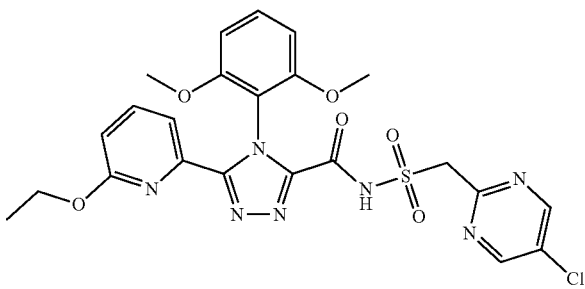 [SMILES: CCOc1cccc(-c2nnc(C(=O)NS(=O)(=O)Cc3ncc(Cl)cn3)n2-c2c(OC)cccc2OC)n1] | N-(((5-chloropyrimidin-2-yl)methyl)sulfonyl)-4-(2,6-dimethoxyphenyl)-5-(6-ethoxypyridin-2-yl)-4H-1,2,4-triazole-3-carboxamide, |
| 44 | 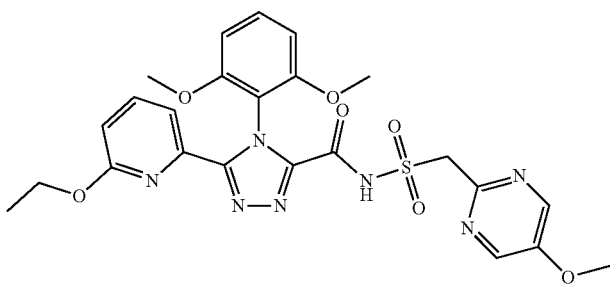 [SMILES: CCOc1cccc(-c2nnc(C(=O)NS(=O)(=O)Cc3ncc(OC)cn3)n2-c2c(OC)cccc2OC)n1] | 4-(2,6-Dimethoxyphenyl)-5-(6-ethoxypyridin-2-yl)-N-(((5-methoxypyrimidin-2-yl)methyl)sulfonyl)-4H-1,2,4-triazole-3-carboxamide, |
| 45 | 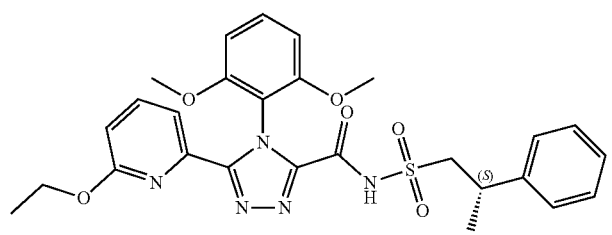 | (S)-4-(2,6-Dimethoxyphenyl)-5-(6-ethoxypyridin-2-yl)-N-((2-phenylpropyl)sulfonyl)-4H-1,2,4-triazole-3-carboxamide, |
| 46 | 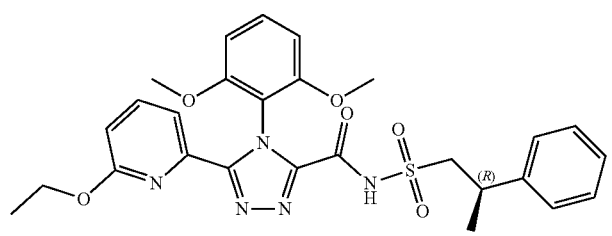 | (R)-4-(2,6-Dimethoxyphenyl)-5-(6-ethoxypyridin-2-yl)-N-((2-phenylpropyl)sulfonyl)-4H-1,2,4-triazole-3-carboxamide, |

| | | |
|---|---|---|
| 47 | 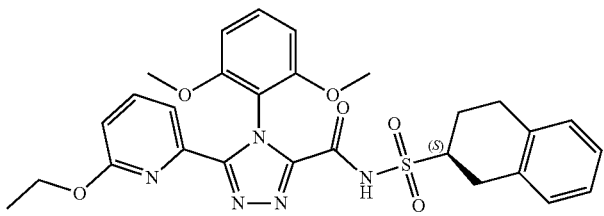 | (S)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide, |
| 48 | 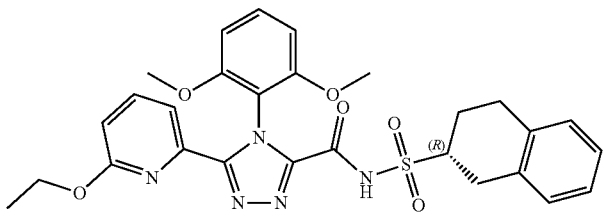 | (R)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide, |
| 49 | 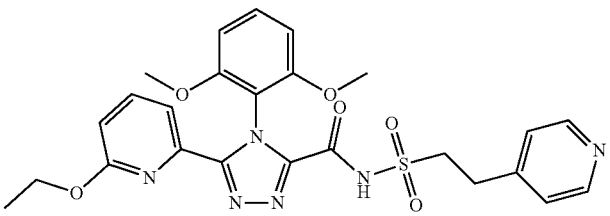 [SMILES: CCOc1cccc(-c2nnc(C(=O)NS(=O)(=O)CCc3ccncc3)n2-c2c(OC)cccc2OC)n1] | 4-(2,6-Dimethoxyphenyl)-5-(6-ethoxypyridin-2-yl)-N-((2-(pyridin-4-yl)ethyl)sulfonyl)-4H-1,2,4-triazole-3-carboxamide, |
| 50 | 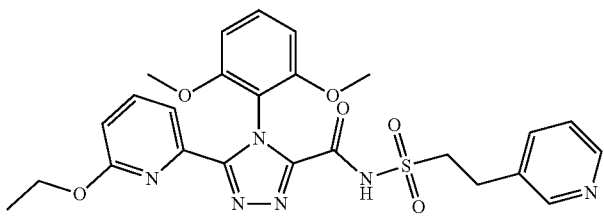 [SMILES: CCOc1cccc(-c2nnc(C(=O)NS(=O)(=O)CCc3cccnc3)n2-c2c(OC)cccc2OC)n1] | 4-(2,6-Dimethoxyphenyl)-5-(6-ethoxypyridin-2-yl)-N-((2-(pyridin-3-yl)ethyl)sulfonyl)-4H-1,2,4-triazole-3-carboxamide, |
| 51 | 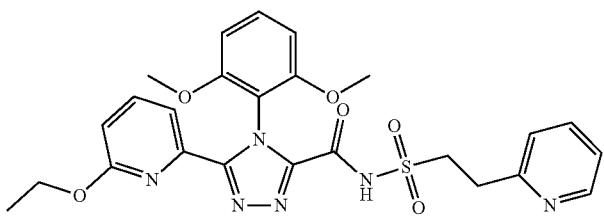 [SMILES: CCOc1cccc(-c2nnc(C(=O)NS(=O)(=O)CCc3ccccn3)n2-c2c(OC)cccc2OC)n1] | 4-(2,6-Dimethoxyphenyl)-5-(6-ethoxypyridin-2-yl)-N-((2-(pyridin-2-yl)ethyl)sulfonyl)-4H-1,2,4-triazole-3-carboxamide, |
| 52 | 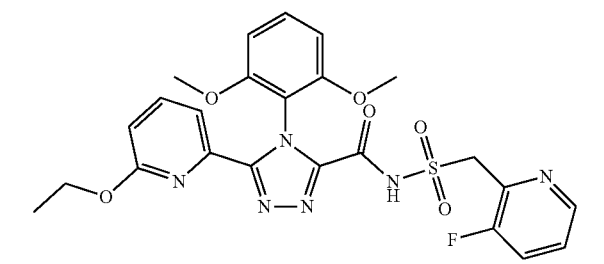 [SMILES: CCOc1cccc(-c2nnc(C(=O)NS(=O)(=O)Cc3ncccc3F)n2-c2c(OC)cccc2OC)n1] | 4-(2,6-Dimethoxyphenyl)-5-(6-ethoxypyridin-2-yl)-N-(((3-fluoropyridin-2-yl)methyl)sulfonyl)-4H-1,2,4-triazole-3-carboxamide, |
| 53 | 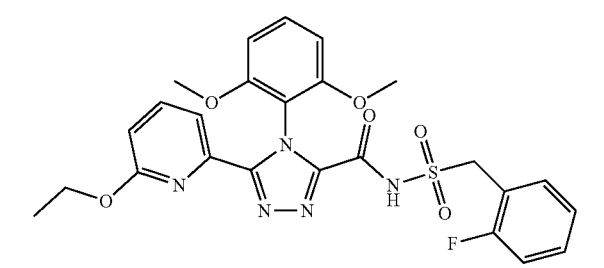 [SMILES: CCOc1cccc(-c2nnc(C(=O)NS(=O)(=O)Cc3ccccc3F)n2-c2c(OC)cccc2OC)n1] | 4-(2,6-Dimethoxyphenyl)-5-(6-ethoxypyridin-2-yl)-N-((2-fluorobenzyl)sulfonyl)-4H-1,2,4-triazole-3-carboxamide |

| | | |
|---|---|---|
| 54 | 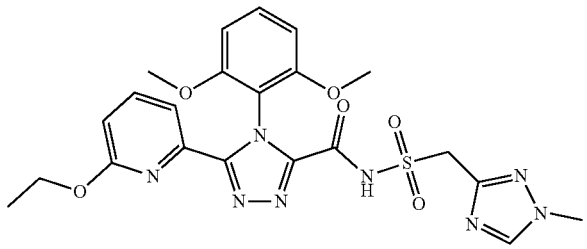 [SMILES: CCOc1cccc(-c2nnc(C(=O)NS(=O)(=O)Cc3ncn(C)n3)n2-c2c(OC)cccc2OC)n1] | 4-(2,6-Dimethoxyphenyl)-5-(6-ethoxypyridin-2-yl)-N-(((1-methyl-1H-1,2,4-triazol-3-yl)methyl)sulfonyl)-4H-1,2,4-triazole-3-carboxamide, |
| 55 | 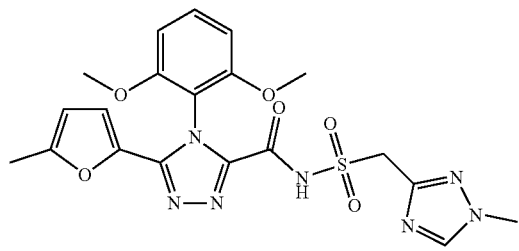 | 4-(2,6-Dimethoxyphenyl)-N-(((1-methyl-1H-1,2,4-triazol-3-yl)methyl)sulfonyl)-5-(5-methylfuran-2-yl)-4H-1,2,4-triazole-3-carboxamide, |
| 56 | 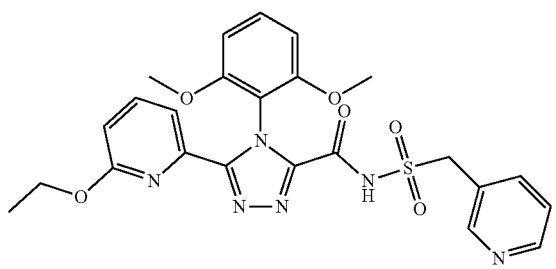 [SMILES: CCOc1cccc(-c2nnc(C(=O)NS(=O)(=O)Cc3cccnc3)n2-c2c(OC)cccc2OC)n1] | 4-(2,6-Dimethoxyphenyl)-5-(6-ethoxypyridin-2-yl)-N-((pyridin-3-ylmethyl)sulfonyl)-4H-1,2,4-triazole-3-carboxamide, |
| 57 | 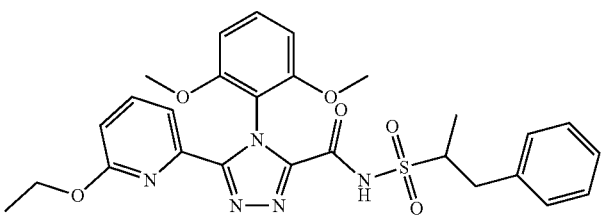 [SMILES: CCOc1cccc(-c2nnc(C(=O)NS(=O)(=O)C(C)Cc3ccccc3)n2-c2c(OC)cccc2OC)n1] | 4-(2,6-Dimethoxyphenyl)-5-(6-ethoxypyridin-2-yl)-N-((1-phenylpropan-2-yl)sulfonyl)-4H-1,2,4-triazole-3-carboxamide, |
| 58 | 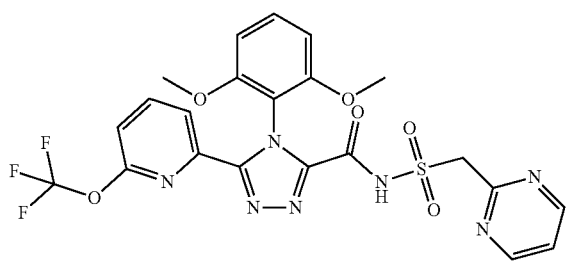 [SMILES: COc1cccc(OC)c1-n1c(C(=O)NS(=O)(=O)Cc2ncccn2)nnc1-c1cccc(OC(F)(F)F)n1] | 4-(2,6-Dimethoxyphenyl)-N-((pyrimidin-2-ylmethyl)sulfonyl)-5-(6-(trifluoromethoxy)pyridin-2-yl)-4H-1,2,4-triazole-3-carboxamide, |
| 59 | 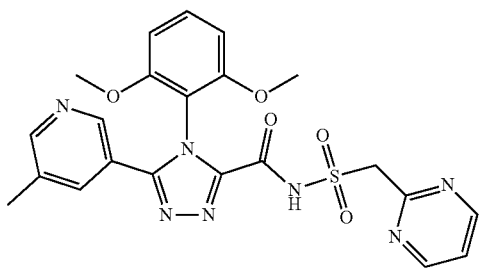 [SMILES: COc1cccc(OC)c1-n1c(C(=O)NS(=O)(=O)Cc2ncccn2)nnc1-c1cncc(C)c1] | 4-(2,6-Dimethoxyphenyl)-5-(5-methylpyridin-3-yl)-N-((pyrimidin-2-ylmethyl)sulfonyl)-4H-1,2,4-triazole-3-carboxamide, |

| | | |
|---|---|---|
| 64 | 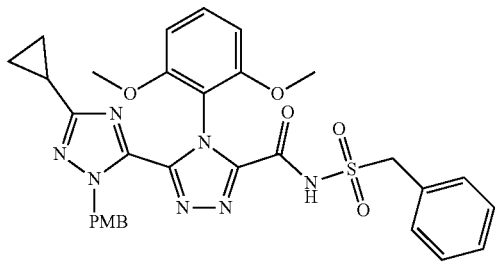 | N-(benzylsulfonyl)-5-cyclopropyl-4'-(2,6-dimethoxyphenyl)-2-(4-methoxybenzyl)-2H,4'H-[3,3'-bi(1,2,4-triazole)]-5'-carboxamide, |
| 65 | 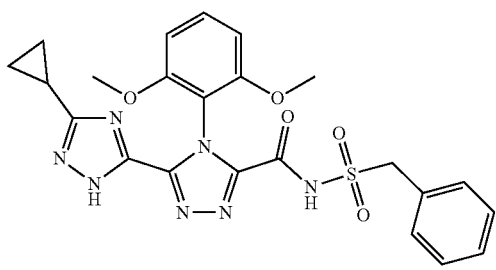 [SMILES: COc1cccc(OC)c1-n1c(C(=O)NS(=O)(=O)Cc2ccccc2)nnc1-c1nc(C2CC2)n[nH]1] | N-(benzylsulfonyl)-5-cyclopropyl-4'-(2,6-dimethoxyphenyl)-2H,4'H-[3,3'-bi(1,2,4-triazole)]-5'-carboxamide, and |
| | 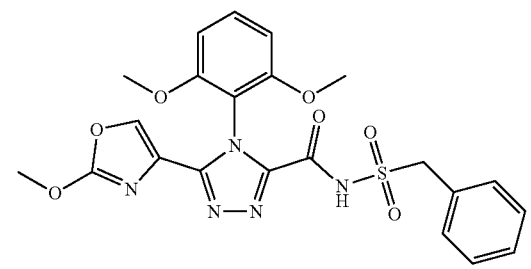 [SMILES: COc1nc(-c2nnc(C(=O)NS(=O)(=O)Cc3ccccc3)n2-c2c(OC)cccc2OC)co1] | N-(benzylsulfonyl)-4-(2,6-dimethoxyphenyl)-5-(2-methoxyoxazol-4-yl)-4H-1,2,4-triazole-3-carboxamide. | or a pharmaceutically acceptable salt thereof.

19. A compound selected from the group consisting of:

| | | |
|---|---|---|
| 1 | 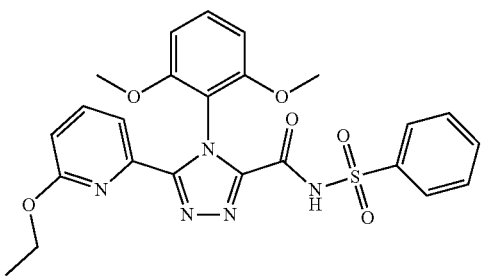 [SMILES: CCOc1cccc(-c2nnc(C(=O)NS(=O)(=O)c3ccccc3)n2-c2c(OC)cccc2OC)n1] | 4-(2,6-dimethoxyphenyl)-5-(6-ethoxypyridin-2-yl)-N-(phenylsulfonyl)-4H-1,2,4-triazole-3-carboxamide, |
| 3 | 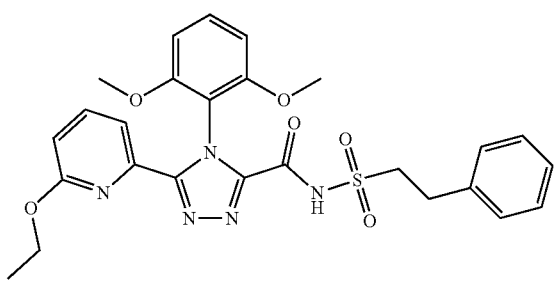 [SMILES: CCOc1cccc(-c2nnc(C(=O)NS(=O)(=O)CCc3ccccc3)n2-c2c(OC)cccc2OC)n1] | 4-(2,6-dimethoxyphenyl)-5-(6-ethoxypyridin-2-yl)-N-(phenethylsulfonyl)-4H-1,2,4-triazole-3-carboxamide, |

| | | |
|---|---|---|
| 17 | 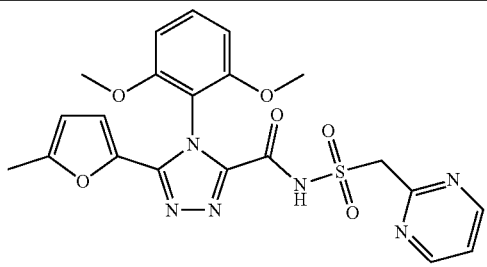 | 4-(2,6-Dimethoxyphenyl)-5-(5-methylfuran-2-yl)-N-((pyrimidin-2-ylmethyl)sulfonyl)-4H-1,2,4-triazole-3-carboxamide, |
| 20 | 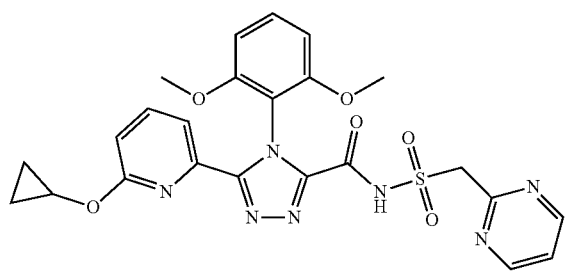 [SMILES: COc1cccc(OC)c1-n1c(C(=O)NS(=O)(=O)Cc2ncccn2)nnc1-c1cccc(OC2CC2)n1] | 5-(6-Cyclopropoxypyridin-2-yl)-4-(2,6-dimethoxyphenyl)-N-((pyrimidin-2-ylmethyl)sulfonyl)-4H-1,2,4-triazole-3-carboxamide, |
| 34 | 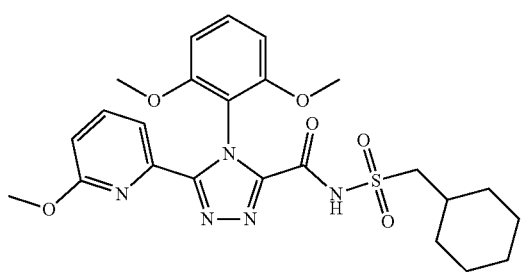 [SMILES: COc1cccc(-c2nnc(C(=O)NS(=O)(=O)CC3CCCCC3)n2-c2c(OC)cccc2OC)n1] | N-((cyclohexylmethyl)sulfonyl)-4-(2,6-dimethoxyphenyl)-5-(6-methoxypyridin-2-yl)-4H-1,2,4-triazole-3-carboxamide, |
| 39 | 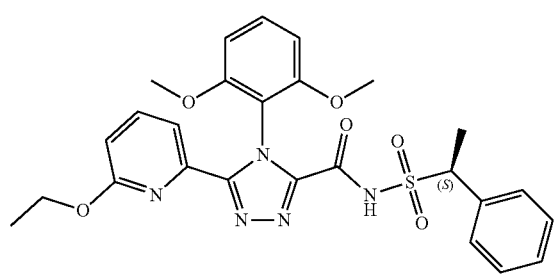 | (S)-4-(2,6-dimethoxyphenyl)-5-(6-ethoxypyridin-2-yl)-N-((1-phenylethyl)sulfonyl)-4H-1,2,4-triazole-3-carboxamide, |
| 40 | 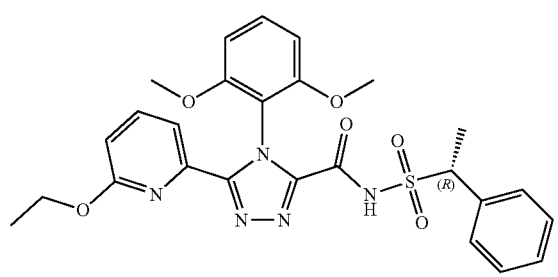 | (R)-4-(2,6-dimethoxyphenyl)-5-(6-ethoxypyridin-2-yl)-N-((1-phenylethyl)sulfonyl)-4H-1,2,4-triazole-3-carboxamide, |
| 41 | 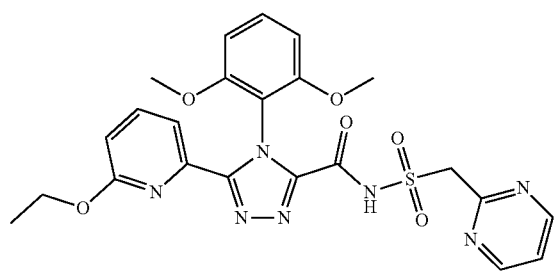 [SMILES: CCOc1cccc(-c2nnc(C(=O)NS(=O)(=O)Cc3ncccn3)n2-c2c(OC)cccc2OC)n1] | 4-(2,6-Dimethoxyphenyl)-5-(6-ethoxypyridin-2-yl)-N-((pyrimidin-2-ylmethyl)sulfonyl)-4H-1,2,4-triazole-3-carboxamide, |

| | | |
|---|---|---|
| 47 | 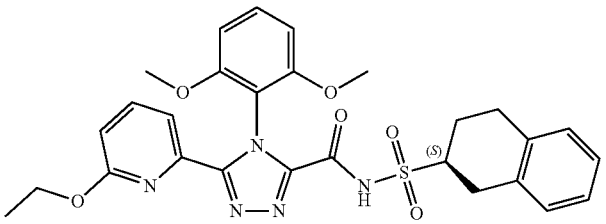 | (S)-4-(2,6-Dimethoxyphenyl)-5-(6-ethoxypyridin-2-yl)-N-((1,2,3,4-tetrahydronaphthalen-2-yl)sulfonyl)-4H-1,2,4-triazole-3-carboxamide, |
| 55 | 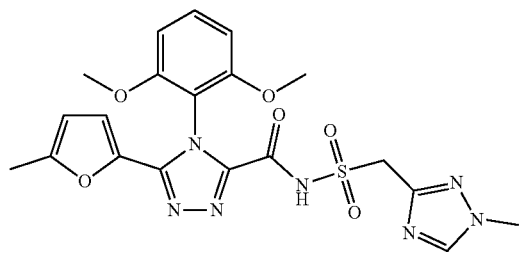 | 4-(2,6-Dimethoxyphenyl)-N-(((1-methyl-1H-1,2,4-triazol-3-yl)methyl)sulfonyl)-5-(5-methylfuran-2-yl)-4H-1,2,4-triazole-3-carboxamide, and |
| 57 | 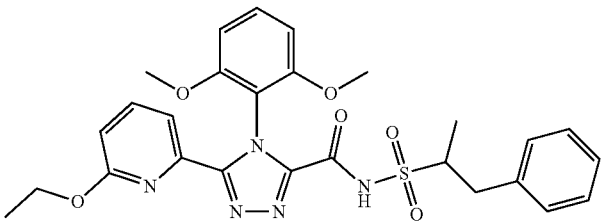 [SMILES: CCOc1cccc(-c2nnc(C(=O)NS(=O)(=O)C(C)Cc3ccccc3)n2-c2c(OC)cccc2OC)n1] | 4-(2,6-Dimethoxyphenyl)-5-(6-ethoxypyridin-2-yl)-N-((1-phenylpropan-2-yl)sulfonyl)-4H-1,2,4-triazole-3-carboxamide. | or a pharmaceutically acceptable salt thereof.

20. A pharmaceutical composition comprising a compound or a pharmaceutically accpetable salt as claimed in claim 1 and one or more pharmaceutically acceptable excipients.

* * * * *